(12) United States Patent
Breitenstein et al.

(10) Patent No.: US 8,163,773 B2
(45) Date of Patent: Apr. 24, 2012

(54) ORGANIC COMPOUNDS

(75) Inventors: Werner Breitenstein, Basel (CH); Claus Erhardt, Lörrach (DE); Juergen Klaus Maibaum, Weil-Haltingen (DE); Nils Ostermann, Binzen (DE); Juerg Zimmermann, Reinach (CH); Keiichi Masuya, Bottmingen (CH); Kazuhide Konishi, Ibaraki (JP); Fumiaki Yokokawa, Ibaraki (JP); Takanori Kanazawa, Ibaraki (JP); Edgar Jacoby, Basel (CH); Andreas Marzinzik, Weil (DE); Philipp Grosche, Inzlingen (DE); Shimpei Kawakami, Ibaraki (JP)

(73) Assignee: Novartis AG, Basel (CH)

( * ) Notice: Subject to any disclaimer, the term of this patent is extended or adjusted under 35 U.S.C. 154(b) by 958 days.

(21) Appl. No.: 11/995,484

(22) PCT Filed: Jul. 10, 2006

(86) PCT No.: PCT/EP2006/006733
§ 371 (c)(1),
(2), (4) Date: Jul. 9, 2008

(87) PCT Pub. No.: WO2007/006534
PCT Pub. Date: Jan. 18, 2007

(65) Prior Publication Data
US 2009/0233920 A1 Sep. 17, 2009

(30) Foreign Application Priority Data
Jul. 11, 2005 (GB) .................................. 0514203.9

(51) Int. Cl.
*A61K 31/445* (2006.01)
*C07D 401/00* (2006.01)
(52) U.S. Cl. ...................................... 514/317; 546/208
(58) Field of Classification Search .................. 514/317; 546/208
See application file for complete search history.

(56) References Cited

U.S. PATENT DOCUMENTS

| | | | |
|---|---|---|---|
| 5,389,647 A * | 2/1995 | Baker et al. ................... | 514/326 |
| 6,150,526 A | 11/2000 | Binggeli et al. | |
| 6,197,959 B1 | 3/2001 | Breu et al. | |
| 6,376,672 B1 | 4/2002 | Breu et al. | |
| 6,846,839 B1 * | 1/2005 | Tang et al. .................... | 514/397 |
| 2002/0087002 A1 | 7/2002 | Breu et al. | |
| 2004/0077551 A1 | 4/2004 | Campbell et al. | |
| 2004/0204455 A1 | 10/2004 | Cody et al. | |
| 2009/0192148 A1 | 7/2009 | Ehara et al. | |

FOREIGN PATENT DOCUMENTS

| | | |
|---|---|---|
| WO | WO 93/12108 A1 | 6/1993 |
| WO | 97/09311 | 3/1997 |
| WO | WO 99/09984 A1 | 3/1999 |
| WO | WO 00/63173 A1 | 10/2000 |
| WO | 00/64887 | 11/2000 |
| WO | WO 01/70673 A2 | 9/2001 |
| WO | WO 02/062525 A1 | 8/2002 |
| WO | WO 02/076440 A2 | 10/2002 |
| WO | WO 02/088101 A2 | 11/2002 |
| WO | WO 03/093267 A1 | 11/2003 |
| WO | 2004/002957 | 1/2004 |
| WO | 2004/089903 | 10/2004 |
| WO | WO 2004/089915 A1 | 10/2004 |
| WO | WO 2004/096116 A2 | 11/2004 |
| WO | WO 2004/096366 A1 | 11/2004 |
| WO | WO 2004/096769 A1 | 11/2004 |
| WO | WO 2004/096799 A1 | 11/2004 |
| WO | WO 2004/096803 A1 | 11/2004 |
| WO | WO 2004/096804 A1 | 11/2004 |
| WO | 2005/051911 | 6/2005 |
| WO | WO 2005/051911 A | 6/2005 |
| WO | WO 2005/061457 A | 7/2005 |
| WO | 2006/005741 | 1/2006 |
| WO | WO 2006/005741 A2 | 1/2006 |
| WO | 2006/066896 | 6/2006 |
| WO | 2006/069788 | 7/2006 |

(Continued)

OTHER PUBLICATIONS

Park et al. CAS: 139: 7132, 2003.*
Marki, et al., "Piperidine Renin" Il Farmaco, vol. 56, No. 1-2, 2001, pp. 21-27.
Maibaum, et al., "Renin inhibitors as novel treatment for cardiovascular diseases" Expert Opinion on Therapeutic Patents, vol. 13, No. 5, 2003, pp. 589-603.
Specker, Edgar, "De Novo Design und Synthese neuer Leitstrukturen als Ubergangszustandsmimetika zur selektiven Inhibition der HIV-1 Protease und Cathepsin D", Dissertation von Edgar Specker, 2004, 1-149.

(Continued)

*Primary Examiner* — Rei-tsang Shiao
(74) *Attorney, Agent, or Firm* — Sophie Binet Cross

(57) ABSTRACT

The invention relates to 3,5-substituted piperidine compounds, these compounds for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations comprising a 3,5-substituted piperidine compound, and/or a method of treatment comprising administering a 3,5-substituted piperidine compound, a method for the manufacture of a 3,5-substituted piperidine compound, and novel intermediates and partial steps for its synthesis. The preferred compounds (which can also be present as salts) have the formula I wherein R1, R2, T, R3 and R4 are as defined in the specification.

(I)

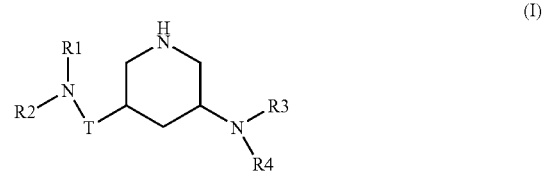

15 Claims, No Drawings

FOREIGN PATENT DOCUMENTS

| | | |
|---|---|---|
| WO | 2006/074924 | 7/2006 |
| WO | 2006/094763 | 9/2006 |
| WO | 2006/100036 | 9/2006 |
| WO | 2006/103273 | 10/2006 |
| WO | 2006/103275 | 10/2006 |
| WO | 2006/103277 | 10/2006 |
| WO | 2006/125621 | 11/2006 |
| WO | WO 2006/117183 A | 11/2006 |
| WO | 2006/128659 | 12/2006 |

OTHER PUBLICATIONS

Park, J.S. et al. "An efficient synthesis of 3(S)-aminopiperidine-f(R)-carbozxlic acid as a cyclic Beta, y-diamino acid", Tetrahedron Letters, 2003, 44, No. 8 pp. 1611-1614.

Abstract: 2003: 91169 Caplus of Tetrahedron Letters, vol. 44, No. 8, 2003.

International Search Report provided by the European Patent Office for priority application PCT/EP2006/006733 mailed Jan. 30, 2007.

* cited by examiner

ORGANIC COMPOUNDS

This application is the National Stage of Application No. PCT/EP2006/006733, filed on Jul. 10, 2006, which claims benefit of GB 0514203.9, filed July 11, 2005. The contents of which are incorporated herein by reference in their entirety.

The invention relates to 3,5-substituted piperidine compounds, these compounds for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations comprising a 3,5-substituted piperidine compound, and/or a method of treatment comprising administering a 3,5-substituted piperidine compound, a method for the manufacture of a 3,5-substituted piperidine compound, and novel intermediates and partial steps for its synthesis.

The present invention relates to a compound of the formula I

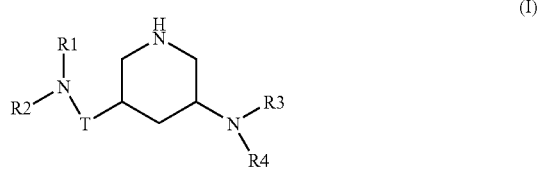

wherein

R1 is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;

R2 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;

R3 is hydrogen, unsubstituted or substituted aryl or unsubstituted or substituted alkyl, R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl; and T is methylene ($CH_2$) or carbonyl (C(=O)); or a (preferably pharmaceutically acceptable) salt thereof.

The compounds of the present invention exhibit inhibitory activity on the natural enzyme renin. Thus, compounds of formula I may be employed for the treatment (this term also including prophylaxis) of one or more disorders or diseases especially selected from the diseases given in detail below, especially as far as these diseases can be modulated (more especially beneficially influenced) by renin inhibition.

Listed below are definitions of various terms used to describe the compounds of the present invention as well as their use and synthesis, starting materials and intermediates and the like. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

The term "lower" or "$C_1$-$C_7$" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl or tert-butyl.

Halo or halogen is preferably fluoro, chloro, bromo or iodo, most preferably fluoro, chloro or bromo. If not explicitly or implicitly stated otherwise, halo can also stand for more than one halogen substituent in moieties such as alkyl, alkanoyl and the like (e.g. in trifluoromethyl, trifluoroacetyl).

Unsubstituted or substituted alkyl is preferably $C_1$-$C_{20}$-alkyl, more preferably $C_1$-$C_7$-alkyl, that is straight-chained or branched (one or, where appropriate, more times), which is unsubstituted or substituted by one or more, e.g. up to three moieties selected from unsubstituted or substituted heterocyclyl as described below, especially pyrrolyl, furanyl, thienyl (=thiophenyl), thiazolyl, pyrazolyl, triazolyl, tetrazolyl, oxetidinyl, 3-($C_1$-$C_7$-alkyl)-oxetidinyl, pyridyl, pyrimidinyl, morpholino, thiomorpholino, piperidinyl, piperazinyl, pyrrolidinyl, tetrahydrofuranoyl, tetrahydro-pyranyl, 1H-indazanyl, benzofuranyl, benzothiophenyl, (more preferably) isoquinolinyl, quinolinyl or especially indolyl, each of which is unsubstituted or substituted as described below for unsubstituted or substituted heterocyclyl, e.g. by one to three substitutents independently selected from hydroxy, halo, such as chloro, $C_1$-$C_7$-alkyl, such as methyl, cyano and $C_1$-$C_7$-alkanoyl, such as acetyl; from unsubstituted or substituted cycloalkyl as described below, especially cyclopropyl, cyclobutyl, cyclopentyl or cyclohexyl each of which is unsubstituted or substituted as described below for unsubstituted or substituted cycloalkyl, especially by up to four $C_1$-$C_7$-alkyl moieties; from unsubstituted or substituted aryl as described below, especially unsubstituted or substituted phenyl, naphthyl, indenyl or indanyl; and from the group consisting of $C_2$-$C_7$-alkenyl, $C_2$-$C_7$-alkinyl, halo, hydroxy, $C_1$-$C_7$-alkoxy, halo-$C_1$-$C_7$-alkoxy, such as trifluoromethoxy, hydroxy-$C_1$-$C_7$-alkoxy, $C_1$-$C_7$-alkoxy-$C_1$-$C_7$-alkoxy, phenyl- or naphthyloxy, phenyl- or naphthyl-$C_1$-$C_7$-alkyloxy, $C_1$-$C_7$-alkanoyloxy, ($C_1$-$C_7$-alkyl, hydroxy-$C_2$-$C_7$-alkyl (with the hydroxy not in 1-position), $C_1$-$C_7$-alkoxy-$C_1$-$C_7$-alkyl, phenyl and/or phenyl-$C_1$-$C_7$-alkyl)-aminocarbonyloxy, benzoyl- or naphthyloxy, $C_1$-$C_7$-alkylthio, halo-$C_1$-$C_7$-alkthio, such as trifluoromethylthio, hydroxy-$C_1$-$C_7$-alkylthio, $C_1$-$C_7$-alkoxy-$C_1$-$C_7$-alkylthio, phenyl- or naphthylthio, phenyl- or naphthyl-$C_1$-$C_7$-alkylthio, nitro, amino, mono- or di-($C_1$-$C_7$-alkyl, phenyl, naphthyl, phenyl-$C_1$-$C_7$-alkyl, naphthyl-$C_1$-$C_7$-alkyl, hydroxy-$C_2$-$C_7$-alkyl (with the hydroxy not in 1-position) and/or $C_1$-$C_7$-alkoxy-$C_1$-$C_7$-alkyl)-amino, $C_1$-$C_7$-alkanoylamino, benzoyl- or naphthoylamino, $C_1$-$C_7$-alkylsulfonylamino, phenyl- or naphthylsulfonylamino, phenyl- or naphthyl-$C_1$-$C_7$-alkylsulfonylamino, phenyl- or naphthyl-$C_1$-$C_7$-alkyl-carbonylamino, carboxyl, $C_1$-$C_7$-alkyl-carbonyl, $C_1$-$C_7$-alkoxy-carbonyl, phenyl- or naphthyloxycarbonyl, phenyl- or naphthyl-$C_1$-$C_7$-alkoxycarbonyl, carbamoyl, N-mono- or N,N-di-($C_1$-$C_7$-alkyl)-aminocarbonyl, N-mono- or N,N-di-(naphthyl- or phenyl-$C_1$-$C_7$-alkyl, hydroxy-$C_2$-$C_7$-alkyl (with the hydroxy not in 1-position) and/or $C_1$-$C_7$-alkoxy-$C_1$-$C_7$-alkyl)-aminocarbonyl, cyano, sulfenyl (—S—OH), sulfonyl (—S(=O)—OH), $C_1$-$C_7$-alkylsulfinyl ($C_1$-$C_7$-alkyl-S(=O)—), phenyl- or naphthylsulfinyl, phenyl- or naphthyl-$C_1$-$C_7$-alkylsulfinyl, sulfonyl, $C_1$-$C_7$-alkylsulfonyl, phenyl- or naphthylsulfonyl, phenyl- or naphthyl-$C_1$-$C_7$-alkylsulfonyl, sulfamoyl, N-mono or N,N-di-($C_1$-$C_7$-alkyl, phenyl-, naphthyl, phenyl-$C_1$-$C_7$-alkyl, naphthyl-$C_1$-$C_7$-alkyl, hydroxy-$C_2$-$C_7$-alkyl and/or $C_1$-$C_7$-alkoxy-$C_1$-$C_7$-alkyl)-aminosulfonyl, N-mono-, N'-mono-, N,N-di- or N,N,N'-tri-($C_1$-$C_7$-alkyl, hydroxy-$C_2$-$C_7$-alkyl (with the hydroxy not in 1-position), $C_1$-$C_7$-alkoxy-$C_1$-$C_7$-alkyl, phenyl and/or phenyl-$C_1$-$C_7$-alkyl)-aminocarbonylamino or -aminocarbonyloxy and N-mono-, N'-mono-, N,N-di- or N,N,N'-tri-($C_1$-$C_7$-alkyl, hydroxy-$C_2$-$C_7$-alkyl (with the hydroxy not in 1-position), $C_1$-$C_7$-alkoxy-$C_1$-$C_7$-alkyl, phenyl and/or phenyl-$C_1$-$C_7$-alkyl)-aminosulfonylamino;

where any phenyl, naphthyl, indenyl, indanyl, pyridyl or indolinyl mentioned as substituent of or as part of a substituent of substituted alkyl (mentioned in the preceding paragraph) is unsubstituted or substituted by one or more, preferably up to three, moieties independently selected from the group consisting of $C_1$-$C_7$-alkyl, $C_1$-$C_7$-alkoxy-$C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, $C_1$-$C_7$-alkoxy-$C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$ alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycarbonyl, phenyl-$C_1$-$C_7$-alkyloxycarbonyl, naphthyl-$C_1$-$C_7$ alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfonyl, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-amino-sulfonyl and nitro, or preferably, where preferred substituents are mentioned, by one or more of these mentioned substituents. Very especially preferred, unsubstituted or substituted alkyl (especially as R2 or as part of acyl R4) is phenylmethyl, 2-cyclohexyl-2-phenyl-ethyl, 2,2-diphenylethyl, 2,2-diphenyl-n-butyl, 2,3-diphenyl-n-propyl, naphthylmethyl, 2-phenyl-2-pyridylethyl, indolylmethyl, 2-$C_1$-$C_7$-alkoxycarbonyl-2,2-diphenyl-ethyl, 4-methyl-2-phenyl-n-pentyl or 5-$C_1$-$C_7$-alkoxy-2-diphenylmethylpentyl, where any phenyl, naphthyl, pyridyl or indolyl mentioned as substituent of substituted alkyl is unsubstituted or substituted by one or more, especially up to three, moieties independently selected from the group consisting of $C_1$-$C_7$-alkyl, hydroxy-$C_1$-$C_7$-alkyl, $C_1$-$C_7$-alkoxy-$C_1$-$C_7$-alkyl, 107 -hydroxy-$C_2$-$C_7$-alkoxy-$C_1$-$C_7$-alkyl, halo-$C_1$-$C_7$-alkyl, oxo-$C_1$-$C_7$-alkyl, $C_1$-C-alkanoyl, phenyl, halo, especially chloro or bromo, hydroxy, $C_1$-$C_7$-alkoxy, $C_1$-$C_7$-alkoxy-$C_1$-$C_7$-alkoxy, phenoxy, halo-$C_1$-$C_7$-alkoxy, amino, $C_1$-$C_7$-alkanoylamino, $C_1$-$C_7$-alkanesulfonyl and cyano (where preferably any moiety mentioned before comprising an O, halo, or S via which it is bound is not bound to a ring nitrogen).

Unsubstituted or substituted alkenyl is preferably $C_2$-$C_{20}$-alkenyl, more preferably $C_2$-$C_7$-alkenyl with one or, if possible, more double bonds, that is straight-chained or branched (one or, where appropriate, more times), which is unsubstituted or substituted by one or more, e.g. up to three moieties selected from those mentioned as substituents for substituted alkyl and from unsubstituted or substituted aryl, each preferably as described above or below. Substituents with an active hydrogen (e.g. hydroxy or amino) are preferably present in the form of tautomers in equilibrium if bound directly to a carbon with a double bond, preferably at such positions substituents with active hydrogen are avoided.

Unsubstituted or substituted alkynyl is preferably $C_2$-$C_{20}$-alkynyl, more preferably $C_2$-$C_7$ alkynyl with one or, if possible, more triple bonds, that is straight-chained or branched (one or, where appropriate, more times), which is unsubstituted or substituted by one or more, e.g. up to three moieties selected from those mentioned as substituents for substituted alkyl and from unsubstituted or substituted aryl, each preferably as described above or below. Substituents with an active hydrogen (e.g. hydroxy or amino) are preferably present in the form of tautomers in equilibrium if bound directly to a carbon with a triple bond, preferably at such positions substituents with active hydrogen are avoided.

Unsubstituted or substituted aryl preferably is a mono- or bicyclic aryl with 6 to 22 carbon atoms, especially phenyl, indenyl, indanyl or naphthyl, and is unsubstituted or substituted by one or more, especially one to three, moieties, preferably independently selected from the group consisting of a substituent of the formula —($C_0$-$C_7$-alkylene)-(X)$_r$—($C_1$-$C_7$-alkylene)-(Y)$_s$—($C_0$-$C_7$-alkylene)-H (especially in substituted aryl or substituted aryl-alkyl as R2) where $C_0$-alkylene means that a bond is present instead of bound alkylene, alkylene in each case may be straight-chained or branched and unsubstituted or (with lower preference) substituted e.g. by one or more moieties as defined for substituted alkyl, especially by halo, especially fluoro, hydroxy, $C_1$-$C_7$-alkoxy, phenyloxy, naphthyloxy, $C_1$-$C_7$-alkanoyloxy, benzoyloxy, naphthyloxy, amino, mono- or di-($C_1$-$C_7$-alkyl, $C_1$-$C_7$-alkanoyl, phenyl-$C_1$-$C_7$-alkanoyl, naphthyl-$C_1$-$C_7$-alkanoyl, phenyl, naphthyl, phenyl-$C_1$-$C_7$-alkyl and/or naphthyl-$C_1$-$C_7$-alkyl)-amino, carboxy, $C_1$-$C_7$-alkoxycarbonyl or cyano, r and s, each independently of the other, are 0 or 1 and each of X and Y, if present and independently of the others, is —O—, —NV—, —S—, —O—CO—, —CO—O—, —NV—CO—; —CO—NV—; —NV—SO$_2$—, —SO$_2$—NV; —NV—CO—NV—, —NV—CO—O—, —O—CO—NV—, —NV—SO$_2$—NV— wherein V is hydrogen or unsubstituted or substituted alkyl as defined above, especially $C_1$-$C_7$-alkyl, or is phenyl, naphthyl, phenyl- or naphthyl-$C_1$-$C_7$-alkyl or halo-$C_1$-$C_7$-alkyl; where said substitutent —($C_0$-$C_7$-alkylene)-(X)$_r$—($C_1$-$C_7$-alkylene)-(Y)$_s$—($C_0$-$C_7$-alkylene)-His preferably $C_1$-$C_7$-alkyl, such as methyl, ethyl, n-propyl, isopropyl, n-butyl, isobutyl, sec-butyl or tert-butyl, halo-$C_1$-$C_7$-alkyl, such as trifluoromethyl, hydroxy-$C_1$-$C_7$-alkyl, $C_1$-$C_7$-alkoxy-$C_1$-$C_7$-alkyl, such as 3-methoxypropyl or 2-methoxyethyl, ω-hydroxy-$C_2$-$C_7$-alkoxy-$C_1$-$C_7$-alkyl, $C_1$-$C_7$-alkoxy-$C_1$-$C_7$-alkoxy-$C_1$-$C_7$-alkyl, phenyloxy- or naphthyloxy-$C_1$-$C_7$-alkyl, $C_1$-$C_7$-alkanoyloxy-$C_1$-$C_7$-alkyl, amino-$C_1$-$C_7$ alkyl, such as aminomethyl, $C_1$-$C_7$-alkoxy-$C_1$-$C_7$-alkylamino-$C_1$-$C_7$-alkyl, mono- or di-($C_1$-$C_7$ alkyl-, naphthyl-, phenyl, naphthyl-$C_1$-$C_7$-alkyl and/or phenyl-$C_1$-$C_7$-alkyl)-amino-$C_1$-$C_7$-alkyl, $C_1$-$C_7$-alkanoylamino-$C_1$-$C_7$-alkyl, $C_1$-$C_7$-alkyl-O—CO—NH—$C_1$-$C_7$-alkyl, $C_1$-$C_7$-alkylsulfonylamino-$C_1$-$C_7$-alkyl, $C_1$-$C_7$-alkyl-NH—CO—NH—$C_1$-$C_7$-alkyl, $C_1$-$C_7$-alkyl-NH—SO$_2$—NH—$C_1$-$C_7$-alkyl, $C_1$-$C_7$-alkoxy, hydroxy-$C_1$-$C_7$-alkoxy, $C_1$-$C_7$-alkoxy-$C_1$-$C_7$-alkoxy, $C_1$-$C_7$-alkanoyloxy, halo-$C_1$-$C_7$-alkoxy, such as trifluoromethoxy, phenyl- or naphthyl-$C_1$-$C_7$-alkanoyloxy, phenyl- or naphthyl-$C_1$-$C_7$-alkylaminocarbonyloxy, halo-$C_1$-$C_7$-alkylthio, such as trifluoromethylthio, phenyl- or naphthyl-$C_1$-$C_7$-alkylthio, mono- or di-($C_1$-$C_7$-alkyl-, naphthyl-$C_1$-$C_7$-alkyl-, phenyl-$C_1$-$C_7$-alkyl- and/or $C_1$-$C_7$-alkoxy-$C_1$-$C_7$-alkyl-) amino, $C_1$-$C_7$-alkanoylamino, $C_1$-$C_7$-alkylsulfonylamino, phenyl- or naphthyl-$C_1$-$C_7$-alkanoylamino, phenyl- or naphthyl-$C_1$-$C_7$-alkylaminocarbonyl-amino, carboxy-$C_1$-

$C_7$-alkyl, $C_1$-$C_7$-alkoxy-carbonyl, hydroxy-$C_1$-$C_7$-alkoxycarbonyl, $C_1$-$C_7$-alkoxy-$C_1$-$C_7$-alkoxycarbonyl, amino-$C_1$-$C_7$-alkoxycarbonyl, (N—) mono-($C_1$-$C_7$-alkyl)-amino-$C_1$-$C_7$-alkoxycarbonyl, $C_1$-$C_7$-alkanoylamino-$C_1$-$C_7$-alkoxycarbonyl, N-mono- or N,N-di-($C_1$-$C_7$-alkyl, naphthyl-$C_1$-$C_7$-alkyl and/or phenyl-$C_1$-$C_7$-alkyl)-aminocarbonyl, $C_1$-$C_7$-alkylsulfonyl, halo-$C_1$-$C_7$-alkylsulfonyl, hydroxy-$C_1$-$C_7$-alkylsulfonyl, $C_1$-$C_7$-alkoxy-$C_1$-$C_7$-alkylsulfonyl, amino-$C_1$-$C_7$-alkylsulfonyl, N-mono- or di-($C_1$-$C_7$-alkyl)-amino-$C_1$-$C_7$-alkylsulfonyl, $C_1$-$C_7$ alkanoylamino-$C_1$-$C_7$-alkylsulfonyl, N—$C_1$-$C_7$-alkoxy-$C_1$-$C_7$-alkylcarbamoyl or N-mono- or N,N-di-($C_1$-$C_7$-alkyl)-aminosulfonyl;

from $C_2$-$C_7$-alkenyl, $C_2$-$C_7$-alkynyl, phenyl, naphthyl, heterocyclyl, especially as defined below for heterocyclyl, preferably selected from pyrrolyl, furanyl, thienyl, pyrimidine-2,4-dione-1-, -3- or -5-yl and tetrahydrofuranyl, [phenyl- or naphthyl- or heterocyclyl or trihalo(especially trifluoro)methoxy]-$C_1$-$C_7$-alkyl or —$C_1$-$C_7$-alkyloxy wherein phenyl or naphthyl is preferably unsubstituted or substituted, preferably by $C_1$-$C_7$-alkoxy and/or halo and wherein heterocyclyl is as defined below, preferably selected from pyrrolyl, furanyl, tetrahydrofuranyl, tetrahydropyranyl and thienyl; such as benzyl or naphthylmethyl, tetrahydrofuranyl- or tetrahydropyranyl-$C_1$-$C_7$-alkyl, benzoyl- or naphthoylamino-$C_1$-$C_7$-alkyl, (phenyl- or naphthyl- or heterocyclyl)-sulfonylamino-$C_1$-$C_7$-alkyl wherein phenyl or naphthyl or heterocyclyl is unsubstituted or substituted, preferably by one or more, especially one to three, $C_1$-$C_7$-alkyl moieties, (phenyl or naphthyl or heterocyclyl)-$C_1$-$C_7$-alkylsulfonylamino-$C_1$-$C_7$-alkyl, halo, hydroxy, (heterocyclyl or phenyl or naphthyl)-oxy, naphthyl-$C_1$-$C_7$-alkyloxy, benzoyl or naphthoyl or heterocyclylcarbonyl)-oxy, (phenyl or naphthyl or heterocyclyl)-aminocarbonyloxy, (phenyl or naphthyl or heterocyclyl)-thio, (benzoyl or naphthoyl or heterocyclyl)-thio, nitro, amino, di-((naphthyl or phenyl or heterocyclyl)-$C_1$-$C_7$-alkyl)-amino, (benzoyl or naphthoyl or heterocyclyl)-amino, (phenyl or naphthyl or heterocyclyl)-$C_1$-$C_7$-carbonylamino, (phenyl or naphthyl or heterocyclyl)-sulfonylamino wherein phenyl or naphthyl is unsubstituted or substituted preferably by one or more, especially one to three, $C_1$-$C_7$-alkyl moieties, (phenyl or naphthyl or heterocyclyl)-$C_1$-$C_7$-alkylsulfonylamino, (phenyl or naphthyl or heterocyclyl)-aminocarbonylamino, (phenyl or naphthyl or heterocyclyl)-$C_1$-$C_7$-aminocarbonylamino, (phenyl or naphthyl or heterocyclyl)-oxycarbonylamino, (phenyl or naphthyl or heterocyclyl)-$C_1$-$C_7$-alkyloxycarbonylamino, carboxyl, $C_1$-$C_7$-alkyl-carbonyl, halo-$C_1$-$C_7$-alkylcarbonyl, hydroxy-$C_1$-$C_7$-alkylcarbonyl, $C_1$-$C_7$-alkoxy-$C_1$-$C_7$-alkylcarbonyl, amino-$C_1$-$C_7$-alkylcarbonyl, (N-) mono- or (N,N-) di-($C_1$-$C_7$-alkyl)-amino-$C_1$-$C_7$-alkylcarbonyl, $C_1$-$C_7$-alkanoylamino-$C_1$-$C_7$-alkylcarbonyl, halo-$C_1$-$C_7$-alkoxycarbonyl, (phenyl or naphthyl or (especially mono- or bicyclic) heterocyclyl)-oxycarbonyl, (phenyl or naphthyl or heterocyclyl)-$C_1$-$C_7$-alkoxycarbonyl, (N,N-) di-($C_1$-$C_7$-alkyl)-amino-$C_1$-$C_7$-alkoxycarbonyl, carbamoyl, N-mono or N,N-di-(naphthyl or phenyl or heterocyclyl)-aminocarbonyl, cyano, $C_1$-$C_7$-alkylene which is unsubstituted or substituted by up to four $C_1$-$C_7$-alkyl substituents and bound to two adjacent ring atoms of the aryl moiety, sulfenyl, sulfinyl, $C_1$-$C_7$-alkylsulfinyl, (phenyl or naphthyl or heterocyclyl)-sulfinyl wherein phenyl or naphthyl is unsubstituted or substituted preferably by one or more, especially one to three, $C_1$-$C_7$-alkyl moieties, phenyl- or naphthyl-$C_1$-$C_7$-alkylsulfinyl, sulfonyl, (phenyl or naphthyl or heterocyclyl)-sulfonyl wherein phenyl or naphthyl is unsubstituted or substituted preferably by one or more, especially one to three, $C_1$-$C_7$-alkyl moieties, (phenyl or naphthyl or heterocyclyl)$C_1$-$C_7$-alkylsulfonyl, sulfamoyl and N-mono or N,N-di-($C_1$-$C_7$-alkyl, phenyl-, naphthyl, heterocyclyl, phenyl-$C_1$-$C_7$-alkyl, naphthyl-$C_1$-$C_7$-alkyl and/or heterocyclyl-$C_1$-$C_7$ alkyl)-aminosulfonyl;

where any phenyl or naphthyl or heterocyclyl (which heterocyclyl is preferably as defined for heterocyclyl, more preferably is selected from pyrrolyl, furanyl, tetrahydrofuranyl, tetrahydropyranyl and thienyl) mentioned as substituent of or as part of a substituent of substituted aryl mentioned in one of the two preceding paragraphs is unsubstituted or substituted by one or more, preferably up to three, moieties independently selected from the group consisting of $C_1$-$C_7$-alkyl, $C_1$-$C_7$-alkenyl, $C_1$-$C_7$-alkynyl, halo-$C_1$-$C_7$-alkyl, such as trifluoromethyl, halo, especially fluoro, chloro, bromo or iodo, hydroxy, $C_1$-$C_7$-alkoxy, phenyloxy, naphthyloxy, phenyl- or naphthyl-$C_1$-$C_7$-alkoxy, $C_1$-$C_7$-alkanoyloxy, phenyl- or naphthyl-$C_1$-$C_7$-alkanoyloxy, amino, mono- or di-($C_1$-$C_7$-alkyl, phenyl, naphthyl, phenyl-$C_1$-$C_7$-alkyl, naphthyl-$C_1$-$C_7$-alkyl, $C_1$-$C_7$-alkanoyl and/or phenyl- or naphthyl-$C_1$-$C_7$-alkanoyl)-amino, carboxy, $C_1$-$C_7$-alkoxycarbonyl, phenoxycarbonyl, naphthyloxycarbonyl, phenyl-$C_1$-$C_7$-alkyloxycarbonyl, naphthyl-$C_1$-$C_7$-alkoxycarbonyl, carbamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminocarbonyl, cyano, sulfonyl, sulfamoyl, N-mono- or N,N-di-($C_1$-$C_7$-alkyl, phenyl, naphthyl, phenyl-$C_1$-$C_7$-alkyl and/or naphthyl-$C_1$-$C_7$-alkyl)-aminosulfonyl and nitro, or preferably, where preferred substituents are mentioned, by one or more of these mentioned substituents.

Unsubstituted or substituted heterocyclyl is preferably a mono- or bicyclic heterocyclic moiety with an unsaturated, partially saturated or saturated ring system with preferably 3 to 22 (more preferably 3 to 14) ring atoms and with one or more, preferably one to four, heteroatoms independently selected from nitrogen (=N—, —NH— or substituted —NH—), oxygen and sulfur (—S—, S(=O)— or S—(=O)$_2$—) which is unsubstituted or substituted by one or more, e.g. up to three, substitutents preferably independently selected from the substitutents mentioned above for aryl (where preferably such substituents that comprise an S, O or halo which binds to heterocyclyl are not bound via a ring nitrogen) and from oxo (=O) and thioxo (=S). Preferably, unsubstituted or substituted heterocyclyl is selected from the following moieties:

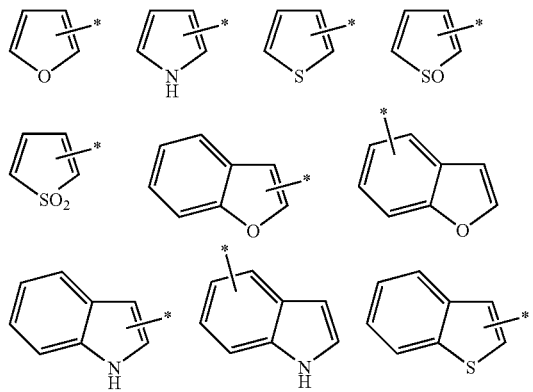

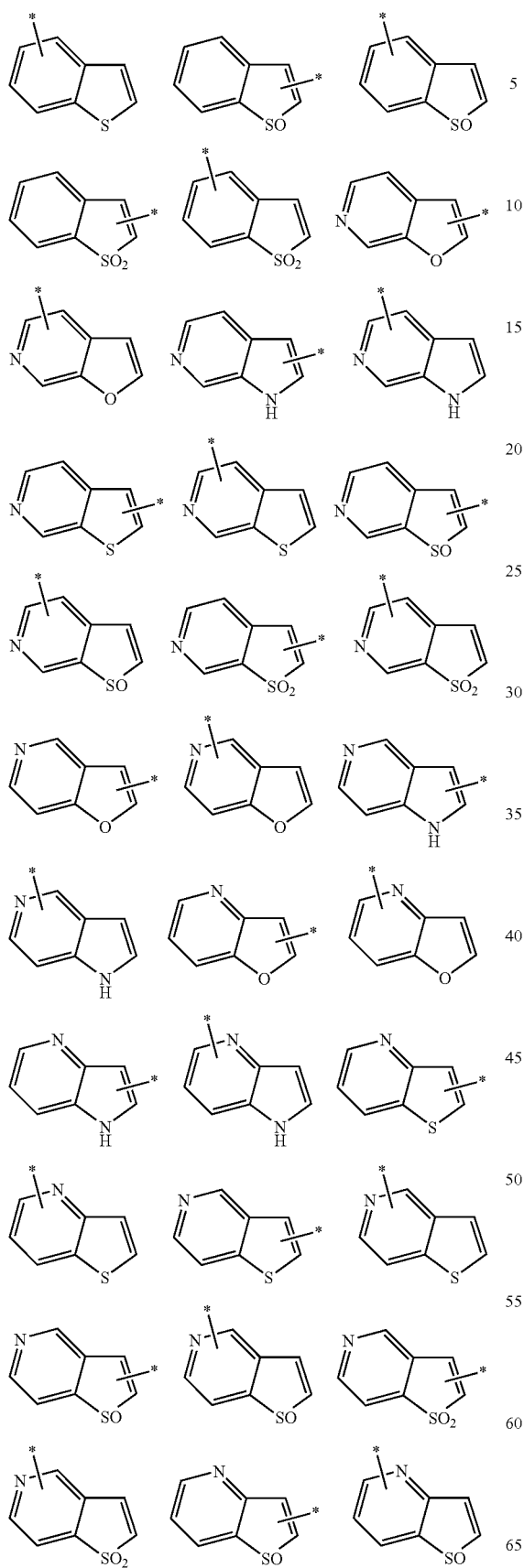
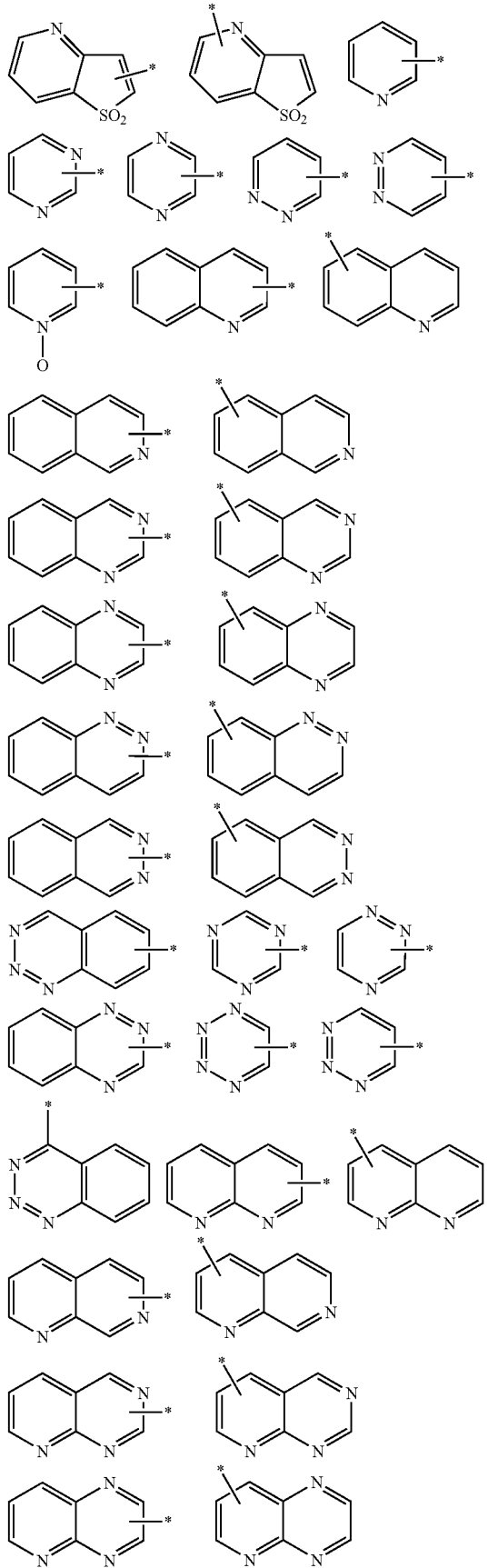

-continued
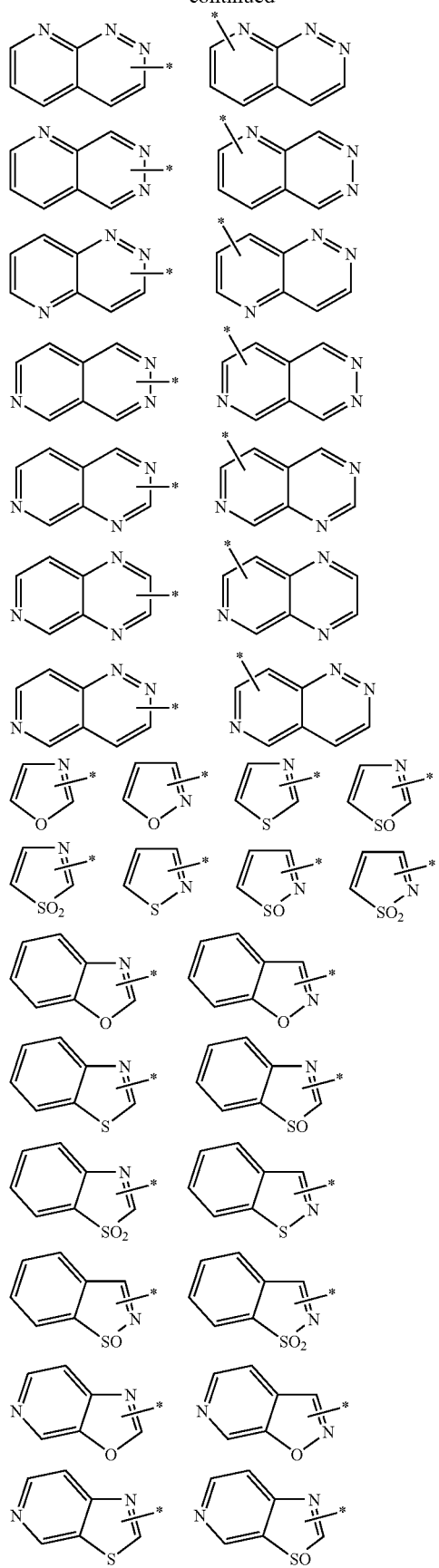
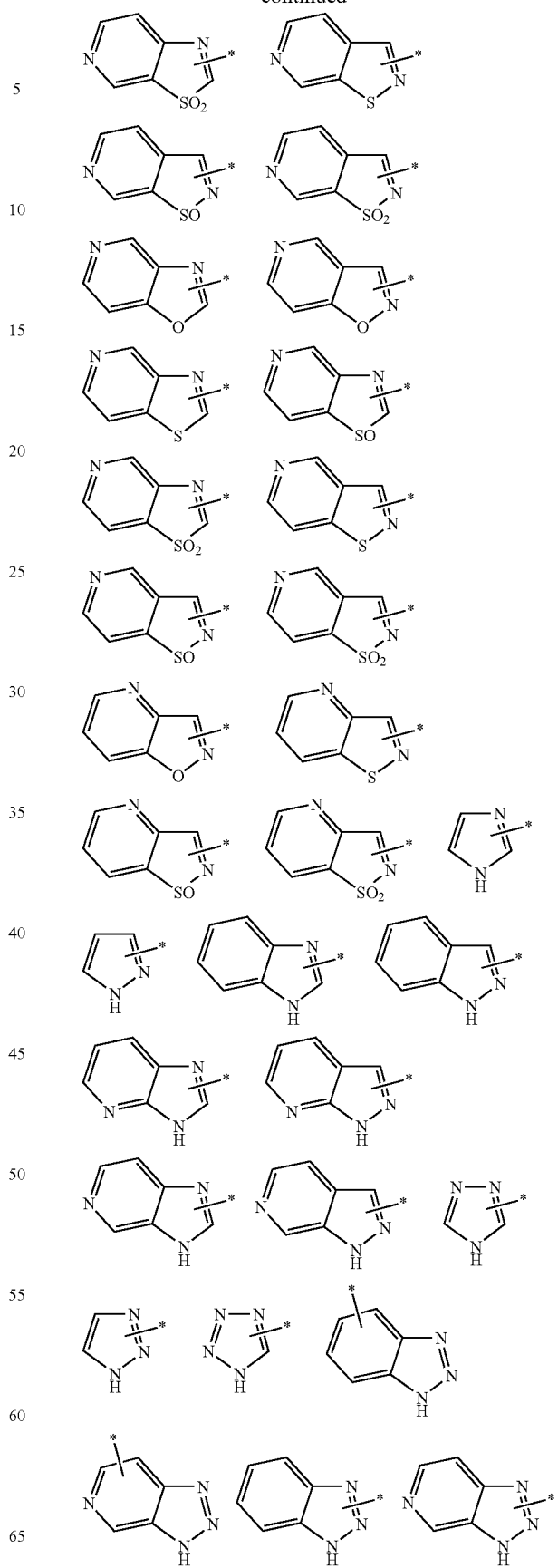

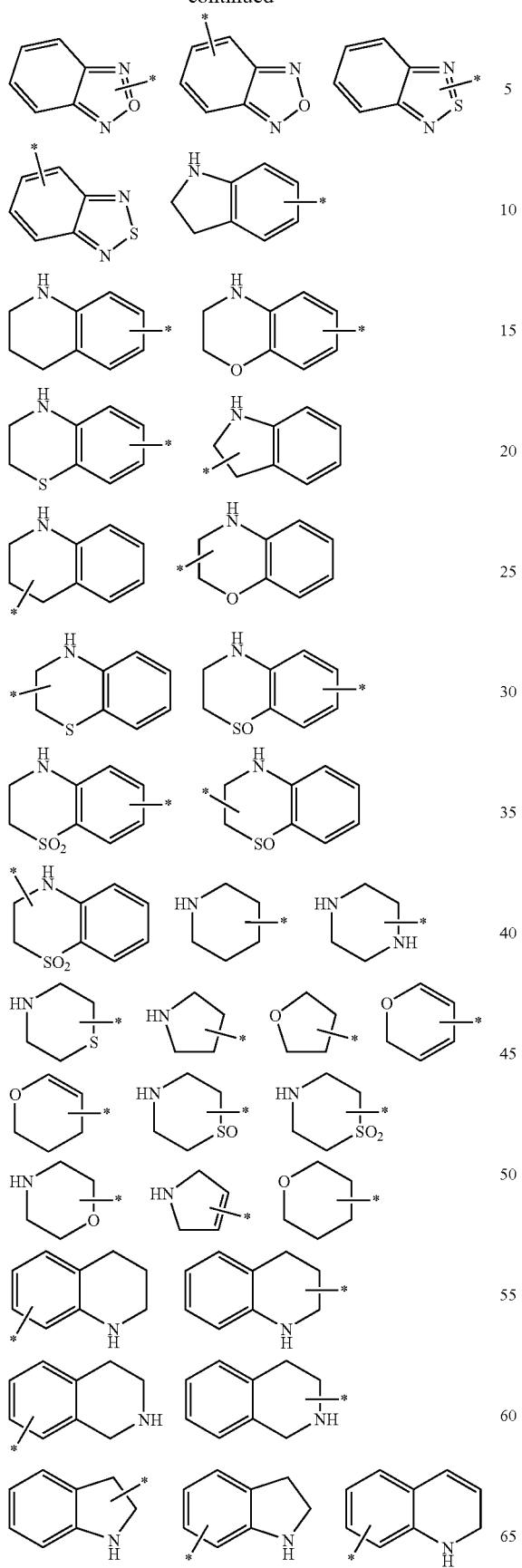
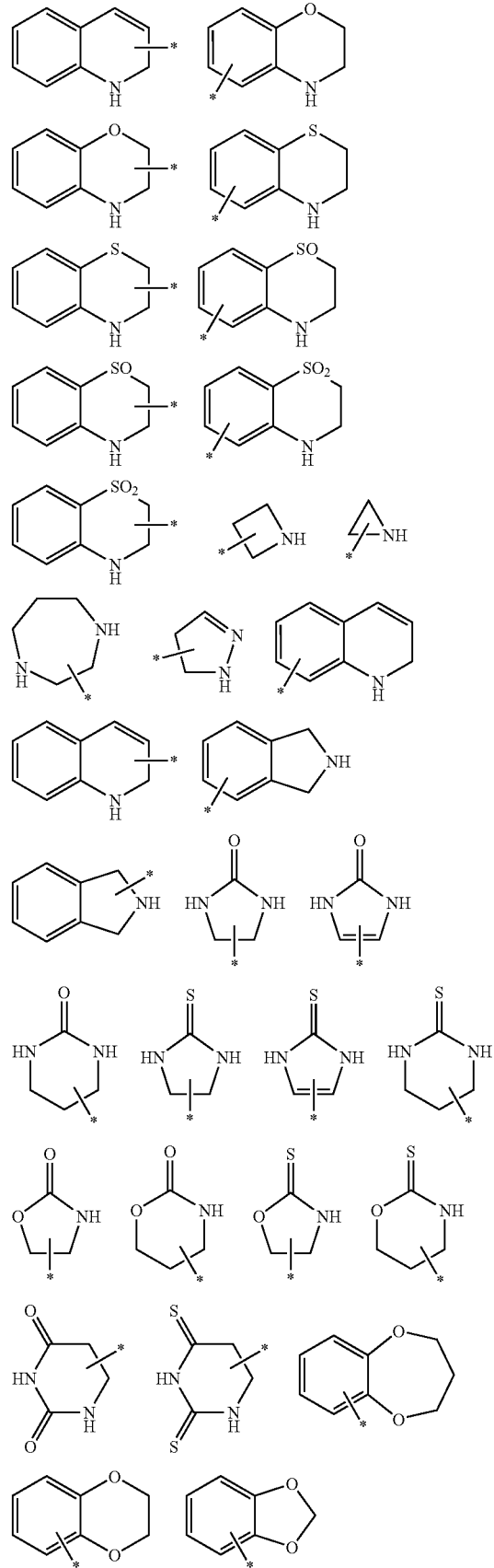

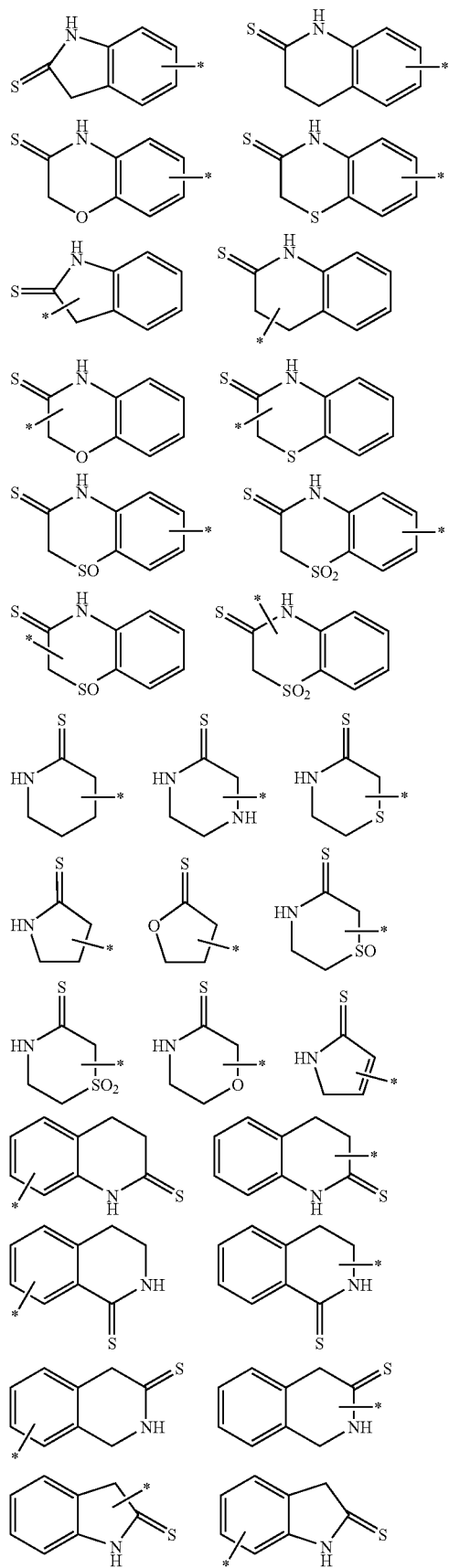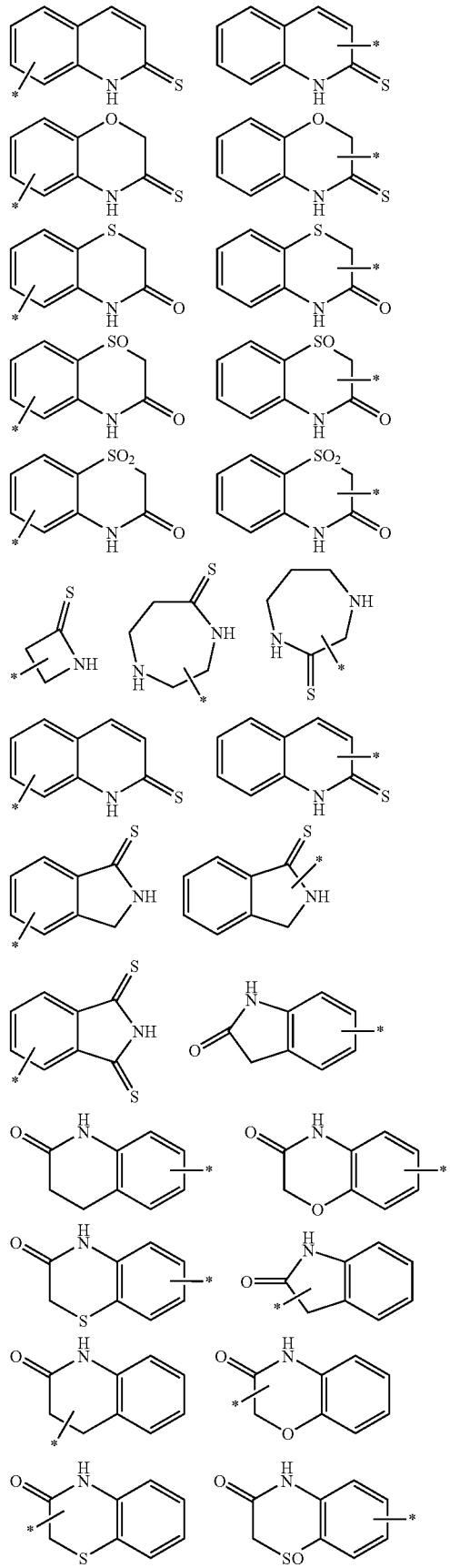

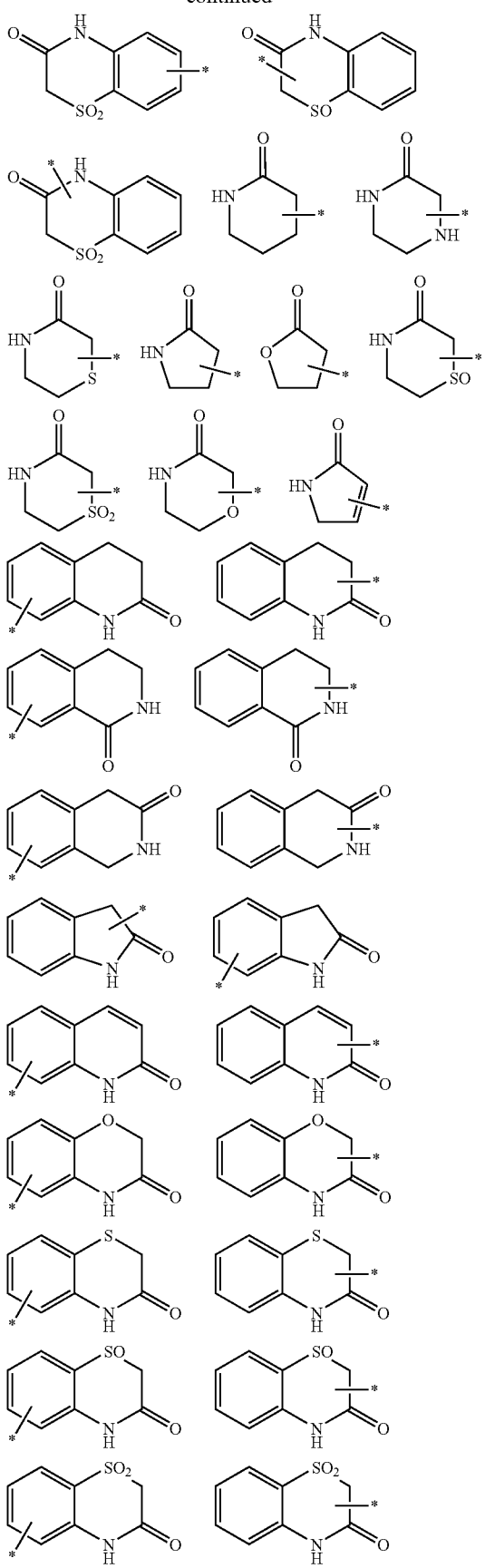
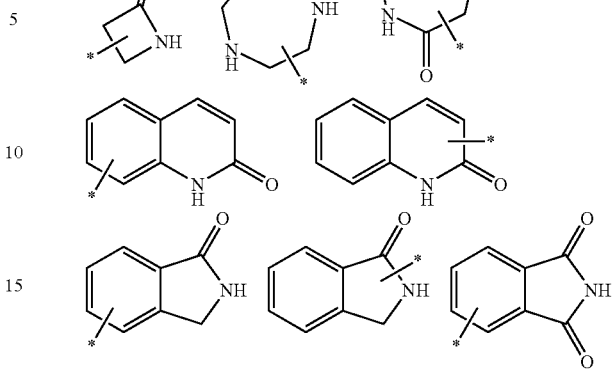

where in each case where an H is present bound to a ring atom the bond with the asterisk connecting the respective heterocyclyl moiety to the rest of the molecule the H may be replaced with said bond and if present one or more further H atoms bound to a ring atom may be replaced by one or more substituents as just described. Very preferred as unsubstituted or substituted heterocyclyl are tetrahydrofuranyl, tetrahydropyranyl, piperidinyl, pyridyl, thiophenyl, thiazolyl, pyrazolyl, indolyl, quinolinyl or 2H-1,4-benzoxazin-3(4H)-onyl, each of which is unsubstituted or substituted by one or more, especially up to three substituents independently selected from the substituents mentioned for substituted aryl above, especially by one or more, especially up to three, moieties independently selected from the group consisting of $C_1$-$C_7$-alkyl, $C_1$-$C_7$-alkoxy-$C_1$-$C_7$-alkyl, halo-$C_1$-$C_7$-alkyl, oxo-$C_1$-$C_7$-alkyl, $C_1$-$C_7$-alkanoyl, phenyl, halo, especially chloro or bromo, hydroxy, $C_1$-$C_7$-alkoxy, $C_1$-$C_7$-alkoxy-$C_1$-$C_7$-alkoxy, phenoxy, halo-$C_1$-$C_7$-alkoxy, amino, $C_1$-$C_7$-alkanoylamino, $C_1$-$C_7$-alkanesulfonyl and cyano.

Unsubstituted or substituted cycloalkyl is preferably mono- or bicyclic, more preferably monocyclic, $C_3$-$C_{10}$-cycloalkyl which may include one or more double (e.g. in cycloalkenyl) and/or triple bonds (e.g. in cycloalkynyl), and is unsubstituted or substituted by one or more, e.g. one to four substitutents preferably independently selected from those mentioned above as substituents for aryl, especially $C_3$-$C_8$-cycloalkyl that is unsubstituted or substituted by up to four substituents selected from $C_1$-$C_7$-alkyl, from phenyl (which is unsubstituted or substituted by one or more, especially up to three, substituents independently selected from the group consisting of $C_1$-$C_7$-alkyl, $C_1$-$C_7$-alkoxy-$C_1$-$C_7$-alkyl, halo-$C_1$-$C_7$-alkyl, oxo-$C_1$-$C_7$ alkyl, $C_1$-$C_7$-alkanoyl, phenyl, halo, such as chloro, hydroxy, $C_1$-$C_7$-alkoxy, $C_1$-$C_7$-alkoxy-$C_1$-$C_7$-alkoxy, halo-$C_1$-$C_7$-alkoxy, phenoxy, amino, $C_1$-$C_7$-alkanoylamino, carbamoyl, $C_1$-$C_7$-alkanesulfonyl and cyano), from carbamoyl and from cyano. Preferred is cyclopropyl, cyclobutyl, cyclopentyl, cyclohexyl, cycloheptyl or cyclooctyl that is unsubstituted or substituted by phenyl, halophenyl, carbamoyl and cyano.

Acyl is preferably unsubstituted or substituted aryl-carbonyl (aryl-C(=O)—) or -sulfonyl (aryl-$SO_2$—), unsubstituted or substituted heterocyclylcarbonyl (heterocyclyl-C(=O)—) or -sulfonyl (heterocyclyl-$SO_2$—), unsubstituted or substituted cycloalkylcarbonyl (cycloalkyl-C(=O)—) or -sulfonyl (cycloalkyl-$SO_2$—), formyl or (unsubstituted or substituted alkyl, unsubstituted or substituted aryl-$C_1$-$C_7$-alkyl, unsubstituted or substituted heterocyclyl-$C_1$-$C_7$-alkyl or unsubstituted or substituted cycloalkyl-$C_1$-$C_7$-alkyl)-carbonyl or -sulfonyl, or (especially if bound to N, S or O) unsubstituted or substituted alkyloxycarbonyl, unsubstituted or substituted aryloxycarbonyl, unsubstituted or substituted heterocyclyloxycarbonyl, unsubstituted or substituted cycloalkyloxycarbonyl, unsubstituted or substituted aryl-$C_1$-$C_7$-oxycarbonyl, unsubstituted or substituted heterocyclyl-$C_1$-$C_7$-oxycarbonyl, unsubstituted or substituted cycloalkyl-$C_1$-$C_7$-oxycarbonyl or N-mono- or N,N-di-(unsubstituted or substituted aryl, unsubstituted or substituted heterocyclyl, unsubstituted or substituted cycloalkyl, unsubstituted or substituted aryl-$C_1$-$C_7$-alkyl, unsubstituted or substituted heterocyclyl-$C_1$-$C_7$-alkyl, unsubstituted or substituted cycloalkyl-$C_1$-$C_7$-alkyl or unsubstituted or substituted alkyl)-aminocarbonyl or -aminosulfonyl, with the proviso that-oxycarbonyl bound moieties are preferably bound to a nitrogen in the rest of the molecule. Examples of preferred acyl moieties are $C_1$-$C_7$-alkanoyl that is unsubstituted or substituted by one or more, especially up to three, e.g. one or two moieties independently selected from the group consisting of hydroxy, amino, N-mono- or N,N-di-$C_1$-$C_7$-alkylamino and $C_1$-$C_7$-alkanoylamino, such as acetyl, 2-methyl-propionyl, 2-ethyl-butyryl, 3-methyl-butyryl, 3,3-dimethyl-butyryl, 2,2-dimethyl-propionyl, 3,3-dimethyl-butyryl 3-hydroxy-2,2-dimethyl-propionyl, N,N-dimethyl-amino-acetyl or 2-(N-acetylamino)-4-methyl-butyryl, unsubstituted or mono-, di- or tri-(halo, $C_1$-$C_7$-alkoxy and/or $C_1$-$C_7$-alkyl)-substituted benzoyl or naphthoyl, such as 4-methyl-benzoyl, or 3,4-dimethoxybenzoyl, phenyl- or naphthyl-$C_2$-$C_7$-alkanoyl wherein phenyl or naphthyl is unsubstituted or substituted by one or more, especially up to three, $C_1$-$C_7$-alkoxy substitutents, such as 3-phenyl-propionyl, 2,2-dimethyl-2-phenylacetyl or 3-ethoxyphenylacetyl, $C_3$-$C_8$-cycloalkylcarbonyl (=cycloalkanesulfonyl) that is unsubstituted or substituted by one or more, e.g. up to four, substituents independently selected from the group consisting of $C_1$-$C_7$-alkyl, carbamoyl and cyano, such as cyclopropylcarbonyl, 2,2,3,3-tetramethyl-cyclopropylcarbonyl, 1-carbamoyl-cyclopropylcarbonyl, cyclobutylcarbonyl or 1-cyano-cyclopropylcarbonyl, benzo[b]thiophenylcarbonyl, such as benzo[b]thiophen-2-carbonyl, tetrahydrofuranylcarbonyl, such as tetrahydrofuran-2-carbonyl, piperidinylcarbonyl which is unsubstituted or substituted by $C_1$-$C_7$-alkanoyl, such as 1-acetyl-piperidine-4-carbonyl, $C_1$-$C_7$-alkylsulfonyl, such as methylsulfonyl (=methanesulfonyl), (phenyl- or naphthyl)-$C_1$-$C_7$-alkylsulfonyl, such as phenylmethanesulfonyl, or (unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri-)substituted) (phenyl- or naphthyl)-sulfonyl wherein if more than one substituent is present the substituents are selected independently from those mentioned, such as methanesulfonyl, phenylmethanesulfonyl, phenylsulfonyl (=benzenesulfonyl), naphthalene-1-sulfonyl, naphthalene-2-sulfonyl, toluene-4-sulfonyl, 4-isopropyl-benzenesulfonyl, biphenyl-4-sulfonyl, 2-trifluoromethyl-benzenesulfonyl, 3-trifluoromethyl-benzenesulfonyl, 4-trifluoromethylsulfonyl, 4-chloro-benzenesulfonyl, 3-chloro-benzenesulfonyl, 2-chloro-benzenesulfonyl, 2,4-difluoro-benzenesulfonyl, 2,6-difluoro-benzenesulfonyl, 2,5-dichloro-benzenesulfonyl, 2,4-dichlorobenzenesulfonyl, 3,4-dichloro-benzenesulfonyl, 3,5-dichloro-benzenesulfonyl, 2,3-dichloro-benzenesulfonyl, 3-methoxy-benzenesulfonyl, 4-methoxy-benzenesulfonyl, 2,5-dimethoxy-benzenesulfonyl, 2,4-dimethoxybenzenesulfonyl, 4-trifluoromethoxy-benzenesulfonyl, 2-benzyloxy-benzenesulfonyl, 4-phenoxy-benzenesulfonyl, 4-(2-oxo-propyl)-benzenesulfonyl, 3-acetyl-benzenesulfonyl, 4-acetylamino-benzenesulfonyl, 4-cyano-benzenesulfonyl, 3-cyano-benzenesulfonyl, 2-cyano-benzenesulfonyl or 4-methanesulfonyl-benzenesulfonyl; halo-thiophene-2-sulfonyl, such as 5-chloro-thiophene-2-sulfonyl, quinoline-sulfonyl, such as quinoline-8-sulfonyl, ($C_1$-$C_7$-alkanoylamino and/or $C_1$-$C_7$-alkyl)-substituted thiazolesulfonyl, such as 2-acetylamino-4-methyl-thiazole-5-sulfonyl, (halo and/or $C_1$-$C_7$-alkyl)-substituted pyrazolesulfonyl, such as 5-chloro-1,3-dimethyl-1H-pyrazole-4-sulfonyl, pyridine-sulfonyl, such as pyridine-3-sulfonyl, N-mono- or N,N-di-($C_1$-$C_7$-alkyl, (unsubstituted or $C_1$-$C_7$-alkyl- and/or halo-substituted) phenyl or naphthyl, phenyl-$C_1$-$C_7$-alkyl, naphthyl-$C_1$-$C_7$-alkyl or $C_3$-$C_8$-cycloalkyl)-aminocarbonyl, such as $C_1$-$C_7$-alkylaminocarbonyl, especially N-tert-butyl-aminocarbonyl, N-phenyl-aminocarbonyl, N-(3-chloro-phenyl)-aminocarbonyl or phenyl-$C_1$-$C_7$-alkylaminocarbonyl, especially N-benzyl-aminocarbonyl, or ($C_1$-$C_7$-alkyl, phenyl, naphthyl, phenyl-$C_1$-$C_7$-alkyl, napthyl-$C_1$-$C_7$-alkyl and/or $C_1$-$C_7$-alkoxy-$C_1$-$C_7$-alkyl)-oxycarbonyl, e.g. $C_1$-$C_7$-alkoxycarbonyl, such as methoxyethylcarbonyl, isopropyloxycarbonyl, tert-butyloxycarbonyl isobutyloxycarbonyl or 2-(methoxy)-ethoxycarbonyl, or phenyl-$C_1$-$C_7$-alkyloxycarbonyl, such as benzyloxycarbonyl.

T is methylene ($CH_2$) or preferably carbonyl ($C(=O)$).

In all definitions above and below the person having skill in the art will, without undue experimentation or effort, be able to recognize which are especially relevant (e.g. those that if present provide compounds that are sufficiently stable for the manufacture of pharmaceuticals, e.g. having a half-life of more than 30 seconds, preferably of more than a week) and thus are preferably encompassed by the present claims and that only chemically feasible bonds and substitutions (e.g. in the case of double or triple bonds, hydrogen carrying amino or hydroxy groups and the like can be avoided in order to avoid tautomerism) are encompassed, as well as tautomeric forms where present, especially in equilibrium. For example, preferably, for reasons of stability or chemical feasibility, directly vicinal atoms in chains preferably are not selected from oxy plus oxy, thio plus oxy, oxy plus thio or thio plus thio, except where ring systems or the like are present that are sufficiently stable. Substitutents binding via an O (e.g. in $C_1$-$C_7$-alkoxy) or S that is part of them are preferably not bound to nitrogen e.g. in rings.

Salts are especially the pharmaceutically acceptable salts of compounds of formula I. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula I with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfonyl, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between the compounds in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula I or their precursors, is to be understood as referring also to one or more salts thereof or a mixture of a corresponding free compound and one or more salts thereof, each of which is intended to include also any solvate, metabolic precursor such as ester or amide of the compound of formula I, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is intended to include the plural (for example also different configuration isomers of the same compound, e.g. enantiomers in racemates or the like) or preferably the singular ("one").

The compounds of the present invention can possess two or more asymmetric centers depending on the choice of the substituents. The preferred absolute configurations are as indicated herein specifically. However, any possible isolated or pure diastereoisomers, enantiomers or geometric enantiomers, and mixtures thereof, e.g., mixtures of enantiomers, such as racemates, are encompassed by the present invention.

As described above, the compounds of the present invention are inhibitors of renin activity and, thus, may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, Alzheimer's disease, dementia, anxiety states and cognitive disorders, and the like, especially where inhibition of (especially inappropriate) renin activity is required.

"Inappropriate" renin activity preferably relates to a state of a warm-blooded animal, especially a human, where renin shows a renin activity that is too high in the given situation (e.g. due to one or more of misregulation, overexpression e.g. due to gene amplification or chromosome rearrangement or infection by microorganisms such as virus that express an aberrant gene, abnormal activity e.g. leading to an erroneous substrate specificity or a hyperactive renin e.g. produced in normal amounts, too low activity of renin activity product removing pathways, high substrate concentration and/or the like) and/or leads to or supports a renin dependent disease or disorder as mentioned above and below, e.g. by too high renin activity. Such inappropriate renin activity may, for example, comprise a higher than normal activity, or further an activity in the normal or even below the normal range which, however, due to preceding, parallel and or subsequent processes, e.g. signaling, regulatory effect on other processes, higher substrate or product concentration and the like, leads to direct or indirect support or maintenance of a disease or disorder, and/or an activity that supports the outbreak and/or presence of a disease or disorder in any other way. The inappropriate activity of renin may or may not be dependent on parallel other mechanisms supporting the disorder or disease, and/or the prophylactic or therapeutic effect may or may include other mechanisms in addition to inhibition of renin. Therefore "dependent" can be read as "dependent inter alia", (especially in cases where a disease or disorder is really exclusively dependent only on renin) preferably as "dependent mainly", more preferably as "dependent essentially only". A disease dependent on (especially inappropriate) activity of renin may also be one that simply responds to modulation of renin activity, especially responding in a beneficial way (e.g. lowering the blood pressure) in case of renin inhibition.

Where a disease or disorder dependent on (=that "depends on", "depending") (especially inappropriate) activity of a renin is mentioned (such in the definition of "use" in the following paragraph and also especially where a compound of the formula I is mentioned for use in the diagnostic or therapeutic treatment which is preferably the treatment of a disease or disorder dependent on inappropriate renin activity, this refers preferably to any one or more diseases or disorders that depend on inappropriate activity of natural renin and/or one or more altered or mutated forms thereof.

Where subsequently or above the term "use" is mentioned (as verb or noun) (relating to the use of a compound of the formula I or of a pharmaceutically acceptable salt thereof, or a method of use thereof), this (if not indicated differently or to be read differently in the context) includes any one or more of the following embodiments of the invention, respectively (if not stated otherwise): the use in the treatment of a disease or disorder that depends on (especially inappropriate) activity of renin, the use for the manufacture of pharmaceutical compositions for use in the treatment of a disease or disorder that depends on (especially inappropriate) activity of renin; a method of use of one or more compounds of the formula I in the treatment of a disease or disorder that depends on (especially inappropriate) activity of renin; a pharmaceutical preparation comprising one or more compounds of the formula I for the treatment of a disease or disorder that depends on (especially inappropriate) activity of renin; and one or more compounds of the formula I for use in the treatment of a disease or disorder in a warm-blooded animal, especially a human, preferably a disease that depends on (especially inappropriate) activity of renin; as appropriate and expedient, if not stated otherwise.

The terms "treat", "treatment" or "therapy" refer to the prophylactic (e.g. delaying or preventing the onset of a disease or disorder) or preferably therapeutic (including but not limited to preventive, delay of onset and/or progression, palliative, curing, symptom-alleviating, symptom-reducing, patient condition ameliorating, renin-modulating and/or renin-inhibiting) treatment of said disease(s) or disorder(s), especially of the one or more diseases or disorders mentioned above or below.

PREFERRED EMBODIMENTS ACCORDING TO THE INVENTION

The groups of preferred embodiments of the invention mentioned below are not to be regarded as exclusive, rather, e.g., in order to replace general expressions or symbols with more specific definitions, parts of those groups of compounds can be interchanged or exchanged using the definitions given above, or omitted, as appropriate, and each of the more specific definitions, independent of any others, may be introduced independently of or together with one or more other more specific definitions for other more general expressions or symbols.

The invention preferably relates to a compound of the formula I wherein the moieties T-NR1R2 and NR3R4 are bound in the cis configuration (as pure isomer or mixture of the cis isomers) or alternatively wherein these moieties are bound in trans configuration (as pure isomer of as mixture of the trans isomers) with regard to the central piperidine ring.

The invention thus more preferably relates to a compound of the formula I as defined hereinbefore or hereinafter which has the configuration shown in the following formula IA,

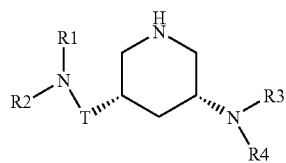

(IA)

or a (preferably pharmaceutically acceptable) salt thereof,
or alternatively the configuration shown in the following formula IB,

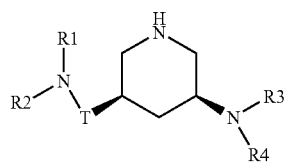

(IB)

or a (preferably pharmaceutically acceptable) salt thereof, where in formula IA and formula IB R1, R2, T, R3 and R4 are as defined above or below for a compound of the formula I.

Alternatively and also more preferably, the invention relates to a compound of the formula I as defined hereinbefore or hereinafter which has the configuration shown in the following formula IC,

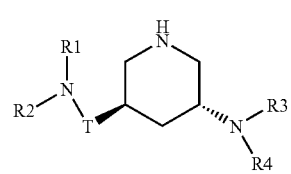

(IC)

or a pharmaceutically acceptable salt thereof,
or alternatively the configuration shown in the following formula ID,

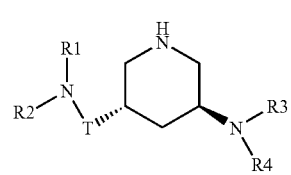

(ID)

or a (preferably pharmaceutically acceptable) salt thereof, where in formula IC and formula ID R1, R2, T, R3 and R4 are as defined above or below for a compound of the formula I.

In a first preferred embodiment, the invention especially relates to a compound of the formula I wherein
R1 is hydrogen, unsubstituted or substituted alkyl or unsubstituted or substituted cycloalkyl;
R2 is unsubstituted or substituted alkyl, unsubstituted or substituted aryl, unsubstituted or substituted heterocyclyl or unsubstituted or substituted cycloalkyl;
R3 is hydrogen or unsubstituted or substituted alkyl,
R4 is unsubstituted or substituted alkyl or acyl; and
T is carbonyl (C(=O));
or a (preferably pharmaceutically acceptable) salt thereof;
where preferably unsubstituted or substituted alkyl, unsubstituted or substituted cycloalkyl, unsubstituted or substituted aryl and/or acyl are as defined as given above as preferred definitions.

Highly preferred is a compound of the formula I, wherein
R1 is hydrogen, $C_1$-$C_7$-alkyl, $C_3$-$C_8$-cycloalkyl or phenyl-$C_1$-$C_7$-alkyl,
R2 is phenyl-$C_1$-$C_7$-alkyl, naphthyl-$C_1$-$C_7$-alkyl, di-(phenyl)-$C_1$-$C_7$-alkyl, indenyl-$C_1$-$C_7$-alkyl, (phenyl-$C_3$-$C_8$-cycloalkyl)-$C_1$-$C_7$-alkyl, (phenyl)-(pyridyl)-$C_1$-$C_7$-alkyl, indolyl-$C_1$-$C_7$-alkyl, 4H-benzo[1,4]oxazin-3-on-yl, ($C_1$-$C_7$-alkoxy)-di(phenyl)-$C_1$-$C_7$-alkyl or ($C_1$-$C_7$-alkoxycarbonyl)-di-(phenyl)-$C_1$-$C_7$-alkyl where each phenyl, naphthyl, pyridyl, indolyl or 4H-benzo[1,4]oxazin-3-on-yl mentioned for R2 so far is unsubstituted or substituted by one or more, especially up to three, moieties independently selected from the group consisting of $C_1$-$C_7$-alkyl, $C_1$-$C_7$ alkoxy-$C_1$-$C_7$-alkyl, phenyl, halo, hydroxy, $C_1$-$C_7$-alkoxy and $C_1$-$C_7$-alkoxy-$C_1$-$C_7$-alkoxy;
R3 is hydrogen, $C_1$-$C_7$-alkyl or phenyl-$C_1$-$C_7$-alkyl wherein phenyl is unsubstituted or substituted by one or more, especially up to three, moieties independently selected from the group consisting of $C_1$-$C_7$-alkyl, halo, hydroxy, $C_1$-$C_7$-alkoxy, carboxy, $C_1$-$C_7$-alkoxycarbonyl and cyano; and
R4 is phenyl-$C_1$-$C_7$-alkyl wherein phenyl is unsubstituted or substituted by one or more, e.g. up to three, moieties independently selected from the group consisting of halo and $C_1$-$C_7$-alkoxy, such as 2-, 3- or 4-chlorophenylmethyl, $C_1$-$C_7$-alkanoyl that is unsubstituted or substituted by one or more, especially up to three, e.g. one or two moieties independently selected from the group consisting of hydroxy, amino, N-mono- or N,N-di-$C_1$-$C_7$-alkylamino and $C_1$-$C_7$-alkanoylamino, such as acetyl, 2-methyl-propionyl, 2-ethyl-butyryl, 3-methyl-butyryl, 3,3-dimethyl-butyryl, 2,2-dimethyl-propionyl, 3,3-dimethyl-butyryl, 3-hydroxy-2,2-dimethyl-propionyl, N,N-dimethyl-amino-acetyl, 2-(N-acetylamino)-4-methyl-butyryl, unsubstituted or mono-, di- or tri-(halo, $C_1$-$C_7$-alkoxy and/or $C_1$-$C_7$-alkyl)-substituted benzoyl or naphthoyl, such as 4-methyl-benzoyl or 3,4-dimethoxybenzoyl, phenyl- or naphthyl-$C_2$-$C_7$-alkanoyl wherein phenyl or naphthyl is unsubstituted or substituted by one or more, especially up to three, $C_1$-$C_7$-alkoxy substitutents, such as 3-phenyl-propionyl, 2,2-dimethyl-2-phenylacetyl or 3-ethoxyphenylacetyl, $C_3$-$C_8$-cycloalkylcarbonyl (=cycloalkanecarbonyl) that is unsubstituted or substituted by one or more, e.g. up to four, substituents independently selected from the group consisting of $C_1$-$C_7$-alkyl, carbamoyl and cyano, such as cyclopropylcarbonyl, 2,2,3,3-tetramethyl-cyclopropylcarbonyl, 1-carbamoyl-cyclopropylcarbonyl, cyclobutylcarbonyl or 1-cyano-cyclopropylcarbonyl, benzo[b]thiophenylcarbonyl, such as benzo[b]thiophen-2-carbonyl, tetrahydrofuranylcarbonyl, such as tetrahydrofuran-2-carbonyl, piperidinylcarbonyl which is unsubstituted or substituted by $C_1$-$C_7$-alkanoyl, such as 1-acetyl-piperidine-4-carbonyl, $C_1$-$C_7$-alkylsulfonyl, such as methylsulfonyl (=methanesulfonyl), (phenyl- or naphthyl)-$C_1$-$C_7$-alkylsulfonyl, such as phenylmethanesulfonyl, or (unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri-)substituted) (phenyl- or naphthyl)-sulfonyl wherein if more than one substituent is present the substituents are selected independently from those mentioned, such as methanesulfonyl, phenylmethanesulfonyl, phenylsulfonyl (=benzenesulfonyl), naphthalene-1-sulfonyl, naphthalene-2-sulfonyl, toluene-4-sulfonyl, 4-isopropyl-benzenesulfonyl, biphenyl-4-sulfonyl, 2-trifluoromethyl-benzenesulfonyl, 3-trifluoromethyl-benzenesulfonyl, 4-trifluoromethylsulfonyl, 4-chloro-benzenesulfonyl, 3-chlorobenzenesulfonyl, 2-chloro-benzenesulfonyl, 2,4-difluoro-benzenesulfonyl, 2,6-difluoro-benzenesulfonyl, 2,5-dichloro-benzenesulfonyl, 2,4-dichlorobenzenesulfonyl, 3,4-dichloro-benzenesulfonyl, 3,5-dichloro-benzenesulfonyl, 2,3-dichloro-benzenesulfonyl, 3-methoxy-benzenesulfonyl, 4-methoxy-benzenesulfonyl, 2,5-dimethoxy-benzenesulfonyl, 2,4-dimethoxybenzenesulfonyl, 4-trifluoromethoxy-benzenesulfonyl, 2-benzyloxy-benzenesulfonyl, 4-phenoxy-benzenesulfonyl, 4-(2-oxo-propyl)-benzenesulfonyl, 3-acetyl-benzenesulfonyl, 4-acetylamino-benzenesulfonyl, 4-cyano-benzenesulfonyl, 3-cyano-benzenesulfonyl, 2-cyano-benzenesulfonyl or 4-methanesulfonyl-benzenesulfonyl; halo-thiophene-2-sulfonyl, such as 5-chloro-thiophene-2-sulfonyl, quinoline-sulfonyl, such as quinoline-8-sulfonyl, ($C_1$-$C_7$-alkanoylamino and/or $C_1$-$C_7$-alkyl)-substituted thiazol-sulfonyl, such as 2-acetylamino-4-methyl-thiazole-5-sulfonyl, (halo and/or $C_1$-$C_7$-alkyl)-substituted pyrazolesulfonyl, such as 5-chloro-1,3-dimethyl-1H-pyrazole-4-sulfonyl, pyridine-sulfonyl, such as pyridine-3-sulfonyl, N-mono- or N,N-di-($C_1$-$C_7$-alkyl, (unsubstituted or $C_1$-$C_7$-alkyl- and/or halo-substituted) phenyl or naphthyl, phenyl-$C_1$-$C_7$-alkyl, naphthyl-$C_1$-$C_7$-alkyl or $C_3$-$C_8$-cycloalkyl)-aminocarbonyl, such as $C_1$-$C_7$-alkylaminocarbonyl, especially N-tert-butyl-aminocarbonyl, N-phenyl-aminocarbonyl, N-(3-chloro-phenyl)-aminocarbonyl or phenyl-$C_1$-$C_7$-alkylaminocarbonyl, especially N-benzyl-aminocarbonyl, or ($C_1$-$C_7$-alkyl, phenyl, naphthyl, phenyl-$C_1$-$C_7$-alkyl, napthyl-$C_1$-$C_7$ alkyl and/or $C_1$-$C_7$-alkoxy-$C_1$-$C_7$-alkyl)-oxycarbonyl, e.g. $C_1$-$C_7$-alkoxycarbonyl, such as methoxyethylcarbonyl, isopropyloxycarbonyl, tert-butyloxycarbonyl, isobutyloxycarbonyl or 2-(methoxy)-ethoxycarbonyl, or phenyl-$C_1$-$C_7$-alkyloxycarbonyl, such as benzyloxycarbonyl; and T is carbonyl;

or a (preferably pharmaceutically acceptable) salt thereof.

Preferred Definitions for R1

Preferably, R1 is hydrogen, unsubstituted or substituted alkyl or unsubstituted or substituted cycloalkyl; more preferably hydrogen, $C_1$-$C_7$-alkyl, $C_3$-$C_8$-cycloalkyl or phenyl-$C_1$-$C_7$-alkyl, When R1 is unsubstituted or substituted alkyl, it is preferably $C_1$-$C_7$-alkyl, more preferably $C_1$-$C_4$-alkyl such as methyl or ethyl.

When R1 is cycloalkyl, it is preferably $C_3$-$C_8$-cycloalkyl such as preferably $C_3$, $C_4$, $C_5$, and $C_6$-cycloalkyl, most preferably cyclopropyl.

When R1 is phenyl-$C_1$-$C_7$-alkyl, it is preferably benzyl. When R1 is phenyl-$C_1$-$C_7$-alkyl, the R2 is preferably with phenyl substituted alkyl as defined herein.

Preferred Definitions for R2

Preferably, R2 is unsubstituted or substituted alkyl, unsubstituted or substituted aryl, unsubstituted or substituted heterocyclyl or unsubstituted or substituted cycloalkyl, more preferably phenyl-$C_1$-$C_7$-alkyl, naphthyl-$C_1$-$C_7$-alkyl, di-(phenyl)-$C_1$-$C_7$-alkyl, indenyl-$C_1$-$C_7$ alkyl, (phenyl-$C_3$-$C_8$-cycloalkyl)-$C_1$-$C_7$-alkyl, (phenyl)-(pyridyl)-$C_1$-$C_7$-alkyl, indolyl-$C_1$-$C_7$-alkyl, 4H-benzo[1,4]oxazin-3-on-yl, ($C_1$-$C_7$-alkoxy)-di(phenyl)-$C_1$-$C_7$-alkyl or ($C_1$-$C_7$-alkoxycarbonyl)-di-(phenyl)-$C_1$-$C_7$-alkyl where each phenyl, naphthyl, pyridyl, indolyl or 4H-benzo[1,4]oxazin-3-on-yl mentioned for R2 so far is unsubstituted or substituted by one or more, especially up to three, moieties preferably independently selected from the group consisting of $C_1$-$C_7$-alkyl, $C_1$-$C_7$-alkoxy-$C_1$-$C_7$-alkyl, phenyl, halo, hydroxy, $C_1$-$C_7$-alkoxy and $C_1$-$C_7$-alkoxy-$C_1$-$C_7$-alkoxy.

Preferred Definitions for T

Preferably T is carbonyl (C(=O)).

Preferred Definitions for R3

Preferably, R3 is hydrogen or unsubstituted or substituted alkyl; more preferably hydrogen, $C_1$-$C_7$-alkyl, pheny-$C_1$-$C_7$-alkyl or $C_3$-$C_7$-cycloalkyl-$C_1$-$C_7$-alkyl wherein phenyl or cycloalkyl are unsubstituted or substituted by one or more, especially up to three, moieties independently selected from the group consisting of $C_1$-$C_7$-alkyl, halo, hydroxy, $C_1$-$C_7$-alkoxy, carboxy, $C_1$-$C_7$-alkoxycarbonyl and cyano; still more preferably hydrogen, $C_1$-$C_7$-alkyl or pheny-$C_1$-$C_7$-alkyl wherein phenyl is unsubstituted or substituted by one or more, especially up to three, moieties independently selected from the group consisting of $C_1$-$C_7$-alkyl, halo, hydroxy, $C_1$-$C_7$-alkoxy, carboxy, $C_1$-$C_7$-alkoxycarbonyl and cyano; most preferably R3 is hydrogen, methyl, isobutyl, benzyl or —$CH_2$-cyclopropyl.

Most preferably R3 is hydrogen.

When R3 is unsubstituted or substituted alkyl, it is preferably $C_1$-$C_7$-alkyl, more preferably $C_1$-$C_4$-alkyl. The alkyl moiety can be substituted as described herein, preferably by phenyl or or $C_3$-$C_7$cycloalkyl wherein phenyl or cycloalkyl are unsubstituted or substituted.

When R3 is pheny-$C_1$-$C_7$-alkyl, then R4 is preferably unsubstituted or substituted alkyl, such as pheny-$C_1$-$C_7$-alkyl, or acyl, such as $C_1$-$C_7$-alkyl-carbonyl, or unsubstituted or substituted cycloalkyl-carbonyl.

When R3 is $C_1$-$C_7$-alkyl, then R4 is preferably unsubstituted or substituted alkyl, such as pheny-$C_1$-$C_7$-alkyl, or acyl, such as $C_1$-$C_7$-alkyl-carbonyl, unsubstituted or substituted arylsulfonyl, N-mono- or N,N-di-(unsubstituted or substituted aryl-$C_1$-$C_7$-alkyl)-aminocarbonyl or unsubstituted or substituted cycloalkyl-carbonyl.

Preferred Definitions for R4

Preferably, R4 is unsubstituted or substituted alkyl, unsubstituted or substituted aryl, unsubstituted or substituted heterocyclyl, unsubstituted or substituted cycloalkyl or acyl; such as unsubstituted or substituted alkyl or acyl, still more preferably phenyl-$C_1$-$C_7$-alkyl wherein phenyl is unsubstituted or substituted by one or more, e.g. up to three, moieties independently selected from the group consisting of halo and $C_1$-$C_7$-alkoxy, especially 2-, 3- or 4-chlorophenylmethyl, $C_1$-$C_7$-alkanoyl that is unsubstituted or substituted by one or more, especially up to three, e.g. one or two moieties independently selected from the group consisting of hydroxy, amino, N-mono- or N,N-di-$C_1$-$C_7$-alkylamino and $C_1$-$C_7$-alkanoylamino, especially acetyl, 2-methyl-propionyl, 2-ethyl-butyryl, 3-methyl-butyryl, 3,3-dimethyl-butyryl, 2,2-dimethyl-propionyl, 3,3-dimethyl-butyryl, 3-hydroxy-2,2-dimethyl-propionyl, N,N-dimethylamino-acetyl, 2-(N-acetylamino)-4-methyl-butyryl, unsubstituted or mono-, di- or tri-(halo, $C_1$-$C_7$-alkoxy and/or $C_1$-$C_7$-alkyl)-substituted benzoyl or naphthoyl, especially 4-methyl-benzoyl or 3,4-dimethoxybenzoyl, phenyl- or naphthyl-$C_2$-$C_7$-alkanoyl wherein phenyl or naphthyl is unsubstituted or substituted by one or more, especially up to three, $C_1$-$C_7$-alkoxy substitutents, especially 3-phenyl-propionyl, 2,2-dimethyl-2-phenylacetyl or 3-ethoxyphenylacetyl, $C_3$-$C_8$-cycloalkylcarbonyl (=cycloalkanecarbonyl) that is unsubstituted or substituted by one or more, e.g. up to four, substituents independently selected from the group consisting of $C_1$-$C_7$-alkyl, carbamoyl and cyano, especially cyclopropylcarbonyl, 2,2,3,3-tetramethyl-cyclopropylcarbonyl, 1-carbamoyl-cyclopropylcarbonyl, cyclobutylcarbonyl or 1-cyano-cyclopropylcarbonyl, benzo[b]thiophenylcarbonyl, especially benzo[b]thiophen-2-carbonyl, tetrahydrofuranylcarbonyl, especially tetrahydrofuran-2-carbonyl, piperidinylcarbonyl which is unsubstituted or substituted by $C_1$-$C_7$-alkanoyl, such as 1-acetyl-piperidine-4-carbonyl, $C_1$-$C_7$-alkylsulfonyl, such as methylsulfonyl, (phenyl- or naphthyl)-$C_1$-$C_7$-alkylsulfonyl, especially phenylmethanesulfonyl, or (unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri-)substituted)(phenyl- or naphthyl)-sulfonyl wherein if more than one substituent is present the substituents are selected independently from those mentioned, especially methanesulfonyl, phenylmethanesulfonyl, phenylsulfonyl, naphthalene-1-sulfonyl, naphthalene-2-sulfonyl, toluene-4-sulfonyl, 4-isopropyl-benzenesulfonyl, biphenyl-4-sulfonyl, 2-trifluoromethyl-benzenesulfonyl, 3-trifluoromethyl-benzenesulfonyl, 4-trifluoromethylsulfonyl, 4-chloro-benzenesulfonyl, 3-chloro-benzenesulfonyl, 2-chloro-benzenesulfonyl, 2,4-difluoro-benzenesulfonyl, 2,6-difluoro-benzenesulfonyl, 2,5-dichloro-benzenesulfonyl, 2,4-dichlorobenzenesulfonyl, 3,4-dichloro-benzenesulfonyl, 3,5-dichloro-benzenesulfonyl, 2,3-dichloro-benzenesulfonyl, 3-methoxy-benzenesulfonyl, 4-methoxy-benzenesulfonyl, 2,5-dimethoxy-benzenesulfonyl, 2,4-dimethoxybenzenesulfonyl, 4-trifluoromethoxy-benzenesulfonyl, 2-benzyloxy-benzenesulfonyl, 4-phenoxy-benzenesulfonyl, 4-(2-oxo-propyl)-benzenesulfonyl, 3-acetyl-benzenesulfonyl, 4-acetylamino-benzenesulfonyl, 4-cyano-benzenesulfonyl, 3-cyano-benzenesulfonyl, 2-cyano-benzenesulfonyl or 4-methanesulfonyl-benzenesulfonyl; halo-thiophene-2-sulfonyl, especially 5-chloro-thiophene-2-sulfonyl, quinoline-sulfonyl, especially quinoline-8-sulfonyl, ($C_1$-$C_7$-alkanoylamino and/or $C_1$-$C_7$-alkyl)-substituted thiazol-sulfonyl, especially 2-acetylamino-4-methyl-thiazole-5-sulfonyl, (halo and/or $C_1$-$C_7$-alkyl)-substituted pyrazolesulfonyl, especially 5-chloro-1,3-dimethyl-1H-pyrazole-4-sulfonyl, pyridine-sulfonyl, such as pyridine-3-sulfonyl, N-mono- or N,N-di-($C_1$-$C_7$-alkyl, (unsubstituted or $C_1$-$C_7$-alkyl- and/or halo-substituted) phenyl or naphthyl, phenyl-$C_1$-$C_7$-alkyl, naphthyl-$C_1$-$C_7$-alkyl or $C_3$-$C_8$-cycloalkyl)-aminocarbonyl, especially $C_1$-$C_7$-alkylaminocarbonyl, especially N-tert-butyl-aminocarbonyl, N-phenyl-aminocarbonyl, N-(3-chlorophenyl)-aminocarbonyl or phenyl-$C_1$-$C_7$-alkylaminocarbonyl, especially N-benzyl-aminocarbonyl, or ($C_1$-$C_7$ alkyl, phenyl, naphthyl, phenyl-$C_1$-$C_7$-alkyl and/or napthyl-$C_1$-$C_7$-alkyl)-oxycarbonyl, e.g. $C_1$-$C_7$-alkoxycarbonyl, especially tert-butyloxycarbonyl or isobutyloxycarbonyl, or phenyl-$C_1$-$C_7$ alkyloxycarbonyl.

In a first embodiment, R4 is acyl. Preferred examples are selected from the group consisting of (a) to (o):

(a) Unsubstituted or Substituted Mono- or Bicyclic aryl-carbonyl

Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono- or di-substituted. Suitable substituents are as defined herein, preferably $C_1$-$C_7$-alkyl, such as methyl, —O—$C_1$-$C_7$-alkyl, such as OMe, halo-$C_1$-$C_7$-alkyl, halo, such as Cl, —O—$C_1$-$C_7$-alkylene-O-alkyl, such as O—$C_3H_6$OCH$_3$, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano, unsubstituted or substituted, preferably unsubstituted, heterocyclyl or unsubstituted or substituted, preferably unsubstituted, heterocyclyl-$C_1$-$C_4$-alkyl, such as heterocyclyl-CH$_2$, whereby the heterocyclyl moiety in each case is preferably monocyclic 5- or 6-membered heterocyclyl, preferably containing an N and/or O atom, such as tetrahydrofuranyl or tetrahydropyranyl, piperidinyl, pyrrolidinyl, piperazinyl or morpholinyl, most preferably $C_1$-$C_7$-alkyl and/or —O—$C_1$-$C_7$-alkyl.

(b) Unsubstituted or Substituted Mono- or Bicyclic heterocyclylcarbonyl

Preferred examples for the heterocyclyl moiety are mono- or bicyclic rings. Preferred are 3 to 14, more preferably 5 to 11 membered ring systems. The heterocyclyl moiety may be saturated, partially saturated or aromatic ring systems. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrrolidin-2-onyl, pyrrolyl, piperidyl, furanyl, pyrimidyl, pyridyl, pyrazinyl, isoxazolyl, pyrrolidin-2-onyl, tetrahydrofuranyl, or tetrahydropyranyl, in particular tetrahydrofuranyl, or tetrahydropyranyl or pyridyl; or 9- to 11-membered bicyclic ring systems preferably containing at least one nitrogen and/or S atom, in particular indolyl, 2,3-dihydrobenzo[1,4]dioxinyl, benzofuranyl, 4H-benzo[1,4]oxazin-3-onyl, benzooxazolyl, benzo[1,2,5]oxadiazolyl, benzimidazolyl or benzothiopenyl, more preferably benzothiopenyl. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, such as acetyl, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, unsubstituted or substituted, preferably unsubstituted, heterocyclyl or unsubstituted or substituted, preferably unsubstituted, heterocyclyl-$C_1$-$C_4$-alkyl, such as heterocyclyl-$CH_2$, whereby the heterocyclyl moiety in each case is preferably monocyclic 5- or 6-membered heterocyclyl, preferably containing an N and/or O atom, such as tetrahydrofuranyl or tetrahydropyranyl, piperidinyl, pyridyl, pyrrolidinyl, piperazinyl or morpholinyl, most preferably $C_1$-$C_7$-alkanoyl, cyano, or pyridyl. Most preferably the heterocyclyl moiety is unsubstituted or is mono-substituted as described above.

(c) Unsubstituted or Substituted Mono- or Bicyclic cycloalkylcarbonyl

Preferred examples for the cycloalkyl moiety are monocyclic rings, preferably $C_3$-$C_8$-cycloalkyl, more preferably $C_3$, $C_4$, $C_5$, and $C_6$-cycloalkyl. The cycloalkyl moiety may be substituted or unsubstituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted, preferably unsubstituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, unsubstituted or substituted, preferably unsubstituted, heterocyclyl or unsubstituted or substituted, preferably unsubstituted, heterocyclyl-$C_1$-$C_4$-alkyl, such as heterocyclyl-$CH_2$, whereby the heterocyclyl moiety in each case is preferably monocyclic 5- or 6-membered heterocyclyl, preferably containing an N and/or O atom, such as tetrahydrofuranyl or tetrahydropyranyl, piperidinyl, pyridyl, tetrazolyl, pyrrolidinyl, piperazinyl or morpholinyl, nitro, amino, amino-$C_1$-$C_7$-alkyl, carbamoyl, $C_1$-$C_7$-alkanoylamino, carboxyl, and cyano, whereby suitable phenyl substituents include $C_1$-$C_7$-alkyl, such as methyl, —O—$C_1$-$C_7$-alkyl, halo-$C_1$-$C_7$-alkyl, halo, hydroxyl and amino, most preferably cycloalkyl is unsubstituted or substituted by carbamoyl, cyano, pyridyl, tetrazolyl or phenyl.

(d) Unsubstituted or Substituted alkylcarbonyl

Preferred examples for the alkyl moiety are branched or straight chain $C_1$-$C_7$-alkyl which may be substituted or unsubstituted. In one embodiment, the alkyl moiety is branched alkyl such as isopropyl, isobutyl, sec-butyl or tert-butyl, isopentyl, 1-ethylpropyl, 2,2-dimethyl-propyl, 1,2-dimethyl-propyl, 1-ethyl-2-methyl-propyl, or 3-methyl-butyl. In another embodiment the alkyl moiety is straight chain alkyl such as methyl, ethyl, n-propyl, n-butyl or n-pentyl, preferably methyl, ethyl or n-propyl. When the alkyl moiety is substituted, it is preferably mono, di- or tri-substituted, more preferably mono-substituted. Suitable substituents for the alkyl moiety are as defined herein, preferably O—$C_1$-$C_4$-alkyl, such as OMe, halo, hydroxy, unsubstituted or substituted phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, aminocarbonyl, N-mono- or N,N-di-substituted aminocarbonyl, such as CONHMe, N-mono- or N,N-di-substituted amino, such as $NMe_2$, carboxyl, $C_1$-$C_7$-alkyloxycarbonyl, such as COOMe, cyano, unsubstituted or substituted, preferably unsubstituted, heterocyclyl-$C_1$-$C_4$-alkyl, such as heterocyclyl-$CH_2$, whereby the heterocyclyl moiety in each case is preferably monocyclic 5- or 6-membered heterocyclyl, preferably containing an N and/or O atom, such as tetrahydrofuranyl or tetrahydropyranyl, piperidinyl, pyridyl, tetrazolyl, pyrrolidinyl, piperazinyl or morpholinyl, and whereby suitable phenyl or heterocyclyl substituents include $C_1$-$C_7$-alkyl, such as methyl, —O—$C_1$-$C_7$-alkyl, halo-$C_1$-$C_7$-alkyl, halo, hydroxyl and amino, preferably $C_1$-$C_7$-alkyl, and whereby suitable amino substituents include $C_1$-$C_7$-alkyl, such as methyl, phenyl or cyclopropyl, preferably $C_1$-$C_7$ alkyl. Most preferably the alkyl moiety is unsubstituted or mono-substituted by —O—$C_1$-$C_7$-alkyl, hydroxyl, $C_1$-$C_7$-alkanoylamino, unsubstituted or substituted phenyloxy, tetrahydropyranyloxy, pyridyloxy or N-mono- or N,N-di-substituted amino.

(e) Unsubstituted or Substituted Mono- or Bicyclic aryl-$C_1$-$C_7$-alkylcarbonyl Preferably aryl alkyl is aryl-$C_{1-6}$ alkyl, more preferably aryl-$C_{1-4}$ alkyl, in particular aryl-$CH_2$—, aryl-$CH_2CH_2$—, aryl-$CH(CH_3)$—, aryl-$CH_2CH(CH_3)$— or aryl-$C(CH_3)_2$—, most preferably aryl-$CH_2$—. The alkyl moiety, in particular when aryl alkyl is aryl-$CH_2$— or aryl-$CH_2CH_2$—, may be substituted, preferably mono-substituted. Examples of preferred substituents include O—$C_1$-$C_4$-alkyl, such as OMe, halo, hydroxy, nitro, amino, amino-$C_1$-$C_7$-alkyl, $C_1$-$C_7$-alkanoylamino, such as —NHCOMe, carboxyl, and cyano most preferably $C_1$-$C_7$-alkanoylamino, O—$C_1$-$C_4$-alkyl or hydroxyl.

Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl or naphthyl. When the aryl moiety is substituted, it is preferably mono-, di- or tri-substituted. In particular, phenyl is preferably unsubstituted, mono-, di- or tri-substituted, and naphthyl is preferably unsubstituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, unsubstituted or substituted, preferably substituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$ alkanoylamino, such as —NHCOMe, carboxyl, and cyano. Suitable substituents for the phenyl and naphthyl substituent on the aryl moiety of aryl alkylcarbonyl include $C_1$-$C_7$-alkyl, —O—$C_1$-$C_7$-alkyl, halo-$C_1$-$C_7$-alkyl, halo, hydroxyl and amino. Most preferably the aryl moiety is unsubstituted or substituted by —O—$C_1$-$C_7$-alkyl, halo-$C_1$-$C_7$-alkyl, substituted phenyl, $C_1$-$C_7$-alkanoylamino and/or halo.

(f) Unsubstituted or Substituted Mono- or Bicyclic heterocyclyl-$C_1$-$C_7$-alkylcarbonyl Preferably heterocyclyl alkyl is heterocyclyl-$C_{1-6}$alkyl, more preferably heterocyclyl-$C_{1-4}$ alkyl, in particular heterocyclyl-$CH_2$—, heterocyclyl-$CH_2CH_2$— or heterocyclyl-$CH_2C(CH_3)_2$—, most preferably heterocyclyl-$CH_2$—.

Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrimidyl, pyridyl, pyrazinyl, isoxazolyl, pyrrolidin-2-onyl, pyrrolyl, piperidyl, furanyl, tetrahydrofuranyl, or tetrahydropyranyl; or 9- to 11-membered bicyclic ring systems preferably containing at least one nitrogen and/or oxygen atom, in particular 4H-benzo[1,4]oxazin-3-onyl, benzooxazolyl, indolyl, 2,3-dihydro-benzo[1,4]dioxinyl, chromanyl, 2H-chromenyl, 3,4-dihydro-1H-quinolin-2-onyl, benzo[d]isoxazolyl, 4,5,6,7-tetrahydro-benzo[d]isoxazolyl, 3a,4,5,6,7,7a-hexahydro-benzo[d]isoxazolyl, 1,4,5,6-tetrahydro-cyclopentapyrazolyl, 3,4-dihydro-2H-benzo[b][1,4]dioxepinyl, benzofuranyl, benzo[1,2,5]oxadiazolyl, benzimidazolyl or 3,4-dihydro-2H-benzo[1,4]oxazinyl, more preferably pyrrolidinyl, pyrrolidin-2-onyl, pyrrolyl, piperidyl, furanyl, tetrahydrofuranyl, tetrahydropyranyl, 4H-benzo[1,4]oxazin-3-onyl or benzooxazolyl, most preferably tetrahydropyranyl or pyridyl. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, cyano, more preferably —$C_1$-$C_7$-alkyl. Suitable phenyl substituents include $C_1$-$C_7$-alkyl, —O—$C_1$-$C_7$-alkyl, halo-$C_1$-$C_7$-alkyl, halo, hydroxyl and amino. Most preferably the heterocyclyl moiety is unsubstituted or is mono-substituted with —$C_1$-$C_7$-alkyl.

(g) Unsubstituted or Substituted Mono- or Bicyclic cycloalkyl-$C_1$-$C_7$-alkylcarbonyl Preferably cycloalkyl alkyl is cycloalkyl-$C_{1-6}$ alkyl, more preferably cycloalkyl-$C_{1-4}$ alkyl, in particular cycloalkyl-$CH_2$—, cycloalkyl-$CH_2CH_2$— or cycloalkyl-$CH_2C(CH_3)_2$—, most preferably cycloalkyl-$CH_2$—. The alkyl moiety may be substituted, preferably mono-substituted, including on the carbon where the cycloalkyl moiety is attached. Examples of preferred substituents include O—$C_1$-$C_4$-alkyl, such as OMe, halo, hydroxy, nitro, amino, amino-$C_1$-$C_7$-alkyl, carboxyl, and cyano, most preferably O—$C_1$-$C_4$-alkyl or hydroxyl. Preferred examples for the cycloalkyl moiety are monocyclic rings, preferably $C_3$-$C_7$-cycloalkyl, more preferably $C_3$, $C_5$ and $C_6$-cycloalkyl. The cycloalkyl moiety may be substituted or unsubstituted. $C_3$-cycloalkyl is preferably unsubstituted and $C_5$ and $C_6$-cycloalkyl are preferably unsubstituted or substituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, —NHCOEt or —NHCOCHCH$_3$)$_2$, carboxyl, and cyano, most preferably amino, O—$C_1$-$C_4$-alkyl or hydroxy.

(h) Unsubstituted or Substituted alkyloxycarbonyl

Preferred examples for the alkyl moiety are branched or straight chain $C_1$-$C_7$-alkyl which may be substituted or unsubstituted. In one embodiment, the alkyl moiety is branched alkyl such as isopropyl, isobutyl, sec-butyl or tert-butyl, isopentyl, 1-ethylpropyl, 2,2-dimethyl-propyl and 1,2-dimethyl-propyl. In another embodiment the alkyl moiety is straight chain alkyl such as methyl, ethyl, n-propyl, n-butyl or n-pentyl, preferably methyl or ethyl. When the alkyl moiety is substituted, it is preferably mono-, di- or tri-substituted, more preferably mono-substituted. Suitable substituents for the alkyl moiety are as defined herein, preferably O—$C_1$-$C_4$-alkyl, such as OMe, halo, hydroxy, unsubstituted or substituted phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, aminocarbonyl, N-mono- or N,N-di-substituted aminocarbonyl, such as CONHMe, carboxyl, $C_1$-$C_7$ alkyloxycarbonyl, such as COOMe, and cyano, whereby suitable phenyl or naphthyl substituents include $C_1$-$C_7$-alkyl, such as methyl, —O—$C_1$-$C_7$-alkyl, halo-$C_1$-$C_7$-alkyl, halo, hydroxyl and amino, preferably $C_1$-$C_7$-alkyl, and whereby suitable amino substituents include $C_1$-$C_7$-alkyl, such as methyl, phenyl or cyclopropyl, preferably $C_1$-$C_7$-alkyl. Most preferably the alkyl moiety is unsubstituted or mono-substituted by —O—$C_1$-$C_7$-alkyl.

(i) Unsubstituted or Substituted Mono- or Bicyclic heterocyclyloxycarbonyl

Preferred examples for the heterocyclyl moiety are mono- or bicyclic rings. Preferred are 3 to 14, more preferably 5 to 11 membered ring systems. The heterocyclyl moiety may be saturated, partially saturated or aromatic, in particular if a monocyclic moiety is contemplated, aromatic or saturated, more preferably saturated, rings, or, in particular if a bicyclic moiety is contemplated, aromatic or partially saturated ring systems, in particular whereby one of the rings is aromatic and the other is saturated or partially saturated. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrrolidin-2-onyl, pyrrolyl, piperidyl, furanyl, pyrimidyl, pyridyl, pyrazinyl, isoxazolyl, pyrrolidin-2-onyl, tetrahydrofuranyl, or tetrahydropyranyl; more preferably tetrahydrofuranyl or tetrahydropyranyl. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, more preferably phenyl, —$C_1$-$C_7$-alkyl or $C_3$-$C_8$-cycloalkyl. Suitable phenyl and cycloalkyl substituents include $C_1$-$C_7$-alkyl, —O—$C_1$-$C_7$-alkyl, halo-$C_1$-$C_7$-alkyl, halo, hydroxyl and amino. Most preferably the heterocyclyl moiety is unsubstituted.

(j) Unsubstituted or Substituted Mono- or Bicyclic aryl-$C_1$-$C_7$-alkyloxycarbonyl Preferably aryl alkyl is aryl-$C_{1-6}$alkyl, more preferably aryl-$C_{1-4}$ alkyl, in particular aryl-$CH_2$—, aryl-$CH_2CH_2$—, aryl-$CH(CH_3)$—, aryl-$CH_2CH(CH_3)$— or aryl-$CH(CH_2CH_3)$—, most preferably aryl-$CH_2$—. Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono-, di- or tri-substituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, unsubstituted or substituted, preferably substituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, carboxyl, and cyano. Suitable substituents for the phenyl and naphthyl substituent on the aryl moiety of aryl alkylcarbonyl include $C_1$-$C_7$-alkyl, —O—$C_1$-$C_7$-alkyl, halo-$C_1$-$C_7$-alkyl, halo, hydroxyl and amino.

(k) N-mono- or N,N-di-(Unsubstituted or Substituted Mono- or Bicyclic aryl, Unsubstituted or Substituted Mono- or Bicyclic cycloalkyl, Unsubstituted or Substituted Mono- or Bicyclic aryl-$C_1$-$C_7$-alkyl and/or Unsubstituted or Substituted alkyl)-aminocarbonyl Preferred examples for the alkyl moiety of the unsubstituted or substituted alkyl aminocarbonyl are branched or straight chain $C_1$-$C_7$-alkyl which may be substituted or unsubstituted. In one embodiment, the alkyl moiety is branched alkyl such as isopropyl, isobutyl, sec-butyl or tert-butyl, isopentyl, 1-ethylpropyl, 2,2-dimethyl-propyl and 1,2-dimethyl-propyl, most preferably tert-butyl. In another embodiment the alkyl moiety is straight chain alkyl such as methyl, ethyl, n-propyl, n-butyl or n-pentyl, preferably methyl or ethyl. When the alkyl moiety is substituted, it is preferably mono-, di- or tri-substituted, more preferably mono-substituted. Suitable substituents for the alkyl moiety are as defined herein, preferably O—$C_1$-$C_4$-alkyl, such as OMe, halo, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, aminocarbonyl, N-mono- or N,N-di-substituted aminocarbonyl, such as CONHMe, carboxyl, $C_1$-$C_7$-alkyloxycarbonyl, such as COOMe, and cyano. Most preferably the alkyl moiety is unsubstituted.

Preferred examples of the aryl moiety of the unsubstituted or substituted aryl aminocarbonyl include mono- or bicyclic aryl with 6 to 22 carbon atoms, whereby one of the rings of the bicyclic aryl may be a partially or fully saturated ring condensed to the other aromatic ring, especially phenyl or naphthyl, more preferably phenyl. When the aryl moiety is substituted, it is preferably mono- or di-substituted. Suitable substituents are as defined herein, preferably $C_1$-$C_7$-alkyl, —O—$C_1$-$C_7$-alkyl, such as OMe, halo-$C_1$-$C_7$-alkyl, halo, such as Cl, —O—$C_1$-$C_7$-alkylene-O-alkyl, such as O—$C_3H_6OCH_3$, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano. Most preferably aryl is unsubstituted or substituted with Cl.

Preferred examples for the cycloalkyl moiety of the unsubstituted or substituted cycloalkyl aminocarbonyl are monocyclic rings, preferably $C_3$-$C_8$-cycloalkyl, more preferably $C_3$, $C_4$, $C_5$, $C_6$ and $C_7$-cycloalkyl, most preferably $C_6$-cycloalkyl. The cycloalkyl moiety may be substituted or unsubstituted, preferably unsubstituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted phenyl, naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, carboxyl, and cyano, most preferably O—$C_1$-$C_4$-alkyl or hydroxy. Most preferably cycloalkyl is unsubstituted.

Preferably the aryl alkyl moiety of the unsubstituted or substituted aryl alkyl aminocarbonyl is aryl-$C_{1-6}$ alkyl, more preferably aryl-$C_{1-4}$ alkyl, in particular aryl-$CH_2$—, aryl-$CH_2CH_2$—, or aryl-$CH(CH_2CH_3)$—, most preferably aryl-$CH_2$—. Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl or naphthyl, more preferably phenyl. When the aryl moiety is substituted, it is preferably mono-, di- or tri-substituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, nitro, amino, amino-$C_1$-$C_7$-alkyl, $C_1$-$C_7$-alkanoylamino, such as —NHCOMe, carboxyl, and cyano, more preferably —O—$C_1$-$C_7$-alkyl or halo.

It is preferred that the aminocarbonyl group is N-mono-(unsubstituted or substituted mono- or bicyclic aryl, unsubstituted or substituted mono- or bicyclic cycloalkyl, unsubstituted or substituted mono- or bicyclic aryl-$C_1$-$C_7$-alkyl, or unsubstituted or substituted alkyl)-aminocarbonyl.

(l) Unsubstituted or Substituted Mono- or Bicyclic arylsulfonyl

Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, or naphthyl, more preferably phenyl. When the aryl moiety is substituted, it is preferably mono- or di-substituted. Suitable substituents are as defined herein, preferably $C_1$-$C_7$-alkyl, such as methyl or isopropyl, —O—$C_1$-$C_7$-alkyl, such as OMe, halo-$C_1$-$C_7$-alkyl, such as $CF_3$, halo-$C_1$-$C_7$-alkoxy, such as $OCF_3$, halo, such as Cl or F, —O—$C_1$-$C_7$-alkylene-O-alkyl, such as O—$C_3H_6OCH_3$, hydroxy, unsubstituted or substituted, preferably unsubstituted, phenyl- or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, such as phenyl-$CH_2$—O—, nitro, amino, amino-$C_1$-$C_7$-alkyl, $C_1$-$C_7$-alkanoyl-$C_1$-$C_7$-alkyl, such as $CH_2C(O)Me$, $C_1$-$C_7$-alkanoyl-amino, such as $NHC(O)Me$, $C_1$-$C_7$-alkanoyl, such as acetyl, carboxyl, $C_1$-$C_7$-alkyl-sulfonyl, such as —S(O)$_2$Me, and/or cyano, most preferably $C_1$-$C_7$-alkyl, —O—$C_1$-$C_7$-alkyl, halo-$C_1$-$C_7$-alkyl, halo-$C_1$-$C_7$-alkoxy, halo, unsubstituted or substituted, preferably unsubstituted, phenyl- or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, $C_1$-$C_7$-alkanoyl-$C_1$-$C_7$-alkyl, $C_1$-$C_7$-alkanoyl-amino, $C_1$-$C_7$-alkanoyl, $C_1$-$C_7$-alkyl-sulfonyl and/or cyano.

(m) Unsubstituted or Substituted Mono- or Bicyclic heterocyclylsulfonyl

Preferred examples for the heterocyclyl moiety are mono- or bicyclic rings. Preferred are 3 to 14, more preferably 5 to 11 membered ring systems. The heterocyclyl moiety may be saturated, partially saturated or aromatic ring systems. The heterocyclyl moiety has preferably 1, 2 or 3, more preferably 1 or 2 heteroatoms selected from O, N or S, more preferably S or N. Particularly preferred examples include 5- or 6-membered rings preferably containing a nitrogen or an sulfur atom, in particular pyrrolidinyl, oxazolyl, pyrrolidin-2-onyl, pyrrolyl, piperidyl, pyrimidyl, pyridyl, pyrazinyl, pyrazolyl, isoxazolyl, pyrrolidin-2-onyl, thiazolyl, or thiophenyl, in particular thiophenyl, thiazolyl, pyridyl or pyrazolyl; or 9- to 11-membered bicyclic ring systems preferably containing at least one nitrogen and/or S atom, in particular indolyl, 2,3-dihydro-benzo[1,4]dioxinyl, benzofuranyl, quinolinyl, 4H-benzo[1,4]oxazin-3-onyl, benzooxazolyl, benzo[1,2,5]oxadiazolyl, benzimidazolyl or benzothiophenyl, more preferably quinolinyl. When the heterocyclyl moiety is substituted, it is preferably mono-substituted. Suitable substituents for the heterocyclyl moiety are as defined herein, preferably —$C_1$-$C_7$-alkyl, such as methyl, halo, such as Cl, hydroxy, $C_1$-$C_7$-alkanoyl, such as acetyl, $C_1$-$C_7$-alkanoylamino, such as NHC(O)Me, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano, most preferably $C_1$-$C_7$-alkanoyl, cyano, or pyridyl. Most preferably the heterocyclyl moiety is unsubstituted or is substituted by $C_1$-$C_7$-alkyl, halo, and/or $C_1$-$C_7$ alkanoylamino.

(n) Unsubstituted or Substituted Mono- or Bicyclic aryl-$C_1$-$C_7$-alkylsulfonyl Preferably aryl alkyl is aryl-$C_{1-6}$ alkyl, more preferably aryl-$C_{1-4}$ alkyl, in particular aryl-$CH_2$—, aryl-$CH_2CH_2$—, aryl-CH($CH_3$)—, aryl-$CH_2$CH($CH_3$)— or aryl-CH($CH_2CH_3$)—, most preferably aryl-$CH_2$—. Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono-, di- or tri-substituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$-alkylene-O-alkyl, such as O—$C_3H_6OCH_3$, hydroxy, unsubstituted or substituted, preferably substituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, carboxyl, and cyano. Suitable substituents for the phenyl and naphthyl substituent on the aryl moiety of aryl alkylcarbonyl include $C_1$-$C_7$-alkyl, —O—$C_1$-$C_7$-alkyl, halo-$C_1$-$C_7$-alkyl, halo, hydroxyl and amino. Most preferably, aryl is unsubstituted.

(o) Unsubstituted or Substituted $C_1$-$C_7$-alkylsulfonyl

Preferred examples for the alkyl moiety are branched or straight chain $C_1$-$C_7$-alkyl which may be substituted or unsubstituted. In one embodiment, the alkyl moiety is branched alkyl such as isopropyl, isobutyl, sec-butyl or tert-butyl, isopentyl, 1-ethylpropyl, 2,2-dimethyl-propyl and 1,2-dimethyl-propyl, most preferably tert-butyl. In another embodiment the alkyl moiety is straight chain alkyl such as methyl, ethyl, n-propyl, n-butyl or n-pentyl, preferably methyl or ethyl. When the alkyl moiety is substituted, it is preferably mono-, di- or tri-substituted, more preferably mono-substituted. Suitable substituents for the alkyl moiety are as defined herein, preferably O—$C_1$-$C_4$-alkyl, such as OMe, halo, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, aminocarbonyl, N-mono- or N,N-di-substituted aminocarbonyl, such as CONHMe, carboxyl, $C_1$-$C_7$-alkyloxycarbonyl, such as COOMe, and cyano. Most preferably the alkyl moiety is unsubstituted.

In a second embodiment, R4 is unsubstituted or substituted mono- or bicyclic aryl-$C_1$-$C_7$-alkyl.

Preferably aryl alkyl is aryl-$C_{1-6}$ alkyl, more preferably aryl-$C_{1-4}$ alkyl, in particular aryl-$CH_2$—, aryl-$CH_2CH_2$—, aryl-CH($CH_3$)—, aryl-$CH_2$CH($CH_3$)— or aryl-CH($CH_2CH_3$)—, most preferably aryl-$CH_2$—. Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono-, di- or tri-substituted. In one embodiment, phenyl is preferably unsubstituted. Suitable substituents are as defined herein, preferably $C_1$-$C_7$-alkyl, —O—$C_1$-$C_7$-alkyl, such as OMe, halo-$C_1$-$C_7$-alkyl, such as $CF_3$, halo, such as Cl or F, —O—$C_1$-$C_7$ alkylene-O-alkyl, such as O—$C_3H_6OCH_3$, hydroxy, unsubstituted or substituted, preferably substituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, $C_1$-$C_7$-alkanoylamino, such as —NHCOMe, carboxyl, and cyano. Suitable substituents for the phenyl and naphthyl substituent on the aryl moiety of aryl alkylcarbonyl include $C_1$-$C_7$-alkyl, —O—$C_1$-$C_7$-alkyl, halo-$C_1$-$C_7$-alkyl, halo, hydroxyl and amino. Most preferably, aryl is unsubstituted.

In a third embodiment, R4 is unsubstituted or substituted mono- or bicyclic cycloalkyl.

Preferred examples for the cycloalkyl moiety are monocyclic rings, preferably $C_3$-$C_8$-cycloalkyl, more preferably $C_3$, $C_4$, $C_5$, and $C_6$-cycloalkyl, most preferably $C_6$-cycloalkyl. The cycloalkyl moiety may be substituted or unsubstituted. When the cycloalkyl moiety is substituted, it is preferably mono-substituted. Suitable substituents for the cycloalkyl moiety are as defined herein, preferably O—$C_1$-$C_4$-alkyl, such as OMe, halo, hydroxy, unsubstituted or substituted, preferably unsubstituted, phenyl or naphthyl, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carbamoyl, $C_1$-$C_7$-alkanoylamino, carboxyl, and cyano, whereby suitable phenyl substituents include $C_1$-$C_7$-alkyl, such as methyl, —O—$C_1$-$C_7$-alkyl, halo-$C_1$-$C_7$-alkyl, halo, hydroxyl and amino, most preferably cycloalkyl is unsubstituted.

In a fourth embodiment, R4 is unsubstituted or substituted mono- or bicyclic aryl.

Preferred examples of the aryl moiety include mono- or bicyclic aryl with 6 to 22 carbon atoms, whereby one of the rings of the bicyclic aryl may be a partially or fully saturated ring condensed to the other aromatic ring, especially phenyl, indanyl, indenyl, 1,2,3,4-tetrahydronaphthyl or naphthyl, more preferably phenyl. When the aryl moiety is substituted, it is preferably mono- or di-substituted. Suitable substituents are as defined herein, preferably $C_1$-$C_7$-alkyl, such as methyl, —O—$C_1$-$C_7$-alkyl, such as OMe, halo-$C_1$-$C_7$-alkyl, halo, such as Cl, —O—$C_1$-$C_7$-alkylene-O-alkyl, such as O—$C_3H_6OCH_3$, hydroxy, unsubstituted or substituted, preferably unsubstituted, phenyl- or naphthyloxy, unsubstituted or substituted, preferably unsubstituted, phenyl- or naphthyl-$C_1$-$C_7$-alkyloxy, nitro, amino, amino-$C_1$-$C_7$-alkyl, carboxyl, and cyano. Most preferably, aryl is unsubstituted.

In a fifth embodiment, R4 is unsubstituted or substituted mono- or bicyclic heterocyclyl.

Preferred examples for the heterocyclyl moiety are mono- or bicyclic rings. Preferred are 3 to 14, more preferably 5 to 11 membered ring systems. The heterocyclyl moiety may be saturated, partially saturated or aromatic ring systems. The heterocyclyl moiety has preferably 1, 2 or 3, more preferably 1 or 2 heteroatoms selected from O, N or S, more preferably O or N. Particularly preferred examples include 5- or 6-membered rings preferably containing a nitrogen or an oxygen atom, in particular pyrrolidinyl, oxazolyl, pyrrolidin-2-onyl, pyrrolyl, piperidyl, furanyl, pyrimidyl, pyridyl, pyrazinyl, isoxazolyl, pyrrolidin-2-onyl, tetrahydrofuranyl, or tetrahydropyranyl, in particular pyrimidyl or pyridyl; or 9- to 11-membered bicyclic ring systems preferably containing at least one nitrogen and/or S atom, in particular indolyl, 2,3-dihydro-benzo[1,4]dioxinyl, benzofuranyl, 4H-benzo[1,4]oxazin-3-onyl, benzooxazolyl, benzo[1,2,5]oxadiazolyl, benzimidazolyl or benzothiopenyl, more preferably benzothiopenyl. When the heterocyclyl moiety is substituted, it is preferably mono-substituted. Suitable substituents for the heterocyclyl moiety are as defined herein, preferably —$C_1$-$C_7$-alkyl, such as methyl, halo, hydroxy, $C_1$-$C_7$-alkanoyl, such as acetyl, unsubstituted or substituted, preferably unsubstituted, phenyl, unsubstituted or substituted, preferably unsubstituted, phenyl- or naphthyloxy, unsubstituted or substituted, preferably unsubstituted, phenyl- or naphthyl-$C_1$-$C_7$-alkyl, unsubstituted or substituted, preferably unsubstituted, $C_3$-$C_8$-cycloalkyl, such as cyclopropyl, nitro, amino, amino-$C_1$-$C_7$-alkyl, carboxyl, and cyano. Most preferably the heterocyclyl moiety is unsubstituted or is mono-substituted as described above, e.g. by halo.

Alternatively, R3 and R4 may form a nitrogen containing ring as described herein, preferably, R3 and R4 form together a pyrrolidine, imidazolidine or piperidine ring that is unsubstituted or substituted and may preferably contain an oxo moiety. When the ring is substituted, it is preferably substituted by up to four moieties selected from $C_1$-$C_7$-alkyl, hydroxyl, halo, hydroxy-$C_1$-$C_7$-alkyl, halo-$C_1$-$C_7$-alkyl and cyano. Preferably the ring is unsubstituted.

Particular embodiments of the invention, especially of compounds of the formula I and/or salts thereof, are provided in the Examples—the invention thus, in a very preferred embodiment, relates to a compound of the formula I, or a salt thereof, selected from the compounds given in the Examples, as well as the use thereof according to the invention.

Process of Manufacture

A compound of formula I, or a salt thereof, is prepared analogously to methods that, for other compounds, are in principle known in the art, so that for the novel compounds of the formula I the process is novel at least as analogy process, especially as described or in analogy to methods described herein in the illustrative Examples, or modifications thereof, preferably in general by a) for the manufacture of a compound of the formula I wherein R1 is hydrogen, and R2, R3, R4 and T are as defined for a compound of the formula I hereinabove or hereinbelow (preferably with the proviso that R4 has one of the meanings given herein other than N-mono- or N,N-di-(unsubstituted or substituted aryl, unsubstituted or substituted heterocyclyl, unsubstituted or substituted cycloalkyl or unsubstituted or substituted alkyl)-aminocarbonyl), reacting a compound of the formula II,

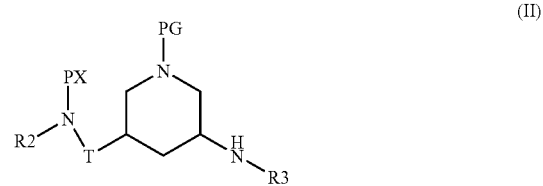

(II)

wherein R2, R3 and T are as defined for a compound of the formula I, PX is R1 as defined for a compound of the formula I, a protecting group or a bound resin and PG is a protecting group, with a compound of the formula III,

R4-A (III)

wherein R4 is as defined for a compound of the formula I hereinabove or hereinbelow and A is activated hydroxy; or b) reacting a compound of the formula IV,

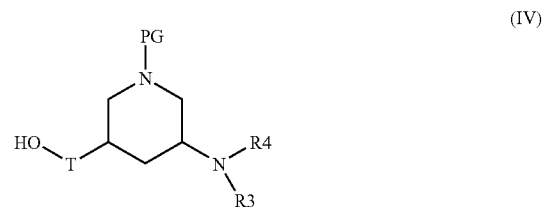

(IV)

wherein T is methylene or preferably carbonyl, PG is a protecting group and R3 and R4 are as defined for a compound of the formula I, or (preferably) an activated derivative thereof, with a compound of the formula V,

R1-NH—R2 (V)

wherein R1 and R2 are as defined for a compound of the formula I; or c) for the manufacture of a compound of the formula I wherein R1 is hydrogen, R4 is N-mono- or N,N-di-(unsubstituted or substituted aryl, unsubstituted or substituted heterocyclyl, unsubstituted or substituted cycloalkyl or unsubstituted or substituted alkyl)-aminocarbonyl and R2, R3 and T are as defined for a compound of the formula I hereinabove or hereinbelow, reacting a compound of the formula II as given under a) above with a compound of the formula VI,

R4*-NCO (VI)

wherein R4* is unsubstituted or substituted aryl, unsubstituted or substituted heterocyclyl, unsubstituted or substituted cycloalkyl or unsubstituted or substituted alkyl; or d) for the manufacture of a compound of the formula I wherein R1 is hydrogen, R4 is unsubstituted or substituted alkyl bound via a methylene group (which may be the alkyl of unsubstituted or substituted alkyl or form part of it) and R2, R3 and T are as defined for a compound of the formula I hereinabove or hereinbelow, reacting a compound of the formula II as given under a) above with an oxo compound of the formula VII,

R4-C(=O)R4* (VII)

wherein R4 and R4* with the carbon atom binding independently are hydrogen or a moiety completing an unsubstituted or substituted alkyl moiety R4 bound via the carbon carrying the oxo (=O) group in formula VII, under conditions of reductive amination;

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials (especially of the formulae II to VII), in addition to specific protecting groups mentioned, further protecting groups may be present, and any protecting groups or bound resins are removed at an appropriate stage in order to obtain a corresponding compound of the formula I, or a salt thereof.

Preferred Reaction Conditions

The preferred reaction conditions for the reactions mentioned above, as well as for the transformations and conversions, are as follows (or analogous to methods used in the Examples or as described there):

The reaction under a), the reaction conditions and reactants can be of customary type, e.g., they can preferably be as follows: activated hydroxy A in formula III can preferably be halogen, such as chloro, bromo or iodo, or in the case that R4 is a moiety as defined for R4 herein other than acyl the moiety of a sulfonic acid bound via an oxygen, such as toluolsulfonyloxy or methanesulfonyloxy, or if R4 is an acyl moiety the activated hydroxy may be the moiety of an organic carbonic or sulfonic acid (preferably $C_1$-$C_7$-alkanoyl thus forming a symmetric or mixed anhydride or the acyl moiety of the same acid, thus forming a symmetric anhydride) bound via oxygen, a moiety completing an activated ester, such as the hydroxybenzotriazole (HOBT), pentafluorophenyl, 4-nitrophenyl or N-hydroxysuccinimide ester, or the activated hydroxy can be formed in situ from the corresponding hydroxy, e.g. by contacting the compounds of formulae II and III with a suitable solvent, for example a halogenated hydrocarbon, such as methylene chloride, N,N-dimethylformamide, N,N-dimethylacetamide, N-methyl-2-pyrrolidone, dimethylaminopyridine, methylene chloride, or a mixture of two or more such solvents, and by the addition of a suitable base, for example pyridine, triethylamine, diisopropylethylamine (DIEA) or N-methylmorpholine and, if the reactive derivative of the acid of the formula III is formed in situ, a suitable coupling agent that forms a preferred reactive derivative of the carbonic acid of formula III in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt), HOAt alone, 4-(4,6-dimethoxy-1,3,5-triazin-2-yl)-4-methylmorpholinium chloride (DMT-MM), propylphosphonic anhydride or with 1-chloro-2-methyl-propenyl)-dimethylamine (=1-chloro-N,N,2-trimethyl-1-propenylamine). For review of some other possible coupling agents, see e.g. Klauser; Bodansky, *Synthesis* 1972, 453-463.

Preferably, A in formula III is halo, such as chloro or bromo. The reaction mixture is preferably stirred at a temperature of between approximately −20 and 60° C., especially between 0° C. and 50° C., e.g. between room temperature and 40° C. The solvent is a customary solvent, for example a halogenated hydrocarbon, such as methylene chloride, N,N-dimethyl-formamide, N,N-dimethylacetamide, N-methyl-2-pyrrolidone, dimethylaminopyridine, methylene chloride, or a mixture of two or more such solvents, and a suitable base, for example pyridine, triethylamine, diisopropylethylamine (DIEA) or N-methylmorpholine, is added preferably. The reaction may be carried out under an inert gas, e.g. nitrogen or argon.

A protecting group PX may be selected from customary amino protecting groups, such as lower alkoxycarbonyl or other such protecting groups as deducible e.g. from the standard textbooks mentioned below under General Process Conditions. The removal of such a protecting group after the reaction between a compound of the formula II and a compound of the formula III can take place under customary conditions, e.g. as described in the standard textbooks just referenced. For example, $C_1$-$C_7$-alkoxycarbonyl, such as tert-butoxycarbonyl, can be removed by reaction with an acid, such as hydrochloric acid, in an appropriate solvent, such as dioxane or methylene chloride, at customary temperatures, e.g. in the range from 0 to 50° C., for example at room temperature, or using $CF_3SO_3Si(CH_3)_3$ or the like in an appropriate solvent, such as methylene chloride, in the presence of 2,6-lutidine, where the temperatures may be in the same range as just described.

Where PX is a resin, this may include any resin that is appropriate and binding to which of the rest of the compound of formula II or of the resulting protected compound of the formula I can be reversed (that is, the rest of the molecule can be removed); among the possible resins, polystyrene based resins are especially preferred where binding is possible via appropriate ligating groups, e.g. —$CH_2$—N($CH_3$)—C (=O)—($CH_2$)$_4$—O-(3,5-dimethoxyphenyl-4-methylene or —$CH_2$—O—($CH_2$)$_2$—O-(3,5-dimethoxyphenyl-4-methylene where the last methylene is bound to the nitrogen in formula II and the left handed $CH_2$ is bound to the resin matrix, such as polystyrene. The removal of the moiety PX can then preferably take place in the presence of an acid, such as a strong organic acid, e.g. trifluoroacetic acid, at appropriate temperatures, e.g. from 0 to 50° C., such as at room temperature.

Before or after or simultaneously with the removal of a protecting group or resin PX, the protecting group PG (and, if present, other protecting groups) may be removed under appropriate conditions, e.g. selected from those mentioned in the standard textbooks given under the General Process Conditions. For example, a protecting group 9H-fluoren-9-ylmethyloxycarbonyl may be removed by reacting with an appropriate secondary nitrogen base, such as piperidine, in an appropriate solvent, such as an N,N-di($C_1$-$C_7$-alkyl)-$C_1$-$C_7$-alkanolamide, e.g. dimethylacetamide, at customary temperatures, e.g. from 0 to 50° C., for example at room temperature, $C_1$-$C_7$-alkoxycarbonyl, such as tert-butoxycarbonyl, can be removed by reaction with an acid, such as hydrochloric acid, in an appropriate solvent, such as dioxane or methylene chloride, at customary temperatures, e.g. in the range from 0 to 50° C., for example at room temperature, or using $CF_3SO_3Si(CH_3)_3$ or the like in an appropriate solvent, such as methylene chloride, in the presence of 2,6-lutidine, where the temperatures may be in the same range as just described.

Removal of the protecting groups including PG and a protecting groups PX or a resin PX thus leads to a compound of the formula I, or a salt thereof.

The reaction under b) preferably takes place under customary condensation or substitution conditions.

In the case of a compound of the formula IV wherein T is carbonyl (that is, the compound of the formula IV is a carbonic acid), the reaction preferably takes place with an activated derivative of the compound of the formula IV. As an activated derivative of an acid of the formula IV reactive esters (such as the hydroxybenzotriazole (HOBT), pentafluorophenyl, 4-nitrophenyl or N-hydroxysuccinimide ester), acid halogenides (such as the acid chloride or bromide) or reactive anhydrides (such as mixed anhydrides with lower alkanoic acids or symmetric anhydrides) are preferred. Reactive carbonic acid derivatives can also and preferably be formed in situ. The reaction is carried out by dissolving the compounds of formulae IV and V in a suitable solvent, for example a halogenated hydrocarbon, such as methylene chloride, N,N-dimethylformamide, N,N-dimethylacetamide, N-methyl-2-pyrrolidone, methylene chloride, acetonitrile or a mixture of two or more such solvents, and by the addition of a suitable base, for example triethylamine, diisopropylethylamine (DIPEA) or N-methylmorpholine and, if the reactive derivative of the acid of the formula IV is formed in situ, a suitable coupling agent that forms a preferred reactive derivative of the carbonic acid of formula IV in situ, for example dicyclohexylcarbodiimide/1-hydroxybenzotriazole (DCC/HOBT); bis(2-oxo-3-oxazolidinyl)phosphinic chloride (BOPCI); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt), HOAt alone, 4-(4,6-dimethoxy-1,3,5-triazin-2-yl)-4-methylmorpholinium chloride (DMT-MM), O-(1H-6-chlorobenzo-triazole-1-yl)-1,1,3,3-tetramethyluronium hexafluorophosphate (HCTU), propylphosphonic anhydride or with 1-chloro-2-methyl-propenyl)-dimethylamine (=1-chloro-N,N,2-trimethyl-1-propenylamine). For review of some other possible coupling agents, see e.g. Klauser; Bodansky, *Synthesis* 1972, 453-463. The reaction can take place at a temperature of between approximately −20 and 50° C., especially between 0° C. and 30° C., e.g. at 0° C. to room temperature. The reaction may be carried out under an inert gas, e.g. nitrogen or argon.

In the case of a compound of the formula IV wherein T is methylene, in an activated derivative the OH group is preferably replaced by a leaving group, such as halo, e.g. chloro, bromo or iodo, or organic sulfonyloxy, such as tosyloxy or methanesulfonyloxy. The reaction with a compound of the formula V then preferably takes under standard conditions for nucleophilic substitution.

The removal of protecting groups PG and/or other protecting groups can then in either case take place as described under process a) or the general process conditions.

The reaction under c) between a compound of the formula II and an isocyanate of the formula VI can take place under customary reaction conditions known in the art for analogous reactions. For example, the reaction may take place in an appropriate solvent, such as 1,2-dichloroethane or methylene chloride, in the presence of a base, e.g. a tertiary nitrogen base, such as pyridine, and for example at temperatures from 20° C. to the reflux temperature of the reaction mixture, e.g. from room temperature to 80° C.

The removal of protecting groups PX, resins PX, protecting groups PG and/or other protecting groups can then in either case take place as described under process a) or the general process conditions.

The reaction under d) can take place in one step or first by forming the corresponding ketimine or aldimine that is then reduced to the amine of the formula I. In the first case, the reductive amination preferably takes place under customary conditions for reductive amination, e.g. in the presence of an appropriate hydrogenation agent, such as hydrogen in the presence of a catalyst or a complex hydride, e.g. sodium triacetoxyborohydride or sodium cyanoborohydride, in an appropriate solvent, such as a halogenated hydrocarbon, e.g. methylene chloride or 1,2-dichloroethane, and optionally a carbonic acid, e.g. acetic acid, at preferred temperatures between −10° C. and 50° C., e.g. from 0° C. to room temperature. In the second case, first the reaction (where preferably in formula II PX is a resin) between a compound of the formula II and of the formula VII to a corresponding aldimine or ketimine takes place, e.g. in customary solvents, such as tri-lower alkyl orthoformates, such as trimethyl orthoformate, and/or halogenated hydrocarbons, such as methylene chloride, where the temperatures can, for example, lie in the range from 0 to 50° C., e.g. at room temperature; a resulting aldimine or ketimine intermediate can then, after isolation or without isolation (in the case of PX as a resin e.g. after washing of the resin), be reacted further under reduction to a corresponding amine of the formula I, e.g. in the presence of an appropriate hydrogenating substance, such as an appropriate complex hydride, e.g. borane-pyridine complex, for example in an appropriate solvent, e.g. an alcohol, such as methanol, a halogenated hydrocarbon, such as methylene chloride, and a carbonic acid, such as acetic acid, or mixtures of two or more thereof, where the reaction temperatures can, for example, lie in the range from 0 to 50° C., e.g. at room temperature.

R4 and R4* in a compound of the formula VII with the carbon atom binding independently are hydrogen or a moiety completing an unsubstituted or substituted alkyl moiety R4 bound via the carbon carrying the oxo (=O) group in formula VII means that the moieties R4 and R4*, together with carbon between them, during the reaction or reactions form an unsubstituted or substituted alkyl moiety R4 that is bound via the central carbon which then carries R4, R4* and a hydrogen and the bond binding it to the rest of the molecule [that is, R4 is a moiety of the formula R4-CH(R4*)-]. This moiety is then methyl (R4 and R4* each=H) or other unsubstituted alkyl or is substituted alkyl.

The removal of protecting groups PX, resins PX, protecting groups PG and/or other protecting groups can then in either case take place as described under process a) or the general process conditions.

Optional Reactions and Conversions

Compounds of the formula I, or protected forms thereof directly obtained according to any one of the preceding procedures or after introducing protecting groups anew, which are included subsequently as starting materials for conversions as well even if not mentioned specifically, can be converted into different compounds of the formula I according to known procedures, where required after removal of protecting groups.

Where R1 is hydrogen in a compound of the formula I, this can be converted into the corresponding compound wherein R1 has a meaning other than hydrogen given for compounds of the formula I by reaction with a compound of the formula XVII,

R1*-Q        (XVII)

wherein R1* is defined as R1 in a compound of the formula I other than hydrogen and Q is a leaving group (e.g. preferably selected from halo, e.g. chloro, from unsubstituted or substituted aryl-sulfonyloxy, such as toluolsulfonyloxy, from unsubstituted or substituted alkylsulfonyloxy, such as methylsulfonyloxy or trifluoromethylsulfonyloxy, with the reaction allowed to take place e.g. in the presence of a base, such as an alkali metal salt of a weaker acid, e.g. an alkali metal carbonate and/or an alkali metal hydrogencarbonate, such as sodium or potassium carbonate and/or sodium or potassium hydrogencarbonate ($NaHCO_3$ or $KHCO_3$) in an appropriate solvent, e.g. dimethylacetamide, dioxane and/or $H_2O$, at preferred temperatures between −20 and 50° C., e.g. at −5 to 30° C.), or wherein Q is —CHO (so that the compound of the formula IV is an aldehyde) and then R1* is the complementary moiety for a moiety R1 that includes a methylene group (resulting in a group R1 of the formula R1*-$CH_2$—) e.g. under reductive amination conditions as follows: The reaction preferably takes place under customary conditions for reductive amination, e.g. in the presence of an appropriate hydrogenation agent, such as hydrogen in the presence of a catalyst or a complex hydride, e.g. sodium triacetoxyborohydride or sodium cyanoborohydride, in an appropriate solvent, such as a halogenated hydrocarbon, e.g. methylene chloride or 1,2-dichloroethane, and optionally a carbonic acid, e.g. acetic acid, at preferred temperatures between −10° C. and 50° C., e.g. from 0° C. to room temperature In a compound of the formula I wherein R3 is hydrogen, unsubstituted or substituted alkyl R3 can be introduced by reacting a compound of the formula I wherein R3 is hydrogen and R1, R2, R4 and T are as defined for a compound of the formula I with a compound of the formula XVIII,

R3-Q        (XVIII)

wherein R3 is unsubstituted or substituted alkyl and Q is as defined for a compound of the formula XVII. The reaction conditions are preferably as described for the reaction of a compound of the formula XVII in the preceding paragraph. The reaction preferably takes place in the presence of a protecting group at the nitrogen of the central piperidine ring, that is, with a compound of the formula I in protected form wherein R3 is hydrogen which is subsequently removed.

In some cases, the conversions preferably take place with compounds of the formula I in protected form; the subsequent removal of protecting group can be achieved as described above for the condensation reaction between a compound of the formula II and a compound of the formula III and below under "General Process Conditions", yielding a corresponding compound of the formula I.

Salts of compounds of formula I having at least one salt-forming group may be prepared in a manner known per se. For example, salts of compounds of formula I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

A salt of a compound of the formula I can be converted in customary manner into the free compound; metal and ammonium salts can be converted, for example, by treatment with suitable acids, and acid addition salts, for example, by treatment with a suitable basic agent. In both cases, suitable ion exchangers may be used.

Stereoisomeric mixtures, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Intermediates and final products can be worked up and/or purified according to standard methods, e.g. using chromatographic methods, distribution methods, (re-) crystallization, and the like.

Starting Materials

In the subsequent description of starting materials (this term including also intermediates) and their synthesis, R1, R2, T, R1*, R3, R4, R4, R4*, PG, PX, A and Q have the meanings given above or in the Examples for the respective starting materials or intermediates, if not indicated otherwise directly or by the context. Protecting groups, if not specifically mentioned, can be introduced and removed at appropriate steps in order to prevent functional groups, the reaction of which is not desired in the corresponding reaction step or steps, employing protecting groups, methods for their introduction and their removal are as described above or below, e.g. in the references mentioned under "General Process Conditions". The person skilled in the art will readily be able to decide whether and which protecting groups are useful or required.

A compound of the formula II wherein in PX is a bound resin, a protecting group or R1 as defined for a compound of the formula I can, for example, be prepared by reacting a compound of the formula VIII,

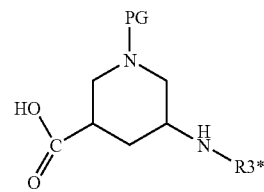

(VIII)

wherein R3* is R3 or a protecting group, or a reactive derivative thereof under condensation conditions with a compound of the formula IX,

   (IX).

The reaction conditions for this condensation reaction and the reactive derivatives of the carbonic acid of the formula VIII can preferably be analogous to those mentioned under process b) above for compounds of the formula IV wherein T is carbonyl and its reaction with a compound of the formula V.

A corresponding compound of the formula II wherein T is methylene can then be obtained by reduction of the obtainable compound of the formula II wherein T is carbonyl. For example, this carbonyl can be reduced to a corresponding methylene by treatment with an appropriate complex hydride of the required specificity, especially borane dimethylsulfide complex, in an appropriate solvent, such as an ether, e.g. tetrahydrofurane, at preferred temperatures between room temperature and the reflux temperature of the reaction mixture or at 140-150° C.

A subsequent removal of protecting group R3* in an obtainable compound of the formula X,

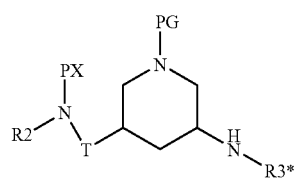   (X)

wherein R3* is a protecting group can be achieved as above for reaction a) and below under "General Process Conditions", yielding a corresponding compound of the formula II wherein R3 is hydrogen. For example, tert-butoxycarbonyl R3* can be removed by reaction with $CF_3SO_3Si(CH_3)_3$/2,6-lutidine under conditions as mentioned above under manufacturing process a).

Where R3* corresponds to a moiety R4 (such as tert-butoxycarbonyl not to be removed), such an obtainable compound of the formula II may already be a compound of the formula I.

A compound of the formula VIII can, for example, be obtained from a corresponding salt, e.g. an ammonium salt of the formula XI,

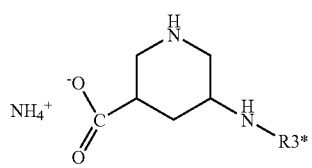   (XI)

wherein R3* is as defined for a compound of the formula VIII, by converting this salt under introduction of a protecting group PG into a corresponding protected compound of the formula VIII, e.g. by introducing a protecting group from an activated form of a carbonic acid that forms the protecting group PG, such as an activated form of "9-fluorenylmethoxycarbonic acid", e.g. N-(9-fluorenylmethoxycarbonyloxy)-succinimide, in the presence of a base, e.g. an alkali metal carbonate and/or hydrogen carbonate, such as sodium carbonate, in an appropriate solvent, such as water, tetrahydrofurane or mixtures of such solvents, e.g. at temperatures in the range from to 50° C., for example at room temperature.

A salt compound of the formula XI can, for example, be obtained by reducing a nicotinic acid derivative of the formula XII,

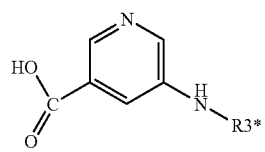   (XII)

in the presence of an appropriate reagent, e.g. hydrogen in the presence of an appropriate catalyst, such as rhodium(III)oxide/platinum(IV)oxide (Nishimura's catalyst) in the presence of ammonium hydroxide and in an aqueous solvent, such as water, e.g. at temperatures from 0 to 50° C., for example at room temperature.

A compound of the formula IX wherein PX is a moiety PX*-CH$_2$ (that is, a moiety PX in the form or a resin, a protecting group or of R1 as defined for a compound of the formula I, in each case comprising and bound via a methylene group) can, for example, be prepared by reacting a compound of the formula XIII,

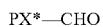   PX*—CHO   (XIII)

wherein PX* is a residue that completes a moiety PX of the formula PX*-CH$_2$ as just defined, under reductive amination conditions with a compound of the formula XIV,

   R2-NH$_2$   (XIV)

wherein R2 is as defined for a compound of the formula I; the reaction can preferably take place under customary conditions for reductive amination, e.g. under formation of the aldimine and its direct reduction in the in the presence of an appropriate hydrogenation agent, such as hydrogen in the presence of a catalyst or a complex hydride, e.g. sodium triacetoxyborohydride or sodium cyanoborohydride, in an appropriate solvent, such as a halogenated hydrocarbon, e.g. methylene chloride or 1,2-dichloroethane, and optionally a carbonic acid, e.g. acetic acid, at preferred temperatures between −10° C. and 50° C., e.g. from 0° C. to room temperature, or first under formation of the aldimine and then (with or without isolation of the aldimine) its reduction to the amine of the formula IX in a separate step—in this second case, first the reaction (where preferably in formula XIII PX* is a resin) between a compound of the formula XIII and of the formula XIV to a corresponding aldimine takes place, e.g. in customary solvents, such as tri-lower alkyl orthoformates, such as trimethyl orthoformate, and/or halogenated hydrocarbons, such as methylene chloride, where the temperatures can, for example, lie in the range from 0 to 80° C., e.g. at room temperature to 60° C., and a resulting aldimine intermediate can then, after isolation or without isolation (in the case of PX* as a resin e.g. after washing of the resin), be reacted further under reduction to a corresponding amine of the formula IX, e.g. in the presence of an appropriate hydrogenating substance, such as an appropriate complex hydride, e.g. borane-pyridine complex, for example in an appropriate solvent, e.g. an alcohol, such as methanol, a halogenated hydrocarbon, such as methylene chloride, and a carbonic acid, such as acetic acid, or mixtures of two or more thereof, where the reaction temperatures can, for example, lie in the range from 0 to 50° C., e.g. at room temperature.

Some examples for compounds of the formula XIII and their manufacture are provided in the examples given below, especially also versions wherein PX is a resin. Other comparable compounds of the formula XIII can be prepared analogously to those described in the examples.

A compound of the formula IV wherein T is carbonyl can, for example, be prepared by removing from a compound of the formula VIII as described above wherein R3* is a protecting group the protecting group, e.g. under conditions described under process a) above or the General Process Conditions, for example tert-butoxycarbonyl in the presence of an acid, such as hydrochloric acid, in an appropriate solvent, e.g. dioxane, at temperatures e.g. from 0 to 50° C., for example at room temperature. If R3* in a compound of the formula VIII is a moiety R3 as defined under formula I, this removal of a protecting group is not required.

A compound of the formula IV wherein T is methylene can be prepared from a compound of the formula VIII by reducing the carboxy function in the presence of an appropriate complex hydride, e.g. borane dimethylsulfide, in an appropriate solvent, e.g. tetrahydrofurane, at preferred temperatures between –20 and 40° C., to the corresponding hydroxymethylene compound.

The reactions in the preceding two paragraphs result in a compound of the formula XVI,

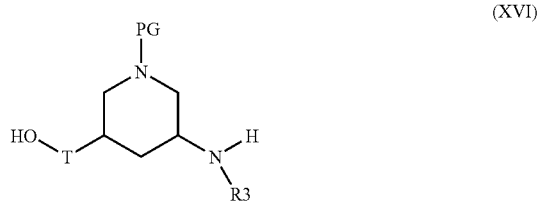

(XVI)

which can then be reacted with a compound of the formula III as shown above under process a) under comparable conditions as those described for process a) to give the corresponding compound of the formula IV.

In a compound of the formula IV wherein R3 is hydrogen, the hydrogen can be replaced by unsubstituted or substituted alkyl R3 as defined herein by reaction with a compound of the formula XVIII,

R3-Q wherein R3 is unsubstituted or substituted alkyl and Q is as defined for a compound of the formula XVII above. The reaction conditions are preferably as described for the reaction of a compound of the formula XVII in the conversion of a compound of the formula I above.

Where for any of the starting materials isomers (e.g. diastereomers, enantiomers) are present, they can be separated according to standard procedures at appropriate stages.

Other starting materials, e.g. compounds of the formula II, V, VI, VII, XII or XVII their synthesis or analogous methods for their synthesis are known in the art, commercially available, and/or they can be found in or derived analogously from the Examples.

General Process Conditions

The following applies in general (where possible) to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about –100° C. to about 190° C., preferably from approximately –80° C. to approximately 150° C., for example at from –80 to –60° C., at room temperature, at from –20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the processes in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the processes of the present invention those starting materials are preferably used which result in compounds of formula I described as being preferred. Special preference is given to reaction conditions that are identical or analogous to those mentioned in the Examples. The invention relates also to novel starting compounds and intermediates described herein, especially those leading to novel compounds of the formula I or compounds of the formula I mentioned as preferred herein.

Pharmaceutical Use, Pharmaceutical Preparations and Methods

As described above, the compounds of the formula I are inhibitors of renin activity and, thus, may be of use for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like. Hypertension, at least as one component of the disease to be treated, is especially preferred, meaning that hypertension alone or in combination with one or more (especially of the mentioned) other diseases may be treated (prophylactically and/or therapeutically).

The present invention further provides pharmaceutical compositions comprising a therapeutically effective amount of a pharmacologically active compound of the formula I, alone or in combination with one or more pharmaceutically acceptable carriers.

The pharmaceutical compositions according to the present invention are those suitable for enteral, such as oral or rectal, transdermal and parenteral administration to mammals, including man, to inhibit renin activity, and for the treatment of conditions associated with (especially inappropriate) renin activity. Such conditions include hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders and the like. Especially preferred is a disease which comprises hypertension, more especially hypertension itself, where treatment with a pharmaceutical composition or the use of a compound of the formula I for its synthesis is useful prophylactically and/or (preferably) therapeutically.

Thus, the pharmacologically active compounds of the formula I may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

Accordingly, the present invention provides pharmaceutical compositions as described above for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, as well as methods of their use.

The pharmaceutical compositions may contain a therapeutically effective amount of a compound of the formula I as defined herein, either alone or in a combination with another therapeutic agent, e.g., each at an effective therapeutic dose as reported in the art. Such therapeutic agents include:

a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) anti-obesity agents such as orlistat; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs*, 2003, 12(4), 623-633, in the FIGS. 1 to 7, which are herein incorporated by reference. A compound of the formula I may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical products or compositions comprising a therapeutically effective amount of a compound of the formula I alone or in combination with a therapeutically effective amount of another therapeutic agent, preferably selected from anti-diabetics, hypolipidemic agents, anti-obesity agents and anti-hypertensive agents, most preferably from antidiabetics, anti-hypertensive agents and hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by (especially inappropriate) renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like.

Thus, the present invention also relates to a compound of formula I for use as a medicament, to the use of a compound of formula I for the preparation of a pharmaceutical composition for the prevention and/or treatment of conditions mediated by (especially inappropriate) renin activity, and to a pharmaceutical composition for use in conditions mediated by (especially inappropriate) renin activity comprising a compound of formula I, or a pharmaceutically acceptable salt thereof, in association with a pharmaceutically acceptable diluent or carrier material.

The present invention further provides a method for the prevention and/or treatment of conditions mediated by (especially inappropriate) renin activity, which comprises administering a therapeutically effective amount of a compound of the formula I to a warm-blooded animal, especially a human, in need of such treatment.

A unit dosage for a mammal of about 50-70 kg may contain between about 1 mg and 1000 mg, advantageously between about 5-600 mg of the active ingredient. The therapeutically effective dosage of active compound is dependent on the species of warm-blooded animal (especially mammal, more especially human), the body weight, age and individual condition, on the form of administration, and on the compound involved.

In accordance with the foregoing the present invention also provides a pharmaceutical product comprising a therapeutic combination, e.g., a kit, kit of parts, e.g., for use in any method as defined herein, comprising a compound of formula I, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition comprising a compound of the formula I according to the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula I, or a pharmaceutically acceptable salt thereof, and at least a second drug substance, said second drug substance preferably being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to a modulation of (especially inappropriate) renin activity, especially one or more of the specific diseases mentioned above.

Finally, the present invention provides a method or use which comprises administering a compound of formula I in combination with a therapeutically effective amount of an anti-diabetic agent, a hypolipidemic agent, an anti-obesity agent or an anti-hypertensive agent.

Ultimately, the present invention provides a method or use which comprises administering a compound of formula I in the form of a pharmaceutical composition as described herein.

The above-cited properties are demonstrable in vitro and in vivo tests using advantageously mammals, e.g., mice, rats, rabbits, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The concentration level in vitro may range between about $10^{-3}$ molar and $10^{-10}$ molar concentrations. A therapeutically effective amount in vivo may range depending on the route of administration, between about 0.001 and 500 mg/kg, preferably between about 0.1 and 100 mg/kg.

As described above, the compounds of the present invention have enzyme-inhibiting properties. In particular, they inhibit the action of the natural enzyme renin. Renin passes from the kidneys into the blood where it effects the cleavage of angiotensinogen, releasing the deca-peptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

The action of renin inhibitors may be demonstrated inter alia experimentally by means of in vitro tests, the reduction in the formation of angiotensin I being measured in various systems (human plasma, purified human renin together with synthetic or natural renin substrate).

Inter alia the following in vitro tests may be used:

Recombinant human renin (expressed in Chinese Hamster Ovary cells and purified using standard methods) at 7.5 nM concentration is incubated with test compound at various concentrations for 1 h at RT in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 2 µM and increase in fluorescence is recorded at an excitation wave-length of 350 nm and at an emission wave-length of 500 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 20 µM.

Alternatively, recombinant human renin (expressed in Chinese Hamster Ovary cells and purified using standard methods) at 0.5 nM concentration is incubated with test compound at various concentrations for 2 h at 37° C. in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 4 µM and increase in fluorescence is recorded at an excitation wave-length of 340 nm and at an emission wave-length of 485 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 20 µM.

In another assay, human plasma spiked with recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I, in this assay, preferably can show $IC_{50}$ values in the range from 1 nM to 20 µM.

In another assay, recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I, in this assay, preferably show $IC_{50}$ values in the range from 1 nM to 20 µM.

In animals deficient in salt, renin inhibitors bring about a reduction in blood pressure. Human renin may differ from the renin of other species. In order to test inhibitors of human renin, primates, e.g., marmosets (*Callithrix jacchus*) may be used, because human renin and primate renin are substantially homologous in the enzymatically active region. Inter alia the following in vivo tests may be used:

Compounds of the formula I can be tested in vivo in primates as described in the literature (see for example by Schnell C R et al. Measurement of blood pressure and heart rate by telemetry in conscious, unrestrained marmosets. Am J Physiol 264 (Heart Circ Physiol 33). 1993: 1509-1516; or Schnell C R et al. Measurement of blood pressure, heart rate, body temperature, ECG and activity by telemetry in conscious, unrestrained marmosets. Proceedings of the fifth FELASA symposium: Welfare and Science. Eds BRIGHTON. 1993.

The following Examples, while in addition representing preferred embodiments of the invention, serve to illustrate the invention without limiting its scope.

EXAMPLES

The following examples serve to illustrate the invention without limiting the scope thereof:

Abbreviations

| | |
|---|---|
| Boc | tert-butoxycarbonyl |
| (Boc)₂O | di-tert-butyl dicarbonate |
| Celite | Celite ® is a filtering aid based on diatomaceous earth (trademark of The Celite Corporation) |
| DIPEA | N-ethyldiisopropylamine |
| DMA | N,N-dimethylacetamide |
| DMAP | 4-(N,N-dimethylamino)-pyridine |
| DMF | N,N-dimethylformamide |
| Fmoc | 9-fluorenylmethoxycarbonyl |
| h | hour(s) |
| HATU | O-(7-azabenzotriazol-1-yl)-N,N,N',N'-tetramethyluronium hexafluorophosphate |
| HCTU | O-(1H-6-chlorobenzotriazole-1-yl)-1,1,3,3-tetramethyluronium hexafluorophosphate |
| HM-N isolute | isolute sorbent from International Sorbent Technology Ltd. |
| mL | milliliter |
| MS | mass spectrometry |
| PS | polystyrene resin |
| RT | room temperature |
| TFA | trifluoroacetic acid |
| THF | tetrahydrofuran |
| Tosyl | para-toluenesulfonyl |
| $t_R$ | retention time |

Temperatures are measured in degrees Celsius. Unless otherwise indicated, the reactions take place at RT.

TLC conditions: $R_f$ values for TLC are measured on 5×10 cm TLC plates, silica gel $F_{254}$, Merck, Darmstadt, Germany.

Scheme 1

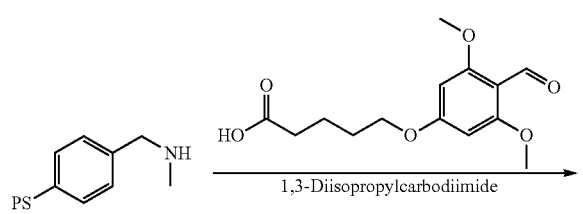

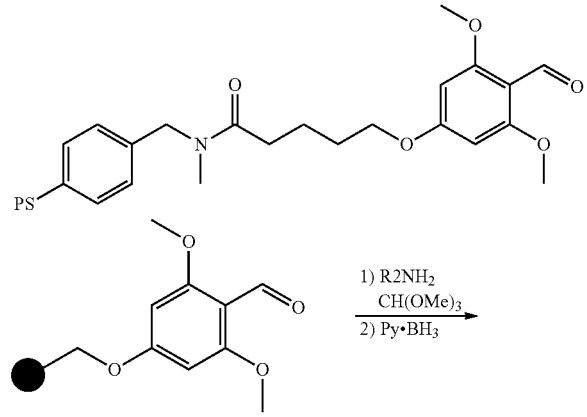

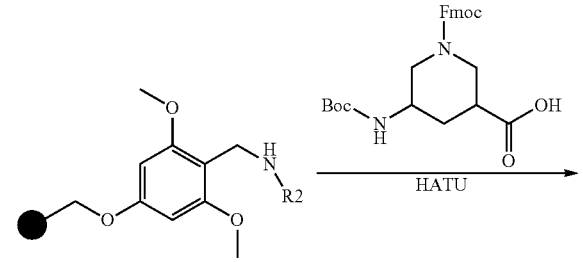

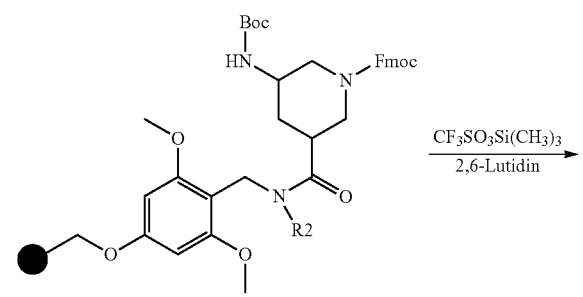

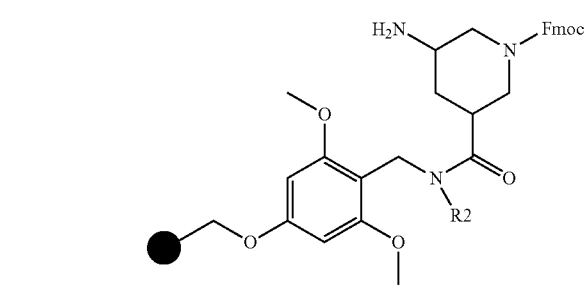

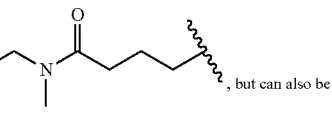

●  is , but can also be

PS stands for the polystyrene resin matrix,
R2 can be as defined in the specification or in the examples.

Starting Material 1: 5-tert-butoxycarbonylamino-1-piperidine-3-carboxylate, ammonium salt

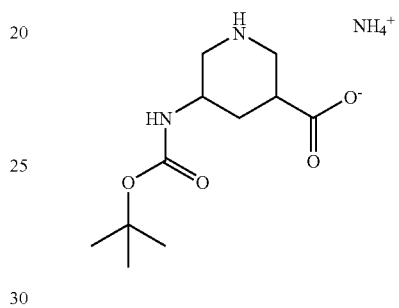

A mixture of 5-tert-butoxycarbonylamino-nicotinic acid (31.8 g, 0.133 mol), Nishimura's catalyst [Rh(III)oxide/Pt (IV)oxide hydrate] (6.37 g) in dist. $H_2O$ (445 mL) and 25% $NH_4OH$ solution (125 mL) is shaken at RT under $H_2$ for 65 h. After addition of a second portion of catalyst (6.37 g) shaking is continued for 25 h. The reaction mixture is filtered through Celite and evaporated in vacuo to yield the title compound as a white powder. MS: 245.1 $[M+H]^+$ Starting Material 2: (3S*,5R*)-5-tert-Butoxycarbonylamino-piperidine-1,3-dicarboxylic acid 1-(9H-fluoren-9-ylmethyl) ester and (3R*,5R*)-5-tert-Butoxycarbonylamino-piperidine-1,3-dicarboxylic acid 1-(9H-fluoren-9-ylmethyl) ester

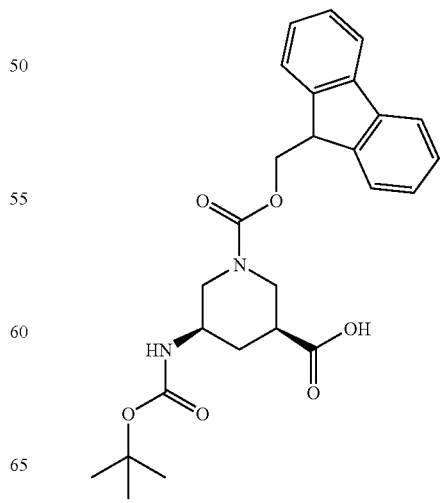

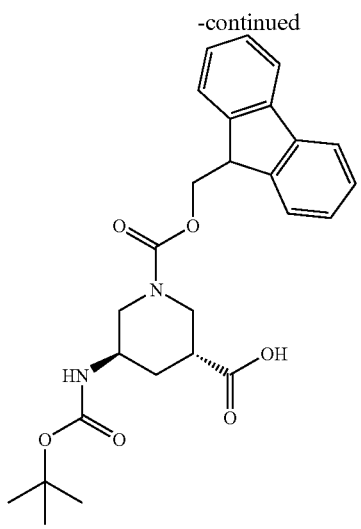

To a stirred mixture of 5-tert-butoxycarbonylamino-1-piperidine-3-carboxylate, ammonium salt (31.76 g, 0.122 mol), NaHCO$_3$ (10.22 g, 0.122 mol), dist. H$_2$O (145 mL) and tetrahydrofurane (290 mL), N-(9-fluorenylmethoxycarbonyloxy)-succinimide (49.25 g, 0.146 mol) is added in several portions. The reaction mixture is stirred for 22 h at RT, and the pH value is then adjusted to 6 by the addition of 1M aqueous HCl. The mixture is diluted with H$_2$O and extracted with ethyl acetate. The organic phase is washed twice with brine, dried (Na$_2$SO$_4$) and evaporated. Crystallisation of the residue from ethyl acetate/hexane yields (3S*,5R*)-5-tert-butoxycarbonylamino-piperidine-1,3-dicarboxylic acid 1-(9H-fluoren-9-ylmethyl) ester as a white powder. t$_R$(HPLC, Nucleosil C18, 5-100% CH$_3$CN+0.1% TFA/H$_2$O+0.1% TFA for 8 min, 100% CH$_3$CN+0.1% TFA for 2 min, flow 1.5 ml/min): 6.64 min. For MS, a sample is treated with TFA/CH$_2$Cl$_2$ for 10 minutes. MS: 367.0 [M+H—C$_5$H$_8$O$_2$]$^+$ The filtrate consists of a ~1:1 mixture of cis and trans isomers.

Separation of the isomers by preparative HPLC (Nucleodur C18, 40-100% CH$_3$CN+0.1% TFA/H$_2$O+0.1% TFA for 36 min) affords besides the above described (3S*,5R*)-cis-isomer also the trans isomer (3R*,5R*)-5-tert-butoxycarbonylamino-piperidine-1,3-dicarboxylic acid 1-(9H-fluoren-9-ylmethyl) ester as a white powder. t$_R$(HPLC, Nucleosil C18, 5-100% CH$_3$CN+0.1% TFA/H$_2$O+0.1% TFA for 8 min, 100% CH$_3$CN+0.1% TFA for 2 min, flow 1.5 ml/min): 6.58 min Starting Material 3A: Polymer-bound (3R*,5S*)-3-amino-5-(2,2-diphenyl-ethylcarbamoyl)-piperidine-1-carboxylic acid 9H-fluoren-9-ylmethyl ester (Resin 1)

N-Methylaminomethyl polystyrene resin (263.5 g, 540 mmol) is washed twice with dimethyl-acetamide and the solvent drained off. A mixture of 1-hydroxybenzotriazole (120.5 g, 892 mmol), 5-(4-formyl-3,5-dimethoxyphenoxy) pentanoic acid (229 g, 811 mmol) and 1,3-diisopropylcarbodiimide (112.6 g, 892 mmol) and dimethylacetamide (1.85 L) is stirred at RT for 30 minutes and then added to the wet resin together with N-ethyldiisopropylamine (152.7 mL, 892 mmol). The suspension is stirred for 2 h at RT and for 16 h at 50° C. The resin is filtered off, washed with DMA (2×), H$_2$O (2×), DMA (1×), THF (2×), CH$_2$Cl$_2$ (4×), CH$_3$OH (2×) and dried under high vacuum at 40° C.

Part of the resulting resin (16.0 g; 14.0 mmol) is washed twice with trimethyl orthoformate (2×150 mL). 2,2-Diphenylethylamine (12.6 g, 64 mmol) in trimethyl orthoformate (70 mL) is added to the wet resin and the suspension shaken for 20 h at RT. The resin is filtered off and washed with trimethyl orthoformate (2×) and CH$_2$Cl$_2$ (4×). A solution of borane-pyridine complex (8 mL, 64 mmol) in CH$_2$Cl$_2$ (70 mL), CH$_3$OH (2.6 mL, 64 mmol) and CH$_3$COOH (3.66 mL, 64 mmol) is added to the wet resin and the suspension shaken for 2 h. The resin is filtered off, washed with CH$_2$Cl$_2$ (2×); DMA (2×); H$_2$O (1×); CH$_3$OH (2×); THF (1×); CH$_2$Cl$_2$ (2×); CH$_3$OH (2×) and dried in vacuo.

Part of the resulting resin (5 g, 3.75 mmol) is swelled with DMA and the solvent drained off.

A mixture of (3S*,5R*)-5-tert-butoxycarbonylamino-piperidine-1,3-dicarboxylic acid 1-(9H-fluoren-9-ylmethyl) ester (3.5 g, 7.5 mmol), DIPEA (2.57 mL, 15 mmol) and O-(7-azabenzotriazol-1-yl)-N,N,N',N'-tetramethyluronium hexafluorophosphate (HATU) (2.85 g, 7.5 mmol) in DMA (30 mL), is pre-activated during 20 minutes at RT by occasional shaking and added to the wet resin. The suspension is shaken for 16 h at RT, the resin is filtered off, washed with DMA (3×), CH$_3$OH (3×) and CH$_2$Cl$_2$ (4×) and dried in vacuo at 50° C.

To a solution of CF$_3$SO$_3$Si(CH$_3$)$_3$ (9 mL, 49.8 mmol) in CH$_2$Cl$_2$ (20 mL), a solution of 2,6-lutidine (8.6 mL, 73.8 mmol) in CH$_2$Cl$_2$ (20 mL) is added. The mixture is diluted up to 100 mL with CH$_2$Cl$_2$. A 50 mL portion of this freshly prepared solution is added to the resin resulting from the last step above (6 g, 3.36 mmol) and the suspension is shaken for 30 minutes at RT. The liquid is drained off, the residue treated with a second portion (50 mL) of the cleavage solution. After shaking for 30 minutes, the resin is filtered off and washed with CH$_2$Cl$_2$ (2×), DMA, CH$_3$OH (3×, alternating) and CH$_2$Cl$_2$ (5×) and dried in vacuo to yield the title compound.

The N-methylaminomethyl polystyrene resin is prepared as follows: To liquid methylamine, kept below −20° C., chloromethylstyrene copolymer (Merrifield resin) is added (~1 g of resin per 10 ml of methylamine). The suspension is shaken in a pressure bottle at RT for 14 h. The resin is filtered off and washed with DMA (2×), H$_2$O (2×), DMA (1×), CH$_3$OH (2×), CH$_2$Cl$_2$ (3×), CH$_3$OH (2×) and dried under high vacuum.

Starting Material 3B: Polymer-bound (3R*,5S*)-3-amino-5-(2,2-diphenyl-ethylcarbamoyl)-piperidine-1-carboxylic acid

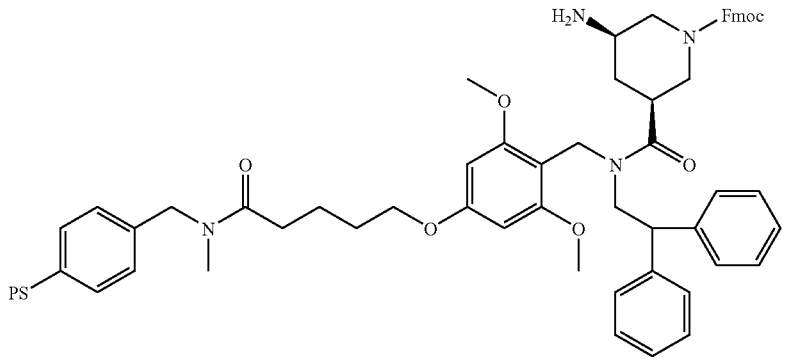

9H-fluoren-9-ylmethyl ester and (3R*,5R*)-3-tert-butoxycarbonylamino-5-(2,2-diphenyl-ethylcarbamoyl)-piperidine-1-carboxylic acid 9H-fluoren-9-ylmethyl ester (Resin 2)

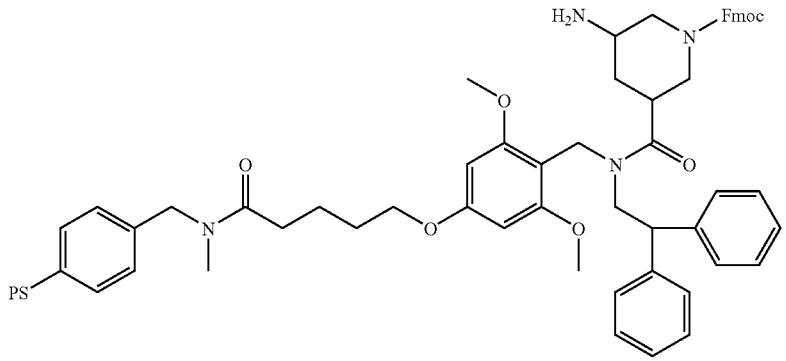

The title resin is prepared analogously as described in Example 3A using a 1:1 mixture of (3S*,5R*)-5-tert-butoxycarbonylamino-piperidine-1,3-dicarboxylic acid 1-(9H-fluoren-9-ylmethyl) ester and (3R*,5R*)-5-tert-butoxycarbonylamino-piperidine-1,3-dicarboxylic acid 1-(9H-fluoren-9-ylmethyl) ester.

Starting Material 4: Polymer-bound (3R*,5S*)-3-Amino-5-[(naphthalen-1-ylmethyl)-carbamoyl]-piperidine-1-carboxylic acid 9H-fluoren-9-ylmethyl ester

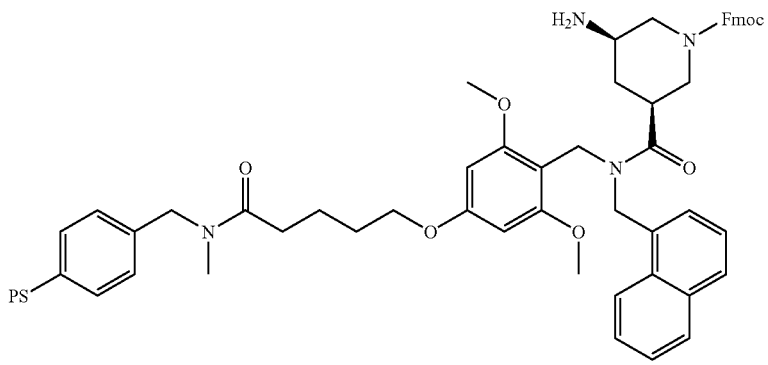

The title compound is prepared analogously as described in Example 3A using 1-naphthalenemethylamine instead of 2,2-diphenylethylamine.

Starting Material 5: Polymer-bound (3R*,5S*)-3-amino-5-(2,2-diphenyl-ethylcarbamoyl)-piperidine-1-carboxylic acid 9H-fluoren-9-ylmethyl ester (Resin 3)

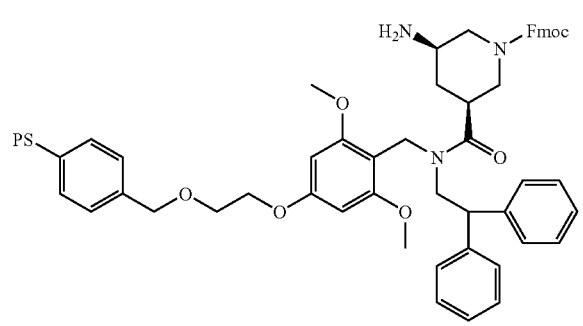

2-(3,5-dimethoxy-4-formylphenoxy)ethoxymethyl polystyrene (10.0 g, 9 mmol) is washed twice with a solution of 30% trimethyl orthoformate in $CH_2Cl_2$ (2×150 mL). A mixture of 2,2-diphenylethylamine (8.88 g, 45 mmol) in a solution of 30% trimethyl orthoformate in $CH_2Cl_2$ (30 mL) is added to the wet resin and the suspension shaken for 14 h at 60° C. The resin is filtered off and washed with a solution of 10% trimethyl orthoformate in $CH_2Cl_2$. A solution of borane-pyridine complex (4.55 mL, ~40 mmol), $CH_3OH$ (1.83 mL, 45 mmol) and $CH_3COOH$ (2.57 mL, 45 mmol) in $CH_2Cl_2$ (40 mL) is added to the wet resin and the suspension shaken for 2 h. The resin is filtered off, washed with DMA, 5% aqueous $CH_3COOH$ (2×, alternating), $H_2O$ (2×), THF (2×), 2% aqueous $NH_4OH$ (2×), $CH_3OH$ (2×), THF (2×), $CH_2Cl_2$ (3×); and dried.

The resulting resin (11 g, 8.25 mmol) is swelled with DMA and the solvent drained off. A mixture of (3S*,5R*)-5-tert-butoxycarbonylamino-piperidine-1,3-dicarboxylic acid 1-(9H-fluoren-9-ylmethyl) ester (7.7 g, 16.5 mmol), DIPEA (5.65 mL, 33 mmol) and O-(1H-6-chlorobenzotriazole-1-yl)-1,1,3,3-tetramethyluronium hexafluorophosphate (HCTU) (7.24 g, 17.5 mmol) in DMA (50 mL) is pre-activated during 20 minutes at RT by occasional shaking and added to the wet resin. The suspension is shaken for 18 h at RT, the resin is filtered off and washed with DMA. A second coupling is performed using half the amount of acid, coupling reagent and DIPEA. After 6 h the resin is filtered off, washed with DMA (2×), $CH_3OH$, THF (3×, alternating), $CH_2Cl_2$ (3×) and dried.

To a solution of $CF_3SO_3Si(CH_3)_3$ (18.75 mL, 103.8 mmol) in $CH_2Cl_2$ (50 mL), 2,6-lutidine (17.9 mL, 153.8 mmol) is added. The mixture is diluted up to 100 mL with $CH_2Cl_2$. A 50 mL portion of this freshly prepared solution is added to the above resin (14.7 g, 8.2 mmol) and the suspension is shaken for 30 minutes at RT. The liquid is drained off, the residue treated with a second portion (50 mL) of the cleavage solution. After shaking for 30 minutes, the resin is filtered off and washed with $CH_2Cl_2$ (2×), DMA, $CH_3OH$ (3×, alternating) and $CH_2Cl_2$ (5×) and dried to yield the title compound.

Example 1

(3S*,5R*)-5-(Toluene-4-sulfonylamino)-piperidine-3-carboxylic acid (2,2-diphenyl-ethyl)-amide, trifluoroacetate

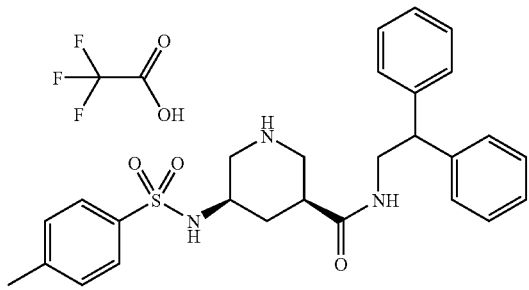

To resin 1 (Starting Material 3A) (3 g, 1.77 mmol), CH₂Cl₂ (15 mL), pyridine (3.55 mL, 44 mmol) and DMAP (244 mg, 2 mmol), followed by a mixture of 4-toluenesulfonyl chloride (7.62 g, 40 mmol) in CH₂Cl₂ (15 mL), are successively added. The reaction mixture is shaken for 40 h at RT. The resin thus obtained is filtered off and washed with DMA/H₂O 1:1 (3×), CH₃OH (3×), THF (2×), CH₂Cl₂ (4×).

The Fmoc group is removed by shaking the wet resin for 15 min at RT with a freshly prepared solution of DMA/piperidine 8:2 (20 mL). After filtration, this procedure is repeated four times using fresh DMA/piperidine solutions. The resin is filtered off and washed successively with DMA and CH₃OH (alternating, 2×), then THF (2×) and then CH₂Cl₂ (4×).

In order to cleave the compound from the polymer, the obtained wet resin is shaken for 15 min with an 8:2 mixture of CH₂Cl₂/95% trifluoroacetic acid (20 mL) and then filtered off. This treatment with acid is repeated twice using each time a fresh mixture of CH₂Cl₂/95% trifluoroacetic acid (20 mL).

The resulting acidic solutions are combined and evaporated in vacuo. The crude product is purified by preparative HPLC (C18 column 250×40 mm, 10-100% CH₃CN+0.1% TFA/H₂O+0.1% TFA/30 min, flow 60 mL/min). The combined pure fractions are evaporated in vacuo to afford the title compound as a white solid. MS: 477.9 [M+H]⁺; t_R(HPLC, Nucleosil C18; 5-100% CH₃CN+0.1% TFA/H₂O+0.1% TFA for 8 min, then 100% CH₃CN+0.1% TFA for 2 min, flow 1.5 ml/min): 5.21 min.

The two enantiomers can be separated on a chiral column (Chiralpak AD-H).

Example 2

(3R*,5R*)-5-(Toluene-4-sulfonylamino)-piperidine-3-carboxylic acid (2,2-diphenyl-ethyl)-amide, trifluoroacetate

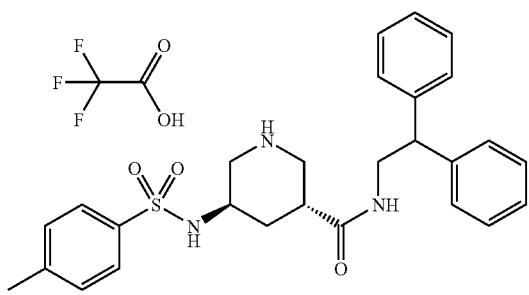

The title compound is prepared analogously as described in Example 1 using resin 2 (Starting Material 3B) and 4-toluenesulfonyl chloride. After cleavage with CH₂Cl₂/95% trifluoroacetic acid (8:2), the acidic solutions are combined and evaporated in vacuo. The crude product is purified by preparative HPLC (C18 column 250×40 mm, 10-100% CH₃CN+0.1% TFA/H₂O+0.1% TFA/30 min, flow 60 mL/min). The combined pure fractions are evaporated in vacuo to afford the title compound (3R*,5R*) and the corresponding (3S*,5R*) isomer. MS: 477.9 [M+H]⁺; t_R(HPLC, Nucleosil C18; 5-100% CH₃CN+0.1% TFA/H₂O+0.1% TFA for 8 min, then 100% CH₃CN+0.1% TFA for 2 min, flow 1.5 ml/min): 5.33 min.

Example 3

(3S*,5R*)-5-(4-Methoxy-benzenesulfonylamino)-piperidine-3-carboxylic acid (2,2-diphenyl-ethyl)-amide, trifluoroacetate

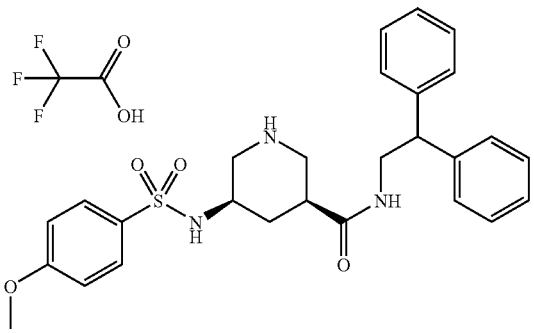

A suspension of resin 3 (Starting Material 5) (30 mg, 77 µmol), CH₂Cl₂ (1.5 mL), pyridine (137 µL, 1.7 mmol), 4-dimethylaminopyridine (9.5 mg, 77 µmol) and 4-methoxy-benzene-sulfonyl chloride (320 mg, 1.55 mmol) is shaken for 40 h at 40° C. The resin is filtered off, washed with DMA/H₂O 1:1 (3×), CH₃OH (3×), THF (2×) and DMA (4×). The Fmoc group is removed by shaking the wet resin for 15 min at RT with a freshly prepared solution of DMA/piperidine 8:2 (1 mL). After filtration, this procedure is repeated four times using fresh DMA/piperidine solutions. The resin is filtered off, washed successively with DMA and CH₃OH (alternating, 2×), then THF (2×) and then CH₂Cl₂ (4×). In order to cleave the compound from the polymer, the wet resin is shaken for 15 min with an 8:2 mixture of CH₂Cl₂/95% trifluoroacetic acid (1 mL) and then filtered off. This treatment with acid is repeated once with a fresh mixture of CH₂Cl₂/95% trifluoroacetic acid (1 mL). The resulting acidic solutions are combined and evaporated in vacuo. The crude product is purified by preparative HPLC (C18 column, 10-100% CH₃CN+0.1% TFA/H₂O+0.1% TFA/20 min, flow 20 mL/min). The combined pure fractions are evaporated in vacuo to afford the title compound. MS: 494.5 [M+H]⁺; t_R (HPLC, Nucleosil C18; 5-100% CH₃CN+0.1% TFA/H₂O+ 0.1% TFA for 8 min, then 100% CH₃CN+0.1% TFA for 2 min, flow 1.5 ml/min): 4.97 min.

Example 4

(3S*,5R*)-5-(5-Chloro-thiophene-2-sulfonylamino)-piperidine-3-carboxylic acid (2,2-diphenyl-ethyl)-amide, trifluoroacetate

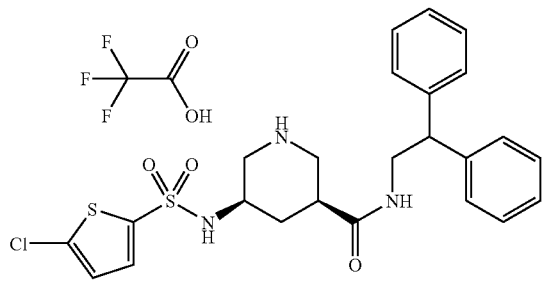

The title compound is prepared analogously as described in Example 3 using 5-chlorothiophene-2-sulfonyl chloride instead of 4-toluenesulfonyl chloride. MS: 504.4 [M+H]$^+$ $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.42 min.

Example 5

(3S*,5R*)-5-(Quinoline-8-sulfonylamino)-piperidine-3-carboxylic acid (2,2-diphenyl-ethyl)-amide, trifluoroacetate

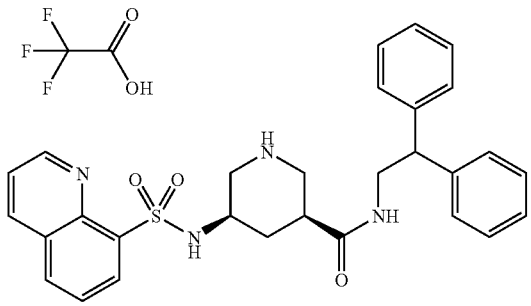

The title compound is prepared analogously as described in Example 3 using quinoline-8-sulfonyl chloride instead of 4-toluenesulfonyl chloride. MS: 515.4 [M+H]$^+$; $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.09 min.

Example 6

(3S*,5R*)-5-Phenylmethanesulfonylamino-piperidine-3-carboxylic acid (2,2-diphenyl-ethyl)-amide, trifluoroacetate

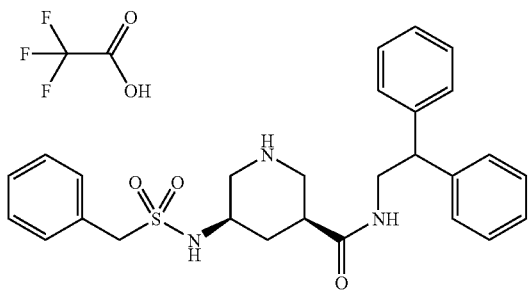

The title compound is prepared analogously as described in Example 3 using phenyl-methanesulfonyl chloride instead of 4-toluenesulfonyl chloride. MS: 478.5 [M+H]$^+$; $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.23 min.

Example 7

(3S*,5R*)-5-(4-Chloro-benzenesulfonylamino)-piperidine-3-carboxylic acid (2,2-diphenyl-ethyl)-amide, trifluoroacetate

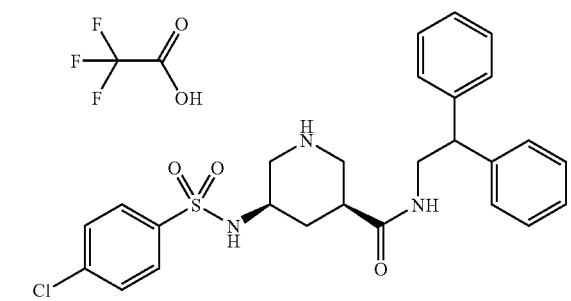

The title compound is prepared analogously as described in Example 8 using 4-chloro-benzenesulfonyl chloride instead of 4-toluenesulfonyl chloride. MS: 498.4 [M+H]$^+$; $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.44 min.

Example 8

(3S*,5R*)-5-(3-Chloro-benzenesulfonylamino)-piperidine-3-carboxylic acid (2,2-diphenyl-ethyl)-amide, trifluoroacetate

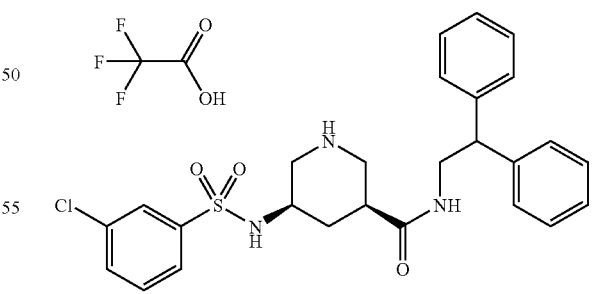

The title compound is prepared analogously as described in Example 3 using 3-chlorobenzenesulfonyl chloride instead of 4-toluenesulfonyl chloride. MS: 498.4 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.43 min.

Example 9

(3S*,5R*)-5-(2-Chloro-benzenesulfonylamino)-piperidine-3-carboxylic acid (2,2-diphenyl-ethyl)-amide, trifluoroacetate

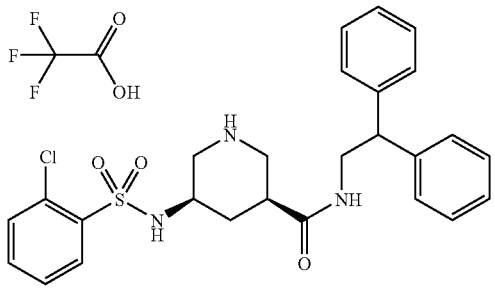

The title compound is prepared analogously as described in Example 3 using 2-chloro-benzenesulfonyl chloride instead of 4-toluenesulfonyl chloride. MS: 498.4 [M+H]$^+$; $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.25 min.

Example 10

(3S*,5R*)-5-(Naphthalene-1-sulfonylamino)-piperidine-3-carboxylic acid (2,2-diphenyl-ethyl)-amide, trifluoroacetate

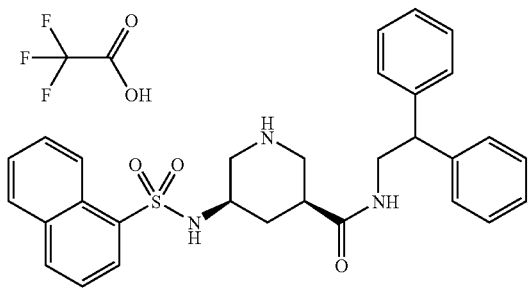

The title compound is prepared analogously as described in Example 8 using 1-naphthalene-sulfonyl chloride instead of 4-toluenesulfonyl chloride. MS: 514.5 [M+H]$^+$; $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.48 min.

Example 11

(3S*,5R*)-5-(4-Methanesulfonyl-benzenesulfonylamino)-piperidine-3-carboxylic acid (2,2-diphenyl-ethyl)-amide, trifluoroacetate

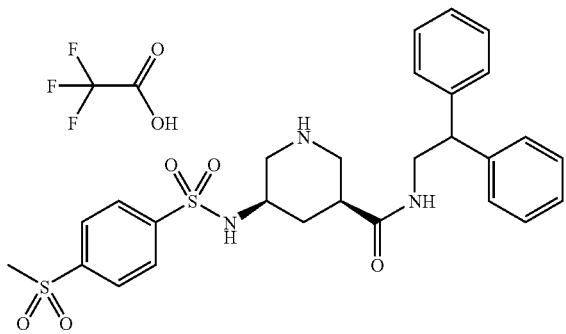

The title compound is prepared analogously as described in Example 3 using 4-methyl-sulfonylbenzenesulfonyl chloride instead of 4-toluenesulfonyl chloride. MS: 542.4 [M+H]$^+$; $t_R$ (HPLC, Nucleosil C18; 5-100% CH$_3$CN+0.1% TFA/H$_2$O+ 0.1% TFA for 8 min, then 100% CH$_3$CN+0.1% TFA for 2 min, flow 1.5 ml/min): 4.94 min.

Example 12

(3S*,5R*)-5-(4-Trifluoromethoxy-benzenesulfonylamino)-piperidine-3-carboxylic acid (2,2-diphenyl-ethyl)-amide, trifluoroacetate

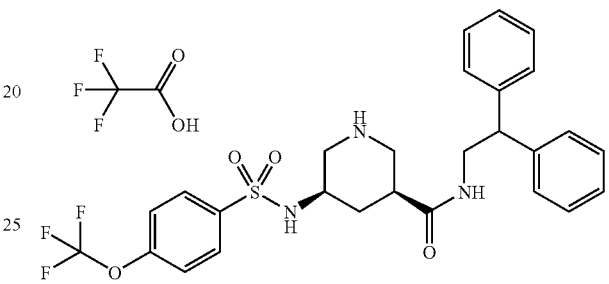

The title compound is prepared analogously as described in Example 3 using 4-(trifluoro-methoxy)benzenesulfonyl chloride instead of 4-toluenesulfonyl chloride. MS: 548.5 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.79 min.

Example 13

(3S*,5R*)-5-(4-Isopropyl-benzenesulfonylamino)-piperidine-3-carboxylic acid (2,2-diphenyl-ethyl)-amide, trifluoroacetate

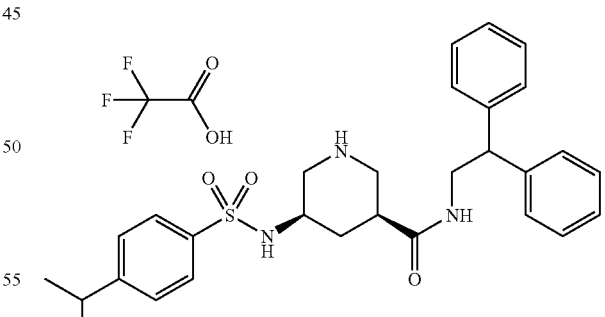

The title compound is prepared analogously as described in Example 3 using 4-isopropyl-benzenesulfonyl chloride instead of 4-toluenesulfonyl chloride. MS: 506.5 [M+H]$^+$; $t_R$(HPLC, Nucleosil C18; 5-100% CH$_3$CN+0.1% TFA/H$_2$O+ 0.1% TFA for 8 min, then 100% CH$_3$CN+0.1% TFA for 2 min, flow 1.5 ml/min): 5.74 min.

Example 14

(3S*,5R*)-5-Methanesulfonylamino-piperidine-3-carboxylic acid (2,2-diphenyl-ethyl)-amide, trifluoroacetate

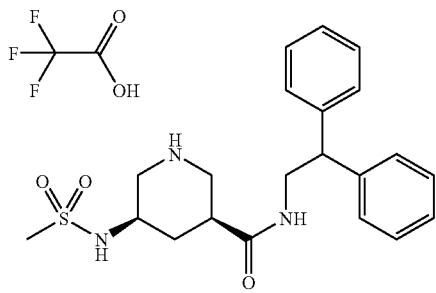

The title compound is prepared analogously as described in Example 3 using methane-sulfonyl chloride instead of 4-toluenesulfonyl chloride. MS: 402.6 [M+H]$^+$; $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 4.56 min.

Example 15

(3S*,5R*)-5-(2-Acetylamino-4-methyl-thiazole-5-sulfonylamino)-piperidine-3-carboxylic acid (2,2-diphenyl-ethyl)-amide, trifluoroacetate

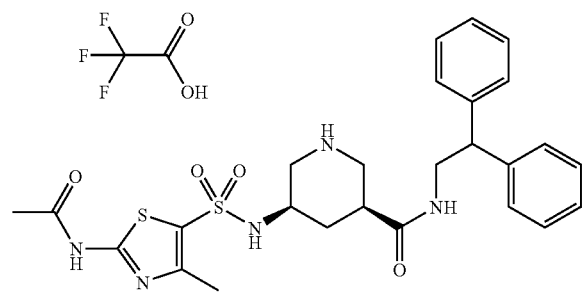

The title compound is prepared analogously as described in Example 3 using 2-acetamido-4-methyl-5-thiazolesulfonyl chloride instead of 4-toluenesulfonyl chloride. MS: 542.4 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 4.79 min.

Example 16

(3S*,5R*)-5-(5-Chloro-1,3-dimethyl-1H-pyrazole-4-sulfonylamino)-piperidine-3-carboxylic acid (2,2-diphenyl)-amide, trifluoroacetate

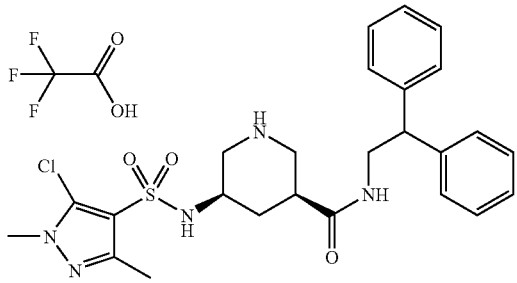

The title compound is prepared analogously as described in Example 2 using 5-chloro-1,3-dimethyl-1H-pyrazole-4-sulfonyl chloride instead of 4-toluenesulfonyl chloride. MS: 516.3 [M+H]$^+$; $t_R$(HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 4.94 min.

Example 17

(3S*,5R*)-5-(2,4-Difluoro-benzenesulfonylamino)-piperidine-3-carboxylic acid (2,2-diphenyl-ethyl)-amide, trifluoroacetate

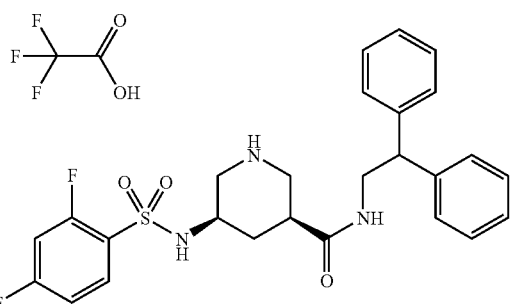

The title compound is prepared analogously as described in Example 3 using 2,4-difluoro-benzenesulfonyl chloride instead of 4-toluenesulfonyl chloride. MS: 500.7 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.33 min.

Example 18

(3S*,5R*)-5-[4-(2-Oxo-propyl)-benzenesulfonylamino]-piperidine-3-carboxylic acid-(2,2-diphenyl-ethyl)-amide, trifluoroacetate

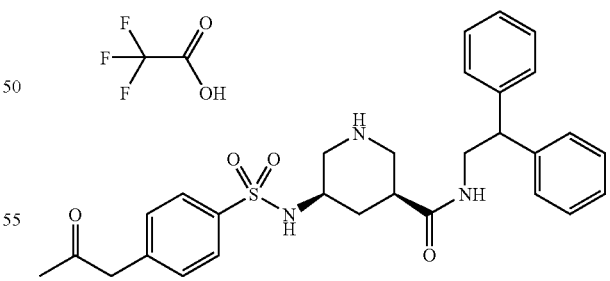

The title compound is prepared analogously as described in Example 3 using 4-(2-oxo-propyl)-benzenesulfonyl chloride instead of 4-toluenesulfonyl chloride. MS: 520.0/521.0 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.07 min.

Example 19

(3S*,5R*)-5-(4-Cyano-benzenesulfonylamino)-piperidine-3-carboxylic acid (2,2-diphenyl-ethyl)-amide, trifluoroacetate

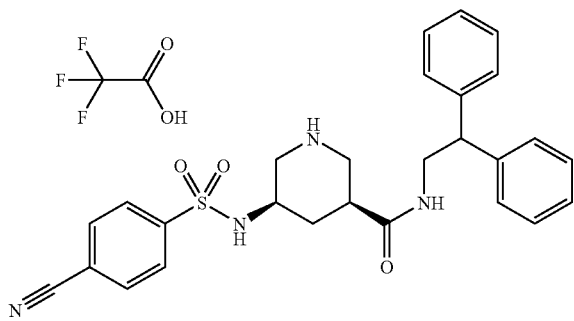

The title compound is prepared analogously as described in Example 2 using 4-cyanobenzenesulfonyl chloride instead of 4-toluenesulfonyl chloride. MS: 489.5 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.03 min.

Example 20

(3S*,5R*)-5-(2,6-Difluoro-benzenesulfonylamino)-piperidine-3-carboxylic acid (2,2-diphenyl-ethyl)-amide, trifluoroacetate

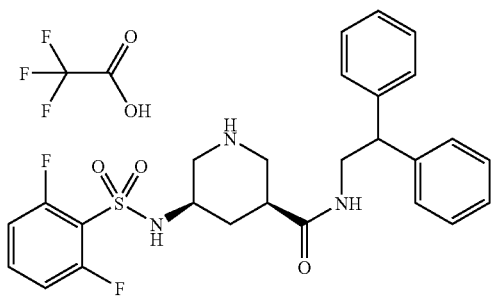

The title compound is prepared analogously as described in Example 3 using 2,6-difluoro-benzenesulfonyl chloride instead of 4-toluenesulfonyl chloride. MS: 500.4 [M+H]$^+$; $t_R$ (HPLC, Nucleosil C18; 5-100% CH$_3$CN+0.1% TFA/H$_2$O+ 0.1% TFA for 8 min, then 100% CH$_3$CN+0.1% TFA for 2 min, flow 1.5 ml/min): 5.02 min.

Example 21

(3S*,5R*)-5-(2-Cyano-benzenesulfonylamino)-piperidine-3-carboxylic acid (2,2-diphenyl-ethyl)-amide, trifluoroacetate

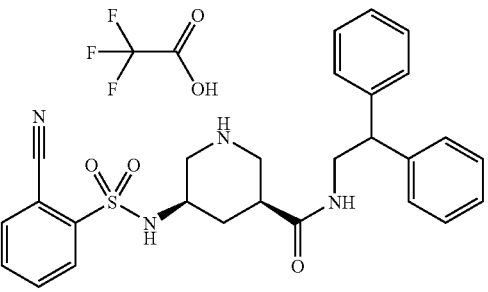

The title compound is prepared analogously as described in Example 3 using 2-cyanobenzenesulfonyl chloride instead of 4-toluenesulfonyl chloride. MS: 489.6 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.01 min.

Example 22

(3S*,5R*)-5-(3-Methoxy-benzenesulfonylamino)-piperidine-3-carboxylic acid (2,2-diphenyl-ethyl)-amide, trifluoroacetate

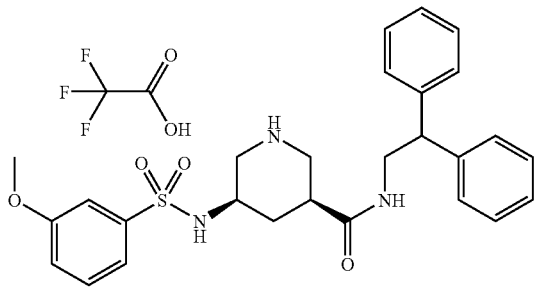

The title compound is prepared analogously as described in Example 3 using 3-methoxy-benzenesulfonyl chloride instead of 4-toluenesulfonyl chloride. MS: 494.6 [M+H]$^+$; $t_R$ (HPLC, Nucleosil C18; 5-100% CH$_3$CN+0.1% TFA/H$_2$O+ 0.1% TFA for 8 min, then 100% CH$_3$CN+0.1% TFA for 2 min, flow 1.5 ml/min): 5.11 min.

Example 23

(3S*,5R*)-5-(2-Trifluoromethyl-benzenesulfonylamino)-piperidine-3-carboxylic acid (2,2-diphenyl-ethyl)-amide, trifluoroacetate

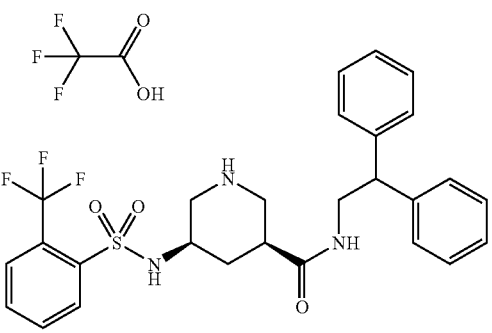

The title compound is prepared analogously as described in Example 3 using 2-(trifluoro-methyl)benzenesulfonyl chloride instead of 4-toluenesulfonyl chloride. MS: 532.6 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.37 min.

Example 24

(3S*,5R*)-5-(4-Acetylamino-benzenesulfonylamino)-piperidine-3-carboxylic acid (2,2-diphenylethyl)-amide, trifluoroacetate

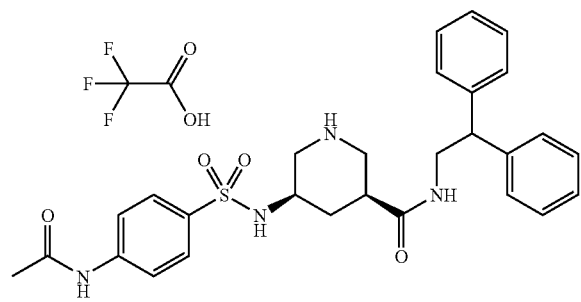

The title compound is prepared analogously as described in Example 3 using 4-acetamido-benzenesulfonyl chloride instead of 4-toluenesulfonyl chloride. MS: 521.5 [M+H]$^+$; $t_R$ (HPLC, Nucleosil C18; 5-100% CH$_3$CN+0.1% TFA/H$_2$O+ 0.1% TFA for 8 min, then 100% CH$_3$CN+0.1% TFA for 2 min, flow 1.5 ml/min): 4.60 min.

Example 25

(3S*,5R*)-5-(Pyridine-3-sulfonylamino)-piperidine-3-carboxylic acid (2,2-diphenyl-ethyl)-amide, trifluoroacetate

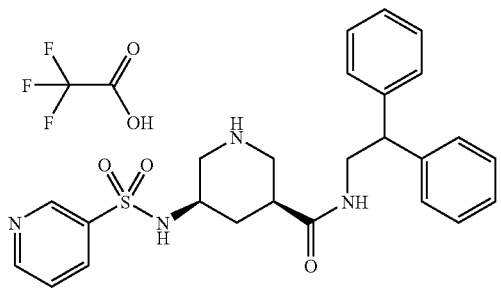

The title compound is prepared analogously as described in Example 3 using pyridine-3-sulfonyl chloride instead of 4-toluenesulfonyl chloride. MS: 465.5 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 4.54 min.

Example 26

(3S*,5R*)-5-(3-Trifluoromethyl-benzenesulfonylamino)-piperidine-3-carboxylic acid (2,2-diphenylethyl)-amide, trifluoroacetate

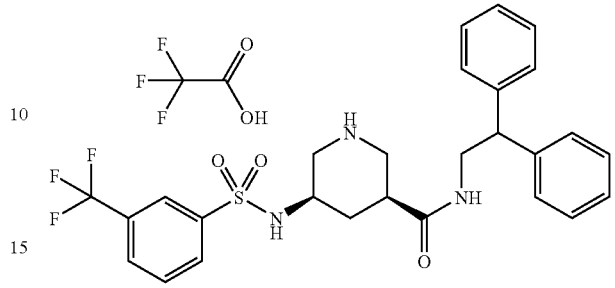

The title compound is prepared analogously as described in Example 3 using 3-(trifluoro-methyl)benzenesulfonyl chloride instead of 4-toluenesulfonyl chloride. MS: 532.5 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.53 min.

Example 27

(3S*,5R*)-5-(Biphenyl-4-sulfonylamino)-piperidine-3-carboxylic acid (2,2-diphenyl-ethyl)-amide, trifluoroacetate

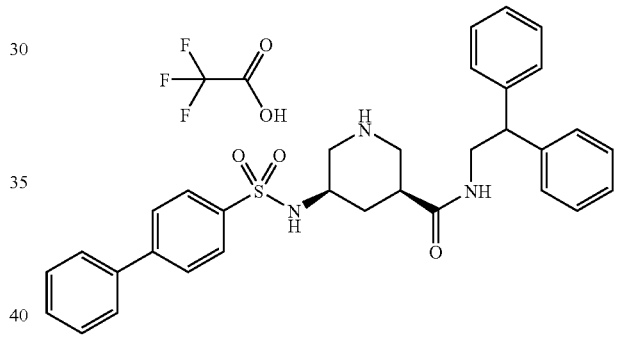

The title compound is prepared analogously as described in Example 3 using biphenyl-4-sulfonyl chloride instead of 4-toluenesulfonyl chloride. MS: 540.5 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.82 min.

Example 28

(3S*,5R*)-5-(3-Cyano-benzenesulfonylamino)-piperidine-3-carboxylic acid (2,2-diphenyl-ethyl)-amide, trifluoroacetate

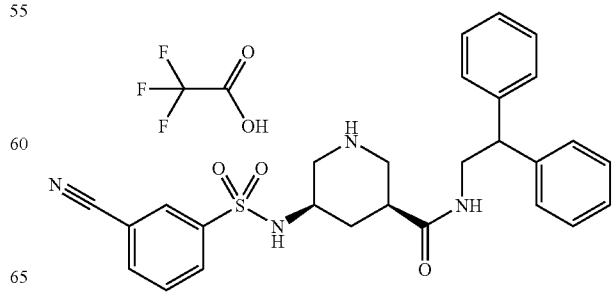

The title compound is prepared analogously as described in Example 3 using 3-cyanobenzenesulfonyl chloride instead of 4-toluenesulfonyl chloride. MS: 489.4 [M+H]⁺; $t_R$ (HPLC, Nucleosil C18; 5-100% CH₃CN+0.1% TFA/H₂O+0.1% TFA for 8 min, then 100% CH₃CN+0.1% TFA for 2 min, flow 1.5 ml/min): 5.20 min.

Example 29

(3S*,5R*)-5-(3,4-Dichloro-benzenesulfonylamino)-piperidine-3-carboxylic acid (2,2-diphenyl-ethyl)-amide, trifluoroacetate

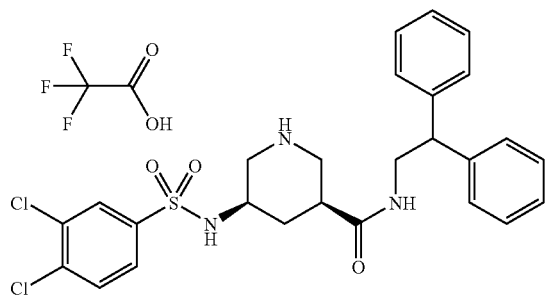

The title compound is prepared analogously as described in Example 3 using 3,4-dichloro-benzenesulfonyl chloride instead of 4-toluenesulfonyl chloride. MS: 532.4/534.3 [M+H]⁺; $t_R$ (HPLC, Nucleosil C18; 5-100% CH₃CN+0.1% TFA/H₂O+0.1% TFA for 8 min, then 100% CH₃CN+0.1% TFA for 2 min, flow 1.5 ml/min): 5.78 min.

Example 30

(3S*,5R*)-5-(2,5-Dimethoxy-benzenesulfonylamino)-piperidine-3-carboxylic acid (2,2-diphenyl-ethyl)-amide, trifluoroacetate

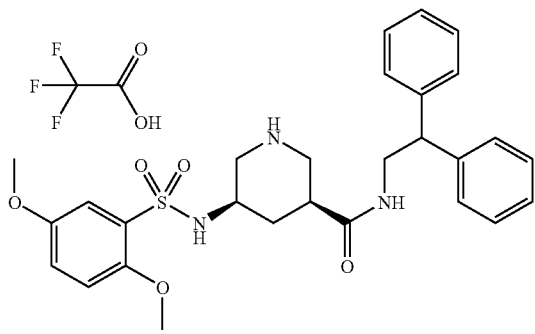

The title compound is prepared analogously as described in Example 3 using 2,5-dimethoxybenzenesulfonyl chloride instead of 4-toluenesulfonyl chloride. MS: 524.5 [M+H]⁺ $t_R$ (HPLC, Nucleosil C18; 5-100% CH₃CN+0.1% TFA/H₂O+ 0.1% TFA for 8 min, then 100% CH₃CN+0.1% TFA for 2 min, flow 1.5 ml/min): 5.25 min.

Example 31

(3S*,5R*)-5-(4-Phenoxy-benzenesulfonylamino)-piperidine-3-carboxylic acid (2,2-diphenyl-ethyl)-amide, trifluoroacetate

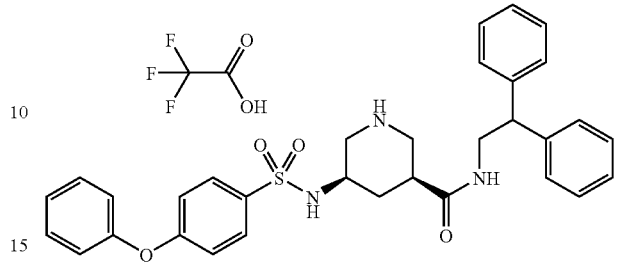

The title compound is prepared analogously as described in Example 3 using 4-phenoxybenzenesulfonyl chloride instead of 4-toluenesulfonyl chloride. MS: 556.5 [M+H]⁺; $t_R$ (HPLC, Nucleosil C18; 5-100% CH₃CN+0.1% TFA/H₂O+0.1% TFA for 8 min, then 100% CH₃CN+0.1% TFA for 2 min, flow 1.5 ml/min): 5.90 min.

Example 32

(3S*,5R*)-5-(2,5-Dichloro-benzenesulfonylamino)-piperidine-3-carboxylic acid (2,2-diphenyl-ethyl)-amide, trifluoroacetate

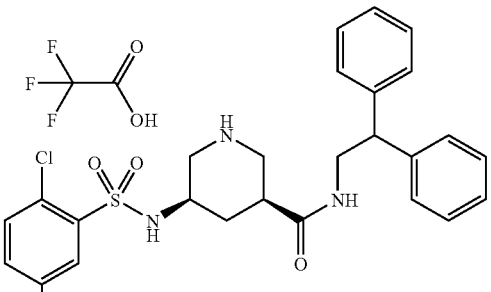

The title compound is prepared analogously as described in Example 3 using 2,5-dichloro-benzenesulfonyl chloride instead of 4-toluenesulfonyl chloride. MS: 532.4/534.3 [M+H]⁺; $t_R$ (HPLC, Nucleosil C18; 5-100% CH₃CN+0.1% TFA/H₂O+0.1% TFA for 8 min, then 100% CH₃CN+0.1% TFA for 2 min, flow 1.5 ml/min): 5.58 min.

Example 33

(3S*,5R*)-5-(3,5-Dichloro-benzenesulfonylamino)-piperidine-3-carboxylic acid (2,2-diphenyl-ethyl)-amide, trifluoroacetate

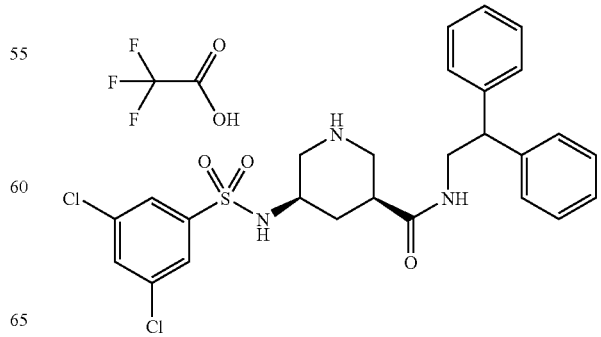

The title compound is prepared analogously as described in Example 3 using 3,5-dichloro-benzenesulfonyl chloride instead of 4-toluenesulfonyl chloride. MS: 532.4/534.2 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.76 min.

Example 34

(3S*,5R*)-5-Benzenesulfonylamino-piperidine-3-carboxylic acid (2,2-diphenyl-ethyl)-amide, trifluoroacetate

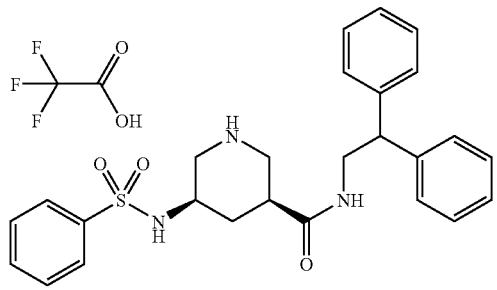

The title compound is prepared analogously as described in Example 3 using benzenesulfonyl chloride instead of 4-toluenesulfonyl chloride. MS: 464.4 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.16 min.

Example 35

(3S*,5R*)-5-(2,4-Dichloro-benzenesulfonylamino)-piperidine-3-carboxylic acid (2,2-diphenyl-ethyl)-amide, trifluoroacetate

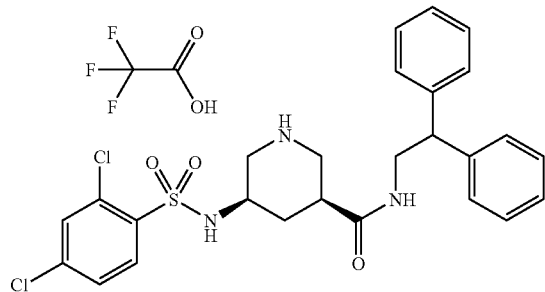

The title compound is prepared analogously as described in Example 3 using 2,4-dichloro-benzenesulfonyl chloride instead of 4-toluenesulfonyl chloride. MS: 532.4/534.3 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.65 min.

Example 36

(3S*,5R*)-5-(Naphthalene-2-sulfonylamino)-piperidine-3-carboxylic acid (2,2-diphenyl-ethyl)-amide, trifluoroacetate

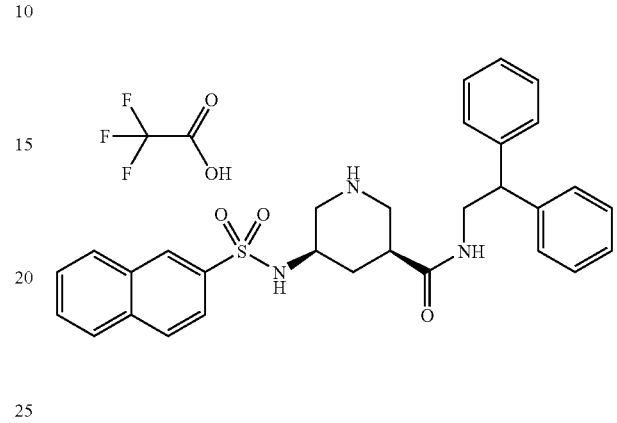

The title compound is prepared analogously as described in Example 3 using naphthalene-2-sulfonyl chloride instead of 4-toluenesulfonyl chloride. MS: 514.5 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.59 min.

Example 37

(3S*,5R*)-5-(2,3-Dichloro-benzenesulfonylamino)-piperidine-3-carboxylic acid (2,2-diphenyl-ethyl)-amide, trifluoroacetate

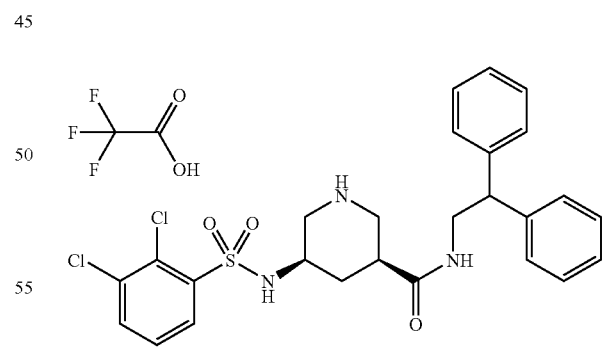

The title compound is prepared analogously as described in Example 3 using 2,3-dichloro-benzenesulfonyl chloride instead of 4-toluenesulfonyl chloride. MS: 532.4/534.3 [M+H]$^+$; $t_R$ (HPLC, Nucleosil C18; 5-100% CH$_3$CN+0.1% TFA/H$_2$O+0.1% TFA for 8 min, flow 1.5 ml/min): 5.62 min.

Example 38

(3S*,5R*)-5-(2-Benzyloxy-benzenesulfonylamino)-piperidine-3-carboxylic acid (2,2-diphenyl-ethyl)-amide, trifluoroacetate

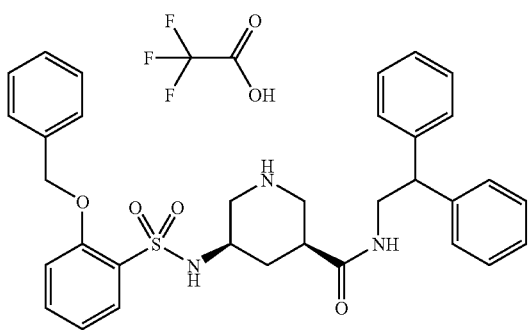

The title compound is prepared analogously as described in Example 3 using 2-benzyloxy-benzenesulfonyl chloride (see WO 02/089749) instead of 4-toluenesulfonyl chloride. MS: 570.3 [M+H]$^+$; $t_R$ (HPLC, Nucleosil C18; 5-100% CH$_3$CN+ 0.1% TFA/H$_2$O+0.1% TFA for 8 min, flow 1.5 ml/min): 5.73 min.

Example 39

(3S*,5R*)-5-(3-Acetyl-benzenesulfonylamino)-piperidine-3-carboxylic acid (2,2-diphenyl-ethyl)-amide, trifluoroacetate

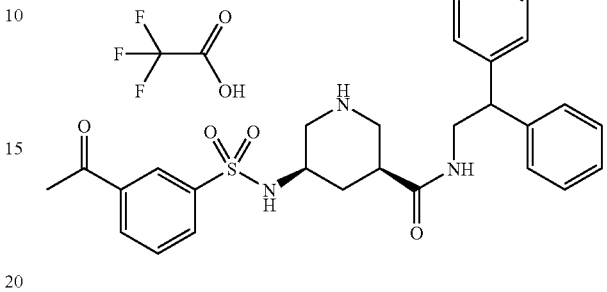

The title compound is prepared analogously as described in Example 3 using 3-acetylbenzenesulfonyl chloride instead of 4-toluenesulfonyl chloride. MS: 506.2. [M+H]$^+$; $t_R$ (HPLC, Nucleosil C18; 5-100% CH$_3$CN+0.1% TFA/H$_2$O+0.1% TFA for 8 min, flow 1.5 ml/min): 5.01 min.

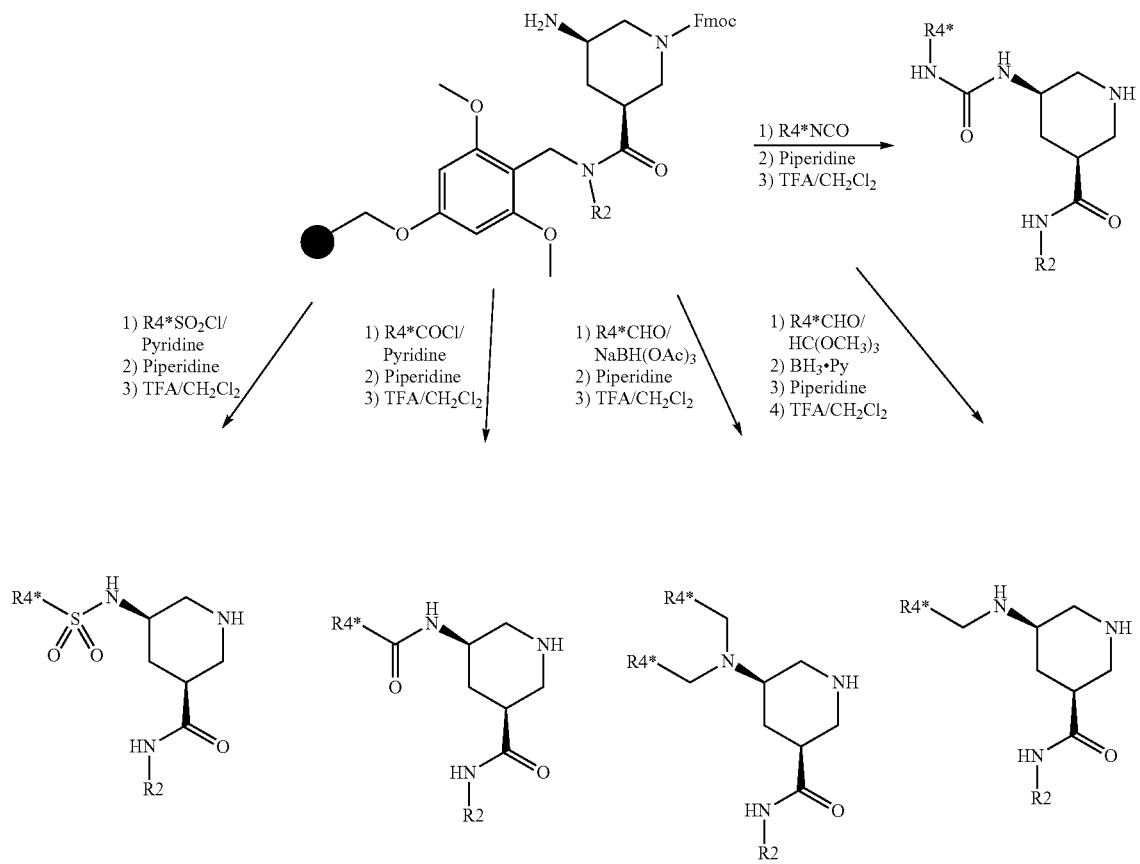

Scheme 2

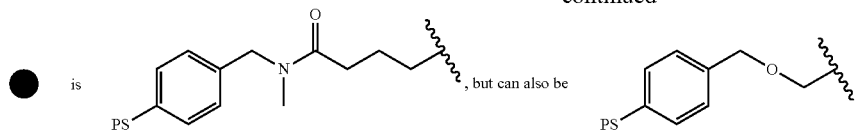

R4* is a moiety completing R4*SO₂—, R4*CO— or R4*—CH₂— to a moiety R4—
PS stands for the polystyrene resin matrix,
R2 can be as defined in the specification or in the examples.

Example 40

(3S*,5R*)-5-[Bis-(3-chloro-benzyl)-amino]-piperidine-3-carboxylic acid (naphthalen-1-ylmethyl)-amide, trifluoroacetate

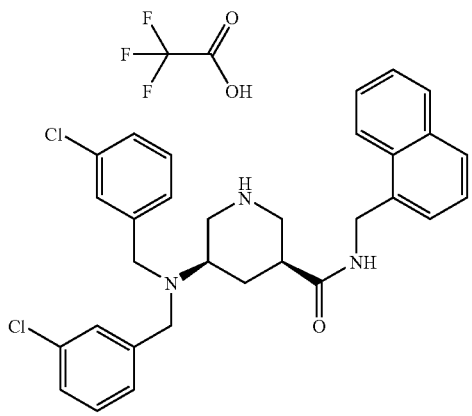

Resin 1 (Starting Material 3A, 200 mg, 0.11 mmol) is washed twice with CH₂Cl₂ and the solvent drained off. CH₂Cl₂ (2 mL) is added to the wet resin followed by 3-chlorobenzaldehyde (113 μL, 1 mmol) and sodium triacetoxyborohydride (212 mg, 1 mmol). The suspension is shaken at RT for 20 h. The resin is filtered off, washed with DMA and H₂O (alternating), then CH₃OH and then CH₂Cl₂ and then dried in vacuo. The resulting resin is swelled with DMA and the solvent drained off. A mixture of DMA/piperidine 8:2 (2 mL) is added to the wet resin and the suspension is shaken for 10 min. After filtration, the resin is shaken with a fresh solution of DMA/piperidine 8:2. This cleavage procedure is repeated 8 times. The resin is filtered off and washed with DMA, CH₃OH and CH₂Cl₂. In order to cleave the compound from the polymer, the wet resin is shaken for 20 min with an 8:2 mixture of CH₂Cl₂/95% trifluoro-acetic acid (3 mL) and then filtered off. This treatment with acid is repeated using a fresh mixture of CH₂Cl₂/95% trifluoroacetic acid (3 mL). The two filtrates are combined and evaporated in vacuo. The crude product is purified by preparative HPLC (C18 column 19×50, 20-100% CH₃CN+0.1% TFA/H₂O+0.1% TFA/30 min, flow 10 mL/min). The combined pure fractions are evaporated in vacuo to afford the title compound. MS: 532.3/534.3 [M+H]⁺; $t_R$ (HPLC, Nucleosil C18; 40-100% CH₃CN+0.1% TFA/H₂O+0.1% TFA for 5 min, flow 1.5 mL/min): 3.69 min.

Example 41

(3S*,5R*)-5-(4-Methyl-benzoylamino)-piperidine-3-carboxylic acid (2,2-diphenyl-ethyl)-amide, trifluoroacetate

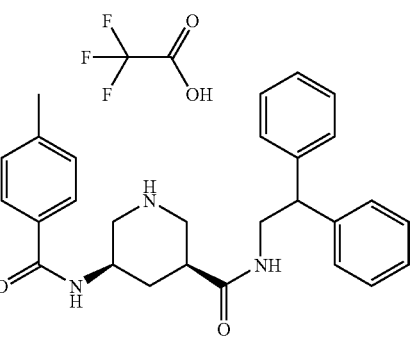

To a suspension of resin 3 (Starting Material 5) (180 mg, 106 μmol), CH₂Cl₂ (1.5 mL), pyridine (188 μL, 2.33 mmol) and 4-dimethylaminopyridine (13 mg, 106 μmol), p-toluoylchloride (210 mg, 1.59 mmol) is added and the mixture is shaken for 40 h at 40° C. The resin is filtered off, washed with DMA/H₂O 1:1 (3×), CH₃OH (3×), THF (2×) and DMA (4×). The Fmoc group is removed by shaking the wet resin for 15 min at RT with a freshly prepared solution of DMA/piperidine 8:2 (1 mL). After filtration, this procedure is repeated four times using fresh DMA/piperidine solutions. The resin is filtered off, washed successively with DMA and CH₃OH (alternating, 2×), then THF (2×) and then CH₂Cl₂ (4×). In order to cleave the compound from the polymer, the wet resin is shaken for 15 min with an 8:2 mixture of CH₂Cl₂/95% trifluoroacetic acid (1 mL) and then filtered off. This acid treatment is repeated once with a fresh 8:2 mixture of CH₂Cl₂/95% trifluoroacetic acid (1 mL). The resulting acidic solutions are combined and evaporated in vacuo. The crude product is purified by preparative HPLC (C18 column, 10-100% CH₃CN+0.1% TFA/H₂O+0.1% TFA/20 min, flow 20 mL/min). The combined pure fractions are evaporated in vacuo to afford the title compound. MS: 442.6 [M+H]⁺; $t_R$ (HPLC, Nucleosil C18; 5-100% CH₃CN+0.1% TFA/H₂O+ 0.1% TFA for 8 min, flow 1.5 ml/min): 5.18 min.

Example 42

(3S*,5R*)-5-(2-Chloro-benzylamino)-piperidine-3-carboxylic acid (2,2-diphenyl-ethyl)-amide, trifluoroacetate

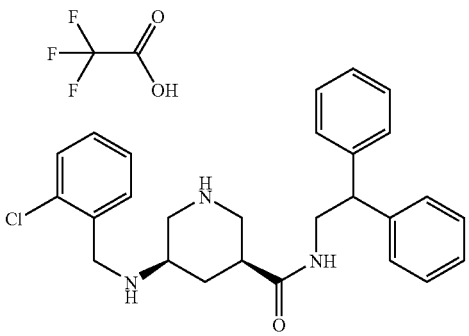

To a suspension of resin 3 (Starting Material 5) (180 mg, 106 μmol) in a mixture of trimethyl orthoformate/CH$_2$Cl$_2$ 3:7 (1.5 mL), 2-chlorobenzaldehyde (59.6 μL, 0.53 mmol) is added and the mixture is shaken for 40 h at 60° C. The resin is filtered off and then washed three times with trimethyl orthoformate/CH$_2$Cl$_2$ (1:9). A mixture of borane-pyridine complex (53.5 μL, ~0.45 mmol), CH$_3$OH (21.5 μL, 0.53 mmol) and CH$_3$COOH (30.3 μL, 0.53 mmol) in CH$_2$Cl$_2$ (1.4 mL) is added to the wet resin and the suspension shaken for 2 h. The resin is filtered off, washed with DMA, 5% aqueous CH$_3$COOH (2×, alternating), H$_2$O (2×), THF (2×), 2% aqueous NH$_4$OH (2×), CH$_3$OH (2×), THF (2×) and DMA (4×). The Fmoc group is then removed by shaking the wet resin for 15 min at RT with a freshly prepared solution of DMA/piperidine 8:2 (1 mL). After filtration, this procedure is repeated four times using fresh DMA/piperidine solutions. The resin is filtered off, washed successively with DMA and CH$_3$OH (alternating, 2×), then THF (2×) and then CH$_2$Cl$_2$ (4×). In order to cleave the compound from the polymer, the wet resin is shaken for 15 min with an 8:2 mixture of CH$_2$Cl$_2$/95% trifluoro-acetic acid (1 mL) and then filtered off. This acid treatment is repeated once with a fresh 8:2 mixture of CH$_2$Cl$_2$/95% trifluoroacetic acid (1 mL). The resulting acidic solutions are combined and evaporated in vacuo. The crude product is purified by preparative HPLC (C18 column, 10-100% CH$_3$CN+0.1% TFA/H$_2$O+0.1% TFA/20 min, flow 20 mL/min). The combined pure fractions are evaporated in vacuo to afford the title compound. MS: 448.4 [M+H]$^+$; t$_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 4.47 min.

Example 43

(3S*,5R*)-5-(3-Chloro-benzylamino)-piperidine-3-carboxylic acid (2,2-diphenyl-ethyl)-amide, trifluoroacetate

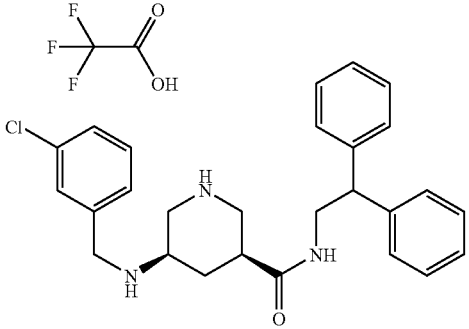

The title compound is prepared analogously as described in Example 42 using 3-chlorobenzaldehyde instead of 2-chlorobenzaldehyde. MS: 448.4 [M+H]$^+$; t$_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 4.65 min.

Example 44

(3S*,5R*)-5-[3-(3-Chloro-phenyl)-ureido]-piperidine-3-carboxylic acid (2,2-diphenyl-ethyl)-amide, trifluoroacetate

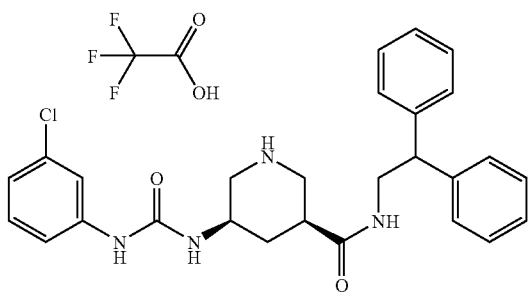

To a suspension of resin 3 (Starting Material 5) (180 mg, 106 μmol), 1,2-dichloroethane (1.5 mL) and pyridine (17 μL, 0.21 mmol), 3-chlorophenyl isocyanate (64.1 μL, 0.53 mmol) is added and the mixture is shaken for 24 h at 75° C. The resin is filtered off, washed with CH$_2$Cl$_2$ (2×), DMA/H$_2$O 1:1 (3×), CH$_3$OH (3×), THF (2×) and DMA (4×). The Fmoc group is removed by shaking the wet resin for 15 min at RT with a freshly prepared solution of DMA/piperidine 8:2 (1 mL). After filtration, this procedure is repeated four times using fresh DMA/piperidine solutions. The resin is filtered off, washed successively with DMA and CH$_3$OH (alternating, 2×), then THF (2×) and then CH$_2$Cl$_2$ (4×). In order to cleave the compound from the polymer, the wet resin is shaken for 15 min with an 8:2 mixture of CH$_2$Cl$_2$/95% trifluoroacetic acid (1 mL) and then filtered off. This acid treatment is repeated once with a fresh 8:2 mixture of CH$_2$Cl$_2$/95% trifluoroacetic acid (1 mL). The resulting acidic solutions are combined and evaporated in vacuo. The crude product is purified by preparative HPLC (C18 column, 10-100% CH$_3$CN+0.1% TFA/H$_2$O+0.1% TFA/20 min, flow 20 mL/min). The combined pure fractions are evaporated in vacuo to afford the title compound. MS: 477.4 [M+H]$^+$; t$_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.41 min.

Scheme 3

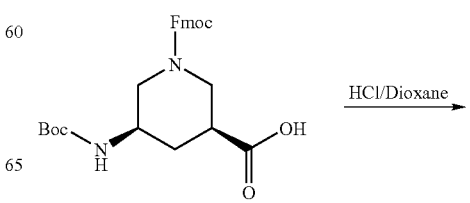

81

-continued

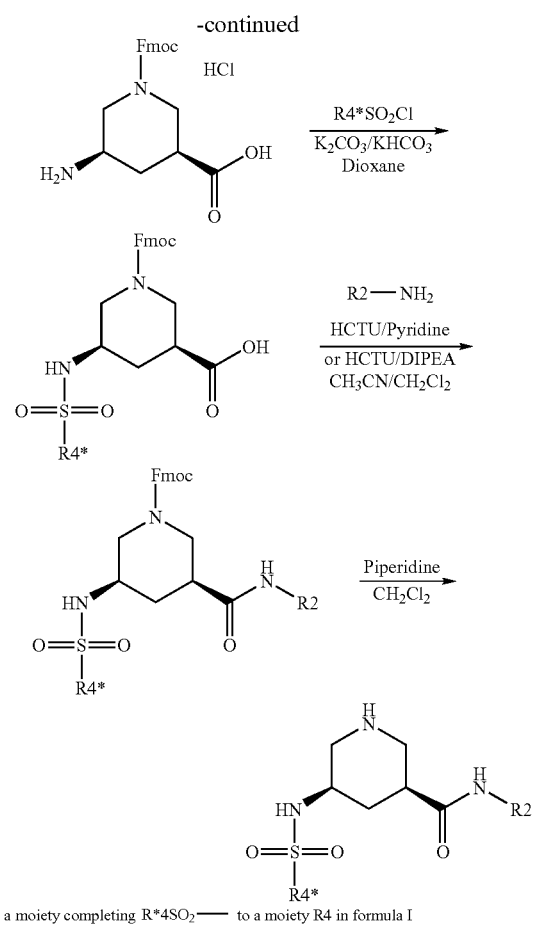

R4* is a moiety completing R*4SO2— to a moiety R4 in formula I

Example 45

(3S*,5R*)-5-(Toluene-4-sulfonylamino)-piperidine-3-carboxylic acid (5,6-diethyl-indan-2-yl)-amide, trifluoroacetate

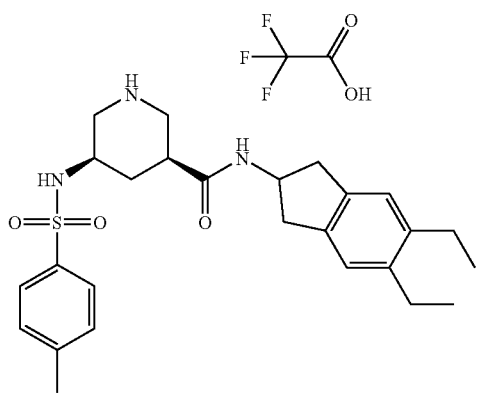

To a stirred, ice-cooled mixture of (3S*,5R*)-5-(toluene-4-sulfonylamino)-piperidine-1,3-dicarboxylic acid 1-(9H-fluoren-9-ylmethyl) ester (190 mg, 0.365 mmol) in pyridine (4 mL), O-(1H-6-chlorobenzotriazole-1-yl)-1,1,3,3-tetramethyluronium hexafluorophosphate (166 mg, 0.40 mmol) is added. The mixture is stirred for 15 min at 0° C. After the addition of 5,6-diethyl-indan-2-ylamine (82 mg, 0.365 mmol) stirring is continued for 5 h at 0° C. The reaction is quenched by the addition of 2N HCl and the acidic mixture is extracted three times with tert-butyl methyl ether. The combined organic layers are washed with an aqueous $NaHCO_3$ solution and brine, dried over $Na_2SO_4$ and evaporated in vacuo to afford an amorphous solid.

To a solution of this compound in $CH_2Cl_2$, piperidine (0.815 mL, 8.25 mmol) is added and the mixture is stirred for 1 h at RT. After evaporation in vacuo, the residue is purified by preparative HPLC (C18 column; 10-100% $CH_3CN$+0.1% TFA/$H_2O$+0.1% TFA/20 min, flow 20 mL/min) to afford the title compound. MS: 470.5 [M−H]⁻; $t_R$ (HPLC, C18 column; 5-100% $CH_3CN$+0.05% TFA/$H_2O$+0.05% TFA for 6 min, flow 1.5 ml/min): 3.74 min.

The starting materials are prepared as follows:

A. (3S*,5R*)-5-Amino-piperidine-1,3-dicarboxylic acid 1-(9H-fluoren-9-ylmethyl) ester, hydrochloride To a mixture of (3S*,5R*)-5-tert-butoxycarbonylamino-piperidine-1,3-dicarboxylic acid 1-(9H-fluoren-9-ylmethyl) ester (4.7 g, 10.1 mmol) (see Starting Material 1 above) in dioxane (25 mL), HCl (4M in dioxane, 25 mL, 100 mmol) is added and the reaction mixture is stirred for 16 h at RT. Hexane (50 mL) is added and the crystals are filtered off, washed with hexane and dried in vacuo to afford the title compound as a white solid. MS: 367.4 [M+H]⁺; $t_R$ (HPLC, Nucleosil C18; 5-100% $CH_3CN$+0.1% TFA/$H_2O$+0.1% TFA for 8 min, flow 1.5 ml/min): 4.48 min.

B. (3S*,5R*)-5-(Toluene-4-sulfonylamino)-piperidine-1,3-dicarboxylic acid 1-(9H-fluoren-9-ylmethyl) ester To a stirred, ice-cooled mixture of (3S*,5R*)-5-amino-piperidine-1,3-dicarboxylic acid 1-(9H-fluoren-9-ylmethyl) ester, hydrochloride (9.67 g, 24 mmol), $K_2CO_3$ (4.98 g, 36 mmol in 50 mL of $H_2O$), $KHCO_3$ (3.6 g, 36 mmol in 36 mL of $H_2O$), and dioxane (85 mL) 4-toluenesulfonyl chloride (5.03 g, 26.4 mmol) is added in several portions at a temperature of 0-5° C. Stirring is continued at this temperature for 1 h. The reaction mixture is diluted with $H_2O$ and acidified with HCl to pH 2. The aqueous phase is extracted three times with ethyl acetate. After washing with brine, the combined organic extracts are dried ($Na_2SO_4$) and the solvent is evaporated in vacuo to afford the title compound as a white solid. MS: 521.1 [M−H]⁻; $t_R$ (HPLC, C18 column; 5-100% $CH_3CN$+0.05% TFA/$H_2O$+0.05% TFA for 6 min, flow 1.5 ml/min): 4.66 min.

Example 46

(3R*,5S*)-5-(Toluene-4-sulfonylamino)-piperidine-3-carboxylic acid (2-phenyl-2-pyridin-2-yl-ethyl)-amide, trifluoroacetate

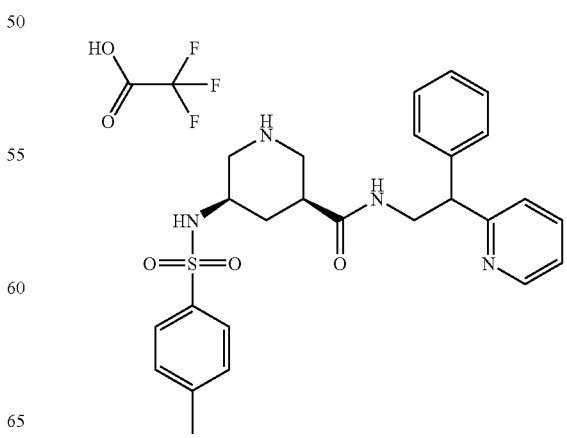

The title compound is prepared analogously as described in Example 45 using 2-phenyl-2-pyridin-2-yl-ethylamine instead of 5,6-diethyl-indan-2-ylamine. MS: 479.5 [M–H]$^-$; $t_R$ (HPLC, C18 column; 5-100% CH$_3$CN+0.05% TFA/H$_2$O+ 0.05% TFA for 6 min, flow 1.5 ml/min): 2.39 min.

Example 47

(3S*,5R*)-5-(3-Chloro-benzenesulfonylamino)-piperidine-3-carboxylic acid [1-(4-chloro-phenyl)-cyclopropylmethyl]-amide, trifluoroacetate

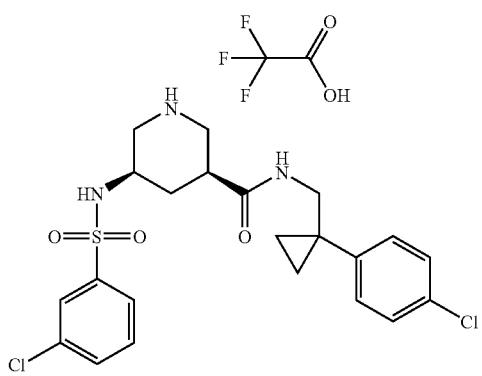

The title compound is prepared analogously as described in Example 45 using C-[1-(4-chloro-phenyl)-cyclopropyl]-methylamine instead of 5,6-diethyl-indan-2-ylamine, and a mixture of CH$_2$Cl$_2$/CH$_3$CN/N-ethyldiisopropylamine instead of pyridine for the coupling step. MS: 482.3/484.1 [M+H]$^+$; $t_R$ (HPLC, Nucleosil C18; 5-100% CH$_3$CN+0.1% TFA/H$_2$O+ 0.1% TFA for 8 min, then 100% CH$_3$CN+0.1% TFA for 2 min, flow 1.5 ml/min): 5.13 min.

Example 48

(3S*,5R*)-5-(Toluene-4-sulfonylamino)-piperidine-3-carboxylic acid [2-(4-methoxy-phenyl)-2-phenyl-ethyl]-amide

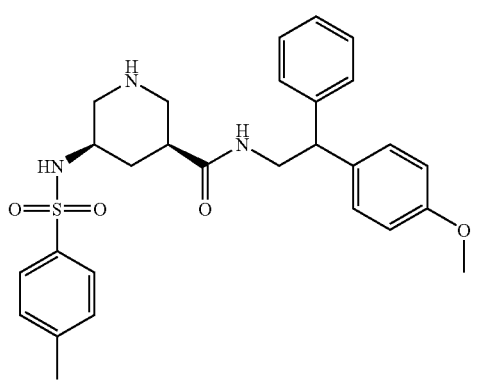

The title compound is prepared analogously as described in Example 45 using 2-(4-methoxy-phenyl)-2-phenyl-ethylamine instead of 5,6-diethyl-indan-2-ylamine and purification by flash chromatography (CH$_2$Cl$_2$/CH$_3$OH). MS: 508.6 [M+H]$^+$; $t_R$ (HPLC, Nucleosil C18; 5-100% CH$_3$CN+0.05% TFA/H$_2$O+0.05% TFA for 6 min, flow 1.5 ml/min): 3.42 min.

Example 49

(3S*,5R*)-5-(Toluene-4-sulfonylamino)-piperidine-3-carboxylic acid {2-[2-(4-methoxy-butoxy)-phenyl]-2-phenyl-ethyl}-amide

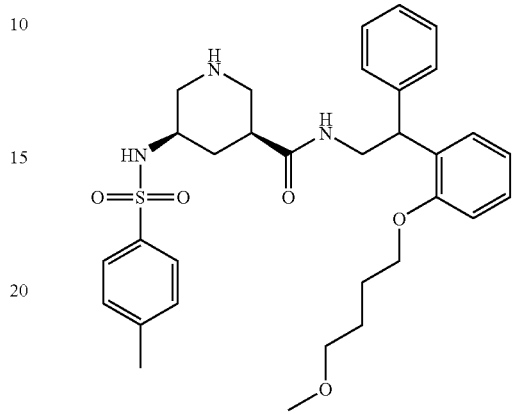

An ice-cooled mixture of (3S*,5R*)-5-(toluene-4-sulfonylamino)-piperidine-1,3-dicarboxylic acid 1-(9H-fluoren-9-ylmethyl) ester (208.2 mg, 0.4 mmol), O-(1H-6-chlorobenzotriazole-1-yl)-1,1,3,3-tetramethyluronium hexafluorophosphate (182 mg, 0.44 mmol) and N-ethyldiisopropylamine (27.4 µL, 0.16 mmol) in CH$_2$Cl$_2$/CH$_3$CN 1:1 (3 mL) is stirred for 10 min. After the addition of 2-[2-(4-methoxy-butoxy)-phenyl]-2-phenyl-ethylamine (119.8 mg, 0.4 mmol), the ice-bath is removed and stirring is continued for 14 h at RT. The reaction mixture is distributed between ethyl acetate and 10% K$_2$CO$_3$ solution. The aqueous layer is separated and extracted twice with ethyl acetate. The combined organic layers are dried over Na$_2$SO$_4$ and evaporated in vacuo. The residue is stirred for 1 h with a freshly prepared mixture of CH$_2$Cl$_2$/piperidine 4:1 (5 mL), evaporated and the residue purified by preparative HPLC (C18 column; 10-100% CH$_3$CN+0.1% TFA/H$_2$O+0.1% TFA/20 min, flow 20 mL/min). The combined pure fractions are treated with Na$_2$CO$_3$, CH$_3$CN is removed in vacuo, and the residual aqueous phase is extracted three times with CH$_2$Cl$_2$. The combined organic layers are dried (Na$_2$SO$_4$) and evaporated to afford the title compound as a slightly beige amorphous solid. MS: 580.4 [M+H]$^+$; $t_R$ (HPLC, Nucleosil C18; 5-100% CH$_3$CN+0.1% TFA/H$_2$O+0.1% TFA for 8 min, flow 1.5 ml/min): 5.61 min.

The starting material named 2-[2-(4-methoxy-butoxy)-phenyl]-2-phenyl-ethylamine is prepared as follows:

a) A solution of [2-(3-methoxy-butoxy)-phenyl]-phenyl-acetonitrile (0.51 g, 1.73 mmol) in ethanol (7 ml) containing 4% concentrated aqueous ammonia is hydrogenated in the presence of Raney-Ni (0.5 g) for 6 hours at room temperature. The mixture is filtered over Celite, washed with ethanol, followed by evaporation of the combined filtrates to give the title product. MS: 300.2 [M+H]$^+$; $t_R$ (HPLC, Nucleosil 100-5 R18; 10-100% CH$_3$CN+0.1% TFA/H$_2$O+ 0.1% TFA for 5 min, flow 1.5 ml/min): 4.44 min.

b) To a stirred solution of 1-benzyl-2-(3-methoxy-butoxy)-benzene (1.05 g, 3.88 mmol) and 2,3-dichloro-5,6-dicyano-1,4-benzoquinone (1.06 g, 4.66 mmol) in CH$_2$Cl$_2$ (10 ml), trimethylsilyl cyanide (1.94 ml, 19.4 mmol) is added, and the reaction mixture is heated at 100° C. for 1 hour in a microwave reactor. After cooling to room temperature, the organics are washed with aqueous NaHCO$_3$ (10%) and water, dried (MgSO$_4$) and concentrated. The product is purified by flash chromatography on silica gel (hexane/EtOAc 97:3 (0.5 L), then hexane/EtOAc 85:15) to give [2-(3-methoxy-butoxy)-phenyl]-phenyl-acetonitrile. MS: 296.2 [M+H]$^+$; t$_R$ (HPLC, Nucleosil 100-5 R18; 10-100% CH$_3$CN+0.1% TFA/H$_2$O+0.1% TFA for 5 min, flow 1.5 ml/min): 5.61 min.

c) To a stirred solution of 2-benzylphenol (0.90 g, 4.89 mmol) in acetonitrile (35 ml), water-free K$_2$CO$_3$ (0.81 g, 5.86 mmol) and toluene-4-sulfonic acid 4-methoxy-butyl ester (1.51 g, 5.86 mmol) are added. The mixture is refluxed overnight and filtered after cooling to room temperature, followed by evaporation. The residue is taken up in CH$_2$Cl$_2$, and the organic phase is subsequently washed with 1 M NaOH (50 ml), water and brine. The combined organics are dried (MgSO$_4$) and evaporated. The residue is purified by flash chromatography on silica gel (hexane/EtOAC 93:3) to give 1-benzyl-2-(3-methoxy-butoxy)-benzene. MS: 271.2 [M+H]$^+$; t$_R$ (HPLC, Nucleosil 100-5 R18; 10-100% CH$_3$CN+0.1% TFA/H$_2$O+0.1% TFA for 5 min, flow 1.5 ml/min): 6.25 min.

Scheme 4

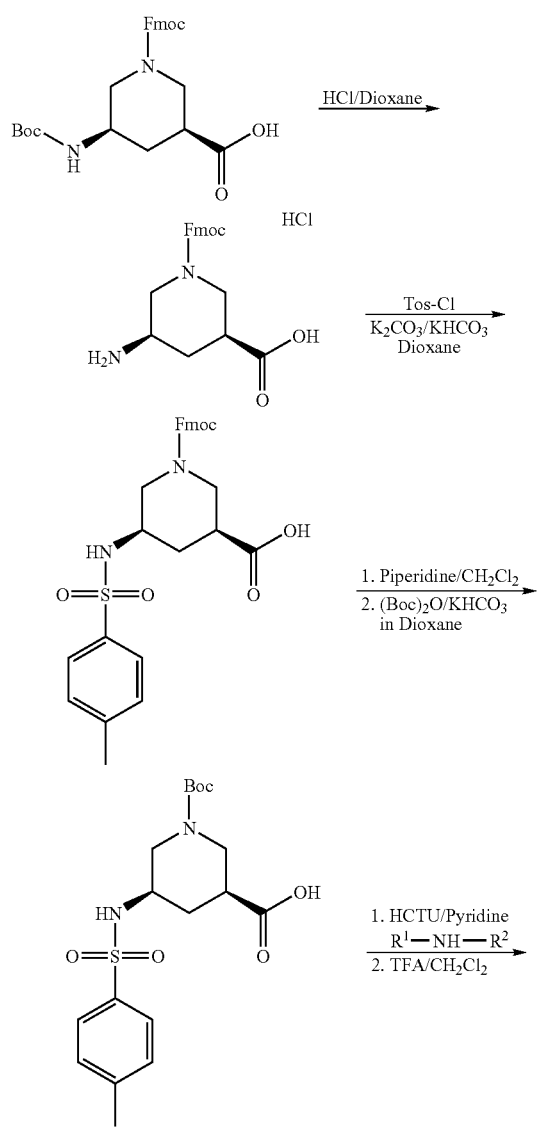

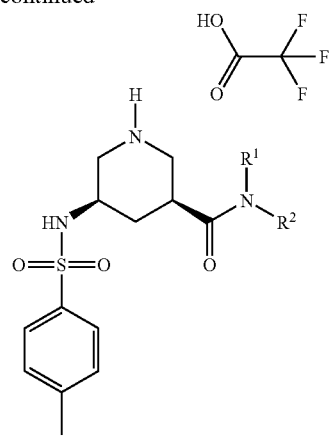

Example 50

(3S*,5R*)-5-(Toluene-4-sulfonylamino)-piperidine-3-carboxylic acid (biphenyl-2-ylmethyl)-amide, trifluoroacetate

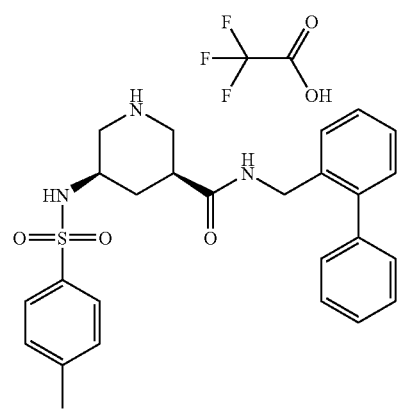

A small part of the residue obtained below under A. (40 mg, 0.1 mmol) is dissolved in pyridine (0.5 mL). The solution is cooled to 2° C., treated with O-(1H-6-chlorobenzotriazole-1-yl)-1,1,3,3-tetramethyluronium hexafluorophosphate and stirred at 2° C. for 1 h. The resulting mixture is added to a precooled solution of 2-phenylbenzylamine (18.3 mg, 0.1 mmol) in pyridine (0.4 mL). The reaction mixture is stirred at 4° C. for 14 h, evaporated in an air stream and the residue evaporated twice with CH$_2$Cl$_2$. The crude product is dissolved in CH$_2$Cl$_2$ (2 mL) and put on a 3 mL HM-N cartridge (isolute) pretreated with an aqueous 10% K$_2$CO$_3$ solution (2 mL). The compound is eluted with CH$_2$Cl$_2$ (2×6 mL). The organic layer is evaporated and dried at RT. A solution of CH$_2$Cl$_2$/trifluoroacetic acid (1:1) is added to the residue, the mixture is shaken for 1 h at RT and evaporated. The residue is purified by preparative HPLC (C18 column, 5-100% CH$_3$CN+0.1% TFA/H$_2$O+0.1% TFA for 8 min, flow 30 ml/min) to afford the title compound. MS: 464.2. [M+H]$^+$; t$_R$ (HPLC, C18 column; 5-100% CH$_3$CN+0.05% TFA/H$_2$O+0.05% TFA for 6 min, flow 1.5 ml/min): 3.36 min.

The starting material is prepared as follows:

A. (3S*,5R*)-5-(Toluene-4-sulfonylamino)-piperidine-1,3-dicarboxylic acid 1-tert-butyl ester A mixture of (3S*,5R*)-5-(toluene-4-sulfonylamino)-piperidine-1,3-dicarboxylic acid 1-(9H-fluoren-9-ylmethyl) ester (11 g, 21.1 mmol) (see Example 45B.), piperidine (62.6 mL, 633 mmol) and CH$_2$Cl$_2$ (170 mL) is stirred for 1 h at RT. The solution is evaporated and the residue is distributed between CH$_2$Cl$_2$ and aqueous 10% KHCO$_3$ solution. After separation, the aqueous layer is washed a second time with CH$_2$Cl$_2$. The combined organic layers are extracted with 10% KHCO$_3$ solution. Total amount of KHCO$_3$ solution: 170 ml (10% solution). The combined aqueous solutions are treated with dioxane (170 mL) and di-tert-butyl dicarbonate (27.3 mL, 120 mmol) and the resulting mixture is stirred for 16 h at RT. After addition of K$_2$CO$_3$ solution (10%, 50 mL), the mixture is washed twice with tert-butyl methyl ether and the aqueous layer is slowly acidified to pH 2 with a 10% NaHSO$_4$ solution. The aqueous layer is extracted three times with CH$_2$Cl$_2$. The combined organic layers are washed with H$_2$O, dried (Na$_2$SO$_4$) and evaporated to give a residue.

Example 51

(3S*,5R*)-5-(Toluene-4-sulfonylamino)-piperidine-3-carboxylic acid [3-(4-methoxy-phenyl)-2-phenyl-propyl]-amide, trifluoroacetate

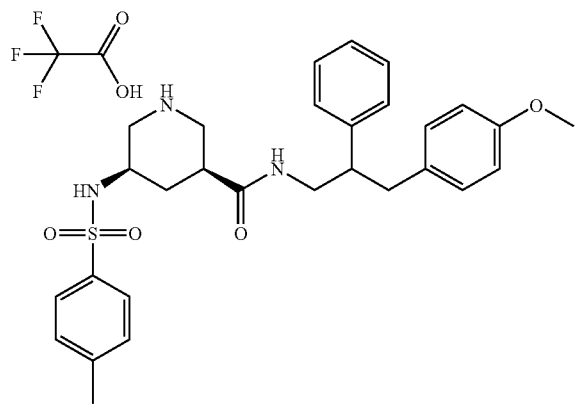

The title compound is prepared analogously as described in Example 50 using 3-(4-methoxy-phenyl)-2-phenyl-propylamine instead of 2-phenylbenzylamine. MS: 522.2 [M+H]$^+$; $t_R$ (HPLC, C18; 5-100% CH$_3$CN+0.05% TFA/H$_2$O+0.05% TFA for 6 min, flow 1.5 ml/min): 3.49 min.

Example 52

(3S*,5R*)-5-(Toluene-4-sulfonylamino)-piperidine-3-carboxylic acid [2-(4-chlorophenyl)-2-phenyl-ethyl]-amide

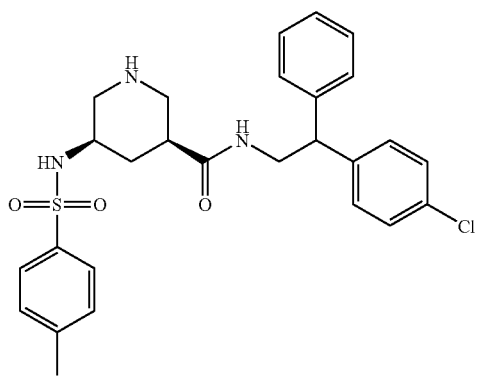

The title compound is prepared analogously as described in Example 45 using 2-(4-chlorophenyl)-2-phenyl-ethylamine.

MS: 512.1/514.1 [M+H]$^+$; $t_R$ (HPLC, Lichrospher RP8 (Merck KGaA, Darmstadt, Germany); 10-100% CH$_3$CN+ 0.1% TFA/H$_2$O+0.1% TFA for 5 min, then 100% CH$_3$CN+ 0.1% TFA for 2.5 min, flow 1.5 ml/min): 5.05 min.

Example 53

(3S*,5R*)-5-(Toluene-4-sulfonylamino)-piperidine-3-carboxylic acid (2-phenyl-bicyclo[3.3.1]non-9-yl)-amide, trifluoroacetate

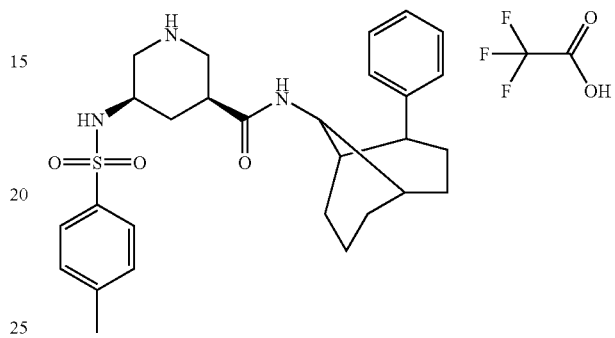

The title compound is prepared analogously as described in Example 50 using 2-phenyl-bicyclo[3.3.1]non-9-ylamine instead of 2-phenylbenzylamine. MS: 496.3 [M+H]$^+$; $t_R$ (HPLC, C18 column; 5-100% CH$_3$CN+0.05% TFA/H$_2$O+ 0.05% TFA for 6 min, flow 1.5 ml/min): 3.79 min.

Scheme 5

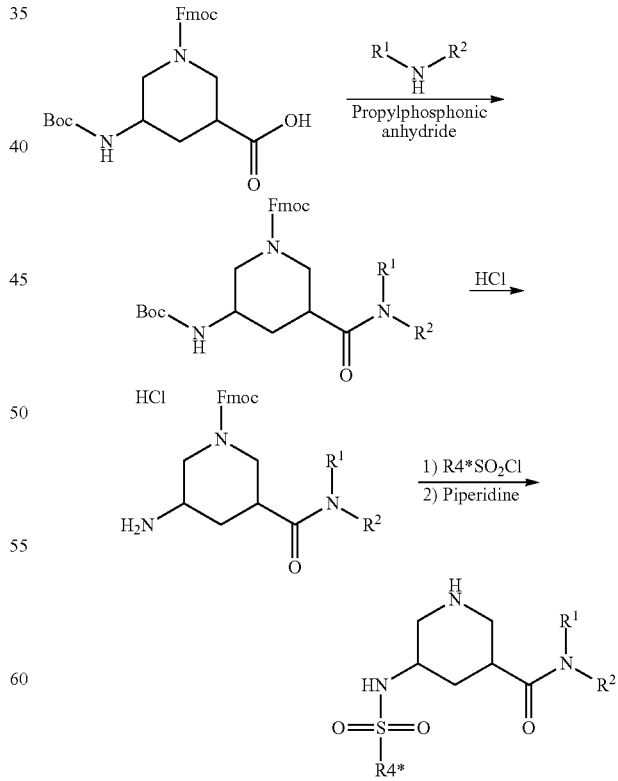

R4* is a moiety completing R4*SO$_2$— to a moiety R4— as given in formula I

Example 54

(3S*,5R*)-5-(3-Chloro-benzenesulfonylamino)-piperidine-3-carboxylic acid (2-chloro-benzyl)-cyclopropyl-amide

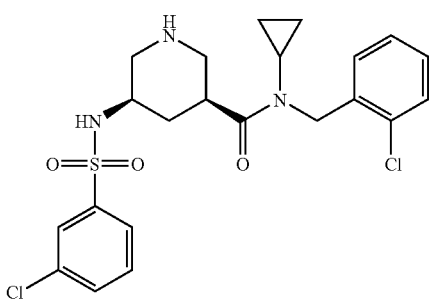

To an ice-cooled mixture of (3R*,5S*)-3-amino-5-[(2-chloro-benzyl)-cyclopropyl-carbamoyl]-piperidine-1-carboxylic acid 9H-fluoren-9-ylmethyl ester (209.3 mg, 0.37 mmol) in pyridine (3 mL), 4-dimethylaminopyridine (12.7 mg, 0.104 mmol) and 3-chlorobenzenesulfonyl chloride (210.5 µL, 1.476 mmol) are added. The reaction mixture is stirred at RT for 14 h, then diluted with H$_2$O and acidified with 1N HCl to pH 2, and the resulting aqueous layer is extracted three times with ethyl acetate. The combined organic layers are washed with brine, dried (Na$_2$SO$_4$) and evaporated to afford the Fmoc protected form or the title compound as a white amorphous solid. To remove the protecting group, the crude compound is stirred during 1 h at RT with a freshly prepared solution of CH$_2$Cl$_2$/piperidine 4:1 (5 mL). The reaction mixture is evaporated in vacuo, and the residue is purified by preparative HPLC (C18 column, 10-100% CH$_3$CN+0.1% TFA/H$_2$O+0.1% TFA, 20 min, flow 20 mL/min). The combined pure fractions are treated with K$_2$CO$_3$, CH$_3$CN is removed in vacuo and the residual aqueous phase is extracted three times with CH$_2$Cl$_2$. The combined organic layers are dried (Na$_2$SO$_4$) and evaporated to afford the title compound as a white amorphous solid. MS: 482.2/484.1 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 5.21 min.

The starting materials are prepared as follows:

A. (3R*,5S*)-3-tert-Butoxycarbonylamino-5-[(2-chloro-benzyl)-cyclopropylcarbamoyl]-piperidine-1-carboxylic acid 9H-fluoren-9-ylmethyl ester To a stirred, ice-cooled mixture of (3S*,5R*)-5-tert-butoxycarbonylamino-piperidine-1,3-dicarboxylic acid 1-(9H-fluoren-9-ylmethyl) ester (233.3 mg, 0.5 mmol), (2-chlorobenzyl)-cyclopropylamine (99.9 mg, 0.55 mmol) and N-ethyldiisopropylamine (685 µL, 4 mmol) in dimethylacetamide (2.5 mL), propylphosphonic anhydride solution (~50% in DMF, 480 µL, ~0.75 mmol) is added. The reaction mixture is stirred for 14 h at RT, diluted with ethyl acetate and washed twice with an aqueous NaHCO$_3$ solution. The combined organic layers are dried (Na$_2$SO$_4$) and evaporated in vacuo, and the residue is purified by preparative HPLC (C18 column, 10-100% CH$_3$CN+0.1% TFA/H$_2$O+0.1% TFA, 20 min, flow 20 mL/min). The combined pure fractions are treated with Na$_2$CO$_3$, CH$_3$CN is removed in vacuo, and the residual aqueous phase is extracted three times with CH$_2$Cl$_2$. The combined organic layers are dried (Na$_2$SO$_4$) and evaporated to afford the title compound as a white amorphous solid. MS: 630.7 [M+H]$^+$; $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 8.24 min.

B. (3R*,5S*)-3-Amino-5-[(2-chloro-benzyl)-cyclopropyl-carbamoyl]-piperidine-1-carboxylic acid 9H-fluoren-9-ylmethyl ester A mixture of (3R*,5S*)-3-tert-butoxycarbonylamino-5-[(2-chloro-benzyl)-cyclopropylcarbamoyl]-piperidine-1-carboxylic acid 9H-fluoren-9-ylmethyl ester (186 mg, 0.295 mmol) and HCl (5M in 2-propanol, 2 mL, 10 mmol) is stirred for 2 h at RT. The mixture is evaporated and the residue dried to afford the title compound as a beige amorphous solid. MS: 530.4 [M+H]$^+$; $t_R$ (HPLC, Nucleosil C18; 5-100% CH$_3$CN+0.1% TFA/H$_2$O+0.1% TFA for 8 min, flow 1.5 ml/min): 6.02 min.

Example 55

(3S*,5R*)-5-(3-Chloro-benzenesulfonylamino)-piperidine-3-carboxylic acid cyclopropyl-(2,2-diphenyl-ethyl)-amide

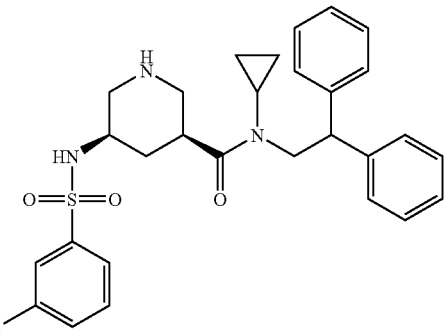

The title compound is prepared analogously as described in Example 54 using cyclopropyl-(2,2-diphenyl-ethyl)-amine instead of 2-(chlorobenzyl)-cyclopropylamine. MS: 538.3 [M+H]$^+$; $t_R$ (HPLC, C18 column; 5-100% CH$_3$CN+0.1% TFA/H$_2$O+0.1% TFA for 8 min, flow 1.5 ml/min): 5.72 min.

Example 56

(3S*,5R*)-5-(Toluene-4-sulfonylamino-piperidine-3-carboxylic acid benzyl-(3-methyl-2-phenyl-butyl)-amide, trifluoroacetate

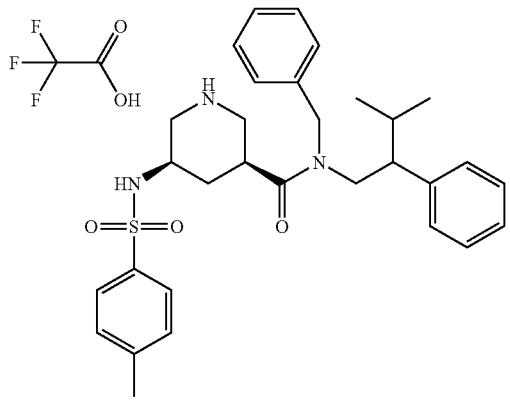

The title compound is prepared analogously as described in Example 54 using benzyl-(3-methyl-2-phenyl-butyl)-amine instead of 2-(chlorobenzyl)-cyclopropylamine. MS: 534.3 [M+H]$^+$; $t_R$ (HPLC, C18 column; 5-100% CH$_3$CN+0.1% TFA/H$_2$O+0.1% TFA for 8 min, flow 1.5 ml/min): 6.17 min.

The starting material is prepared as follows:

A. Benzyl-(3-methyl-2-phenyl-butyl)-amine

The title compound is prepared from 3-methyl-2-phenyl-butylamine and benzaldehyde: A solution of 3-methyl-2-phenyl-butylamine (1.3 g, 8 mmol) and benzaldehyde (0.81 mL, 8 mmol) in $CH_2Cl_2$ (50 mL) is stirred at RT for 20 min. Sodium triacetoxyborohydride (2.52 g, 11.3 mmol) is then added, followed by acetic acid (0.46 mL, 8 mmol). The reaction mixture is stirred at RT for 16 h, then quenched by the addition of saturated $NaHCO_3$ solution. The organic layer is separated and the aqueous phase is extracted twice with $CH_2Cl_2$. The combined organic layers are dried ($Na_2SO_4$) and evaporated. The residue is purified by flash chromatography (hexane/ethyl acetate) to afford benzyl-(3-methyl-2-phenyl-butyl)-amine as a colourless oil. MS: 254.3 $[M+H]^+$; $t_R$ (HPLC, C18 column; 5-100% $CH_3CN$+0.1% $TFA/H_2O$+ 0.1% TFA for 8 min, flow 1.5 ml/min): 5.03 min.

Example 57

(3S*,5R*)-5-(Toluene-4-sulfonylamino)-piperidine-3-carboxylic acid [2,2-bis-(4-methoxy-phenyl)-ethyl]-amide

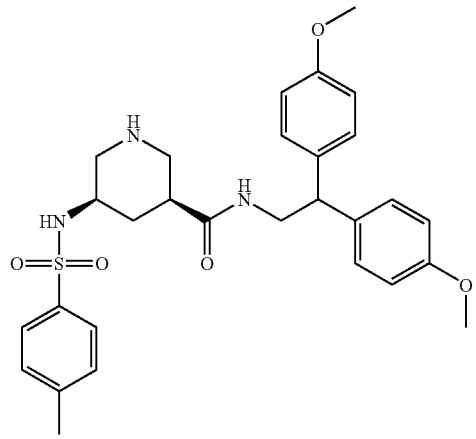

The title compound is prepared analogously as described in Example 45 using 2,2-bis-(4-methoxy-phenyl)-ethylamine. MS: 538.2 $[M+H]^+$; $t_R$ (HPLC, Lichrospher RP8; 10-100% $CH_3CN$+0.1% $TFA/H_2O$+0.1% TFA for 5 min, flow 1.5 ml/min): 4.77 min.

Example 58

(3S,5R)-5-(Toluene-4-sulfonylamino)-piperidine-3-carboxylic acid (2,2-diphenyl-ethyl)-amide, trifluoroacetate

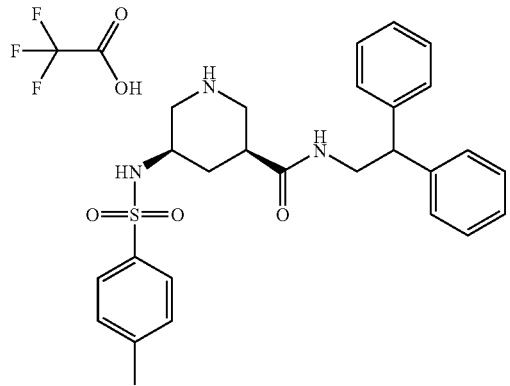

The title compound is prepared analogously as described in Example 54 using 2,2-diphenyl-ethylamine instead of 2-(chlorobenzyl)-cyclopropylamine and (3S,5R)-5-tert-butoxycarbonyl-amino-piperidine-1,3-dicarboxylic acid 1-(9H-fluoren-9-ylmethyl) ester. MS: 478.3 $[M+H]^+$; $t_R$ (HPLC, C18 column; 5-100% $CH_3CN$+0.05% $TFA/H_2O$+ 0.05% TFA for 6 min, flow 1.5 ml/min): 5.34 min.

Scheme 6

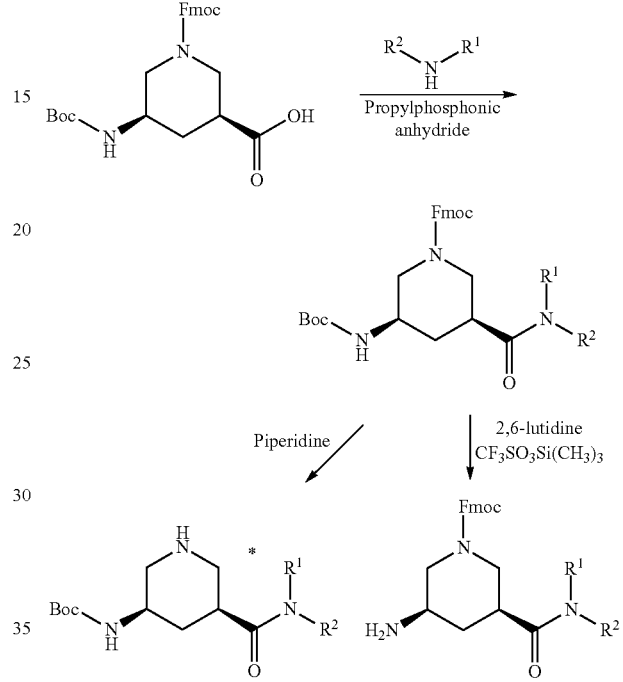

*This compound is also a compound of the formula I

Example 59

{(3R*,5S*)-5-[Benzyl-(3-methyl-2-phenyl-butyl)-carbamoyl]-piperidin-3-yl}-carbamic acid tert-butyl ester

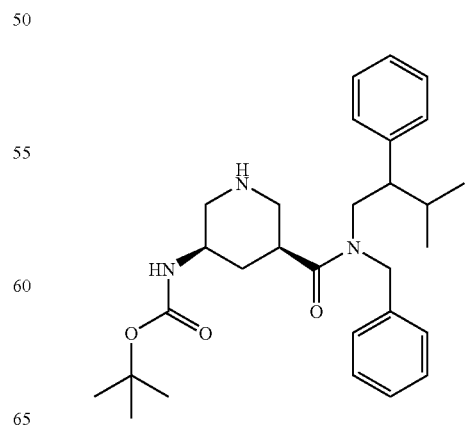

A solution of (3S*,5R*)-3-[benzyl-(3-methyl-2-phenyl-butyl)-carbamoyl]-5-tert-butoxy-carbonylamino-piperidine-1-carboxylic acid 9H-fluoren-9-ylmethyl ester (105.2 mg, 0.15 mmol) is stirred in a mixture of $CH_2Cl_2$/piperidine 4:1 (5 mL) for 1.5 h at RT. The reaction mixture is evaporated, and the residue is purified by preparative HPLC (C18 column, 10-100% $CH_3CN$+0.1% $TFA/H_2O$+0.1% TFA, 20 min, flow 20 mL/min). The combined pure fractions are treated with $K_2CO_3$, $CH_3CN$ is removed in vacuo, and the residual aqueous phase is extracted three times with $CH_2Cl_2$. The combined organic layers are dried ($Na_2SO_4$) and evaporated to afford the title compound as a white amorphous solid. MS: 480.4 $[M+H]^+$; $t_R$ (HPLC, Nucleosil C18; 5-100% $CH_3CN$+0.1% $TFA/H_2O$+0.1% TFA for 8 min, flow 1.5 ml/min): 6.05 min.

The starting material is prepared as follows:
A. (3S*,5R*)-3-[Benzyl-(3-methyl-2-phenyl-butyl)-carbamoyl]-5-tert-butoxycarbonylamino-piperidine-1-carboxylic acid 9H-fluoren-9-ylmethyl ester To a stirred, ice-cooled mixture of (3S*,5R*)-5-tert-butoxycarbonylamino-piperidine-1,3-dicarboxylic acid 1-(9H-fluoren-9-ylmethyl) ester (466.5 mg, 1 mmol), benzyl-(3-methyl-2-phenyl-butyl)-amine (279 mg, 1.1 mmol) and N-ethyldiisopropylamine (1.37 mL, 8 mmol) in dimethylacetamide (6 mL), propylphosphonic anhydride solution (~50% in DMF, 0.95 mL, ~1.5 mmol) is added. The reaction mixture is stirred for 7 h at RT and evaporated in vacuo. The residue is dissolved in ethyl acetate and washed twice with an aqueous 10% $K_2CO_3$ solution. The organic layer is dried ($Na_2SO_4$) and evaporated in vacuo and the residue is purified by flash chromatography (hexane/ethyl acetate). The combined pure fractions are evaporated to afford the title compound as a white amorphous solid. MS: 702.3 $[M+H]^+$; $t_R$ (HPLC, Nucleosil C18; 5-100% $CH_3CN$+0.1% $TFA/H_2O$+ 0.1% TFA for 8 min, then 100% $CH_3CN$+0.1% TFA for 2 min, flow 1.5 ml/min): 8.87 min.

The amine used in Example 59A is prepared as follows:
B. Benzyl-(3-methyl-2-phenyl-butyl)-amine A mixture of 3-methyl-2-phenyl-butylamine (1.3 g, 8 mmol), benzaldehyde (271 µL, 2.66 mmol) and $CH_2Cl_2$ (50 mL) is stirred for 20 min at RT. $NaBH(OAc)_3$ (840 mg, 3.96 mmol) and acetic acid (154 µL, 2.69 mmol) are added. After 2 h the same amounts as indicated above of benzaldehyde, $NaBH(OAc)_3$ and acetic acid are added once again. This procedure is repeated after 4 h. After stirring for 16 h at RT, saturated $NaHCO_3$ solution is added, the $CH_2Cl_2$ layer is removed and the aqueous phase is extracted twice with fresh $CH_2Cl_2$. The combined organic layers are dried ($Na_2SO_4$), evaporated in vacuo and the residue is purified by flash chromatography (hexane/ethyl acetate). The combined pure fractions are evaporated to afford the title compound as a colourless oil. MS: 254.3 $[M+H]^+$; $t_R$ (HPLC, Nucleosil C18; 5-100% $CH_3CN$+0.1% $TFA/H_2O$+0.1% TFA for 8 min, flow 1.5 ml/min): 5.03 min.

Example 60

((3R*,5S*)-5-{Cyclopropyl-[1-(3-methoxy-propyl)-1H-indol-3-ylmethyl]-carbamoyl}-piperidin-3-yl)-carbamic acid tert-butyl ester

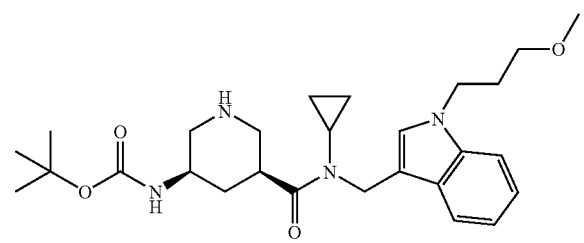

The title compound is prepared analogously as described in Example 59 using cyclopropyl-[1-(3-methoxy-propyl)-1H-indol-3-ylmethyl]-amine instead of benzyl-(3-methyl-2-phenyl-butyl)-amine. MS: 485.4 $[M+H]^+$; $t_R$ (HPLC, C18 column; 5-100% $CH_3CN$+0.1% $TFA/H_2O$+0.1% TFA for 8 min, flow 1.5 ml/min): 5.15 min.

The starting material is prepared as follows:
A. Cyclopropyl-[1-(3-methoxy-propyl)-1H-indol-3-ylmethyl]-amine The title compound is prepared as follows: A mixture of indol-3-carboxaldehyde (4.18 g, 28.8 mmol) and NaH (55-65% in oil, 1.38 g, ~31 mmol) in dimethylacetamide (60 mL) is stirred at 70° C. for 30 min. After cooling to room temperature, toluene-4-sulfonic acid 3-methoxy-propyl ester (7.75 g, 31.7 mmol) and potassium iodide (5.27 g, 31.7 mmol) are added. The reaction mixture is stirred for 2 h at 40° C., then evaporated in vacuo and the residue distributed between $H_2O$ and ethyl acetate. The organic layer is dried over $Na_2SO_4$ and evaporated. Flash chromatography of the residue (hexane/ethyl acetate) and evaporation of the pure fractions afford the 1-substituted indole as an orange oil. A mixture of this intermediate (1.147 g, 6.8 mmol), $CH_2Cl_2$ (50 mL) and cyclopropylamine (1.6 mL, 22.8 mmol) is stirred for 20 min at RT. After addition of sodium triacetoxyborohydride (2.14 g, 9.6 mmol) and acetic acid (0.39 mL, 6.8 mmol), the reaction mixture is stirred 16 h at RT. The reaction is quenched by the addition of saturated $NaHCO_3$ solution. The organic layer is separated and the aqueous phase extracted twice with $CH_2Cl_2$. The combined organic layers are dried ($Na_2SO_4$) and evaporated. The residue is purified by preparative HPLC (C18 column, 10-100% $CH_3CN$+0.1% $TFA/H_2O$+0.1% TFA, 20 min, flow 20 mL/min). The combined pure fractions are treated with $K_2CO_3$, $CH_3CN$ is removed in vacuo, and the residual aqueous phase is extracted three times with $CH_2Cl_2$. The combined organic layers are dried ($Na_2SO_4$) and evaporated to afford cyclopropyl-[1-(3-methoxy-propyl)-1H-indol-3-ylmethyl]-amine as a yellow oil. $t_R$ (HPLC, Nucleosil C18; 5-100% $CH_3CN$+0.1% $TFA/H_2O$+0.1% TFA for 8 min, flow 1.5 ml/min): 4.23 min.

Starting Material 6: (3R*,5S*)-3-Amino-5-{cyclopropyl-[1-(3-methoxy-propyl)-1H-indol-3-ylmethyl]-carbamoyl}-piperidine-1-carboxylic acid 9H-fluoren-9-ylmethyl ester

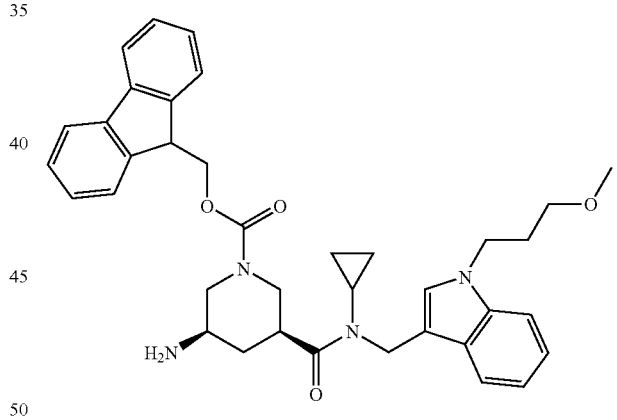

To a stirred, ice-cooled solution of (3R*,5S*)-3-tert-butoxycarbonylamino-5-{cyclopropyl-[1-(3-methoxy-propyl)-1H-indol-3-ylmethyl]-carbamoyl}-piperidine-1-carboxylic acid 9H-fluoren-9-ylmethyl ester (prepared from cyclopropyl-[1-(3-methoxy-propyl)-1H-indol-3-ylmethyl]-amine analogously as described in Example 59A) (1.2 g, 1.7 mmol) in $CH_2Cl_2$ (8 ml), 2,6-lutidine (0.79 mL, 6.8 mmol) is added followed by dropwise addition of trimethylsilyl trifluoromethanesulfonate (0.92 mL, 5.1 mmol). The cooling bath is removed, and the mixture is stirred at RT for 2.5 h. The reaction mixture is diluted with $CH_2Cl_2$ and washed with saturated $NH_4Cl$ solution. The organic layer is dried over $Na_2SO_4$ and evaporated in vacuo to afford the title compound as a brownish solid, which is used without further purification for the next steps. MS: 607.5 $[M+H]^+$; $t_R$ (HPLC, Nucleosil C18; 5-100% $CH_3CN$+0.1% $TFA/H_2O$+0.1% TFA for 8 min, flow 1.5 ml/min): 6.05 min.

Scheme 7

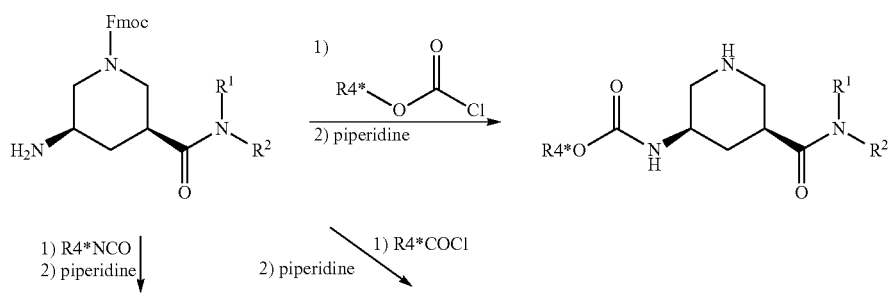

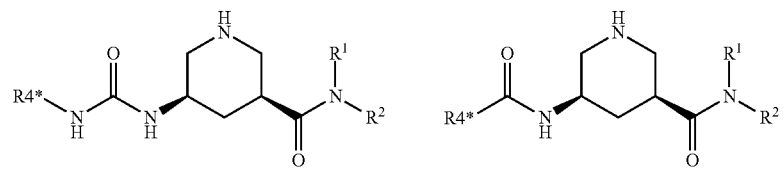

R4* is a moiety completing R4*NH—CO—, R4*—O—CO— or
R4*—CO— to a moiety R4— as given in formula I

Example 61

((3R*,5S*)-5-{Cyclopropyl-[1-(3-methoxy-propyl)-1H-indol-3-ylmethyl]-carbamoyl}-piperidin-3-yl)-carbamic acid 2,2-dimethyl-propyl ester

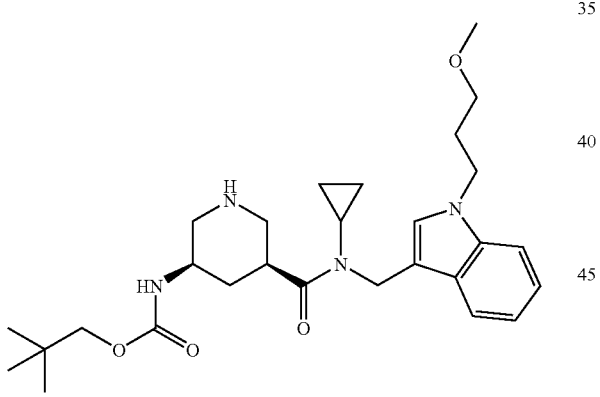

To a mixture of (3R*,5S*)-3-amino-5-{cyclopropyl-[1-(3-methoxy-propyl)-1H-indol-3-yl-methyl]-carbamoyl}-piperidine-1-carboxylic acid 9H-fluoren-9-ylmethyl ester (121.4 mg, 0.2 mmol) (Starting Material 6), N-ethyldiisopropylamine (171.2 µL, 1 mmol) and 4-dimethylaminopyridine (10 mg) in CH$_2$Cl$_2$ (3 mL), neopentyl chloroformate (52.1 µL, 0.35 mmol) is added. After stirring at RT for 14 h, the mixture is diluted with CH$_2$Cl$_2$. The organic layer is washed with 1N HCl and saturated NaHCO$_3$ solution, dried over Na$_2$SO$_4$ and evaporated in vacuo. The crude product is stirred with a solution of CH$_2$Cl$_2$/piperidine 4:1 (5 mL) for 2 h, the mixture is evaporated and the residue purified by preparative HPLC (C18 column, 10-100% CH$_3$CN+0.1% TFA/H$_2$O+0.1% TFA, 20 min, flow 20 mL/min). The combined pure fractions are treated with K$_2$CO$_3$, CH$_3$CN is removed in vacuo, and the residual aqueous phase is extracted three times with CH$_2$Cl$_2$.

The combined organic layers are dried (Na$_2$SO$_4$) and evaporated to afford the title compound as a yellowish solid. MS: 499.2 [M+H]$^+$; t$_R$ (HPLC, Nucleosil C18; 5-100% CH$_3$CN+0.1% TFA/H$_2$O+0.1% TFA for 8 min, flow 1.5 ml/min): 5.45 min.

Example 62

((3R*,5S*)-5-{Cyclopropyl-[1-(3-methoxy-propyl)-1H-indol-3-ylmethyl]-carbamoyl}-piperidin-3-yl)-carbamic acid isobutyl ester

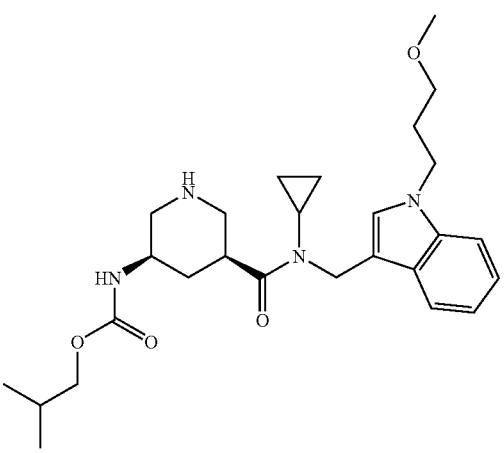

The title compound is prepared analogously as described in Example 61 using isobutyl chloroformate. MS: 485.6 [M+H]$^+$; t$_R$ (HPLC, C18 column; 5-100% CH$_3$CN+0.1% TFA/H$_2$O+0.1% TFA for 8 min, flow 1.5 ml/min): 5.29 min.

Example 63

(3S*,5R*)-5-(2,2-Dimethyl-propionylamino)-piperidine-3-carboxylic acid cyclopropyl-[1-(3-methoxypropyl)-1H-indol-3-ylmethyl]-amide

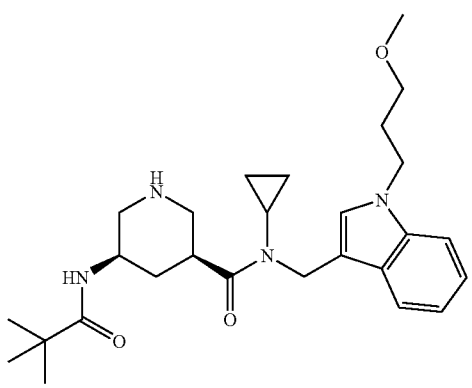

The title compound is prepared analogously as described in Example 61 using pivaloyl chloride. MS: 469.6 [M+H]+.

Example 64

(3S*,5R*)-5-(3,3-Dimethyl-butyrylamino)-piperidine-3-carboxylic acid cyclopropyl-[1-(3-methoxypropyl)-1H-indol-3-ylmethyl]-amide

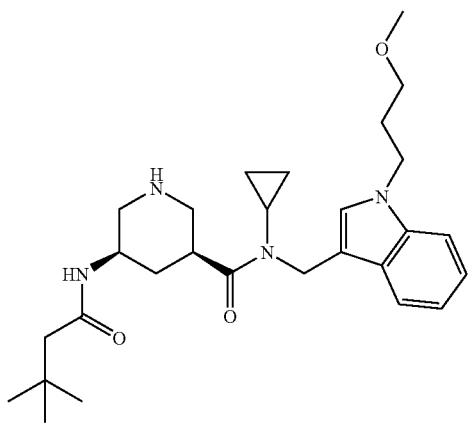

The title compound is prepared analogously as described in Example 61 using tert-butylacetyl chloride. MS: 483.6 [M+H]+; $t_R$ (HPLC, C18 column; 5-100% CH$_3$CN+0.1% TFA/H$_2$O+0.1% TFA for 8 min, flow 1.5 ml/min): 5.02 min.

Example 65

(3S*,5R*)-5-(Cyclobutylcarbonyl-amino)-piperidine-3-carboxylic acid cyclopropyl-[1-(3-methoxypropyl)-1H-indol-3-ylmethyl]-amide

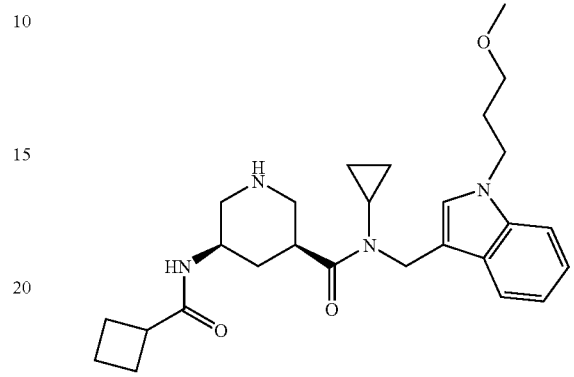

The title compound is prepared analogously as described in Example 61 using cyclobutane-carbonyl chloride. MS: 467.5 [M+H]+; $t_R$ (HPLC, C18 column; 5-100% CH$_3$CN+0.1% TFA/H$_2$O+0.1% TFA for 8 min, flow 1.5 ml/min): 4.79 min.

Example 66

(3S*,5R*)-5-(3-Benzyl-ureido)-piperidine-3-carboxylic acid cyclopropyl-[1-(3-methoxy-propyl)-1H-indol-3-ylmethyl]-amide

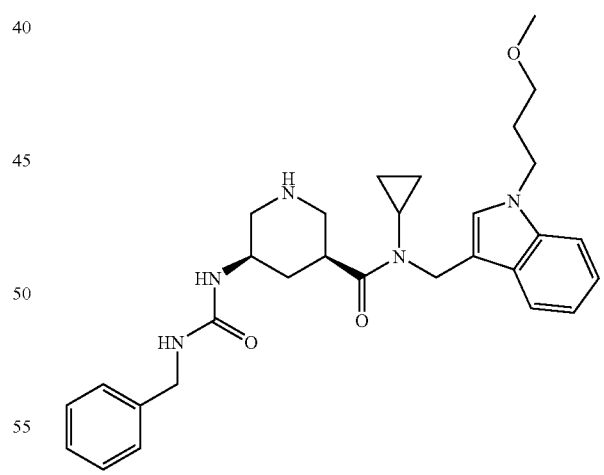

A mixture of (3R*,5S*)-3-amino-5-{cyclopropyl-[1-(3-methoxy-propyl)-1H-indol-3-ylmethyl]-carbamoyl}-piperidine-1-carboxylic acid 9H-fluoren-9-ylmethyl ester (91 mg, 0.15 mmol), dichloroethane (2 mL) and benzyl isocyanate (18.4 µL, 0.15 mmol) is shaken for 14 h at 50° C. A second portion of benzyl isocyanate (9.2 µL, 0.075 mmol) is added and shaking is continued for 5 h at 60° C. The mixture is evaporated in vacuo. The crude product is stirred with a solution of CH$_2$Cl$_2$/piperidine 4:1 (5 mL) for 2 h, the mixture is evaporated and the residue purified by preparative HPLC (C18 column, 10-100% CH$_3$CN+0.1% TFA/H$_2$O+0.1% TFA, 20 min, flow 20 mL/min). The combined pure fractions are treated with K$_2$CO$_3$, CH$_3$CN is removed in vacuo and the residual aqueous phase extracted three times with CH$_2$Cl$_2$. The combined organic layers are dried (Na$_2$SO$_4$) and evaporated to afford the title compound as a yellow resin. MS: 518.3 [M+H]$^+$; $t_R$ (HPLC, Nucleosil C18; 5-100% CH$_3$CN+0.1% TFA/H$_2$O+0.1% TFA for 8 min, flow 1.5 ml/min): 5.05 min.

Example 67

(3S*,5R*)-5-(3-Cyclohexyl-ureido)-piperidine-3-carboxylic acid cyclopropyl-[1-(3-methoxy-propyl)-1H-indol-3-ylmethyl]-amide

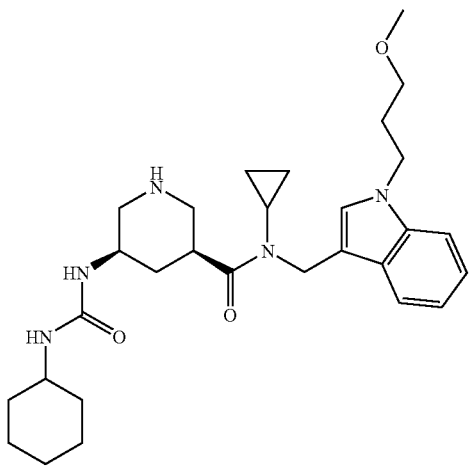

The title compound is prepared analogously as described in Example 66 using cyclohexyl isocyanate. MS: 510.5 [M+H]$^+$; $t_R$ (HPLC, C18 column; 5-100% CH$_3$CN+0.1% TFA/H$_2$O+0.1% TFA for 8 min, flow 1.5 ml/min): 5.15 min.

Example 68

(3S*,5R*)-5-(3-tert-Butyl-ureido)-piperidine-3-carboxylic acid cyclopropyl-[1-(3-methoxy-propyl)-1H-indol-3-ylmethyl]-amide

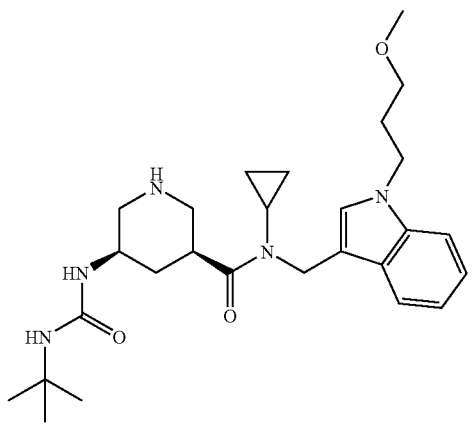

The title compound is prepared analogously as described in Example 66 using tert-butyl isocyanate. MS: 484.6 [M+H]$^+$; $t_R$ (HPLC, C18 column; 5-100% CH$_3$CN+0.1% TFA/H$_2$O+0.1% TFA for 8 min, flow 1.5 ml/min): 4.94 min.

Example 69

(3S*,5R*)-5-[2-(3-Methoxy-phenyl)-acetylamino]-piperidine-3-carboxylic acid cyclopropyl-[1-(3-methoxy-propyl)-1H-indol-3-ylmethyl]-amide

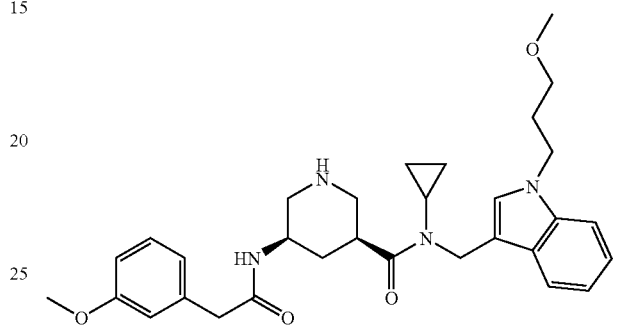

The title compound is prepared analogously as described in Example 61 using 3-methoxy-phenylacetyl chloride. MS: 533.5 [M+H]$^+$; $t_R$ (HPLC, Nucleosil C18; 5-100% CH$_3$CN+0.1% TFA/H$_2$O+0.1% TFA for 8 min, flow 1.5 ml/min): 5.10 min.

Example 70

(3S*,5R*)-5-[(Benzo[b]thiophene-2-carbonyl)-amino]-Piperidine-3-carboxylic acid cyclopropyl-[1-(3-methoxy-propyl)-1H-indol-3-ylmethyl]-amide

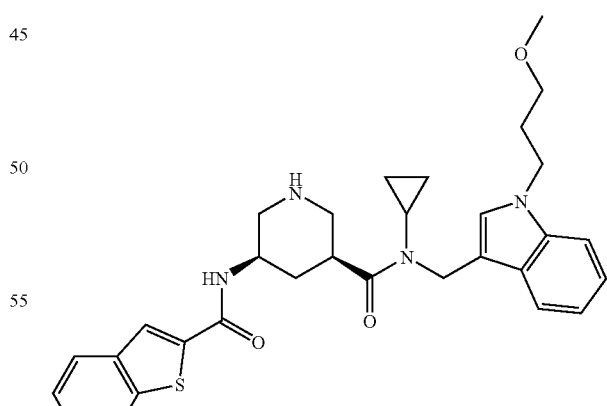

The title compound is prepared analogously as described in Example 61 using benzo[b]thiophene-2-carbonyl chloride. MS: 545.4 [M+H]$^+$; $t_R$ (HPLC, Nucleosil C18; 5-100% CH$_3$CN+0.1% TFA/H$_2$O+0.1% TFA for 8 min, flow 1.5 ml/min): 5.48 min.

Example 71

(3S*,5R*)-5-Benzoylamino-piperidine-3-carboxylic acid cyclopropyl-[1-(3-methoxy-propyl)-1H-indol-3-ylmethyl]-amide

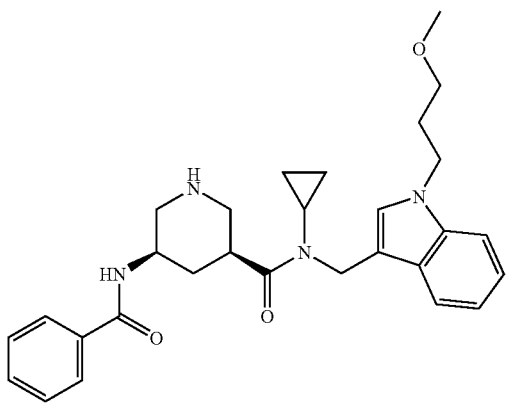

The title compound is prepared analogously as described in Example 61 using benzoyl chloride. MS: 489.3 [M+H]$^+$; $t_R$ (HPLC, Nucleosil C18; 5-100% CH$_3$CN+0.1% TFA/H$_2$O+ 0.1% TFA for 8 min, flow 1.5 ml/min): 4.99 min.

Example 72

(3S*,5R*)-5-Acetylamino-piperidine-3-carboxylic acid cyclopropyl-[1-(3-methoxy-propyl)-1H-indol-3-ylmethyl]-amide

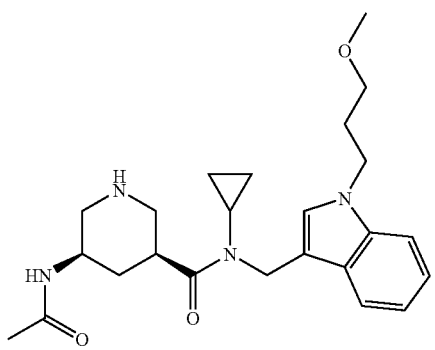

The title compound is prepared analogously as described in Example 61 using acetyl chloride. MS: 427.5 [M+H]$^+$; $t_R$ (HPLC, Nucleosil C18; 5-100% CH$_3$CN+0.1% TFA/H$_2$O+ 0.1% TFA for 8 min, flow 1.5 ml/min): 4.33 min.

Example 73

(3S*,5R*)-5-(3,4-Dimethoxy-benzoylamino)-piperidine-3-carboxylic acid cyclopropyl-[1-(3-methoxy-propyl)-1H-indol-3-ylmethyl]-amide

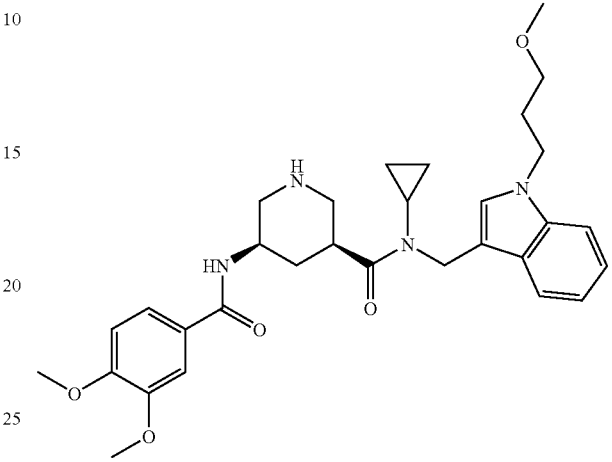

The title compound is prepared analogously as described in Example 61 using 3,4-dimethoxybenzoyl chloride. MS: 549.5 [M+H]$^+$; $t_R$ (HPLC, Nucleosil C18; 5-100% CH$_3$CN+ 0.1% TFA/H$_2$O+0.1% TFA for 8 min, flow 1.5 ml/min): 4.89 min.

Example 74

(3S*,5R*)-5-(3-Phenyl-propionylamino)-piperidine-3-carboxylic acid cyclopropyl-[1-(3-methoxy-propyl)-1H-indol-3-ylmethyl]-amide

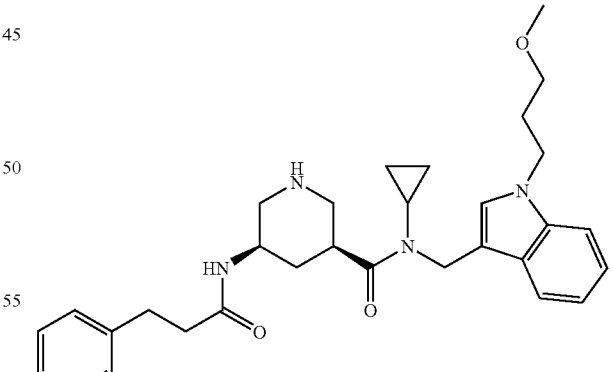

The title compound is prepared analogously as described in Example 61 using 3-pheny-propionyl chloride. MS: 517.5 [M+H]$^+$; $t_R$ (HPLC, Nucleosil C18; 5-100% CH$_3$CN+0.1% TFA/H$_2$O+0.1% TFA for 8 min, flow 1.5 ml/min): 5.17 min.

Example 75

(3S*,5R*)-5-(Cyclohexanecarbonyl-amino)-piperidine-3-carboxylic acid cyclopropyl-[1-(3-methoxy-propyl)-1H-indol-3-ylmethyl]-amide

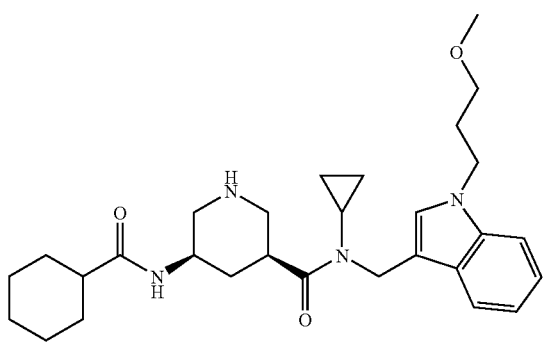

The title compound is prepared analogously as described in Example 61 using cyclohexane-carbonyl chloride. MS: 495.6 [M+H]$^+$; t$_R$ (HPLC, Nucleosil C18; 5-100% CH$_3$CN+0.1% TFA/H$_2$O+0.1% TFA for 8 min, flow 1.5 ml/min): 5.22 min.

Example 76

(3S*,5R*)-5-(3-Methyl-butyrylamino)-piperidine-3-carboxylic acid cyclopropyl-[1-(3-methoxy-propyl)-1H-indol-3-ylmethyl]-amide

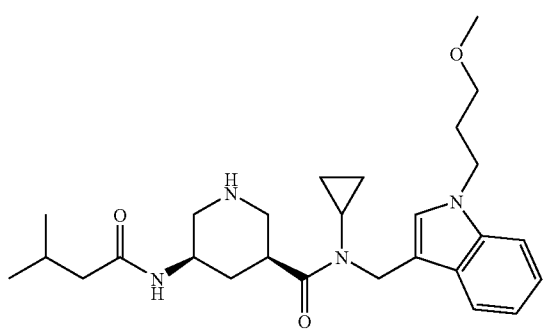

The title compound is prepared analogously as described in Example 61 using isovaleryl chloride. MS: 469.5 [M+H]$^+$; t$_R$ (HPLC, Nucleosil C18; 5-100% CH$_3$CN+0.1% TFA/H$_2$O+0.1% TFA for 8 min, flow 1.5 ml/min): 4.91 min.

Example 77

(3S*,5R*)-5-(2-Ethyl-butyrylamino)-piperidine-3-carboxylic acid cyclopropyl-[1-(3-methoxy-propyl)-1H-indol-3-ylmethyl]-amide

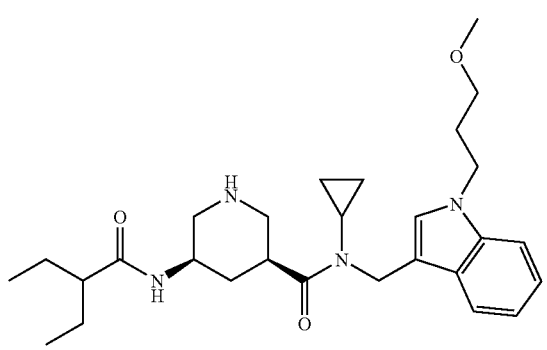

The title compound is prepared analogously as described in Example 61 using 2-ethylbutyryl chloride. MS: 483.7 [M+H]$^+$; t$_R$ (HPLC, Nucleosil C18; 5-100% CH$_3$CN+0.1% TFA/H$_2$O+0.1% TFA for 8 min, flow 1.5 ml/min): 5.05 min.

Example 78

(3S*,5R*)-5-[(2,2,3,3-Tetramethyl-cyclopropanecarbonyl)-amino]-piperidine-3-carboxylic acid cyclopropyl-[1-(3-methoxy-propyl)-1H-indol-3-ylmethyl]-amide

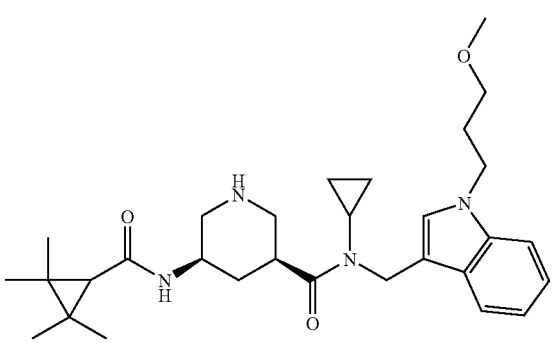

A mixture of 2,2,3,3-tetramethyl-cyclopropanecarboxylic acid (50 mg, 0.35 mmol), O-(1H-6-chlorobenzotriazole-1-yl)-1,1,3,3-tetramethyluronium hexafluorophosphate (HCTU) (145 mg, 0.35 mmol), N-ethyldiisopropylamine (171 µL, 1 mmol) in CH$_2$Cl$_2$ (3 mL) is stirred for 10 min at RT. After the addition of (3R*,5S*)-3-amino-5-{cyclopropyl-[1-(3-methoxy-propyl)-1H-indol-3-ylmethyl]-carbamoyl}piperidine-1-carboxylic acid 9H-fluoren-9-ylmethyl ester (121.4 mg, 0.2 mmol) (Starting Material 6), stirring is continued for 14 h. The mixture is diluted with CH$_2$Cl$_2$, the organic layer washed with saturated NaHCO$_3$ solution, dried over Na$_2$SO$_4$ and evaporated in vacuo. The crude product is stirred with a solution of CH$_2$Cl$_2$/piperidine 4:1 (5 mL) for 2 h, the mixture is evaporated and the residue purified by preparative HPLC (C18 column, 10-100% CH$_3$CN+0.1% TFA/H$_2$O+0.1% TFA, 20 min, flow 20 mL/min). The combined pure fractions are treated with K$_2$CO$_3$, CH$_3$CN is removed in vacuo, and the residual aqueous phase is extracted three times with CH$_2$Cl$_2$. The combined organic layers are dried (Na$_2$SO$_4$) and evaporated to afford the title compound as a yellowish solid. MS: 509.6 [M+H]$^+$; t$_R$ (HPLC, Nucleosil C18; 5-100% CH$_3$CN+0.1% TFA/H$_2$O+0.1% TFA for 8 min, flow 1.5 ml/min): 5.68 min.

Example 79

(3S*,5R*)-5-[(Tetrahydro-furan-2-carbonyl)-amino]-piperidine-3-carboxylic acid cyclopropyl-[1-(3-methoxy-propyl)-1H-indol-3-ylmethyl]-amide

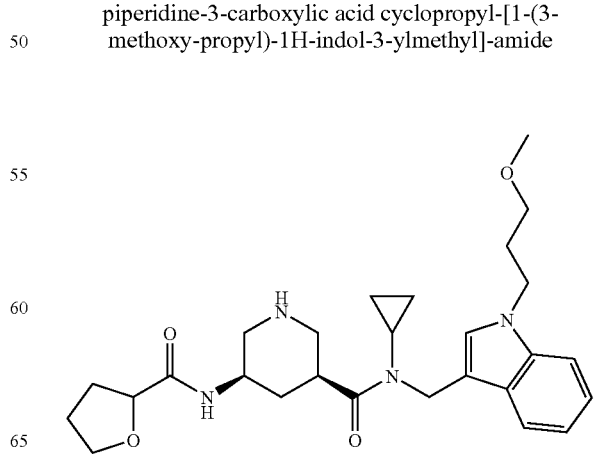

The title compound is prepared analogously as described in Example 61 using tetrahydrofuran-2-carbonyl chloride. MS: 483.6 [M+H]$^+$; t$_R$ (HPLC, Nucleosil C18; 5-100% CH$_3$CN+ 0.1% TFA/H$_2$O+0.1% TFA for 8 min, flow 1.5 ml/min): 4.61 min.

Example 80

(3S*,5R*)-5-Isobutyrylamino-piperidine-3-carboxylic acid cyclopropyl-[1-(3-methoxy-propyl)-1H-indol-3-ylmethyl]-amide

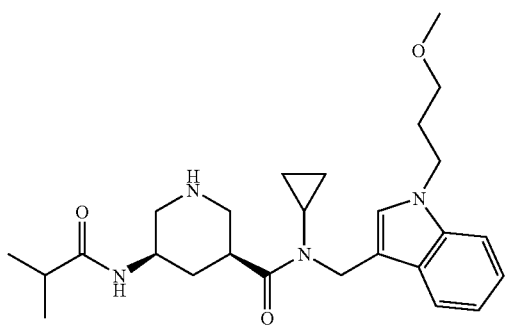

The title compound is prepared analogously as described in Example 61 using isobutyryl chloride. MS: 455.4 [M+H]$^+$; t$_R$ (HPLC, Nucleosil C18; 5-100% CH$_3$CN+0.1% TFA/H$_2$O+ 0.1% TFA for 8 min, flow 1.5 ml/min): 4.75 min.

Example 81

(3S*,5R*)-5-(Cyclopropanecarbonyl-amino)-piperidine-3-carboxylic acid cyclopropyl-[1-(3-methoxy-propyl)-1H-indol-3-ylmethyl]-amide

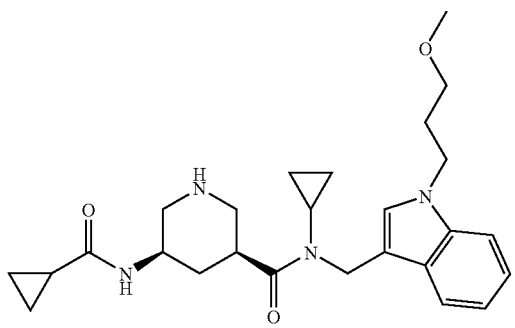

The title compound is prepared analogously as described in Example 61 using cyclopropanecarbonyl chloride. MS: 453.5 [M+H]$^+$; t$_R$ (HPLC, Nucleosil C18; 5-100% CH$_3$CN+0.1% TFA/H$_2$O+0.1% TFA for 8 min, flow 1.5 ml/min): 4.60 min.

Example 82

(3S*,5R*)-5-(2-Methoxy-acetylamino)-piperidine-3-carboxylic acid cyclopropyl-[1-(3-methoxy-propyl)-1H-indol-3-ylmethyl]-amide

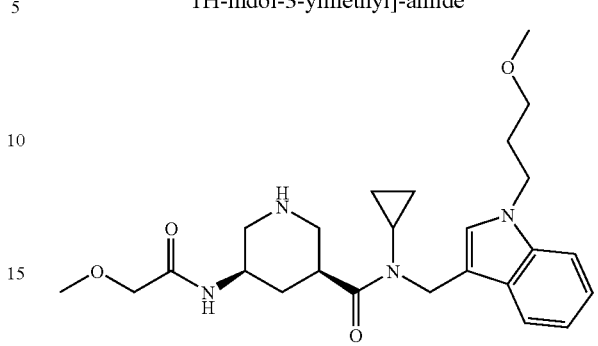

The title compound is prepared analogously as described in Example 61 using methoxy-acetyl chloride. MS: 457.4 [M+H]$^+$; t$_R$ (HPLC, Nucleosil C18; 5-100% CH$_3$CN+0.1% TFA/H$_2$O+0.1% TFA for 8 min, flow 1.5 ml/min): 4.43 min.

Example 83

(3S*,5R*)-5-(2-Methyl-2-phenyl-propionylamino)-piperidine-3-carboxylic acid cyclopropyl-[1-(3-methoxy-propyl)-1H-indol-3-ylmethyl]-amide

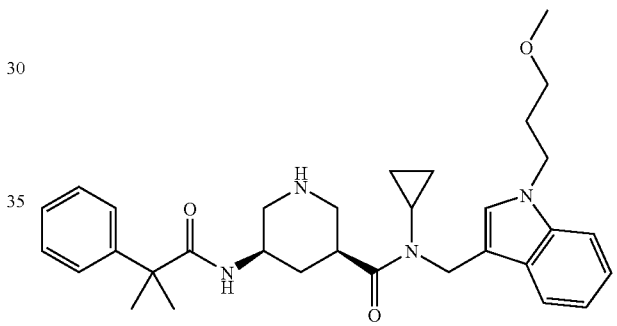

The title compound is prepared analogously as described in Example 78 using 2-methyl-2-phenyl-propionic acid. MS: 531.5 [M+H]$^+$; t$_R$ (HPLC, Nucleosil C18; 5-100% CH$_3$CN+ 0.1% TFA/H$_2$O+0.1% TFA for 8 min, flow 1.5 ml/min): 5.42 min.

Example 84

(3S*,5R*)-5-((S)-2-Acetylamino-4-methyl-pentanoylamino)-piperidine-3-carboxylic acid cyclopropyl-[1-(3-methoxy-propyl)-1H-indol-3-ylmethyl]-amide

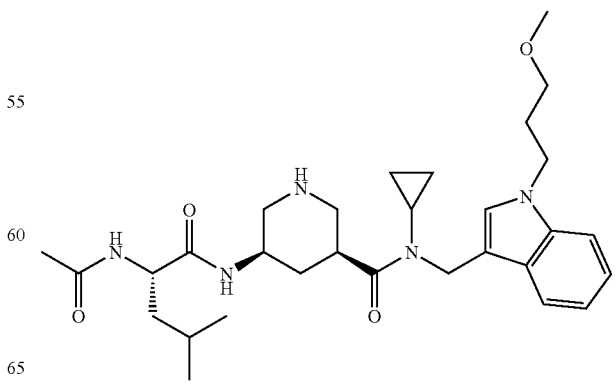

The title compound is prepared analogously as described in Example 78 using N-acetyl-L-leucine. MS: 540.6 [M+H]⁺; $t_R$ (HPLC, Nucleosil C18; 5-100% CH₃CN+0.1% TFA/H₂O+ 0.1% TFA for 8 min, flow 1.5 ml/min): 4.71 min and 4.79 min (mixture of diastereomers).

Example 85

(3S*,5R*)-5-[(1-Acetyl-piperidine-4-carbonyl)-amino]-piperidine-3-carboxylic acid cyclopropyl-[1-(3-methoxy-propyl)-1H-indol-3-ylmethyl]-amide

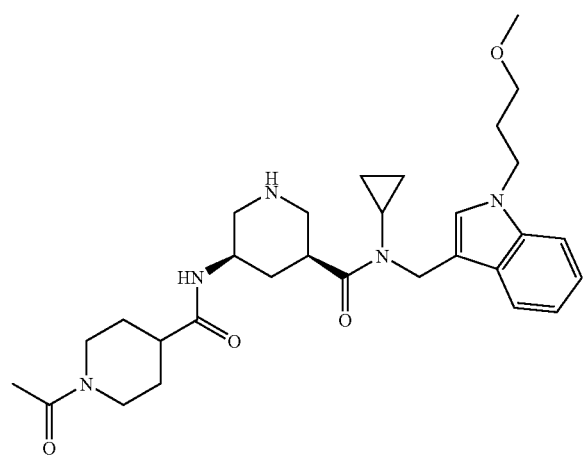

The title compound is prepared analogously as described in Example 78 using 1-acetyl-piperidine-4-carboxylic acid. MS: 538.6 [M+H]⁺; $t_R$ (HPLC, Nucleosil C18; 5-100% CH₃CN+0.1% TFA/H₂O+0.1% TFA for 8 min, flow 1.5 ml/min): 4.31 min.

Example 86

(3S*,5R*)-5-(2-Dimethylamino-acetylamino)-piperidine-3-carboxylic acid cyclopropyl-[1-(3-methoxy-propyl)-1H-indol-3-ylmethyl]-amide

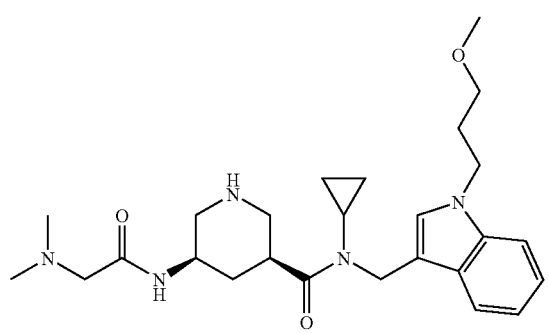

The title compound is prepared analogously as described in Example 78 using N,N-dimethylglycine. MS: 470.4 [M+H]⁺; $t_R$ (HPLC, Nucleosil C18; 5-100% CH₃CN+0.1% TFA/H₂O+ 0.1% TFA for 8 min, flow 1.5 ml/min): 3.88 min.

Example 87

(3S*,5R*)-5-(3-Hydroxy-2,2-dimethyl-propionylamino)-piperidine-3-carboxylic acid cyclopropyl-[1-(3-methoxy-propyl)-1H-indol-3-ylmethyl]-amide

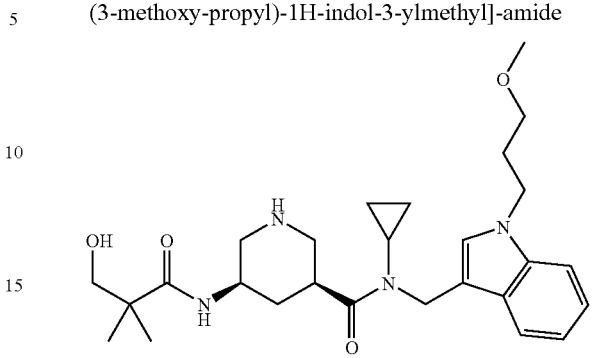

The title compound is prepared analogously as described in Example 78 using 3-hydroxy-2,2-dimethyl-propionic acid. MS: 485.4 [M+H]⁺; $t_R$ (HPLC, Nucleosil C18; 5-100% CH₃CN+0.1% TFA/H₂O+0.1% TFA for 8 min, flow 1.5 ml/min): 4.59 min.

Example 88

Cyclopropane-1,1-dicarboxylic acid amide ((3R*,5S*)-5-{cyclopropyl-[1-(3 methoxy-propyl)-1H-indol-3-ylmethyl]-carbamoyl}piperidin-3-yl)-amide

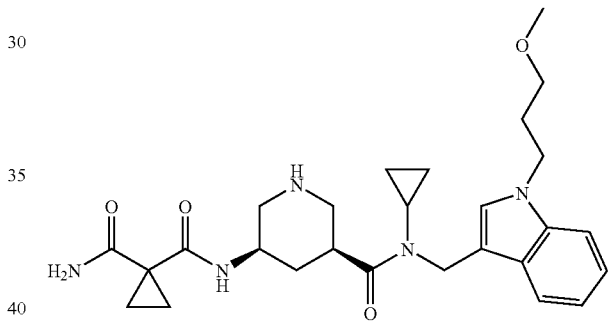

The title compound is prepared analogously as described in Example 78 using 1-carbamoyl-cyclopropanecarboxylic acid. MS: 496.4 [M+H]⁺; $t_R$ (HPLC, Nucleosil C18; 5-100% CH₃CN+0.1% TFA/H₂O+0.1% TFA for 8 min, flow 1.5 ml/min): 4.23 min.

Example 89

(3S*,5R*)-5-[(1-Cyano-cyclopropanecarbonyl)-amino]-piperidine-3-carboxylic acid cyclopropyl-[1-(3-methoxy-propyl)-1H-indol-3-ylmethyl]-amide

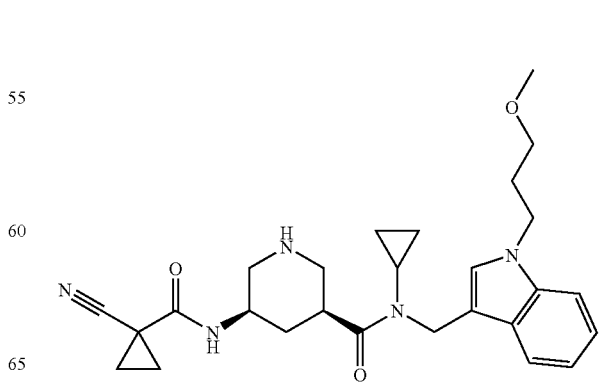

The title compound is prepared analogously as described in Example 78 using 1-cyano-cyclopropanecarboxylic acid. MS: 478.4 [M+H]$^+$; $t_R$ (HPLC, Nucleosil C18; 5-100% CH$_3$CN+0.1% TFA/H$_2$O+0.1% TFA for 8 min, flow 1.5 ml/min): 4.69 min.

Example 90

((3R*,5S*)-5-{Cyclopropyl-[1-(3-methoxy-propyl)-1H-indol-3-ylmethyl]-carbamoyl}-piperidin-3-yl)-carbamic acid benzyl ester

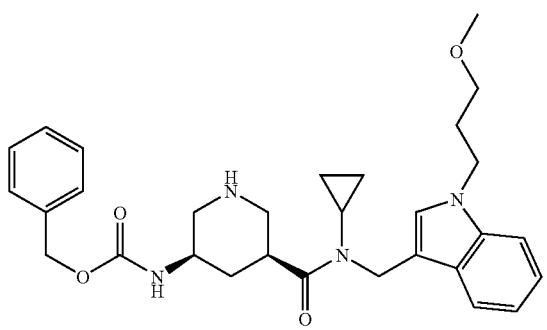

The title compound is prepared analogously as described in Example 61 using benzyl chloroformate. MS (LC-MS): 519.5 [M+H]$^+$; $t_R$ (HPLC, Nucleosil C18; 5-100% CH$_3$CN+0.1% TFA/H$_2$O+0.1% TFA for 8 min, flow 1.5 ml/min): 5.39 min.

Example 91

((3R*,5S*)-5-{Cyclopropyl-[1-(3-methoxy-propyl)-1H-indol-3-ylmethyl]-carbamoyl}-piperidin-3-yl)-carbamic acid 2-methoxy-ethyl ester

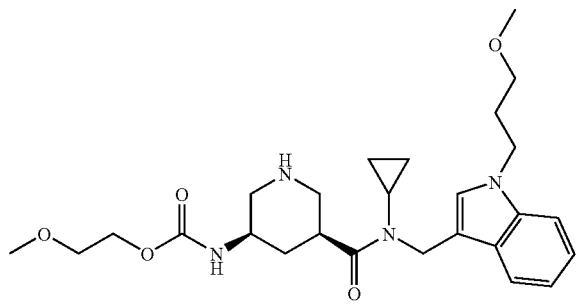

The title compound is prepared analogously as described in Example 61 using 2-methoxy-ethyl chloroformate. MS (LC-MS): 487.7 [M+H]$^+$; $t_R$ (HPLC, Nucleosil C18; 5-100% CH$_3$CN+0.1% TFA/H$_2$O+0.1% TFA for 8 min, flow 1.5 ml/min): 4.68 min.

Example 92

(3S*,5R*)-5-(2,2-Dimethyl-propionylamino)-piperidine-3-carboxylic acid [4-chloro-3-(3-methoxy-propoxy)-benzyl]-cyclopropyl-amide

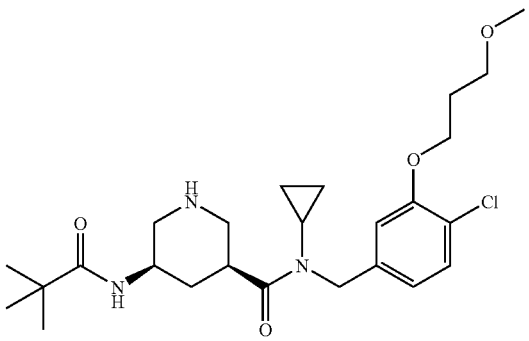

The title compound is prepared analogously as described in Example 61 using (3R*,5S*)-3-amino-5-{[4-chloro-3-(3-methoxy-propoxy)-benzyl]-cyclopropyl-carbamoyl}-piperidine-1-carboxylic acid 9H-fluoren-9-ylmethyl ester, hydrochloride and pivaloyl chloride. MS: 480.4 [M+H]$^+$; $t_R$ (HPLC, Nucleosil C18; 5-100% CH$_3$CN+0.1% TFA/H$_2$O+ 0.1% TFA for 8 min, flow 1.5 ml/min): 5.29 min.

The starting materials are prepared as follows:

A. (3R*,5S*)-3-amino-5-{[4-chloro-3-(3-methoxy-propoxy)-benzyl]-cyclopropyl-carbamoyl}-piperidine-1-carboxylic acid 9H-fluoren-9-ylmethyl ester, hydrochloride A mixture of (3S*,5R*)-5-tert-butoxycarbonylamino-piperidine-1,3-dicarboxylic acid 1-(9H-fluoren-9-ylmethyl) ester (1.78 g, 3.82 mmol), HCTU (1.75 g, 4.23 mmol) and DIPEA (265.3 µl, 1.55 mmol) in a 1:1 mixture of CH$_2$Cl$_2$/CH$_3$CN (20 ml) is stirred for 10 min at RT. After cooling to 5° C., [4-chloro-3-(3-methoxy-propoxy)-benzyl]-cyclopropyl-amine (1.04 g, 3.86 mmol) is added in one portion. The ice-bath is removed and the mixture stirred for 14 h at RT. The reaction mixture is diluted with ethyl acetate and washed twice with K$_2$CO$_3$ solution. The organic layer is dried (Na$_2$SO$_4$) and evaporated. The crude oil thus obtained is stirred with HCl (5M in 2-propanol, 12 ml, 60 mmol) for 1 h and then evaporated to afford the title compound as a yellow oil. $t_R$ (HPLC, Nucleosil C18; 5-100% CH$_3$CN+0.1% TFA/H$_2$O+0.1% TFA for 8 min, flow 1.5 ml/min): 6.31 min.

B. [4-chloro-3-(3-methoxy-propoxy)-benzyl]-cyclopropyl-amine

A mixture of 4-chloro-3-hydroxybenzoic acid (5 g, 29 mmol) and thionyl chloride (31 ml, 0.43 mol) in CH$_2$Cl$_2$/tetrahydrofuran (1:1; 50 ml) is stirred for 2 h at 50° C. The reaction mixture is evaporated in vacuo. After addition of CH$_2$Cl$_2$ (50 ml), the mixture is cooled to 5° C. and treated by dropwise addition of cyclopropylamine (8.1 ml, 115 mmol) during 1 h. The cooling bath is removed and the reaction stirred for 14 h at RT. After dilution with CH$_2$Cl$_2$, the organic phase is washed with a saturated NaHCO$_3$-solution and part of the solvent is removed in vacuo. The crystals thus formed are filtered off and dried to afford 4-chloro-N-cyclopropyl-3-hydroxy-benzamide as white crystals. MS: 212.2 [M+H]$^+$; $t_R$ (HPLC, Nucleosil C18; 5-100% CH$_3$CN+0.1% TFA/H$_2$O+ 0.1% TFA for 8 min, flow 1.5 ml/min): 4.12 min. DMA (50 ml) is added to the amide (4.6 g, 21.7 mmol) followed by K₂CO₃ (4.8 g, 34.7 mmol) and toluene-4-sulfonic acid 3-methoxy-propyl ester (6.89 g, 28.2 mmol). The mixture is stirred for 14 h at 140° C., DMA is removed in vacuo and the residue distributed between ethyl acetate and H₂O. The aqueous layer is separated and extracted twice with ethyl acetate. The combined organic layers are dried (Na₂SO₄) and evaporated to afford 4-chloro-N-cyclopropyl-3-(3-methoxy-propoxy)-benzamide as a brownish oil which crystallises when kept at room temperature. MS: 284.3 [M+H]⁺; $t_R$ (HPLC, Nucleosil C18; 5-100% CH₃CN+0.1% TFA/H₂O+0.1% TFA for 8 min, flow 1.5 ml/min): 5.31 min. The crude intermediate (3 g, 10.6 mmol) is diluted with tetrahydrofuran (28 ml), the mixture is stirred, cooled to −10° C. and treated dropwise under N₂ during 1 h with a borane tetrahydrofuran complex solution (~1 M in tetrahydrofuran, 31.8 ml, 31.8 mmol). Stirring is continued for 80 min at −10° C. and for 14 h at RT. The reaction is quenched with H₂O, acidified with 2N HCl, basified with 2N NaOH and extracted three times with ethyl acetate. The combined organic extracts are dried (Na₂SO₄) and evaporated. The borane complex thus received is treated with methanol (40 ml) and kept for 6 h at reflux temperature. Methanol is distilled off and the residue stirred for 10 min with 1N HCl. The mixture is basified with 1N NaOH and extracted three times with ethyl acetate. The combined organic extracts are dried (Na₂SO₄) and evaporated to yield [4-chloro-3-(3-methoxy-propoxy)-benzyl]-cyclopropyl-amine as a yellow oil. MS: 270.3 [M+H]⁺; $t_R$ (HPLC, Nucleosil C18; 5-100% CH₃CN+0.1% TFA/H₂O+0.1% TFA for 8 min, flow 1.5 ml/min): 4.43 min.

Example 93

((3R*,5S*)-5-{[4-Chloro-3-(3-methoxy-propoxy)-benzyl]-cyclopropyl-carbamoyl}-piperidin-3-yl)-carbamic acid tert-butyl ester

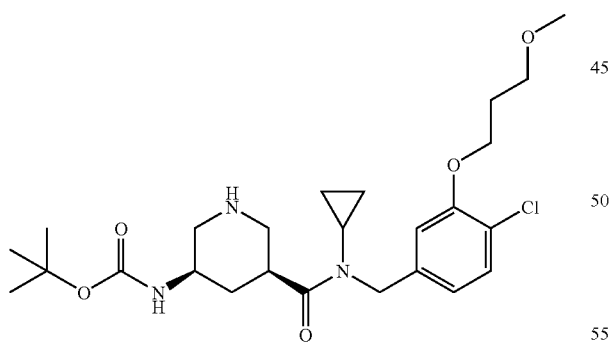

The title compound is prepared analogously as described in Example 61 using (3R*,5S*)-3-amino-5-{[4-chloro-3-(3-methoxy-propoxy)-benzyl]-cyclopropyl-carbamoyl}-piperidine-1-carboxylic acid 9H-fluoren-9-ylmethyl ester, hydrochloride (Example 92A.) and di-tert-butyl dicarbonate. MS: 496.4 [M+H]⁺; $t_R$ (HPLC, Nucleosil C18; 5-100% CH₃CN+ 0.1% TFA/H₂O+0.1% TFA for 8 min, flow 1.5 ml/min): 5.41 min.

Example 94

(3S*,5R*)-5-(Cyclopropanecarbonyl-amino)-piperidine-3-carboxylic acid [4-chloro-3-(3-methoxy-propoxy)-benzyl]-cyclopropyl-amide, trifluoroacetate

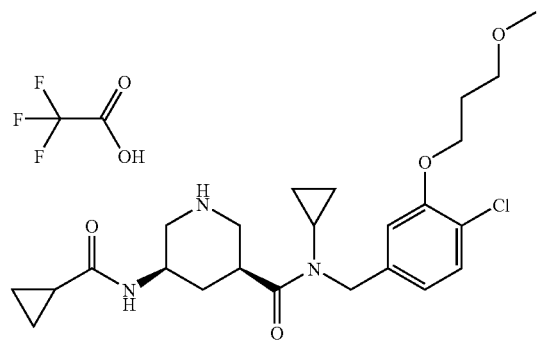

The title compound is prepared analogously as described in Example 61 using (3R*,5S*)-3-amino-5-{[4-chloro-3-(3-methoxy-propoxy)-benzyl]-cyclopropyl-carbamoyl}-piperidine-1-carboxylic acid 9H-fluoren-9-ylmethyl ester, hydrochloride (Example 92A.) and cyclopropane-carbonyl chloride. After preparative HPLC the pure fractions are evaporated without the addition of K₂CO₃. MS: 464.4 [M+H]⁺; $t_R$ (HPLC, Nucleosil C18; 5-100% CH₃CN+0.1% TFA/H₂O+0.1% TFA for 8 min, flow 1.5 ml/min): 4.95 min.

Example 95

(3S*,5R*,5-(Cyclobutanecarbonyl-amino)-piperidine-3-carboxylic acid [4-chloro-3-(3-methoxy-propoxy)-benzyl]-cyclopropyl-amide

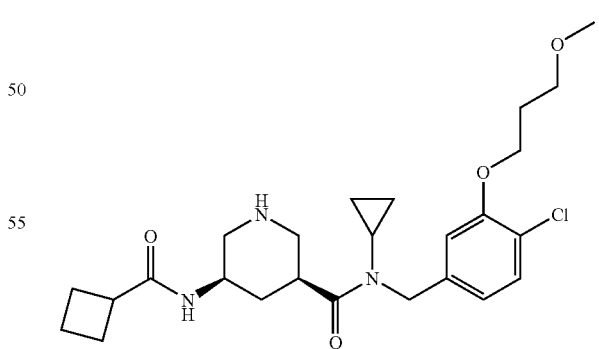

The title compound is prepared analogously as described in Example 61 using (3R*,5S*)-3-amino-5-{[4-chloro-3-(3-methoxy-propoxy)-benzyl]-cyclopropyl-carbamoyl}piperidine-1-carboxylic acid 9H-fluoren-9-ylmethyl ester, hydrochloride (Example 92A.) and cyclobutanecarbonyl chloride. MS: 478.4 [M+H]⁺; $t_R$

Example 96

(3S*,5R*)-5-Isobutyrylamino-piperidine-3-carboxylic acid [4-chloro-3-(3-methoxy-propoxy)-benzyl]-cyclopropyl-amide

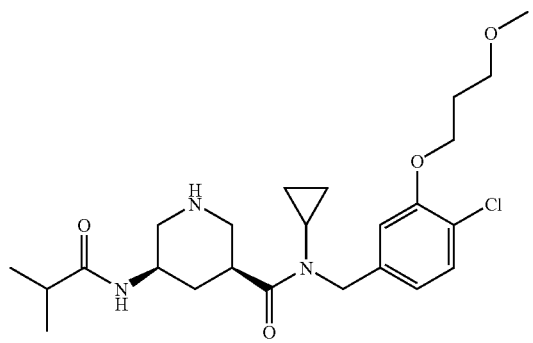

The title compound is prepared analogously as described in Example 61 using (3R*,5S*)-3-amino-5-{[4-chloro-3-(3-methoxy-propoxy)-benzyl]-cyclopropyl-carbamoyl}-piperidine-1-carboxylic acid 9H-fluoren-9-ylmethyl ester, hydrochloride (Example 92A.) and isobutyryl chloride. MS: 466.4 [M+H]$^+$; $t_R$ (HPLC, Nucleosil C18; 5-100% CH$_3$CN+0.1% TFA/H$_2$O+0.1% TFA for 8 min, flow 1.5 ml/min): 5.04 min.

Example 97

(3S*,5R*)-5-(3-tert-Butyl-ureido)-piperidine-3-carboxylic acid [4-chloro-3-(3-methoxy-propoxy)-benzyl]-cyclopropyl-amide, trifluoroacetate

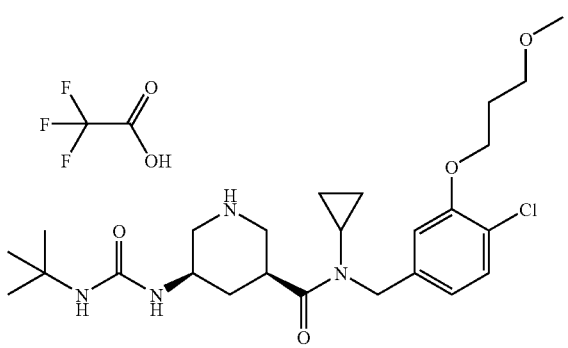

The title compound is prepared analogously as described in Example 98 using (3R*,5S*)-3-amino-5-{[4-chloro-3-(3-methoxy-propoxy)-benzyl]-cyclopropyl-carbamoyl}-piperidine-1-carboxylic acid 9H-fluoren-9-ylmethyl ester, hydrochloride (Example 92A.) and tert-butyl isocyanate. After preparative HPLC the pure fractions are evaporated without the addition of K$_2$CO$_3$. MS: 495.5 [M+H]$^+$; $t_R$ (HPLC, Nucleosil C18; 5-100% CH$_3$CN+0.1% TFA/H$_2$O+0.1% TFA for 8 min, flow 1.5 ml/min): 5.32 min.

Example 98

(3S*,5R*)-5-(3-tert-Butyl-ureido)-piperidine-3-carboxylic acid cyclopropyl-[3-(3-methoxy-propoxy)-4-methyl-benzyl]-amide

MW: 474.6490
MF: C26H42N4O4
NVP-BFQ579-NX-1 WB 5072/1

A mixture of (3R*,5S*)-3-amino-5{-cyclopropyl-[3-(3-methoxy-propoxy)-4-methyl-benzyl]-carbamoyl}-piperidine-1-carboxylic acid 9H-fluoren-9-ylmethyl ester, hydrochloride (110 mg, 0.173 mmol), tert-butyl isocyanate (40 µl, 0.35 mmol), DIPEA (34.2 µl, 0.2 mmol) and 1,2-dichloroethane (2 ml) is shaken for 14 h at 50° C. The mixture is diluted with CH$_2$Cl$_2$ and washed with NaHCO$_3$ solution. The organic layer is dried (Na$_2$SO$_4$) and evaporated. The crude product is stirred with a solution of CH$_2$Cl$_2$/piperidine 4:1 (5 mL) for 1 h, the mixture is evaporated and the residue purified by preparative HPLC (C18 column, 10-100% CH$_3$CN+0.1% TFA/H$_2$O+0.1% TFA, 20 min, flow 20 mL 1 min). The combined pure fractions are treated with K$_2$CO$_3$, CH$_3$CN is removed in vacuo, and the residual aqueous phase is extracted three times with CH$_2$Cl$_2$. The combined organic layers are dried (Na$_2$SO$_4$) and evaporated to afford the title compound as a colorless resin. MS: 475.6 [M+H]$^+$; $t_R$ (HPLC, Nucleosil C18; 5-100% CH$_3$CN+0.1% TFA/H$_2$O+0.1% TFA for 8 min, flow 1.5 ml/min): 5.14 min.

The starting materials are prepared as follows:

A. (3R*,5S*)-3-amino-5-{cyclopropyl-[3-(3-methoxy-propoxy)-4-methyl-benzyl]-carbamoyl}-piperidine-1-carboxylic acid 9H-fluoren-9-ylmethyl ester, hydrochloride The title compound is prepared analogously as described in Example 92A. using (3S*,5R*)-5-tert-butoxycarbonylamino-piperidine-1,3-dicarboxylic acid 1-(9H-fluoren-9-ylmethyl) ester and cyclopropyl-[3-(3-methoxy-propoxy)-4-methyl-benzyl]-amine. MS: 598.6 [M+H]$^+$; $t_R$ (HPLC, Nucleosil C18; 5-100% CH$_3$CN+0.1% TFA/H$_2$O+0.1% TFA for 8 min, flow 1.5 ml/min): 6.35 min.

B. Cyclopropyl-[3-(3-methoxy-propoxy)-4-methyl-benzyl]-amine

The title compound is prepared analogously as described in Example 92B. starting from 3-hydroxy-4-methylbenzoic acid. MS: 250.3 [M+H]$^+$; $t_R$ (HPLC, Nucleosil C18; 5-100% CH$_3$CN+0.1% TFA/H$_2$O+0.1% TFA for 8 min, flow 1.5 ml/min): 4.29 min.

Example 99

(3S*,5R*)-5-(3-Benzyl-ureido)-piperidine-3-carboxylic acid cyclopropyl-[3-(3-methoxy-propoxy)-4-methyl-benzyl]-amide

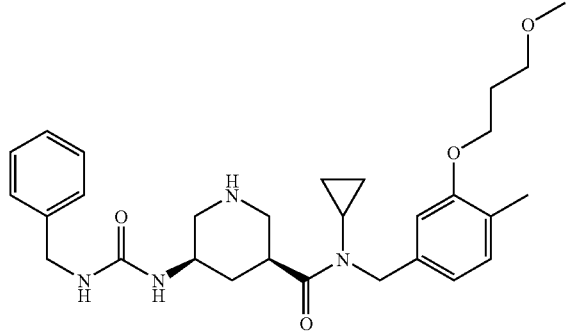

The title compound is prepared analogously as described in Example 98 using (3R*,5S*)-3-amino-5-{cyclopropyl-[3-(3-methoxy-propoxy)-4-methyl-benzyl]-carbamoyl}-piperidine-1-carboxylic acid 9H-fluoren-9-ylmethyl ester, hydrochloride (Example 98A.) and benzylisocyanate. MS: 509.6 [M+H]$^+$; $t_R$ (HPLC, Nucleosil C18; 5-100% CH$_3$CN+0.1% TFA/H$_2$O+0.1% TFA for 8 min, flow 1.5 ml/min): 5.22 min.

Example 100

((3R*,5S*)-5-{Cyclopropyl-[3-(3-methoxy-propoxy)-4-methyl-benzyl]-carbamoyl}-piperidin-3-yl)-carbamic acid isobutyl ester

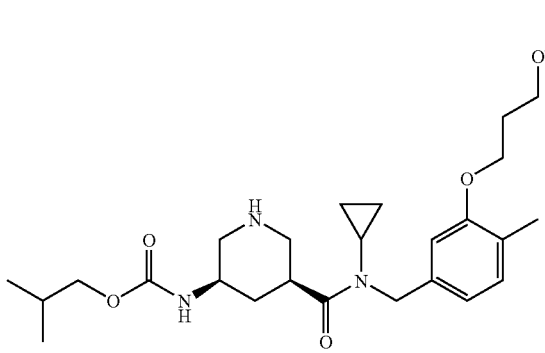

The title compound is prepared analogously as described in Example 61 using (3R*,5S*)-3-amino-5-{cyclopropyl-[3-(3-methoxy-propoxy)-4-methyl-benzyl]-carbamoyl}-piperidine-1-carboxylic acid 9H-fluoren-9-ylmethyl ester, hydrochloride (Example 98A.) and isobutyl chloroformate. MS: 476.6 [M+H]$^+$; $t_R$ (HPLC, Nucleosil C18; 5-100% CH$_3$CN+ 0.1% TFA/H$_2$O+0.1% TFA for 8 min, flow 1.5 ml/min): 5.40 min.

Example 101

(3S*,5R*)-5-(2,2-Dimethyl-propionylamino)-piperidine-3-carboxylic acid cyclopropyl-[3-(3-methoxy-propoxy)-4-methyl-benzyl]-amide

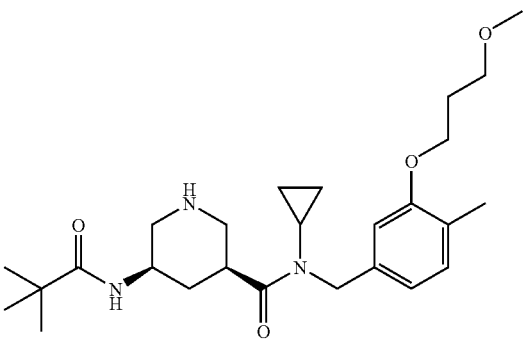

The title compound is prepared analogously as described in Example 61 using (3R*,5S*)-3-amino-5-{cyclopropyl-[3-(3-methoxy-propoxy)-4-methyl-benzyl]-carbamoyl}-piperidine-1-carboxylic acid 9H-fluoren-9-ylmethyl ester, hydrochloride (Example 98A.) and pivaloyl chloride. MS: 460.6 [M+H]$^+$; $t_R$ (HPLC, Nucleosil C18; 5-100% CH$_3$CN+0.1% TFA/H$_2$O+0.1% TFA for 8 min, flow 1.5 ml/min): 5.07 min.

Example 102

(3S*,5R*)-5-(Cyclobutanecarbonyl-amino)-piperidine-3-carboxylic acid cyclopropyl-[3-(3-methoxy-propoxy)-4-methyl-benzyl]-amide

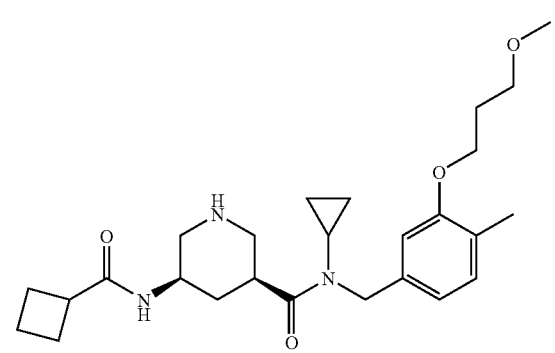

The title compound is prepared analogously as described in Example 61 using (3R*,5S*)-3-amino-5-{cyclopropyl-[3-(3-methoxy-propoxy)-4-methyl-benzyl]-carbamoyl}piperidine-1-carboxylic acid 9H-fluoren-9-ylmethyl ester, hydrochloride (Example 98A.) and cyclobutanecarbonyl chloride. MS: 458.7 [M+H]$^+$; $t_R$ (HPLC, Nucleosil C18; 5-100% CH$_3$CN+0.1% TFA/H$_2$O+0.1% TFA for 8 min, flow 1.5 ml/min): 4.88 min.

Example 103

(3S*,5R*)-5-(3-tert-Butyl-ureido)-piperidine-3-carboxylic acid cyclopropyl-[3-methoxy-5-(3-methoxy-propoxy)-benzyl]-amide, trifluoroacetate

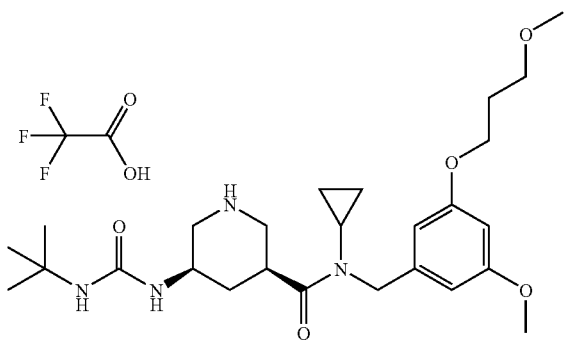

The title compound is prepared analogously as described in Example 98 using (3R*5S*)-3-amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride and tert-butyl isocyanate. After preparative HPLC the fractions are not basified prior to evaporation. MS: 491.5 [M+H]$^+$; $t_R$ (HPLC, Nucleosil C18; 5-100% CH$_3$CN+0.1% TFA/H$_2$O+0.1% TFA for 8 min, flow 1.5 ml/min): 4.75 min.

The starting materials are prepared as follows:
A. (3R*,5S*)-3-Amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride The title compound is prepared analogously as described in Example 92A. using (3S*,5R*)-5-tert-butoxycarbonylamino-piperidine-1,3-dicarboxylic acid 1-(9H-fluoren-9-ylmethyl) ester and cyclopropyl-[3-methoxy-5-(3-methoxy-propoxy)-benzyl]-amine. MS: 614.4 [M+H]$^+$; $t_R$ (HPLC, Nucleosil C18; 5-100% CH$_3$CN+0.1% TFA/H$_2$O+0.1% TFA for 8 min, flow 1.5 ml/min): 5.80 min.

B. Cyclopropyl-[3-methoxy-5-(3-methoxy-propoxy)-benzyl]-amine

A mixture of 3-hydroxy-5-methoxy-benzoic acid methyl ester (4.71 g, 25.9 mmol), K$_2$CO$_3$ (5.72 g, 41.4 mmol) and toluene-4-sulfonic acid 3-methoxy-propyl ester (8.18 g, 33.5 mmol) in DMA (60 ml) is stirred for 14 h at 140° C. The mixture is distributed between ethyl acetate and H$_2$O. The aqueous layer is separated and extracted twice with ethyl acetate. The combined organic layers are dried (Na$_2$SO$_4$) and evaporated to afford crude 3-methoxy-5-(3-methoxy-propoxy)-benzoic acid methyl ester. MS: 255.3 [M+H]$^+$; $t_R$ (HPLC, Nucleosil C18; 5-100% CH$_3$CN+0.1% TFA/H$_2$O+0.1% TFA for 8 min, flow 1.5 ml/min): 6.12 min. A mixture of 3-methoxy-5-(3-methoxy-propoxy)-benzoic acid methyl ester (6.94 g, 27.3 mmol), aqueous 5N NaOH solution (25 ml, 125 mmol) and methanol (50 ml) is stirred for 1 h at 50° C. Methanol is evaporated and the residue distributed between 2N HCl and ethyl acetate. The aqueous layer is separated and extracted twice with ethyl acetate. The combined organic extracts are dried (Na$_2$SO$_4$) and evaporated to afford crude 3-methoxy-5-(3-methoxy-propoxy)-benzoic acid. $t_R$ (HPLC, Nucleosil C18; 5-100% CH$_3$CN+0.1% TFA/H$_2$O+0.1% TFA for 8 min, flow 1.5 ml/min): 4.97 min. A mixture of 3-methoxy-5-(3-methoxy-propoxy)-benzoic acid (6.55 g, 27.3 mmol), thionyl chloride (19.8 ml, 273 mmol) in CH$_2$Cl$_2$/tetrahydrofuran (1:1; 30 ml) is stirred for 2 h at 45° C. The reaction mixture is evaporated in vacuo. After addition of CH$_2$Cl$_2$ (30 ml), the mixture is cooled to 5° C. and treated dropwise with cyclopropylamine. The cooling bath is removed and the reaction stirred for 14 h at RT. After dilution with CH$_2$Cl$_2$, the organic phase is washed with a saturated NaHCO$_3$-solution, dried over Na$_2$SO$_4$ and evaporated to afford N-cyclopropyl-3-methoxy-5-(3-methoxy-propoxy)-benzamide. MS: 280.3 [M+H]$^+$; $t_R$ (HPLC, Nucleosil C18; 5-100% CH$_3$CN+0.1% TFA/H$_2$O+0.1% TFA for 8 min, flow 1.5 ml/min): 4.79 min. N-Cyclopropyl-3-methoxy-5-(3-methoxy-propoxy)-benzamide (7.92 g, 28.4 mmol) is diluted with tetrahydrofuran (50 ml), the mixture is stirred, cooled to −10° C. and treated by dropwise addition under N$_2$ during 1 h of a borane tetrahydrofuran complex solution (~1M in tetrahydrofuran, 85.2 ml, 85.2 mmol). The cooling bath is removed and stirring is continued for 14 h at RT. The reaction is quenched with H$_2$O, acidified with 4N HCl, basified with 4N NaOH and extracted three times with ethyl acetate. The combined organic extracts are dried (Na$_2$SO$_4$) and evaporated. The borane complex thus received is treated with methanol (60 ml) and kept for 5 h at reflux temperature. Methanol is distilled off and the residue is stirred for a few minutes with 4N HCl. The mixture is basified with 4N NaOH and extracted three times with ethyl acetate. The combined organic extracts are dried (Na$_2$SO$_4$) and evaporated to yield cyclopropyl-[3-methoxy-5-(3-methoxy-propoxy)-benzyl]-amine as a brown oil. MS: 266.4 [M+H]$^+$; $t_R$ (HPLC, Nucleosil C18; 5-100% CH$_3$CN+0.1% TFA/H$_2$O+0.1% TFA for 8 min, flow 1.5 ml/min): 3.85 min.

Example 104

(3S*,5R*)-5-(3-Benzyl-ureido)-piperidine-3-carboxylic acid cyclopropyl-[3-methoxy-5-(3-methoxy-propoxy)-benzyl]-amide, trifluoroacetate

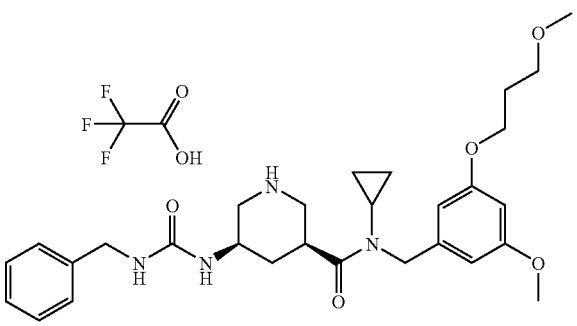

The title compound is prepared analogously as described in Example 98 using (3R*5S*)-3-amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride (Example 103 A.) and benzyl isocyanate. After preparative HPLC the fractions are not basified prior to evaporation. MS: 525.5 [M+H]$^+$; $t_R$ (HPLC, Nucleosil C18; 5-100% CH$_3$CN+0.1% TFA/H$_2$O+0.1% TFA for 8 min, flow 1.5 ml/min): 4.86 min.

Example 105

((3R*,5S*)-5-{Cyclopropyl-[3-methoxy-5-(3-methoxy-propoxy)-benzyl]-carbamoyl}-piperidin-3-yl)-carbamic acid isobutyl ester, trifluoroacetate

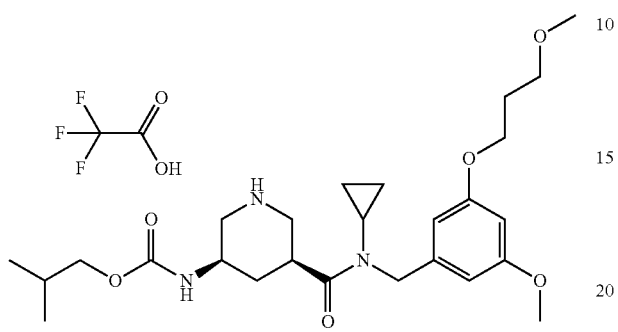

MW: 491.6332 114.0243
MF: C26H41N3O6•C2HF3O2
NVP-BFQ886-Al-1 WB 5082/1

The title compound is prepared analogously as described in Example 61 using (3R*5S*)-3-amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride (Example 103 A.) and isobutyl chloroformate. After preparative HPLC the fractions are not basified prior to evaporation. MS: 492.5 [M+H]⁺; t_R (HPLC, Nucleosil C18; 5-100% CH₃CN+0.1% TFA/H₂O+0.1% TFA for 8 min, flow 1.5 ml/min): 5.05 min.

Example 106

((3R*,5S*)-5-{Cyclopropyl-[3-methoxy-5-(3-methoxy-propoxy)-benzyl]-carbamoyl}-piperidin-3-yl)-carbamic acid tert-butyl ester

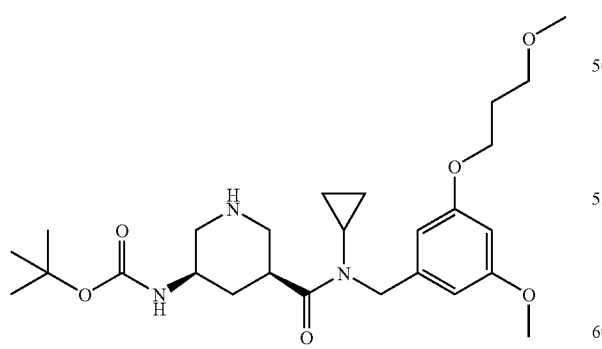

The title compound is prepared analogously as described in Example 61 using (3R*5S*)-3-amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride (Example 103 A.) and di-tert-butyl dicarbonate. MS: 492.4 [M+H]⁺; t_R (HPLC, Nucleosil C18; 5-100% CH₃CN+0.1% TFA/H₂O+0.1% TFA for 8 min, flow 1.5 ml/min): 5.01 min.

Example 107

(3S*,5R*)-5-(3,3-Dimethyl-butyrylamino)-piperidine-3-carboxylic acid cyclopropyl-[3-methoxy-5-(3-methoxy-propoxy)-benzyl]-amide, trifluoroacetate

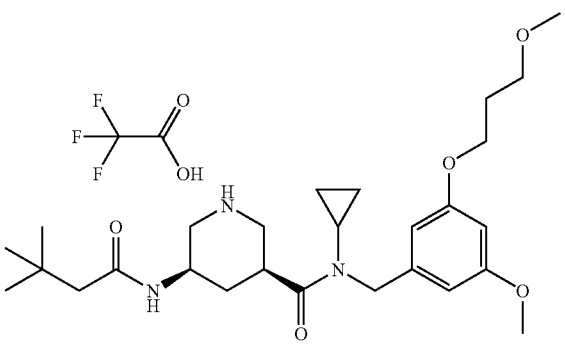

The title compound is prepared analogously as described in Example 61 using (3R*5S*)-3-amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride (Example 103 A.) and tert-butyl-acetyl chloride. After preparative HPLC the fractions are not basified prior to evaporation. MS: 490.4 [M+H]⁺; t_R (HPLC, Nucleosil C18; 5-100% CH₃CN+0.1% TFA/H₂O+0.1% TFA for 8 min, flow 1.5 ml/min): 4.81 min.

Example 108

(3S*,5R*-5-(Cyclobutanecarbonyl-amino)-piperidine-3-carboxylic acid cyclopropyl-[3-methoxy-5-(3-methoxy-propoxy)-benzyl]-amide, trifluoroacetate

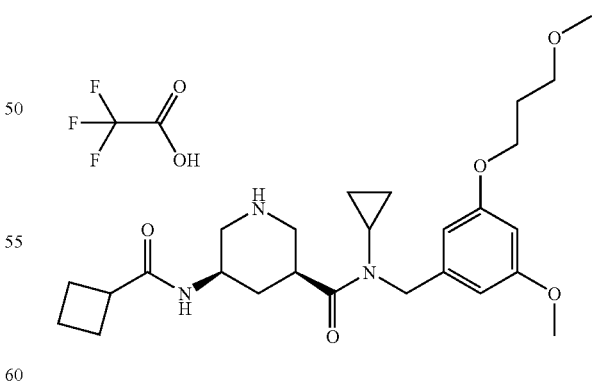

The title compound is prepared analogously as described in Example 61 using (3R*5S*)-3-amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride (Example 103 A.) and cyclobutanecarbonyl chloride. After preparative HPLC the fractions are not basified prior to evaporation. MS: 474.5 [M+H]⁺; t_R (HPLC,

Example 109

(3S*,5R*)-5-(2,2-Dimethyl-propionylamino)-piperidine-3-carboxylic acid cyclopropyl-[3-methoxy-5-(3-methoxy-propoxy)-benzyl]-amide, trifluoroacetate

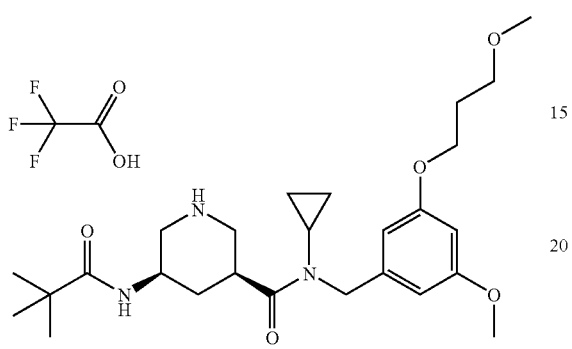

The title compound is prepared analogously as described in Example 61 using (3R*5S*)-3-amino-5-{cyclopropyl-[3-methoxy-5-(3-methoxy-propoxy)-benzyl]-carbamoyl}-piperidine-1-carboxylic acid 9H-fluoren-9-ylmethyl ester, hydrochloride (Example 103 A.) and pivaloyl chloride. After preparative HPLC the fractions are not basified prior to evaporation. MS: 476.4 [M+H]+; $t_R$ (HPLC, Nucleosil C18; 5-100% CH$_3$CN+0.1% TFA/H$_2$O+0.1% TFA for 8 min, flow 1.5 ml/min): 4.72 min.

Example 110

(3S*,5R*)-5-(3,3-Dimethyl-butyrylamino)-piperidine-3-carboxylic acid cyclopropyl-(2,3-dichloro-benzyl)-amide

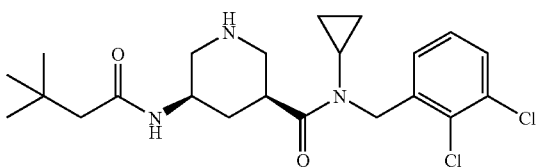

The title compound is prepared analogously as described in Example 61 using (3R*,5S*)-3-amino-5-[cyclopropyl-(2,3-dichloro-benzyl)-carbamoyl]-piperidine-1-carboxylic acid 9H-fluoren-9-ylmethyl ester; hydrochloride and tert-butyl acetyl chloride. MS (LC-MS): 440.5/442.4 [M+H]+; $t_R$ (HPLC, Nucleosil C18; 5-100% CH$_3$CN+0.1% TFA/H$_2$O+ 0.1% TFA for 8 min, flow 1.5 ml/min): 5.28 min.

The starting material is prepared as follows:

A. (3R*,5S*)-3-amino-5-[cyclopropyl-(2,3-dichloro-benzyl)-carbamoyl]-piperidine-1-carboxylic acid 9H-fluoren-9-ylmethyl ester; hydrochloride To a stirred, ice-cooled mixture of (3S*,5R*)-5-tert-butoxycarbonylamino-piperidine-1,3-dicarboxylic acid 1-(9H-fluoren-9-ylmethyl) ester (2.33 g, 5 mmol), cyclopropyl-(2,3-dichloro-benzyl)-amine (see WO 03/093267) (1.12 g, 5.2 mmol) and N-ethyldiisopropylamine (6.85 ml, 40 mmol) in dimethylacetamide (30 ml), propylphosphonic anhydride solution (~50% in DMF, 4.8 ml, ~7.5 mmol) is added. After stirring for 14 h at RT, DMA is evaporated and the residue is distributed between ethyl acetate and 10% aqueous K$_2$CO$_3$ solution. The organic layer is dried (Na$_2$SO$_4$), evaporated in vacuo and the residue purified by preparative HPLC (YMC-Pack, Pro C18, 10-100% CH$_3$CN+0.1% TFA/H$_2$O+0.1% TFA, 20 min, flow 20 ml/min). The combined pure fractions are treated with solid K$_2$CO$_3$, CH$_3$CN is removed in vacuo and the residual aqueous layer is extracted twice with CH$_2$Cl$_2$. The combined organic layers are dried (Na$_2$SO$_4$) and evaporated. The residue is stirred with HCl in 2-propanol (5 N, 10 ml, 50 mmol) and evaporated to afford the title compound as a white amorphous solid. $t_R$ (HPLC, Nucleosil C18; 5-100% CH$_3$CN+0.1% TFA/H$_2$O+0.1% TFA for 8 min, flow 1.5 ml/min): 6.22 min.

Example 111

{(3R*,5S*)-5-[Cyclopropyl-(2,3-dichloro-benzyl)-carbamoyl]-piperidin-3-yl}-carbamic acid 2-methoxy-ethyl ester

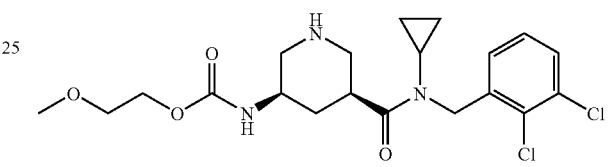

The title compound is prepared analogously as described in Example 61 using (3R*,5S*)-3-amino-5-[cyclopropyl-(2,3-dichloro-benzyl)-carbamoyl]-piperidine-1 carboxylic acid 9H-fluoren-9-ylmethyl ester; hydrochloride and 2-methoxy-ethyl chloroformate. MS (LC-MS): 444.2/446.1 [M+H]+; $t_R$ (HPLC, Nucleosil C18; 5-100% CH$_3$CN+0.1% TFA/H$_2$O+ 0.1% TFA for 8 min, flow 1.5 ml/min): 4.74 min.

Example 112

{(3R*,5S*)-5-[Cyclopropyl-(2,3-dimethyl-benzyl)-carbamoyl]-piperidin-3-yl}-carbamic acid tert-butyl ester

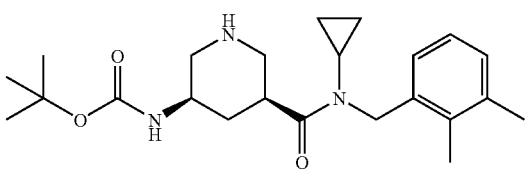

To a stirred, ice-cooled mixture of (3S*,5R*)-5-tert-butoxycarbonylamino-piperidine-1,3-dicarboxylic acid 1-(9H-fluoren-9-ylmethyl) ester (5.0 g, 10.7 mmol), cyclopropyl-(2,3-dimethyl-benzyl)-amine (CAS 625437-38-9) (4.41 g, 11.8 mmol) and N-ethyldiisopropylamine (14.7 ml, 85.7 mmol) in dimethylacetamide (50 ml), propylphosphonic anhydride solution (~50% in DMF, 10 ml, ~16 mmol) is added. After stirring for 14 h at RT, the residue is distributed between ethyl acetate and 10% aqueous K$_2$CO$_3$ solution. The organic layer is dried (Na$_2$SO$_4$) and evaporated in vacuo. Part of the residue (365 mg, 0.58 mmol) is treated with a mixture of CH$_2$Cl$_2$/piperidine (4:1; 10 ml) and stirred at RT for 1 h. The reaction mixture is then evaporated and the residue purified via preparative HPLC to afford the title compound. MS: 402.5

[M+H]⁺; $t_R$ (HPLC, Nucleodur 100; 10-100% CH₃CN+0.1% TFA/H₂O+0.1% TFA for 10 min, flow 1.5 ml/min): 4.77 min.

Example 113

(3S*,5R*)-5-(3,3-Dimethyl-butyrylamino)-piperidine-3-carboxylic acid cyclopropyl-(2,3-dimethyl-benzyl)-amide, trifluoroacetate

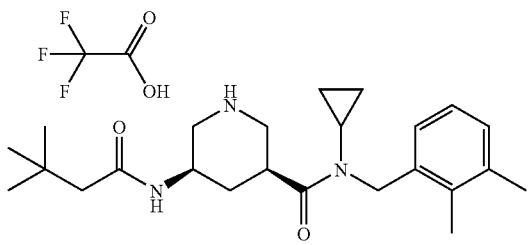

The title compound is prepared analogously as described in Example 61 using (3R*,5S*)-3-amino-5-[cyclopropyl-(2,3-dimethyl-benzyl)-carbamoyl]-piperidine-1-carboxylic acid 9H-fluoren-9-ylmethyl ester; hydrochloride and tert-butylacetyl chloride. MS: 400.6 [M+H]⁺; $t_R$ (HPLC, Nucleodur 100; 10-100% CH₃CN+0.1% TFA/H₂O+0.1% TFA for 10 min, flow 1.5 ml/min): 8.6 min.

Starting Material:

A. (3R*,5S*)-3-Amino-5-[cyclopropyl-(2,3-dimethyl-benzyl)-carbamoyl]-piperidine-1-carboxylic acid 9H-fluoren-9-ylmethyl ester; hydrochloride The starting material is prepared analogously as described in Example 110 A. using (3S*,5R*)-5-tert-butoxycarbonylamino-piperidine-1,3-dicarboxylic acid 1-(9H-fluoren-9-ylmethyl) ester and cyclopropyl-(2,3-dimethyl-benzyl)-amine. MS: 524.5 [M+H]⁺.

Starting Materials 2A and 2B: Enantiomerically pure starting materials

Racemic (3S*,5R*)-5-tert-butoxycarbonylamino-piperidine-1,3-dicarboxylic acid 1-(9H-fluoren-9-ylmethyl) ester (cf. starting material 2) is separated into its enantiomers on a Chiralcel OJ column with n-hexane/ethanol 8:2 (containing 0.1% TFA). Thus, (3R,5S)-5-tert-butoxycarbonylamino-piperidine-1,3-dicarboxylic acid 1-(9H-fluoren-9-ylmethyl) ester and (3S,5R)-5-tert-butoxycarbonylamino-piperidine-1,3-dicarboxylic acid 1-(9H-fluoren-9-ylmethyl) ester are obtained.

Faster running peak (Peak 1): $t_R$ (Chiralcel OJ; 80% n-hexane+0.1% TFA/20% ethanol+0.1% TFA for 30 min, flow 1 ml/min): 9.06 min.

Optical rotation: $[a]_D^{25°}$=−8.2 (c=1.0, CH₃OH)

Peak 2: $t_R$ (Chiralcel OJ; 80% n-hexane+0.1% TFA/20% ethanol+0.1% TFA for 30 min, flow 1 ml/min): 19.66 min.

Optical rotation: $[a]_D^{25°}$=+7.4 (c=1.0, CH₃OH)

Example 114

(3R,5S)-5-(2,2-Dimethyl-propionylamino)-piperidine-3-carboxylic acid cyclopropyl-[1-(3-methoxy-propyl)-1H-indol-3-ylmethyl]-amide

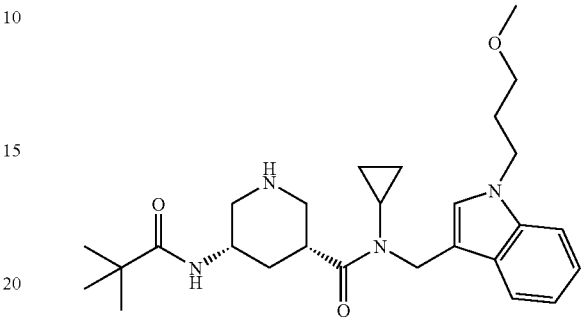

To a stirred mixture of (3S,5R)-3-amino-5-{cyclopropyl-[1-(3-methoxy-propyl)-1H-indol-3-ylmethyl]-carbamoyl}-piperidine-1-carboxylic acid 9H-fluoren-9-ylmethyl ester (374 mg, 0.62 mmol), N-ethyldiisopropylamine (503 µl, 2.94 mmol) and 4-dimethylaminopyridine (31 mg) in CH₂Cl₂ (8 ml), pivaloylchloride (126 µl, 1.02 mmol) is added. After stirring for 14 h at RT, the mixture is diluted with CH₂Cl₂. The organic layer is washed with 1N HCl and saturated NaHCO₃ solution, dried over Na₂SO₄ and evaporated in vacuo. The crude product is stirred with a solution of CH₂Cl₂/piperidine 4:1 (6 ml) for 1 h, the mixture is evaporated and the residue purified by preparative HPLC (YMC Pack Pro C18, 10-100% CH₃CN+0.1% TFA/H₂O+0.1% TFA, 20 min, flow 20 ml/min). The combined pure fractions are treated with K₂CO₃, CH₃CN is removed in vacuo, and the residual aqueous layer is extracted three times with CH₂Cl₂. The combined organic layers are dried (Na₂SO₄) and evaporated to afford the title compound as a yellowish resin. MS: 469.4 [M+H]⁺; $t_R$ (HPLC, Nucleosil C18; 5-100% CH₃CN+0.1% TFA/H₂O+0.1% TFA for 8 min, flow 1.5 ml/min): 5.03 min.

The starting material is prepared as follows:

A. (3S,5R)-3-amino-5-{cyclopropyl-[1-(3-methoxy-propyl)-1H-indol-3-ylmethyl]-carbamoyl}-piperidine-1-carboxylic acid 9H-fluoren-9-ylmethyl ester A mixture of (3R,5S)-5-tert-butoxycarbonylamino-piperidine-1,3-dicarboxylic acid 1-(9H-fluoren-9-ylmethyl) ester (Example 114, peak 2) (401 mg, 0.86 mmol), HCTU (356 mg, 0.86 mmol) and DIPEA (59.9 µl, 0.35 mmol) in a 1:1 mixture of CH₂Cl₂/CH₃CN (6 ml) is stirred for 10 min at 5° C. Cyclopropyl-[1-(3-methoxy-propyl)-1H-indol-3-ylmethyl]-amine (242 mg, 0.94 mmol) is added in one portion, the ice-bath is removed and the mixture stirred for 14 h at RT. The reaction mixture is diluted with CH₂Cl₂ and washed twice with K₂CO₃ solution. The organic layer is dried (Na₂SO₄) and evaporated. CH₂Cl₂ (6 ml) is added to the residue, and a freshly prepared solution of 2,6-lutidine (508 µl, 4.36 mmol) and trimethylsilyl trifluoromethanesulfonate (591 µl, 3.27 mmol) in CH₂Cl₂ (6 ml) is added dropwise during 5 min. The mixture is stirred at RT for 2 h, diluted with CH₂Cl₂ and washed with saturated NH₄Cl solution and brine. The organic layer is dried over Na₂SO₄ and evaporated in vacuo to afford the title compound as a brown oil. MS (LC-MS): 607.5

[M+H]⁺; $t_R$ (HPLC, Nucleosil C18; 5-100% CH$_3$CN+0.1% TFA/H$_2$O+0.1% TFA for 8 min, flow 1.5 ml/min): 6.07 min.

Example 115

(3R,5S)-5-(3-tert-Butyl-ureido)-piperidine-3-carboxylic acid cyclopropyl-[1-(3-methoxy-propyl)-1H-indol-3-ylmethyl]-amide

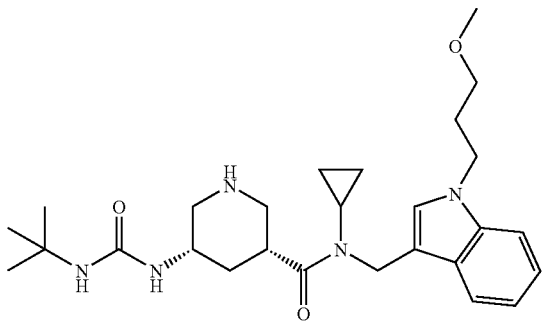

A mixture of (3S,5R)-3-amino-5-{cyclopropyl-[1-(3-methoxy-propyl)-1H-indol-3-ylmethyl]-carbamoyl}-piperidine-1-carboxylic acid 9H-fluoren-9-ylmethyl ester (115 A.) (374 mg, 0.62 mmol), dichloroethane (5 mL) and tert-butyl isocyanate (142 µl, 1.24 mmol) is shaken for 14 h at 50° C. The mixture is diluted with CH$_2$Cl$_2$ and washed with 1 N HCl and saturated NaHCO$_3$ solution. The organic layer is dried (Na$_2$SO$_4$) and evaporated. The crude product is stirred with a solution of CH$_2$Cl$_2$/piperidine 4:1 (6 ml) for 1 h, the mixture is evaporated and the residue purified by preparative HPLC (YMC Pack Pro C18, 10-100% CH$_3$CN+0.1% TFA/H$_2$O+ 0.1% TFA, 20 min, flow 20 mL/min). The combined pure fractions are treated with K$_2$CO$_3$, CH$_3$CN is removed in vacuo and the residual aqueous phase is extracted three times with CH$_2$Cl$_2$. The combined organic layers are dried (Na$_2$SO$_4$) and evaporated to afford the title compound as a yellow resin. MS: 484.2 [M+H]⁺; $t_R$ (HPLC, Nucleosil C18; 5-100% CH$_3$CN+0.1% TFA/H$_2$O+0.1% TFA for 8 min, flow 1.5 ml/min): 5.05 min.

Example 116

(3S*,5R*)-5-(2,2-Dimethyl-propionylamino)-piperidine-3-carboxylic acid ethyl-[4-(3-methoxy-propyl)-3-oxo-3,4-dihydro-2H-benzo[1,4]oxazin-6-yl]-amide

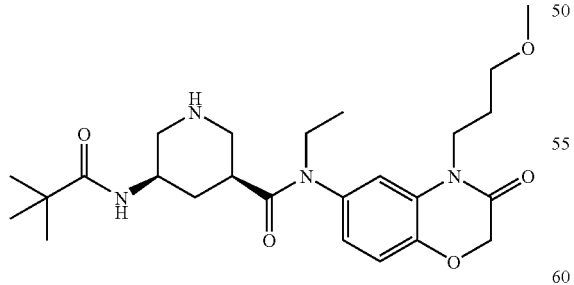

The title compound is prepared analogously as described in Example 61 using (3R*,5S*)-3-amino-5-{ethyl-[4-(3-methoxy-propyl)-3-oxo-3,4-dihydro-2H-benzo[1,4]oxazin-6-yl]-carbamoyl}-piperidine-1-carboxylic acid 9H-fluoren-9-ylmethyl ester, trifluoroacetate and pivaloyl chloride. MS: 475.4 [M+H]⁺; $t_R$ (HPLC, Nucleosil C18; 5-100% CH$_3$CN+0.1% TFA/H$_2$O+0.1% TFA for 8 min, flow 1.5 ml/min): 4.29 min.

The starting materials are prepared as follows:
A. (3R*,5S*)-3-Amino-5-{ethyl-[4-(3-methoxy-propyl)-3-oxo-3,4-dihydro-2H-benzo[1,4]oxazin-6-yl]-carbamoyl}-piperidine-1-carboxylic acid 9H-fluoren-9-ylmethyl ester, trifluoroacetate The title compound is prepared analogously as described in Example 92A. using (3S*,5R*)-5-tert-butoxycarbonylamino-piperidine-1,3-dicarboxylic acid 1-(9H-fluoren-9-ylmethyl) ester and 6-ethylamino-4-(3-methoxy-propyl)-4H-benzo[1,4]oxazin-3-one. The product is purified by preparative HPLC (YMC Pack Pro C18, 10-100% CH$_3$CN+ 0.1% TFA/H$_2$O+0.1% TFA, 20 min, flow 20 ml/min); $t_R$ (HPLC, Nucleosil C18; 5-100% CH$_3$CN+0.1% TFA/H$_2$O+ 0.1% TFA for 8 min, flow 1.5 ml/min): 5.47 min.

B. 6-Ethylamino-4-(3-methoxy-propyl)-4H-benzo[1,4]oxazin-3-one

A mixture of 6-nitro-4H-benzo[1,4]oxazin-3-one (5 g, 25.8 mmol) and NaH (~60% moistened with oil, 911 mg, ~23 mmol) in DMA (30 ml) is stirred at 5° C. for 30 min. Toluene-4-sulfonic acid 3-methoxy-propyl ester (6.87 g, 28.1 mmol) in DMA (10 ml) is added, followed by potassium iodide (4.67 g, 28.1 mmol). The ice-bath is removed and the mixture stirred for 3 h at 60° C. The solvent is distilled off in vacuo and the residue partitioned between H$_2$O and ethyl acetate. The organic layer is dried (Na$_2$SO$_4$) and the solvent evaporated. Part of the crude product (5 g, 18.8 mmol) is dissolved in a mixture of acetic acid (50 ml) and ethyl acetate (50 ml). The solution is added dropwise to a suspension of Fe powder (6 g, 107 mmol) in 5% aqueous acetic acid (50 ml). The resultant mixture is kept at 70° C. for 5 h. After cooling to RT, the Fe powder is filtered off, and the filtrate diluted with H$_2$O. The aqueous layer is extracted with ethyl acetate. The organic layer is washed with NaHCO$_3$ solution, dried (Na$_2$SO$_4$) and evaporated. The residue is purified by column chromatography (SiO$_2$, CH$_2$Cl$_2$/CH$_3$OH 100:0-80:20) to afford 6-amino-4-(3-methoxy-propyl)-4H-benzo[1,4]oxazin-3-one as a dark brown oil. MS: 237.3 [M+H]⁺; $t_R$ (HPLC, Nucleosil C18; 5-100% CH$_3$CN+0.1% TFA/H$_2$O+0.1% TFA for 8 min, flow 1.5 ml/min): 2.66 min. Part of this intermediate (1 g, 4.2 mmol) is diluted with methanol (15 ml). Acetaldehyde (166 µl, 2.94 mmol), acetic acid (480 µl, 8.4 mmol) and NaBH$_3$CN (396 mg, 6.3 mmol) are added. The mixture is stirred for 1.5 h at RT, quenched with 5% KHSO$_4$ solution and extracted with ethyl acetate. The organic layer is washed with NaHCO$_3$ solution and brine, dried over Na$_2$SO$_4$ and evaporated in vacuo. Purification of the product by column chromatography (SiO$_2$, CH$_2$Cl$_2$/CH$_3$OH) affords the title compound as a purple oil. MS: 265.3 [M+H]⁺; $t_R$ (HPLC, Nucleosil C18; 5-100% CH$_3$CN+0.1% TFA/H$_2$O+0.1% TFA for 8 min, flow 1.5 ml/min): 3.41 min

Example 117

(3S*,5R*)-5-[Methyl-(toluene-4-sulfonyl)-amino]-piperidine-3-carboxylic acid (2,2-diphenyl-ethyl)-amide, trifluoroacetate

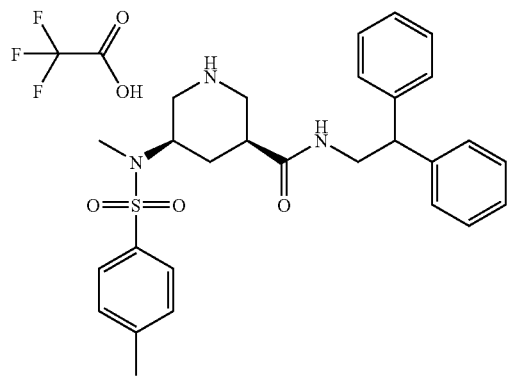

A mixture of (3S*,5R*)-5-[methyl-(toluene-4-sulfonyl)-amino]-piperidine-1,3-dicarboxylic acid 1-tert-butyl ester (40 mg, 0.097 mmol) and HCTU (44 mg, 0.107 mmol) in pyridine (1 ml) is stirred at RT for 15 min. 2,2-Diphenylethylamine (21 mg, 0.107 mmol) is added and the mixture is stirred at RT for 2 h. The reaction is quenched by adding 10% HCl, and the aqueous layer is extracted three times with methyl tert-butyl ether. The combined organic extracts are dried ($Na_2SO_4$) and the solvent is distilled off. The residue is stirred with TFA (0.965 ml) in $CH_2Cl_2$ (1 ml) for 1 h and is then evaporated. The residue is purified by preparative HPLC (SunFire; 20-70% $CH_3CN$+0.1% TFA/$H_2O$+0.1% TFA for 10 min, flow 30 ml/min) to afford the title compound. MS (LC-MS): 492.5 [M+H]$^+$; $t_R$ (HPLC, Symmetry C18; 5-100% $CH_3CN$+0.1% TFA/$H_2O$+0.1% TFA for 7 min, flow 1.5 ml/min): 3.62 min.

The starting material is prepared as follows:

A. (3S*,5R*)-5-[methyl-(toluene-4-sulfonyl)-amino]-piperidine-1,3-dicarboxylic acid 1-tert-butyl ester A mixture of (3S*,5R*)-5-(toluene-4-sulfonylamino)-piperidine-1,3-dicarboxylic acid 1-tert-butyl ester (Example 50A.) (150 mg, 0.376 mmol), $K_2CO_3$ (0.52 g, 3.76 mmol) and methyl iodide (0.234 ml, 3.76 mmol) in DMA (3 ml) is agitated in a closed vessel at 80° C. during 14 h. Aqueous $NaHSO_4$ solution is added and the mixture is extracted three times with methyl tert-butyl ether. The combined organic layers are washed with a 5% $Na_2S_2O_3$ solution and brine, dried over $Na_2SO_4$ and evaporated in vacuo to afford (3S*,5R*)-5-[methyl-(toluene-4-sulfonyl)-amino]-piperidine-1,3-dicarboxylic acid 1-tert-butyl ester 3-methyl ester.

A mixture of this ester (160 mg, 0.375 mmol), ethanol (4 ml) and 1N LiOH solution (1.88 ml, 1.88 mmol) is stirred for 14 h at RT. The mixture is diluted with $H_2O$ and extracted with methyl tert.-butyl ether. The organic layer is discarded, the aqueous phase acidified to pH 2 with a 10% $NaHSO_4$ solution and extracted three times with methyl tert-butyl ether. The combined organic extracts are dried ($Na_2SO_4$) and evaporated to afford the title compound. MS (LC-MS): 413.4 [M+H]$^+$; $t_R$ (HPLC, Symmetry C18; 5-100% $CH_3CN$+0.1% TFA/$H_2O$+0.1% TFA for 7 min, flow 1.5 ml/min): 4.31 min.

Example 118

(3S*,5R*)-5-(Toluene-4-sulfonylamino)-piperidine-3-carboxylic acid (2-cyclohexyl-2-phenyl-ethyl)-amide

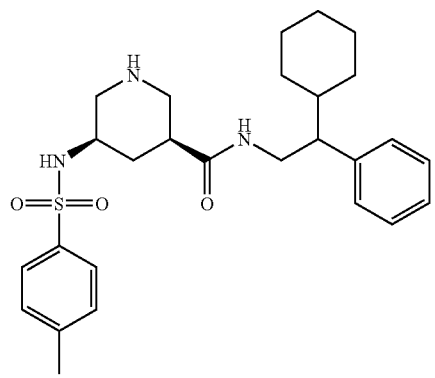

The title compound is prepared analogously as described in Example 45 using 2-cyclohexyl-2-phenyl-ethylamine. MS: 484.2 [M+H]$^+$; $t_R$ (HPLC, Lichrospher RP8; 10-100% $CH_3CN$+0.1% TFA/$H_2O$+0.1% TFA for 5 min, then 100% $CH_3CN$+0.1% TFA for 2.5 min, flow 1.5 ml/min): 5.26 min.

Example 119

(3S*,5R*)-5-(Toluene-4-sulfonylamino)-piperidine-3-carboxylic acid[2-(3-methoxymethyl-phenyl)-2-phenyl-ethyl]-amide

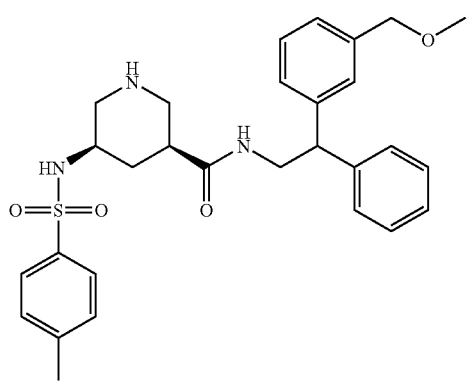

The title compound is prepared analogously as described in Example 45 using 2-(3-methoxymethyl-phenyl)-2-phenyl-ethylamine. MS: 522.2 [M+H]$^+$; $t_R$ (HPLC, Lichrospher RP8; 10-100% $CH_3CN$+0.1% TFA/$H_2O$+0.1% TFA for 5 min, flow 1.5 ml/min): 4.77 min. The starting 2-(3-methoxymethyl-phenyl)-2-phenyl-ethylamine is prepared as follows:

a) A solution of (3-methoxymethyl-phenyl)-phenyl-acetonitrile (0.50 g, 2.11 mmol) in ethanol (10 ml) containing 4% concentrated aqueous ammonia is hydrogenated in the presence of Raney-Ni (0.2 g) for 22 hours at room temperature. The mixture is filtered over Celite, washed with ethanol, followed by evaporation of the combined filtrates. The residue is purified by flash chromatography on silica gel ($CH_2Cl_2$/MeOH/conc. $NH_3$ 95:5:0.5) to give the title product. MS: 242.1 [M+H]$^+$; $t_R$ (HPLC, Nucleosil 100-5 R18; 10-100% $CH_3CN$+0.1% TFA/$H_2O$+0.1% TFA for 5 min, flow 1.5 ml/min): 4.16 min.

Example 120

(3S*,5R*)-5-(Toluene-4-sulfonylamino)-piperidine-3-carboxylic acid (2,2-diphenyl-butyl)-amide

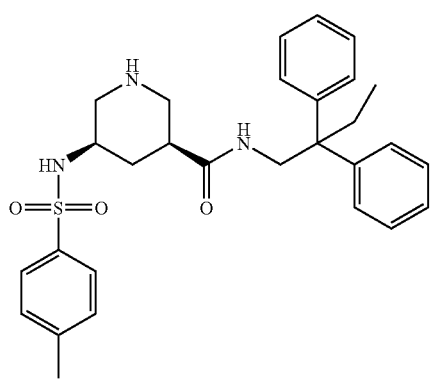

The title compound is prepared analogously as described in Example 45 using 2,2-diphenyl-butylamine. MS: 506.2 [M+H]$^+$; $t_R$ (HPLC, Lichrospher RP8; 10-100% CH$_3$CN+ 0.1% TFA/H$_2$O+0.1% TFA for 5 min, then 100% CH$_3$CN+ 0.1% TFA for 2.5 min, flow 1.5 ml/min): 5.11 min.

Example 121

(3S*,5R*)-5-(Toluene-4-sulfonylamino)-piperidine-3-carboxylic acid[2-(4-chloro-phenyl)-3-methyl-butyl]-amide

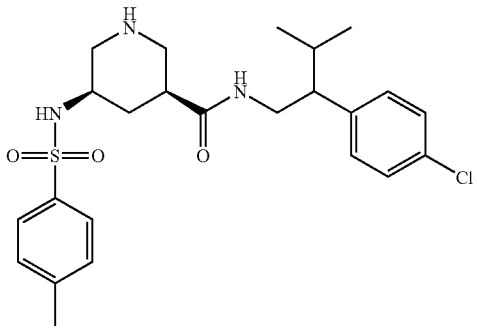

The title compound is prepared analogously as described in Example 45 using 2-(4-chloro-phenyl)-3-methyl-butylamine. MS: 478.1/480.1 [M+H]$^+$; $t_R$ (HPLC, Lichrospher RP8; 10-100% CH$_3$CN+0.1% TFA/H$_2$O+0.1% TFA for 5 min, then 100% CH$_3$CN+0.1% TFA for 2.5 min, flow 1.5 ml/min): 5.02 min.

Example 122

2,2-Diphenyl-3-{[(3S*,5R*)-5-(toluene-4-sulfonylamino)-piperidine-3-carbonyl]-amino}-propionic acid ethyl ester

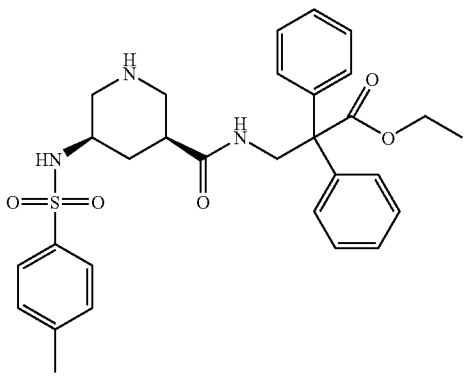

The title compound is prepared analogously as described in Example 45 using 3-amino-2,2-diphenyl-propionic acid ethyl ester, hydrochloride. MS: 550.2 [M+H]$^+$; $t_R$ (HPLC, Lichrospher RP8; 10-100% CH$_3$CN+0.1% TFA/H$_2$O+0.1% TFA for 5 min, flow 1.5 ml/min): 4.96 min.

Example 123

(3S*,5R*)-5-(Toluene-4-sulfonylamino)-piperidine-3-carboxylic acid (4-methyl-2-phenyl-pentyl)-amide

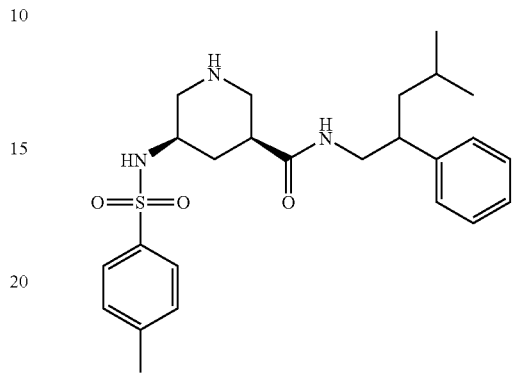

The title compound is prepared analogously as described in Example 45 using 4-methyl-2-phenyl-pentylamine. MS: 458.2 [M+H]$^+$; $t_R$ (HPLC, Lichrospher RP8; 10-100% CH$_3$CN+0.1% TFA/H$_2$O+0.1% TFA for 5 min, flow 1.5 ml/min): 4.98 min.

Example 124

(3S*,5R*)-5-(Toluene-4-sulfonylamino)-piperidine-3-carboxylic acid {2-[2-(3-methoxy-propoxy)-phenyl]-2-phenyl-ethyl}-amide

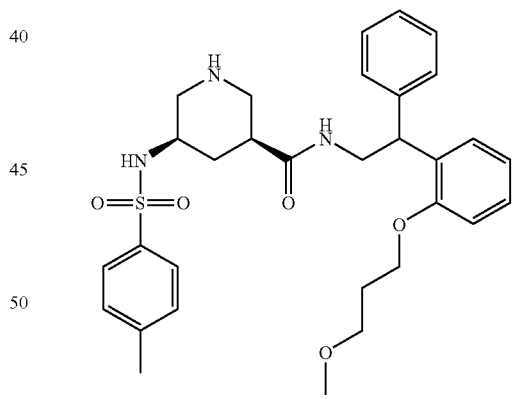

The title compound is prepared analogously as described in Example 45 using 2-[2-(3-methoxy-propoxy)-phenyl]-2-phenyl-ethylamine. MS: 566.2 [M+H]$^+$; $t_R$ (HPLC, Lichrospher RP8; 10-100% CH$_3$CN+0.1% TFA/H$_2$O+0.1% TFA for 5 min, flow 1.5 ml/min): 4.97 min. The starting material 2-[2-(3-methoxy-propoxy)-phenyl]-2-phenyl-ethylamine is prepared as follows:
a) A solution of [2-(3-methoxy-propoxy)-phenyl]-phenyl-acetonitrile (1.85 g, 6.58 mmol) in ethanol (30 ml) containing 4% concentrated aqueous ammonia is hydrogenated in the presence of Raney-Ni (1.85 g) for 8 hours at room temperature. The mixture is filtered over Celite, washed with ethanol, followed by evaporation of the combined filtrates to give the title product. MS: 286.2 [M+H]$^+$; $t_R$ (HPLC, Nucleosil 100-5 R18; 10-100% CH$_3$CN+0.1% TFA/H$_2$O+ 0.1% TFA for 5 min, flow 1.5 ml/min): 4.33 min.

b) To a stirred solution of 1-benzyl-2-(3-methoxy-propoxy)-benzene (4.00 g, 15.6 mmol) and 2,3-dichloro-5,6-dicyano-1,4-benzoquinone (4.25 g, 18.7 mmol) in CH$_2$Cl$_2$ (30 ml), trimethylsilyl cyanide (7.74 g, 78.0 mmol) is added, and the reaction mixture is heated at 100° C. for 1 hour in a microwave reactor. After cooling to room temperature, the organics are washed with aqueous NaHCO$_3$ (10%) and water, dried (MgSO$_4$) and concentrated. The product is purified by flash chromatography on silica gel (hexane/EtOAc 97:3 (1 L), then hexane/EtOAc 85:15) to give [2-(3-methoxy-propoxy)-phenyl]-phenyl-acetonitrile. MS: 282.2 [M+H]$^+$; $t_R$ (HPLC, Nucleosil 100-5 R18; 10-100% CH$_3$CN+0.1% TFA/H$_2$O+0.1% TFA for 5 min, flow 1.5 ml/min): 5.43 min.

c) To a stirred solution of 2-benzylphenol (3.00 g, 16.2 mmol) in acetonitrile (70 ml), water-free K$_2$CO$_3$ (3.38 g, 24.4 mmol) and 3-bromopropylmethylether (3.74 g, 24.4 mmol) are added. The mixture is refluxed overnight, filtered after cooling to room temperature, followed by evaporation of the filtrate. The residue is taken up in EtOAc, and the organic phase is subsequently washed with 0.5 M NaOH (100 ml), water and brine. The combined organics are dried (MgSO$_4$) and evaporated. The residue is purified by flash chromatography on silica gel (hexane/EtOAC 93:3) to give 1-benzyl-2-(3-methoxy-propoxy)-benzene. MS: 257.2 [M+H]$^+$; $t_R$ (HPLC, Nucleosil 100-5 R18; 10-100% CH$_3$CN+0.1% TFA/H$_2$O+0.1% TFA for 5 min, flow 1.5 ml/min): 6.00 min.

Example 125

(3S*,5R*)-5-(Toluene-4-sulfonylamino)-piperidine-3-carboxylic acid [2-(2-methoxy-phenyl)-2-phenyl-ethyl]-amide

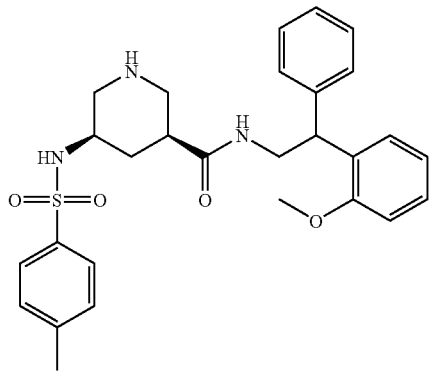

The title compound is prepared analogously as described in Example 45 using 2-(2-methoxy-phenyl)-2-phenyl-ethylamine. MS: 508.2 [M+H]$^+$; $t_R$ (HPLC, Lichrospher RP8; 10-100% CH$_3$CN+0.1% TFA/H$_2$O+0.1% TFA for 5 min, flow 1.5 ml/min): 4.84 min.

Example 126

(3S*,5R*)-5-(Toluene-4-sulfonylamino)-piperidine-3-carboxylic acid (5-methoxy-2,2-diphenyl-pentyl)-amide

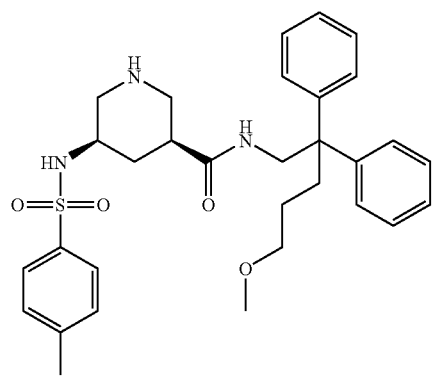

The title compound is prepared analogously as described in Example 45 using 5-methoxy-2,2-diphenyl-pentylamine. MS: 550.2 [M+H]$^+$; $t_R$ (HPLC, Nucleosil C18; 5-100% CH$_3$CN+0.1% TFA/H$_2$O+0.1% TFA for 8 min, flow 1.5 ml/min): 5.35 min.

The starting material 5-methoxy-2,2-diphenyl-pentylamine is prepared as follows:

a) A solution of 5-methoxy-2,2-diphenyl-pentanenitrile (1.50 g, 5.65 mmol) in ethanol (25 ml) containing 4% concentrated aqueous ammonia is hydrogenated in the presence of Raney-Ni (2.0 g) for 20 hours at room temperature. The mixture is filtered over Celite, washed with ethanol, followed by evaporation of the combined filtrates to give the title product. MS: 270.2 [M+H]$^+$; $t_R$ (HPLC, Nucleosil 100-5 R18; 10-100% CH$_3$CN+0.1% TFA/H$_2$O+0.1% TFA for 5 min, flow 1.5 ml/min): 4.46 min.

b) To a stirred mixture of NaH (60% in oil; 1.86 g, 46.6 mmol) in DMF (50 ml) at 0° C., a solution of diphenylacetonitrile (3.00 g, 15.5 mmol) in DMF (10 ml) is added dropwise. The mixture is stirred for 30 min at room temperature and then cooled to 0° C., followed by dropwise addition of a solution of 3-bromopropylmethylether (3.56 g, 23.3 mmol) in DMF (10 ml). The mixture is stirred at room temperature for 30 min and then at 80° C. for 15 min. After cooling to room temperature, the mixture is poured into ice water, followed by extraction of the aqueous phase twice with water. The organic phase is dried (MgSO$_4$), concentrated and the residue is purified by flash chromatography on silica gel (eluent: CH$_2$Cl$_2$) to give 5-methoxy-2,2-diphenyl-pentanenitrile. MS: 266.2 [M+H]$^+$; $t_R$ (HPLC, Nucleosil 100-5 R18; 10-100% CH$_3$CN+0.1% TFA/H$_2$O+ 0.1% TFA for 5 min, flow 1.5 ml/min): 5.53 min.

Example 127

(3S*,5R*)-5-(Toluene-4-sulfonylamino)-piperidine-3-carboxylic acid {2-[2-(2-methoxy-ethoxy)-phenyl]-2-phenyl-ethyl}-amide

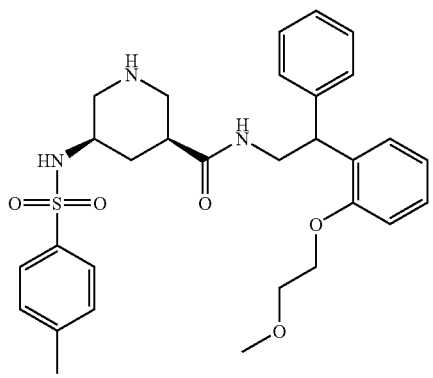

The title compound is prepared analogously as described in Example 45 using 2-[2-(2-methoxy-ethoxy)-phenyl]-2-phenyl-ethylamine. MS: 552.2 [M+H]$^+$; $t_R$ (HPLC, Nucleosil C18; 5-100% CH$_3$CN+0.1% TFA/H$_2$O+0.1% TFA for 8 min, flow 1.5 ml/min): 5.13 min.

The starting material 2-[2-(3-methoxy-ethoxy)-phenyl]-2-phenyl-ethylamine is prepared as follows:

a) A solution of [2-(3-methoxy-ethoxy)-phenyl]-phenyl-acetonitrile (1.46 g, 5.46 mmol) in ethanol (25 ml) containing 4% concentrated aqueous ammonia is hydrogenated in the presence of Raney-Ni (1.46 g) for 6 hours at room temperature. The mixture is filtered over Celite and washed with ethanol, followed by evaporation of the combined filtrates to give the title product. MS: 272.2 [M+H]$^+$; $t_R$ (HPLC, Nucleosil 100-5 R18; 10-100% CH$_3$CN+0.1% TFA/H$_2$O+0.1% TFA for 5 min, flow 1.5 ml/min): 4.37 min.

b) To a stirred solution of 1-benzyl-2-(3-methoxy-ethoxy)-benzene (2.80 g, 11.6 mmol) and 2,3-dichloro-5,6-dicyano-1,4-benzoquinone (3.15 g, 13.9 mmol) in CH$_2$Cl$_2$ (25 ml), trimethyl-silyl cyanide (5.73 g, 57.8 mmol) is added and the reaction mixture is heated at 100° C. for 2 hours in a microwave reactor. After cooling to room temperature, the organics are washed with aqueous NaHCO$_3$ (10%) and water, dried (MgSO$_4$) and concentrated. The product is purified by flash chromatography on silica gel (hexane/EtOAc 97:3 (1 L), then hexane/EtOAc 85:15) to give [2-(3-methoxy-ethoxy)-phenyl]-phenyl-acetonitrile. MS: 268.2 [M+H]$^+$; $t_R$ (HPLC, Nucleosil 100-5 R18; 10-100% CH$_3$CN+0.1% TFA/H$_2$O+0.1% TFA for 5 min, flow 1.5 ml/min): 5.25 min.

c) To a stirred solution of 2-benzylphenol (3.00 g, 16.3 mmol) in acetonitrile (70 ml), water-free K$_2$CO$_3$ (3.38 g, 24.4 mmol) and 2-bromopropylmethylether (3.40 g, 24.4 mmol) are added. The mixture is refluxed overnight and filtered after cooling to room temperature, followed by evaporation of the filtrate. The residue is taken up in EtOAc, and the organic phase is subsequently washed with 0.5 M NaOH (100 ml), water and brine. The combined organics are dried (MgSO$_4$) and evaporated. The residue is purified by flash chromatography on silica gel (hexane/EtOAC 93:3) to give 1-benzyl-2-(3-methoxy-ethoxy)-benzene. MS: 243.2 [M+H]$^+$; $t_R$ (HPLC, Nucleosil 100-5 R18; 10-100% CH$_3$CN+0.1% TFA/H$_2$O+0.1% TFA for 5 min, flow 1.5 ml/min): 5.73 min.

Example 128

{(3R*,5S*)-5-[Cyclopropyl-(2,3-dichloro-benzyl)-carbamoyl]-Piperidin-3-yl}-carbamic acid tert-butyl ester

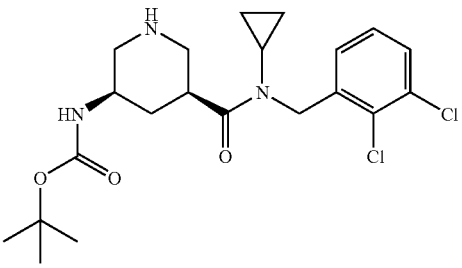

To a stirred, ice-cooled mixture of (3S*,5R*)-5-tert-butoxycarbonylamino-piperidine-1,3-dicarboxylic acid 1-(9H-fluoren-9-ylmethyl) ester (300 mg, 0.643 mmol) in CH$_2$Cl$_2$ (7 mL) a 2M solution of N-ethyldiisopropylamine in 1-methyl-2-pyrrolidone (161 µl, 0.322 mmol) is added, followed by a solution of O-(1H-6-chlorobenzotriazole-1-yl)-1,1,3,3-tetramethyluronium hexafluorophosphate (HCTU) (292 mg, 0.707 mmol) in CH$_3$CN (7 mL). After 15 min cyclopropyl-(2,3-dichloro-benzyl)-amine (139 mg, 0.643 mmol) is added. The mixture is stirred for 15 min at 0° C. and for 14 h at RT. After evaporation of the solvents in vacuo, the residue is diluted with CH$_2$Cl$_2$ and washed with a 10% aqueous K$_2$CO$_3$ solution, 2M HCl solution and brine. The organic layer is dried over Na$_2$SO$_4$, evaporated in vacuo and the residue purified by flash chromatography (SiO$_2$, CH$_2$Cl$_2$/acetone 96:4). Part of the crude product (50 mg, 0.075 mmol) is dissolved in CH$_2$Cl$_2$ (1 mL), treated with piperidine (0.222 mL, 2.25 mmol) and stirred for 1 h at RT. After evaporation in vacuo, the residue is purified by preparative HPLC (YMC Pack Pro C18, 10-100% CH$_3$CN+0.1% TFA/H$_2$O+0.1% TFA, 20 min, flow 20 mL/min). The combined pure fractions are treated with solid K$_2$CO$_3$, CH$_3$CN is removed in vacuo, and the residual aqueous phase is extracted twice with CH$_2$Cl$_2$. The combined organic layers are dried (Na$_2$SO$_4$) and evaporated to afford the title compound as a colourless foam. MS: 442.2/444.2 [M+H]$^+$; $t_R$ (HPLC, Lichrospher RP8; 10-100% CH$_3$CN+0.1% TFA/H$_2$O+0.1% TFA for 5 min, then 100% CH$_3$CN+0.1% TFA for 2.5 min, flow 1.5 ml/min): 5.08 min.

Example 129

(3S*,5R*)-5-(3-Chloro-benzenesulfonylamino)-piperidine-3-carboxylic acid (2,3-diphenyl-propyl)-amide

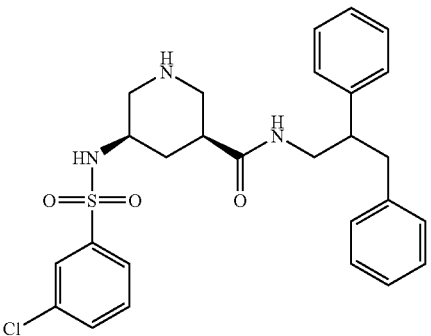

The title compound is prepared analogously as described in Example 45 using 3-chloro-benzenesulfonyl chloride instead of 4-toluenesulfonyl chloride and 2,3-diphenyl-propylamine as amine component. MS: 512.2/514.2 [M+H]$^+$; $t_R$ (HPLC, Lichrospher RP8; 10-100% CH$_3$CN+0.1% TFA/H$_2$O+0.1% TFA for 5 min, then 100% CH$_3$CN+0.1% TFA for 2.5 min flow 1.5 ml/min): 6.24 min.

Example 130

(3S*,5R*)-5-(Toluene-4-sulfonylamino)piperidine-3-carboxylic acid cyclopropyl-(2,3-dichloro-benzyl)-amide

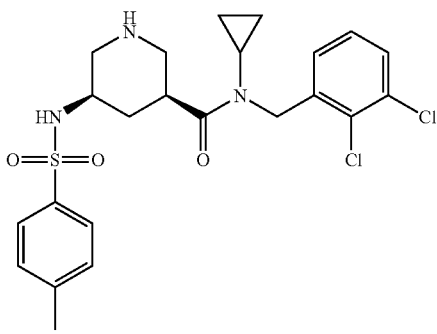

The title compound is prepared analogously as described in Example 54 using O-(1H-6-chlorobenzotriazole-1-yl)-1,1,3,3-tetramethyluronium hexafluorophosphate (HCTU) for the condensation step and cyclopropyl-(2,3-dichloro-benzyl)-amine as amine component. MS: 496.0/498.0 [M+H]$^+$; $t_R$ (HPLC, Lichrospher RP8; 10-100% CH$_3$CN+0.1% TFA/H$_2$O+0.1% TFA for 5 min, flow 1.5 ml/min): 4.90 min Example 131

{(3R*,5R*)-5-[Cyclopropyl-(2,3-dichloro-benzyl)-carbamoyl]-piperidin-3-yl}-carbamic acid tert-butyl ester

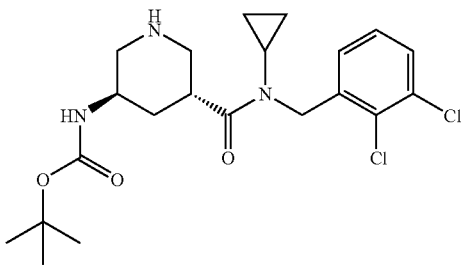

To a stirred, ice-cooled mixture of (3R*,5R*)-5-tert-butoxycarbonylamino-piperidine-1,3-dicarboxylic acid 1-(9H-fluoren-9-ylmethyl) ester (233 mg, 0.5 mmol), cyclopropyl-(2,3-dichloro-benzyl)-amine (112 mg, 0.52 mmol) and N-ethyldiisopropylamine (685 µL, 4 mmol) in dimethylacetamide (3 mL), propylphosphonic anhydride solution (~50% in DMF, 0.48 mL, ~0.75 mmol) is added. The mixture is stirred for 14 h at RT. After evaporation of the solvent in vacuo, the residue is diluted with ethyl acetate and washed with a 10% aqueous K$_2$CO$_3$ solution and brine. The organic layer is dried over Na$_2$SO$_4$, evaporated in vacuo and the residue purified by preparative HPLC (YMC Pack Pro C18, 10-100% CH$_3$CN+0.1% TFA/H$_2$O+0.1% TFA, 20 min, flow 20 mL/min). The combined pure fractions are treated with solid K$_2$CO$_3$, CH$_3$CN is removed in vacuo, and the residual aqueous phase is extracted twice with CH$_2$Cl$_2$. The combined organic layers are dried (Na$_2$SO$_4$) and evaporated to afford (3R*,5R*)-3-tert-butoxycarbonylamino-5-[cyclopropyl-(2,3-dichloro-benzyl)-carbamoyl]piperidine-1-carboxylic acid 9H-fluoren-9-ylmethyl ester as a colourless oil. $t_R$ (HPLC, Nucleosil C18; 5-100% CH$_3$CN+0.1% TFA/H$_2$O+0.1% TFA for 8 min, then 100% CH$_3$CN+0.1% TFA for 2 min, flow 1.5 ml/min): 8.45 min. The product is dissolved in CH$_2$Cl$_2$/piperidine 4:1 (5 mL) and stirred for 1 h at RT. After evaporation in vacuo, the residue is purified by preparative HPLC (YMC Pack Pro C18, 10-100% CH$_3$CN+0.1% TFA/H$_2$O+0.1% TFA, 30 min, flow 20 mL/min). The combined pure fractions are treated with solid K$_2$CO$_3$, CH$_3$CN is removed in vacuo, and the residual aqueous phase is extracted twice with CH$_2$Cl$_2$. The combined organic layers are dried (Na$_2$SO$_4$) and evaporated to afford the title compound as a colourless resin. MS: 442.3/444.2 [M+H]$^+$; $t_R$ (HPLC, Nucleosil C18; 5-100% CH$_3$CN+0.1% TFA/H$_2$O+0.1% TFA for 8 min, flow 1.5 ml/min): 5.58 min.

Example 132

(3R*,5R*)-5-(3-Chloro-benzenesulfonylamino)-piperidine-3-carboxylic acid cyclopropyl-(2,3-dichloro-benzyl)-amide

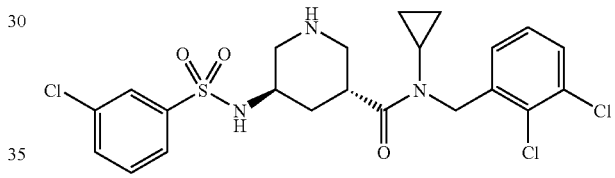

The title compound is prepared analogously as described in Example 54 using cyclopropyl-(2,3-dichloro-benzyl)-amine. MS: 516.2/518.1 [M+H]$^+$; $t_R$ (HPLC, Nucleosil C18; 5-100% CH$_3$CN+0.1% TFA/H$_2$O+0.1% TFA for 8 min, flow 1.5 ml/min): 5.74 min.

Example 133

((3R*,5R*)-5-{Cyclopropyl-[1-(3-methoxy-propyl)-1H-indol-3-ylmethyl]-carbamoyl}-piperidin-3-yl)-carbamic acid tert-butyl ester

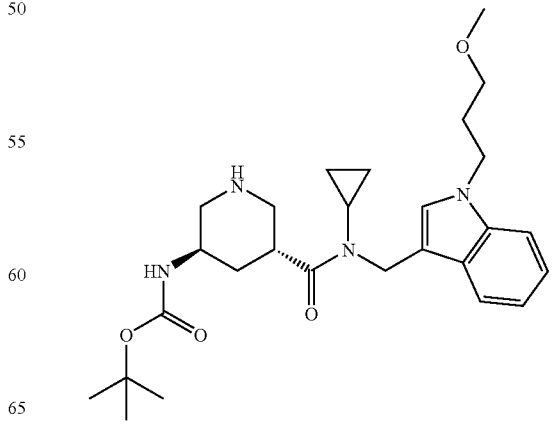

An ice-cooled mixture of (3R*,5R*)-5-tert-butoxycarbonylamino-piperidine-1,3-dicarboxylic acid 1-(9H-fluoren-9-ylmethyl) ester (93.3 mg, 0.2 mmol), O-(1H-6-chlorobenzotriazole-1-yl)-1,1,3,3-tetramethyluronium hexafluorophosphate (HCTU) (91 mg, 0.22 mmol) and ethyldiisopropylamine (17.1 µL, 0.1 mmol) in $CH_2Cl_2/CH_3CN$ 1:1 (2 mL) is stirred for 10 min. Cyclopropyl-[1-(3-methoxypropyl)-1H-indol-3-ylmethyl]-amine (51.7 mg, 0.2 mmol) in $CH_2Cl_2/CH_3CN$ 1:1 (1 mL) is added and the mixture is stirred for 14 h at RT. The mixture is diluted with ethyl acetate, and washed twice with $K_2CO_3$ solution. The organic layer is dried over $Na_2SO_4$ and evaporated in vacuo. The crude product is treated with $CH_2Cl_2$/piperidine 4:1 (5 mL) and stirred for 1 h at RT. After evaporation in vacuo, the residue is purified by preparative HPLC (YMC Pack Pro C18, 10-100% $CH_3CN$+ 0.1% $TFA/H_2O$+0.1% TFA, flow 20 mL/min). The combined pure fractions are treated with solid $K_2CO_3$, $CH_3CN$ is removed in vacuo, and the residual aqueous phase is extracted twice with $CH_2Cl_2$. The combined organic layers are dried ($Na_2SO_4$) and evaporated to afford the title compound. MS: 485.5 $[M+H]^+$; $t_R$ (HPLC, Nucleosil C18; 5-100% $CH_3CN$+ 0.1% $TFA/H_2O$+0.1% TFA for 8 min, flow 1.5 ml/min): 5.33 min.

Scheme 8

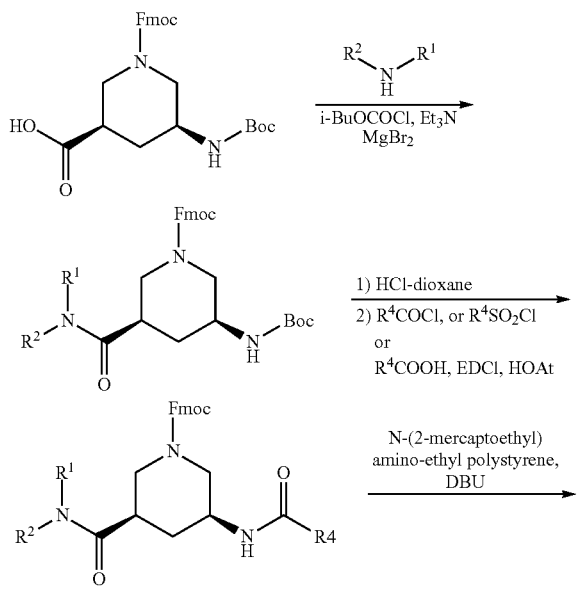

Example 134

(3R,5S)-5-Phenylacetylamino-piperidine-3-carboxylic acid cyclopropyl-[4-(3-methoxy-propyl)-2,2-dimethyl-3-oxo-3,4-dihydro-2H-benzo[1,4]oxazin-6-yl]-amide

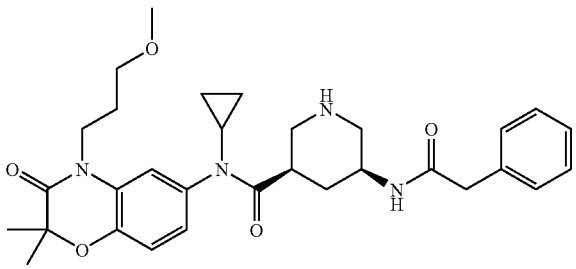

(3R,5S)-3-{Cyclopropyl-[4-(3-methoxy-propyl)-2,2-dimethyl-3-oxo-3,4-dihydro-2H-benzo-[1,4]oxazin-6-yl]-carbamoyl}-5-phenylacetylamino-piperidine-1-carboxylic acid 9H-fluoren-9-ylmethyl ester (90 mg, 0.12 mmol) is treated with 4N HCl/AcOEt (2 mL) at r.t. for 1 hr, then evaporated. The evaporated residue is dissolved in $CH_2Cl_2$ (1 mL). To the solution is added phenylacetyl chloride (20.4 mg, 0.132 mmol) and diisopropyl ethyl amine (32 mg, 0.264 mmol) at 0° C. and stirred for 40 min. After adding 1N HClaq, the mixture is extracted with $CH_2Cl_2$, washed with sat $NaHCO_3$aq, brine and dried ($MgSO_4$). Concentration under vacuum and the evaporated residue is dissolved in THF (1 mL). To the solution is added DBU (9 mg, 0.06 mmol) and N-(2-mercaptoethyl)aminoethyl polystyrene (2.1 mmol/g, 286 mg, 0.6 mmol) and stirred for 1 h at r.t. The reaction mixture is filtered via celite pad and washed with THF. Concentration under vacuum and purification with RP-HPLC gives the title compound. MS: 549 $[M+H]^+$; $t_R$ (HPLC, ACQUITY UPLC™ BEH $C_{18}$ 1.7 µm, 50×2.1 mm; 5% $CH_3CN$+0.1% $TFA/H_2O$+0.1% TFA for 0.5 min then 5-100% $CH_3CN$+0.1% $TFA/H_2O$+0.1% TFA for 5 min then 100% $CH_3CN$+0.1% TFA for 1.5 min, flow 0.5 ml/min): 2.78 min.

The starting material is prepared as follows:

A. (3R,5S)-3-{Cyclopropyl-[4-(3-methoxy-propyl)-2,2-dimethyl-3-oxo-3,4-dihydro-2H-benzo-[1,4]oxazin-6-yl]-carbamoyl}-5-phenylacetylamino-piperidine-1-carboxylic acid 9H-fluoren-9-ylmethyl ester To a solution of (3R,5S)-5-tert-Butoxycarbonylamino-piperidine-1,3-dicarboxylic acid 1-(9H-fluoren-9-ylmethyl) ester (338 mg, 0.73 mmol) in THF (5.0 mL), isobutyl chloroformate (0.1 mL, 0.79 mmol) and $Et_3N$ (0.1 mL, 0.79 mmol) are added at 0° C. After stirring for 1 h at the same temperature, the resulting precipitate is filtered off and the filtrate is concentrated. The evaporated residue is dissolved in THF (5 ml), 6-Cyclopropylamino-4-(3-methoxy-propyl)-2,2-dimethyl-4H-benzo[1,4]oxazin-3-one (200 mg, 0.66 mmol) and $MgBr_2.OEt_2$ (189 mg, 0.73 mmol) are added at room temperature. After stirring for 2 h, the reaction is quenched with $H_2O$ and resulting mixture is extracted with AcOEt, washed with 1N HCl solution, sat. NaHCO3aq and brine. The organic layer is dried ($MgSO_4$), concentrated and purified by silica gel column chromatography to afford the title compound as a white amorphous solid. MS: 753 $[M+H]^+$; $t_R$ (HPLC, CombiScreen ODS-AM 50×4.6 mm; 5-100% $CH_3CN$+0.1% $TFA/H_2O$+0.1% TFA for 5 min then 100% $CH_3CN$+0.1% TFA for 2 min, flow 2.0 ml/min): 4.77 min.

The amine used in Example 134A is prepared as follows:
B. 6-Cyclopropylamino-4-(3-methoxy-propyl)-2,2-dimethyl-4H-benzo[1,4]oxazin-3-one At room temperature, a solution of 2-amino-4-nitro-phenol (82.5 g, 0.54 mol) in DMF (660 ml) is treated with ethyl 2-bromoisobutyrate (160 ml, 1.07 mol) and KF (124.7 g, 2.15 mol), stirred at the same temperature for 1 h, warmed to 60° C., and stirred for 48 h. After pouring the mixture into H₂O (3500 ml), the resulting precipitate is collected by filtration, and washed with H₂O and Et₂O for several times respectively to give 2,2-dimethyl-6-nitro-4H-benzo[1,4]oxazin-3-one (84.8 g, 71%) as yellow solid. $R_f$ (hexane/EtOAc 2:1) 0.42. $^1$H-NMR (400 MHz, DMSO-d6) 1.48 (s), 7.16 (d, J=9.0), 6.42 (d, J=0.4), 8.00 (dd, J=9.0, 0.4). $^{13}$C-NMR (100 MHz, DMSO-d6) 167.7 (s), 147.5 (s), 142.0 (s), 128.0 (s), 119.2 (d), 117.3 (d), 110.3 (d), 78.9 (s), 23.7 (2q).

At 0° C., a solution of 2,2-dimethyl-6-nitro-4H-benzo[1,4]oxazin-3-one (35.8 g, 0.161 mol) and 1-methoxy-3-(p-toluenesulfonyloxy)propane (47.6 g, 0.195 mol) in DMF (720 ml) is treated with KI (5.49 g, 33.1 mmol). After adding 60% of NaH (7.80 g, 0.195 mol) over 10 min, the mixture is stirred at 0° C. for 30 min, warmed to 60° C., stirred for 14 h, and treated with H₂O (3500 ml). After the extraction of the mixture with EtOAc (3×400 ml) and Et₂O (3×400 ml), the combined org. layer is washed with H₂O (2×250 ml), dried (Na₂SO₄), and evaporated. A SiO₂ flash chromatography (2000 g, hexane/EtOAc 5:2) gives 4-(3-methoxy-propyl)-2,2-dimethyl-6-nitro-4H-benzo[1,4]oxazin-3-one (39.0 g, 82%) as yellow oil. $R_f$ (hexane/EtOAc 5:2) 0.45. $^1$H-NMR (400 MHz, CDCl₃) 1.55 (s), 1.91-2.02 (m, 2 H), 3.36 (s), 3.43 (t, J=6.0), 4.07 (t, J=6.0), 7.04 (d, J=9.0), 7.93 (dd, J=9.0, 0.4), 8.09 (d, J=0.4). $^{13}$C-NMR (100 MHz, CDCl₃) 167.6 (s), 148.9 (s), 143.0 (s), 129.5 (s), 119.8 (d), 117.7 (d), 110.4 (d), 78.9 (s), 69.4 (t), 58.7 (q), 39.7 (t), 27.5 (t), 23.7 (2q).

At room temperature, an ethanolic solution (80 ml) of 4-(3-methoxy-propyl)-2,2-dimethyl-6-nitro-4H-benzo[1,4]oxazin-3-one (9.76 g, 33.2 mmol) is treated with H₂O (80 ml), NH₄Cl (3.58 g, 66.9 mmol), and powdered Zn (10.97 g, 0.17 mol), heated to 80° C., stirred for 2 h under reflux, cooled to room temperature, and filtered via celite pad. After washing the cake with CH₂Cl₂ for several times, the both layers of the combined filtrate are separated. The aq. layer is treated with 5N NaOH (6.0 ml) to adjust its pH 9~10, and extracted with CH₂Cl₂ (3×100 ml). The combined org. layer is washed with sat. aqueous solution of NaHCO₃ (100 ml) and brine (50 ml), dried (Na₂SO₄), and evaporated. A SiO₂ flash chromatography (250 g, CH₂Cl₂/acetone 3:1) gives 6-amino-4-(3-methoxy-propyl)-2,2-dimethyl-4H-benzo[1,4]oxazin-3-one (9.23 g, 99%) as brown oil. $R_f$ (CH₂Cl₂/EtOAc 2:1) 0.34. $^1$H-NMR (400 MHz, CDCl₃) 1.39 (s), 1.80-1.91 (m, 2 H), 3.28 (s), 3.35 (t, J=8.0), 3.44 (br. s), 3.88 (t, J=9.0), 6.23 (dd, J=9.0, 0.4), 6.33 (d, J=0.4), 6.68 (d, J=9.0).

At room temperature, a methanolic solution (33 ml) of 6-amino-4-(3-methoxy-propyl)-2,2-dimethyl-4H-benzo[1,4]oxazin-3-one (4.13 g, 15.6 mmol) is treated with AcOH (8.3 ml) and [(1-ethoxycycopropyl)-oxy]trimethylsilane (3.1 ml, 15.6 mmol), warmed to 70° C., stirred for 1.5 h under reflux. At the same temperature, to this mixture is added dropwise a methanolic solution (5.5 ml) of NaBH₃CN (1.10 g, 17.5 mmol) over 5 min, and the resulting mixture is stirred at 70° C. under reflux for 2 h, and treated with CH₂Cl₂ (100 ml) and 5N NaOH (50 ml). After the separation of the both layers, the aq. layer is extracted with CH₂Cl₂ (3×30 ml). The combined org. layer is washed with brine (50 ml), dried (Na₂SO₄), and evaporated. A SiO₂ flash chromatography (200 g, hexane/EtOAc 3:2) gives the title compound (3.03 g, 64%) as light yellow solid. $R_f$(hexane/EtOAc 3:2) 0.48. $^1$H-NMR (400 MHz, CDCl₃) 0.47-0.54 (m, 2 H), 0.68-0.73 (m, 2 H), 1.55 (s), 1.88-1.96 (m, 2 H), 2.36-2.43 (m, 1 H), 3.34 (s), 3.44 (t, J=6.0), 3.97 (t, J=9.0), 4.09 (br. s), 6.45 (dd, J=9.0, 0.4), 6.53 (d, J=0.4), 6.80 (d, J=9.0). $^{13}$C-NMR (100 MHz, CDCl₃) 169.2 (s), 144.3 (s), 135.5 (s), 129.6 (s), 118.1 (d), 107.9 (d), 99.9 (d), 77.2 (s), 70.1 (t), 58.7 (q), 39.2 (t), 27.6 (t), 25.7 (d), 23.6 (2q), 7.3 (2t).

Example 135

(3R,5S)-5-(2-Phenoxy-acetylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide

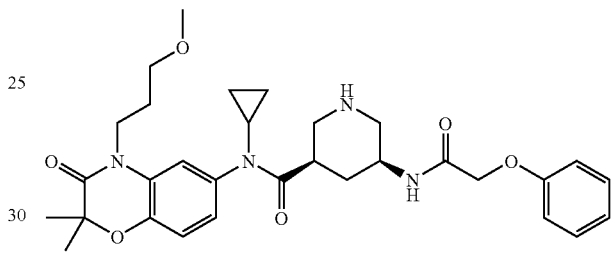

The title compound is prepared analogously as described in Example 134 using phenoxyacetyl chloride. MS: 565 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 2.87 min.

Example 136

(3R,5S)-5-[(1-Phenyl-cyclopropanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

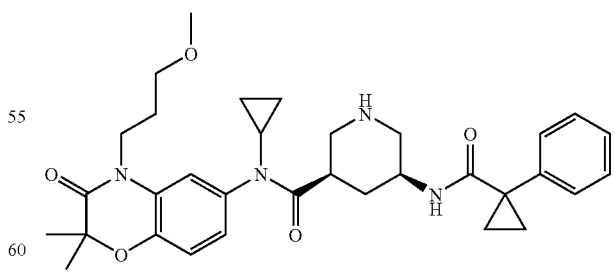

The title compound is prepared analogously as described in Example 134 using 1-phenyl-1-cyclopropyl carboxylic acid as acid component and EDCI and HOAt for the acylation step. MS: 575 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 3.02 min.

Example 137

(3R,5S)-5-(2-Hydroxy-4-methyl-pentanoylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide

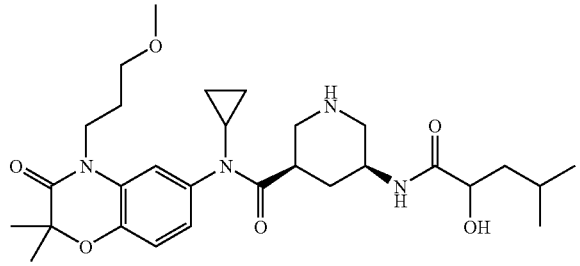

The title compound is prepared analogously as described in Example 134 using DL-leucic acid as acid component and EDCI and HOAt for the acylation step. MS: 545 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 2.64, 2.74 min.

Example 138

(3R,5S)-5-(2-Hydroxy-3-phenyl-propionylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide

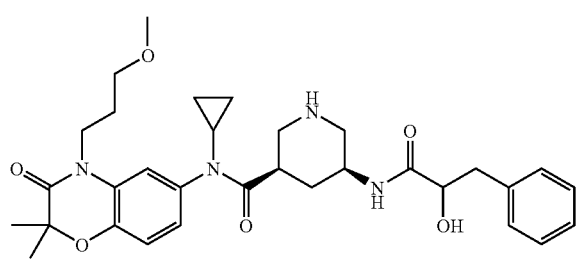

The title compound is prepared analogously as described in Example 134 using DL-phenyllactic acid as acid component and EDCI and HOAt for the acylation step. MS: 579 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 2.70, 2.81 min.

Example 139

(3R,5S)-5-(2-Hydroxy-3-methyl-butyrylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide

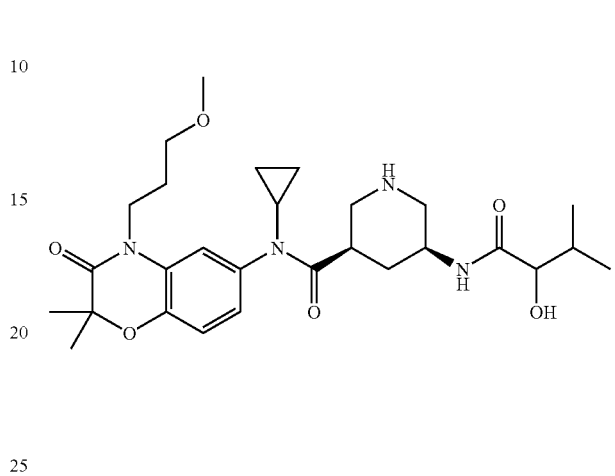

The title compound is prepared analogously as described in Example 134 using DL-valic acid as acid component and EDCI and HOAt for the acylation step. MS: 531 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 2.49, 2.93 min.

Example 140

(3R,5S)-5-[2-(Tetrahydro-pyran-4-yloxy)-acetylamino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

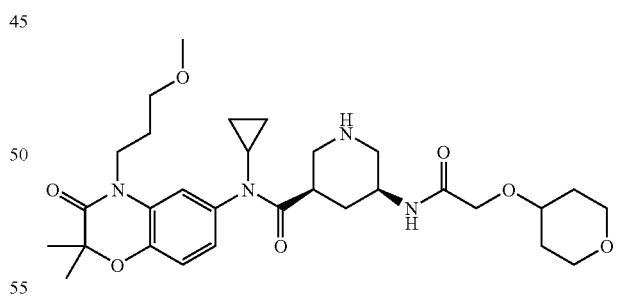

The title compound is prepared analogously as described in Example 134 using [(tetrahydro-2H-pyran-4-yl)oxy]-acetic acid as acid component and EDCI and HOAt for the acylation step. MS: 573 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 2.46 min.

Example 141

((3S,5R)-5{Cyclopropyl-[4-(3-methoxy-propyl)-2,2-dimethyl-3-oxo-3,4-dihydro-2H-benzo[1,4]oxazin-6-yl]-carbamoyl}-piperidin-3-yl)-carbamic acid tetrahydro-pyran-4-yl ester

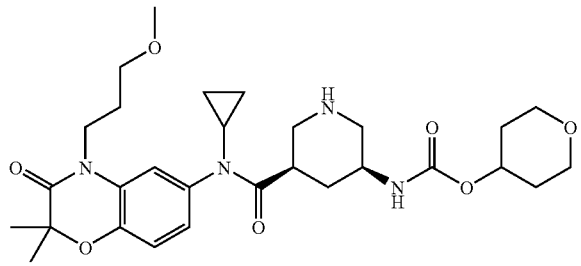

The title compound is prepared analogously as described in Example 134 using Carbonochloridic acid, tetrahydro-2H-pyran-4-yl ester. MS: 599 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 2.53 min.

Example 142

(3R,5S)-5-(2-Hydroxymethyl-3-methyl-butyrylamino)-piperidine-3-carboxylic acid cyclopropyl-[4-(3-methoxy-propyl)-2,2-dimethyl-3-oxo-3,4-dihydro-2H-benzo[1,4]-oxazin-6-yl]-amide

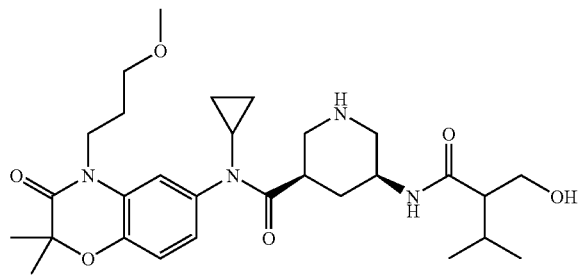

The title compound is prepared by Fmoc deprotection of (3R,5S)-3-{Cyclopropyl-[4-(3-methoxy-propyl)-2,2-dimethyl-3-oxo-3,4-dihydro-2H-benzo[1,4]oxazin-6-yl]-carbamoyl}-5-(2-hydroxymethyl-3-methyl-butyrylamino)-piperidine-1-carboxylic acid 9H-fluoren-9-ylmethyl ester analogously as described in Example 134. MS: 545 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 2.43, 2.61 min.

The starting materials are prepared as follows:

A. (3R,5S)-3-{Cyclopropyl-[4-(3-methoxy-propyl)-2,2-dimethyl-3-oxo-3,4-dihydro-2H-benzo[1,4]oxazin-6-yl]-carbamoyl}-5-(2-hydroxymethyl-3-methyl-butyrylamino)-piperidine-1-carboxylic acid 9H-fluoren-9-ylmethyl ester To a solution of (3R,5S)-3-{Cyclopropyl-[4-(3-methoxy-propyl)-2,2-dimethyl-3-oxo-3,4-di hydro-2H-benzo[1,4]oxazin-6-yl]-carbamoyl}-5-[3-methyl-2-(2-trimethylsilanyl-ethoxymethyl)-butyrylamino]-piperidine-1-carboxylic acid 9H-fluoren-9-ylmethyl ester in $CH_2Cl_2$ is added $BF_3$ $Et_2O$ at room temperature, then the mixture is stirred at room temperature. After 1.5 h, the reaction mixture is diluted with $H_2O$ (10 mL) and extracted with $CH_2Cl_2$ (20 mL). The organic phase is washed with 5% aqueous $KHSO_4$ (10 mL), 5% aqueous $NaHCO_3$, $H_2O$, and brine, then dried over $Na_2SO_4$. The solution is filtered and the solvent is evaporated in vacuo to give the title compound as white amorphous material. MS: 767 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 1.55 min.

B. (3R,5S)-3-{Cyclopropyl-[4-(3-methoxy-propyl)-2,2-dimethyl-3-oxo-3,4-dihydro-2H-benzo[1,4]oxazin-6-yl]-carbamoyl}-5-[3-methyl-2-(2-trimethylsilanyl-ethoxymethyl)-butyrylamino]-piperidine-1-carboxylic acid 9H-fluoren-9-ylmethyl ester The title compound is prepared analogously as described in Example 134 using 3-Methyl-2-(2-trimethylsilanyl-ethoxymethyl)-butyric acid as acid component and EDCI and HOAt for the acylation step. MS: 867 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 5.21 min.

C. 3-Methyl-2-(2-trimethylsilanyl-ethoxymethyl)-butyric acid

To a solution of 3-methylbutyric acid ethyl ester (1.3 g, 10 mmol) in THF (50 mL) is added dropwise LDA solution (2 M in THF/hexane/ethylbenzene, 6 mmol) at −78° C., and the mixture is stirred at −78° C. After 0.5 h, to the reaction mixture is added (2-chloromethoxyethyl)trimethylsilane (2.65 mL, 15 mmol) at −78° C. The reaction mixture is allowed to warm to 0° C. 2 h and then quenched by addition of 100 mL of 5% aqueous $KHSO_4$ and extracted with $Et_2O$ (200 mL). The organic phase is successively washed with 5% aqueous $KHSO_4$, 5% aqueous $NaHCO_3$, $H_2O$, and brine, then dried over $Na_2SO_4$ and concentrated in reduced pressure. A mixture of the residue and 1M aqueous NaOH in MeOH is stirred at 70° C. After 5 h at 70° C., the reaction mixture is quenched by 5% aqueous $KHSO_4$ (100 mL) and extracted with $Et_2O$ (200 mL). The organic phase is successively washed with $H_2O$, and brine, then dried over $Na_2SO_4$. The solution is filtered and the solvent is evaporated in vacuo to afford the title compound.

Example 143

((3S,5R)-5-{Cyclopropyl-[4-(3-methoxy-propyl)-2,2-dimethyl-3-oxo-3,4-dihydro-2H-benzo[1,4]oxazin-6-yl]-carbamoyl}-piperidin-3-yl)-carbamic acid tert-butyl ester

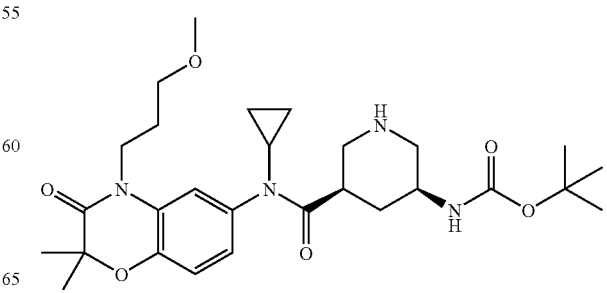

The title compound is prepared by Fmoc deprotection of Example 134A as described in Example 134. MS: 599 [M+H]$^+$; $t_R$ (HPLC, CombiScreen ODS-AM 50×4.6 mm; 5-100% CH$_3$CN+0.1% TFA/H$_2$O+0.1% TFA for 5 min then 100% CH$_3$CN+0.1% TFA for 2 min, flow 2.0 ml/min): 2.70 min.

Example 144

(3R,5S)-5-Acetylamino-piperidine-3-carboxylic acid cyclopropyl-[4-(3-m ethoxy-propyl)-2,2-dimethyl-3-oxo-3,4-dihydro-2H-benzo[1,4]oxazin-6-yl]-amide

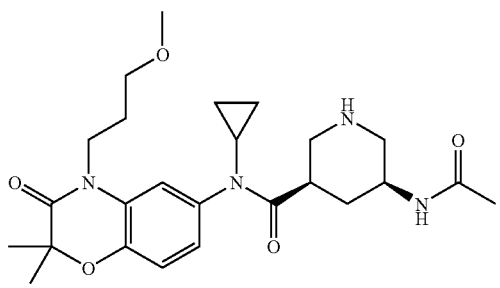

The title compound is prepared analogously as described in Example 134 using acetic anhydride. MS: 473 [M+H]$^+$; $t_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.33 min.

Example 145

(3R,5S)-5-[2-(Pyridin-3-yloxy)-acetylamino]-piperidine-3-carboxylic ac id cyclopropyl-[4-(3-methoxy-propyl)-2,2-dimethyl-3-oxo-3,4-dihydro-2H-benzo[1,4]oxazin-6-yl]-amide

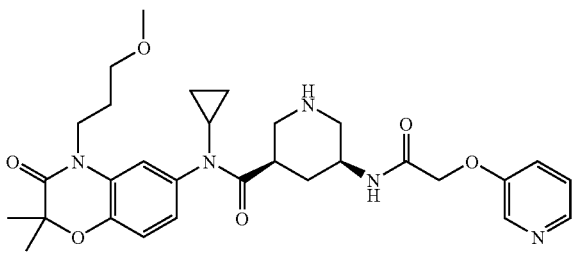

The title compound is prepared analogously as described in Example 134 using (Pyridin-3-yloxy)-acetic acid as acid component and EDCI and HOAt for the acylation step. MS: 566 [M+H]$^+$; $t_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.24 min.

The starting materials are prepared as follows:

A. (Pyridin-3-yloxy)-acetic acid

A mixture of (Pyridin-3-yloxy)-acetic acid tert-butyl ester (60 mg, 0.29 mmol) and HCl in dioxane (4 M, 2 mL) is stirred at room temperature for 1 h. The reaction mixture is concentrated in vacuo to give the title compound. MS: 154 [M+H]$^+$; $t_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 0.40 min.

B. (Pyridin-3-yloxy)-acetic acid tert-butyl ester

A mixture of t-butyl bromoacetate (2 g, 10 mmol), 3-hydroxypyridine (1.5 g, 15 mmol), and K$_2$CO$_3$ (2.9 g, 21 mmol) in THF (20 mL) is stirred at 60° C. After 0.5 h, the reaction mixture is cooled down at room temperature and diluted with H$_2$O, then extracted with EtOAc. The organic phase is washed with H$_2$O, and brine, then dried over Na$_2$SO$_4$. The solution is filtered and the solvent is evaporated in vacuo. The residue is purified by silica gel column chromatography to give the title compound. MS: 210 [M+H]$^+$; $t_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 1.85 min.

Example 146

(3R,5S)-5-(2-Tetrahydro-pyran-4-yl-acetylamino)-piperidine-3-carboxylic acid cyclopropyl-[4-(3-methoxy-propyl)-2,2-dimethyl-3-oxo-3,4-dihydro-2H-benzo-[1,4]oxazin-6-yl]-amide

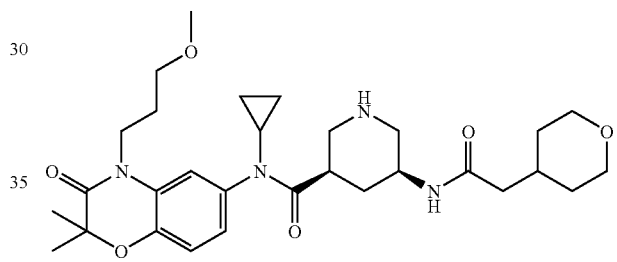

The title compound is prepared analogously as described in Example 134 using (Tetrahydro-pyran-4-yl)-acetic acid as acid component and EDCI and HOAt for the acylation step. MS: 557 [M+H]$^+$; $t_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.78 min.

Example 147

(3R,5S-5-(3-Hydroxy-3-methyl-butyrylamino)-piperidine-3-carboxylic ac id cyclopropyl-[4-(3-methoxy-propyl)-2,2-dimethyl-3-oxo-3,4-dihydro-2H-benzo[1,4]oxazin-6-yl]-amide

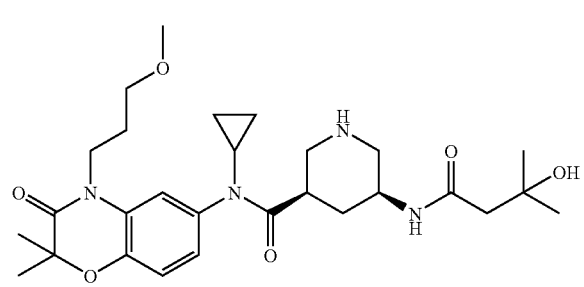

147

The title compound is prepared analogously as described in Example 134 using 3-Hydroxy-3-methyl-butyric acid as acid component and EDCI and HOAt for the acylation step. MS: 531 [M+H]$^+$; t$_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.46 min.

Example 148

(3R,5S)-5-[(Tetrahydro-pyran-4-carbonyl)-amino]-Piperidine-3-carboxylic acid cyclopropyl-[4-(3-methoxy-propyl)-2,2-dimethyl-3-oxo-3,4-dihydro-2H-benzo[1,4]oxazin-6-yl]-amide

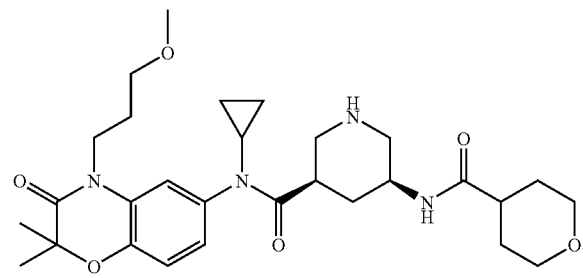

The title compound is prepared analogously as described in Example 134 using Tetrahydro-pyran-4-carboxylic acid as acid component and EDCI and HOAt for the acylation step. MS: 543 [M+H]$^+$; t$_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.48 min.

Example 149

N-((3S,5R)-5-{Cyclopropyl-[4-(3-methoxy-propyl)-2,2-dimethyl-3-oxo-3,4-dihydro-2H-benzo[1,4]oxazin-6-yl]-carbamoyl}-piperidin-3-yl)-nicotinamide

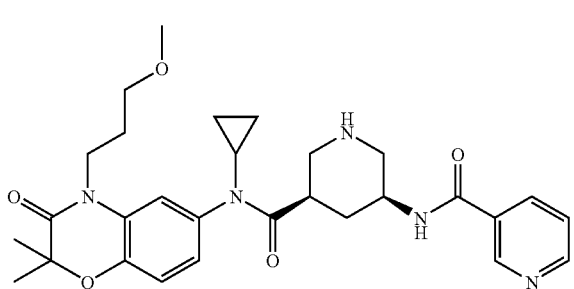

The title compound is prepared analogously as described in Example 134 using Nicotinic acid as acid component and EDCI and HOAt for the acylation step. MS: 536 [M+H]$^+$; t$_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.41 min.

148

Example 150

(3R,5S)-5-Methanesulfonylamino-piperidine-3-carboxylic acid cyclopropyl-[4-(3-methoxy-propyl)-2,2-dimethyl-3-oxo-3,4-dihydro-2H-benzo[1,4]oxazin-6-yl]-amide

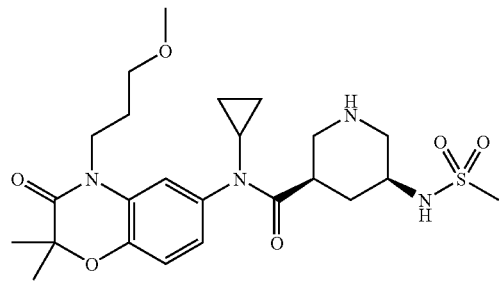

The title compound is prepared analogously as described in Example 134 using methanesulfonyl chloride. MS: 509 [M+H]$^+$; t$_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.44 min.

Example 151

(3R,5S)-5-(2,2-Dimethyl-propionylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide

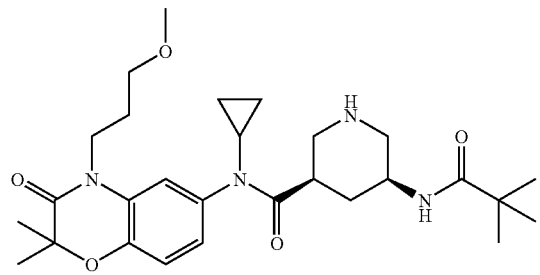

The title compound is prepared analogously as described in Example 134 using pivaloyl chloride. MS: 515 [M+H]$^+$; t$_R$ (HPLC, CombiScreen ODS-AM 50×4.6 mm; 5-100% CH$_3$CN+0.1% TFA/H$_2$O+0.1% TFA for 5 min then 100% CH$_3$CN+0.1% TFA for 2 min, flow 2.0 ml/min): 2.54 min.

Example 152

(3R,5S)-5-[(1-Cyano-cyclopropanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

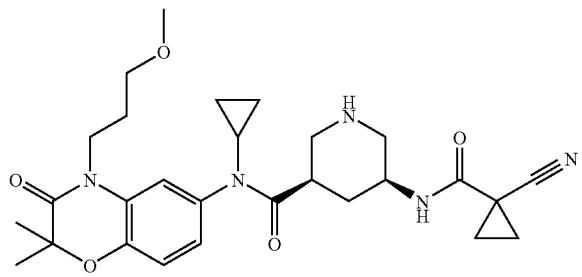

The title compound is prepared analogously as described in Example 134 using 1-cyano-cyclopropanecarboxylic acid as acid component and EDCI and HOAt for the acylation step. MS: 524 [M+H]$^+$; $t_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.54 min.

Example 153

(3R,5S)-5-(4-Methyl-pentanoylamino)-piperidine-3-carboxylic acid cyclo propyl-[4-(3-methoxy-propyl)-2,2-dimethyl-3-oxo-3,4-dihydro-2H-benzo[1,4]oxazin-6-yl]-amide

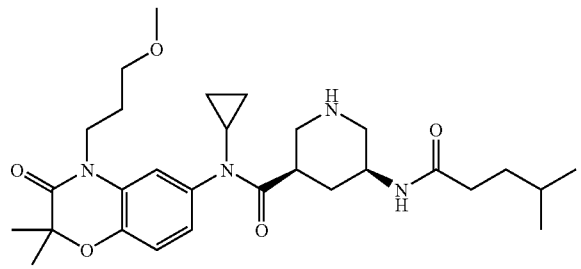

The title compound is prepared analogously as described in Example 134 using 4-Methyl-pentanoic acid as acid component and EDCI and HOAt for the acylation step. MS: 529 [M+H]$^+$; $t_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.87 min.

Example 154

(3R,5S)-5-[(1-Cyano-cyclopentanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

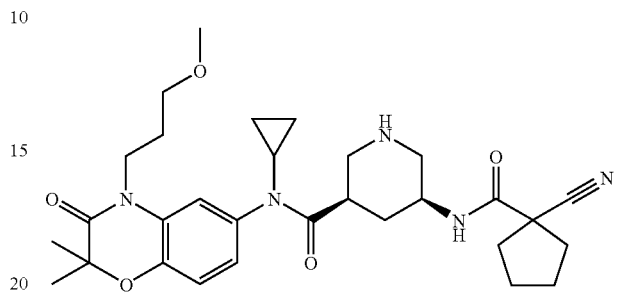

The title compound is prepared analogously as described in Example 134 using 1-Cyano-cyclopentanecarboxylic acid as acid component and EDCI and HOAt for the acylation step. MS: 552 [M+H]$^+$; $t_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.60 min.

Example 155

(3R,5S)-5-[2-(4-Hydroxy-tetrahydro-pyran-4-yl)-acetylamino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

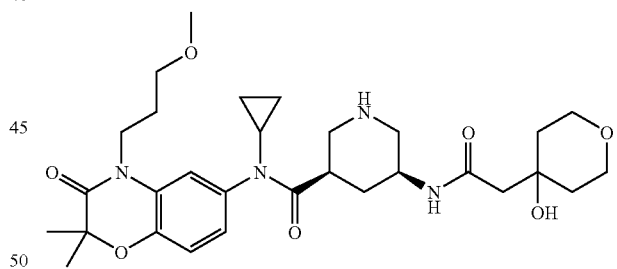

The title compound is prepared analogously as described in Example 134 using (4-Hydroxy-tetrahydro-pyran-4-yl)-acetic acid as acid component and EDCI and HOAt for the acylation step. MS: 573 [M+H]$^+$; $t_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.35 min.

The starting materials are prepared as follows:

A. (4-Hydroxy-tetrahydro-pyran-4-yl)-acetic acid

To a solution of ethyl acetate (2.3 mL, 24 mmol) in THF (60 mL), 1M solution of lithium hexamethyldisilazide in THF (24 mL, 24 mmol) is added at −78° C. After stirring 1 hour at the same temperature, tetrahydro-4H-pyran-4-one (1.9 mL, 20 mmol) is added dropwise, and the reaction mixture is allowed to warm to rt over 2 hours. The reaction mixture is diluted with H$_2$O and extracted with EtOAc. The combined organic phases are washed with H$_2$O and dried over Na$_2$SO$_4$. Concentration under reduced pressure and filtration through silica gel give a crude product. To a solution of (4-hydroxy-tetrahydro-pyran-4-yl)-acetic acid ethyl ester (1.85 g) in 1,4-dioxane (5 mL) and H$_2$O (5 mL), lithium hydroxide (235 mg, 9.8 mmol) is added at 0° C. After stirring for 7 hours at rt, the reaction mixture is diluted with H$_2$O and extracted with Et$_2$O. The aqueous layer is acidified with 1N HCl aq. and extracted with Et$_2$O. The combined organic phases are washed with H$_2$O and dried over Na$_2$SO$_4$. Concentration under reduced pressure and filtration through silica gel give a crude product. The material is used in next step without purification.

Example 156

(3R,5S)-5-(4-Hydroxy-4-methyl-pentanoylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide

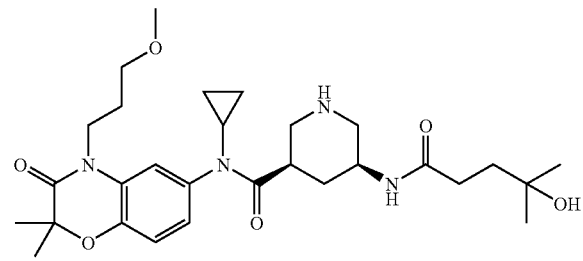

The title compound is prepared analogously as described in Example 134 using 4-Hydroxy-4-methyl-pentanoic acid (Bioorganic & Medicinal Chemistry (2005), 13(24), 6693-6702) as acid component and EDCI and HOAt for the acylation step. MS: 545 [M+H]$^+$; t$_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.41 min.

Example 157

(3R,5S)-5-[(4-Cyano-tetrahydro-pyran-4-carbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

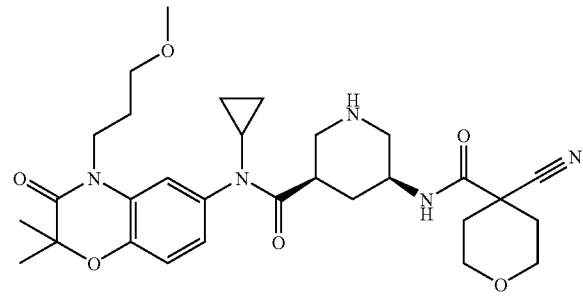

The title compound is prepared analogously as described in Example 134 using 4-Cyano-tetrahydro-pyran-4-carboxylic acid (WO2005058860) as acid component and EDCI and HOAt for the acylation step. MS: 568 [M+H]$^+$; t$_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.53 min.

Example 158

(3R,5S)-5-[2-Methyl-2-(tetrahydro-pyran-4-yl)-propionylamino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

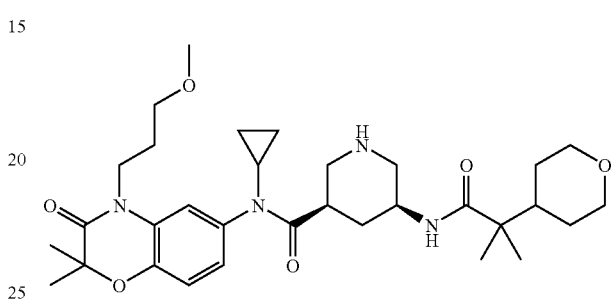

The title compound is prepared analogously as described in Example 134 using 2-Methyl-2-(tetrahydro-pyran-4-yl)-propionic acid chloride (derived from the corresponding carboxylic acid, WO2005070870) for the acylation step. MS: 584 [M+H]$^+$; t$_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.66 min.

Example 159

(3R,5S)-5-(2-Tetrahydro-pyran-4-VI-propionylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide

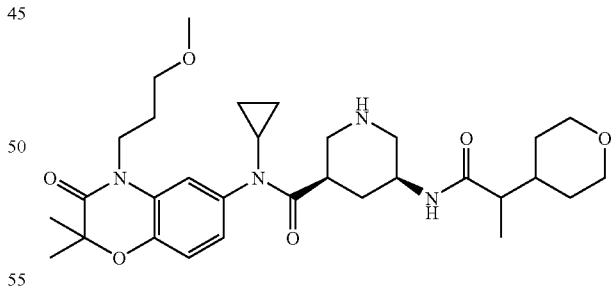

The title compound is prepared analogously as described in Example 134 using 2-(Tetrahydro-pyran-4-yl)-propionic acid as acid component and EDCI and HOAt for the acylation step. MS: 571 [M+H]$^+$; t$_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.56 min.

The starting materials are prepared as follows:
A. 2-(Tetrahydro-pyran-4-yl)-propionic acid
To a solution of (Tetrahydro-pyran-4-yl)-acetic acid ethyl ester (2.0 g, 11.6 mmol) in 50 mL of THF at −78° C. LDA (1.0

M, 17.4 mL, 34.8 mmol) is added dropwise. The solution is stirred for 0.5 h and treated with HMPA (3.2 mL, 9.3 mmol) and MeI (4.94 g, 34.8 mmol). The reaction mixture is stirred at the same temperature for 0.5 h and for 1.5 h at 0° C., acidified with aqueous 1 N aqueous HCl solution, and extracted twice with ether (2×40 mL). The organic phase is washed with saturated aqueous NaCl solution, dried (MgSO$_4$), and concentrated in vacuo to give 1.8 g of 2-(Tetrahydro-pyran-4-yl)-propionic acid ethyl ester which is hydrolyzed without further purification. A solution of the crude ester (500 mg, 2.68 mmol) and 5 N aqueous NaOH solution (2.68 mL, 13.4 mmol) in dioxane-water (4 mL/2 mL) is heated at 60° C. for 2 h. The solution is cooled to room temperature, acidified with 1 N aqueous HCl solution, and extracted with ether. The ether layer is washed with saturated aqueous NaCl solution, dried over anhydrous MgSO$_4$, and concentrated in vacuo to give 400 mg of the title compound. MS: 159 [M+H]$^+$; t$_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.27 min.

Example 160

(3R,5S)-5-[(1-Pyridin-4-yl-cyclopropanecarbonyl)-amino]-piperidine-3-carboxylic acid [4-(3-methoxy-propyl)-2,2-dimethyl-3-oxo-3,4-dihydro-2H-benzo[1,4]oxazin-6-yl]-amide

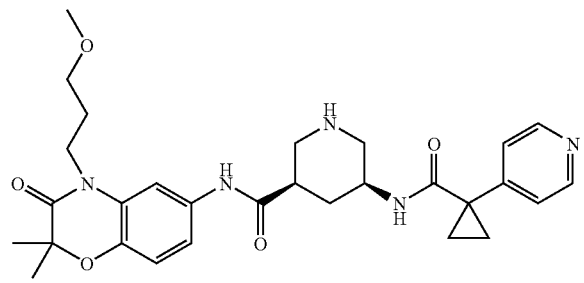

The title compound is prepared analogously as described in Example 134 using 1-pyridin-4-yl-cyclopropanecarboxylic acid component and EDCI and HOAt for the acylation step. MS: 576 [M+H]$^+$; t$_R$ (HPLC, ACQUITY UPLC™ BEH C18 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.24 min.

The starting materials are prepared as follows:

A. 1-pyridin-4-yl-cyclopropanecarboxylic acid

To a mixture of pyridin-4-yl-acetic acid (930 mg, 6.0 mmol) and 1-bromo-2-chloroethane (750 mg, 9.0 mmol) in 50% NaOH aq. solution (5 mL) is added benzyltriethylammonium chloride (680 mg, 3 mmol). The solution is heated to 60° C. and stirred at the temperature for 2 hours. After cooling down to rt, the aqueous layer is removed and the organic layer is neutralized with sat. NH$_4$Cl aq. and extracted with Et$_2$O. The combined organic phases are washed with H$_2$O and dried over Na$_2$SO$_4$. Concentration under reduced pressure gives the title compound. The material is used in a next step without purification.

Example 161

(3R,5S)-5-[(1-Pyridin-4-yl-cyclopropanecarbonyl)-amino]-piperidine-3-carboxylic acid [4-(3-methoxy-propyl)-2,2-dimethyl-3-oxo-3,4-dihydro-2H-benzo[1,4]oxazin-6-yl]-amide

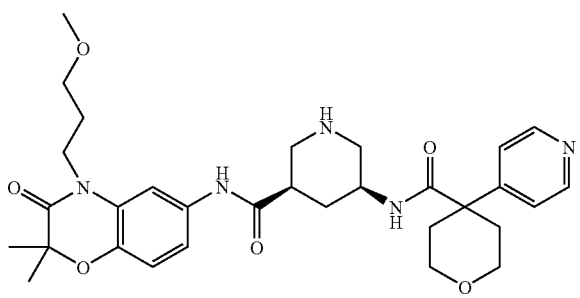

The title compound is prepared analogously as described in Example 134 using 4-pyridin-4-yl-tetrahydro-pyran-4-carboxylic acid component and EDCI and HOAt for the acylation step. MS: 620 [M+H]$^+$; t$_R$ (HPLC, ACQUITY UPLC™ BEH C18 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.26 min.

The starting materials are prepared as follows:

A. 4-Pyridin-4-yl-tetrahydro-pyran-4-carboxylic acid

To a mixture of pyridin-4-yl-acetic acid (930 mg, 6.0 mmol) and bis-(2-chloroethyl)ether 1.1 mL, 9.0 mmol) in 50% NaOH aq. solution (5 mL) is added benzyltriethylammonium chloride (680 mg, 3 mmol). The solution is heated to 60° C. and stirred at the temperature for 2 hours. After cooling down to rt, the aqueous layer is removed and the organic layer is neutralized with sat. NH$_4$Cl aq. and extracted with Et$_2$O. The combined organic phases are washed with H$_2$O and dried over Na$_2$SO$_4$. Concentration under reduced pressure gives the title compound. The material is used in a next step without purification.

Example 162

(3R,5S)-5-[(1-Pyridin-2-yl-cyclopentanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

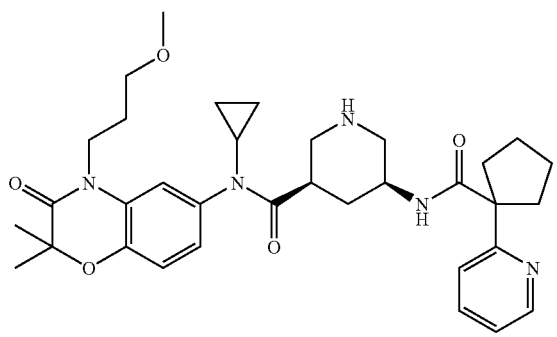

The title compound is prepared analogously as described in Example 134 using 1-Pyridin-2-yl-cyclopentanecarboxylic acid (WO 2002014277) as acid component acid and EDCI and HOAt for the acylation step. MS: 604 [M+H]$^+$; $t_R$ (CombiScreen ODS-AM, 50×4.6 mm; 5% CH$_3$CN+0.1% TFA/ H$_2$O+0.1% TFA for 0.5 min then 5-100% CH$_3$CN+0.1% TFA/H$_2$O+0.1% TFA for 5 min then 100% CH$_3$CN+0.1% TFA for 2 min, flow 2.0 ml/min): 2.23 min.

Example 163

(3R,5R)-5-{2-Oxo-2-[1-(2H-tetrazol-5-yl)-cyclopropyl]-ethyl}-piperidine-3-carboxylic acid cyclopropyl-[4-(3-methoxy-propyl)-2,2-dimethyl-3-oxo-3,4-dihydro-2H-benzo[1,4]oxazin-6-yl]-amide

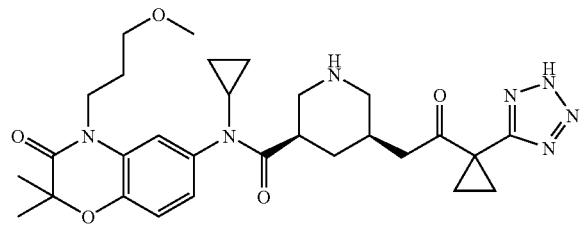

To a solution of (3R,5S)-3-{Cyclopropyl-[4-(3-methoxy-propyl)-2,2-dimethyl-3-oxo-3,4-dihydro-2H-benzo[1,4]oxazin-6-yl]-carbamoyl}-5-{[1-(2H-tetraol-5-yl)-cyclopropane-carbonyl]-amino}-piperidine-1-carboxylic acid 9H-fluoren-9-ylmethyl ester (89 mg, 0.107 mmol) in THF (10 mL) is added DBU (11 mg, 0.0107 mmol) and N-(2-mercaptoethyl)aminoethyl polystyrene (2.1 mmol/g, 340 mg, 0.72 mmol) and stirred for 1 h at r.t. The reaction mixture is filtered via Celite pad and washed with THF. Concentration under vacuum and purification with silica-gel column chromatography gives the title compound as a white solid. MS: 567 [M+H]$^+$; $t_R$ (CombiScreen ODS-AM, 50×4.6 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 2 min, flow 2.0 ml/min): 2.27 min.

The starting materials are prepared as follows:
A. (3R,5S)-3-{Cyclopropyl-[4-(3-methoxy-propyl)-2,2-dimethyl-3-oxo-3,4-dihydro-2H-benzo[1,4]oxazin-6-yl]-carbamoyl}-5-{[1-(2H-tetraol-5-yl)-cyclopropanecarbonyl]-amino}-piperidine-1-carboxylic acid 9H-fluoren-9-ylmethyl ester A microwave vial is charged with (3S,5R)-3-[(1-Cyano-cyclopropanecarbonyl)-amino]-5-{cyclopropyl-[4-(3-methoxy-propyl)-2,2-dimethyl-3-oxo-3,4-dihydro-2H-benzo[1,4]oxazin-6-yl]-carbamoyl}-piperidine-1-carboxylic acid 9H-fluoren-9-ylmethyl ester (80 mg, 0.107 mmol), Azidotrimethylsilane (0.06 mL, 0.645 mmol), Dibutyltin (IV) oxide (2.6 mg, 0.011 mmol) and DME (2 mL). The reaction mixture is heated at 150° C. for 20 min in a CEM Discover microwave. After the mixture is cooled to room temperature, the mixture is concentrated under reduced pressure to give the title compound as a: yellow amorphous, MS: 789 [M+H]$^+$; $t_R$ (CombiScreen ODS-AM, 50×4.6 mm; 5% CH$_3$CN+0.1% TFA/ H$_2$O+0.1% TFA for 0.5 min then 5-100% CH$_3$CN+0.1% TFA/H$_2$O+0.1% TFA for 5 min then 100% CH$_3$CN+0.1% TFA for 2 min, flow 2.0 ml/min): 3.90 min.

B. (3S,5R)-3-[(1-Cyano-cyclopropanecarbonyl)-amino]-5-{cyclopropyl-[4-(3-methoxy-propyl)-2,2-dimethyl-3-oxo-3,4-dihydro-2H-benzo[1,4]oxazin-6-yl]-carbamoyl}-piperidine-1-carboxylic acid 9H-fluoren-9-ylmethyl ester To a solution of (3S,5R)-3-Amino-5-{cyclopropyl-[4-(3-methoxy-propyl)-2,2-dimethyl-3-oxo-3,4-dihydro-2H-benzo[1,4]oxazin-6-yl]-carbamoyl}-piperidine-1-carboxylic acid 9H-fluoren-9-ylmethyl ester hydrochloride salt (100 mg, 0.152 mmol) and 1-Cyano-cyclo-propanecarboxylic acid (20 mg, 0.182 mmol) in DMF (10 mL) is added EDC-HCl (45 mg, 0.227 mmol), HOAt (31 mg, 0.227 mmol) and diisopropylethylamine (0.04 mL, 0.227 mmol) at 0° C. The mixture is stirred for 14 h at r.t. and diluted with ethyl acetate, and washed with H$_2$O. The organic layer is dried over MgSO$_4$ and evaporated in vacuo. The residue is purified by silica-gel column chromatography to afford the title compound as a white solid. MS: 746 [M+H]$^+$; $t_R$ (CombiScreen ODS-AM, 50×4.6 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 2 min, flow 2.0 ml/min): 2.14 min.

Scheme 9

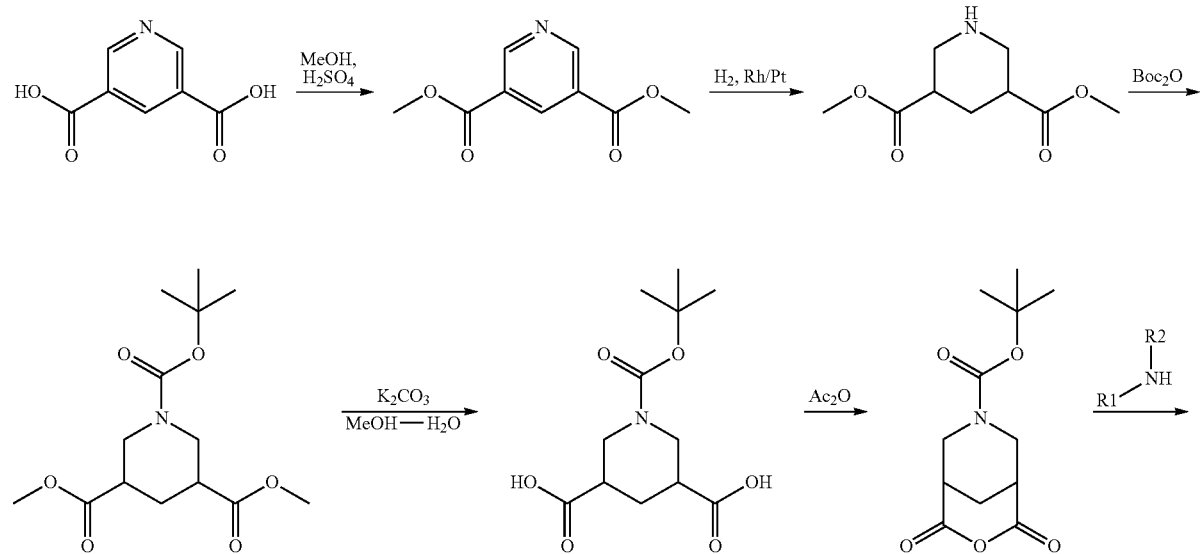

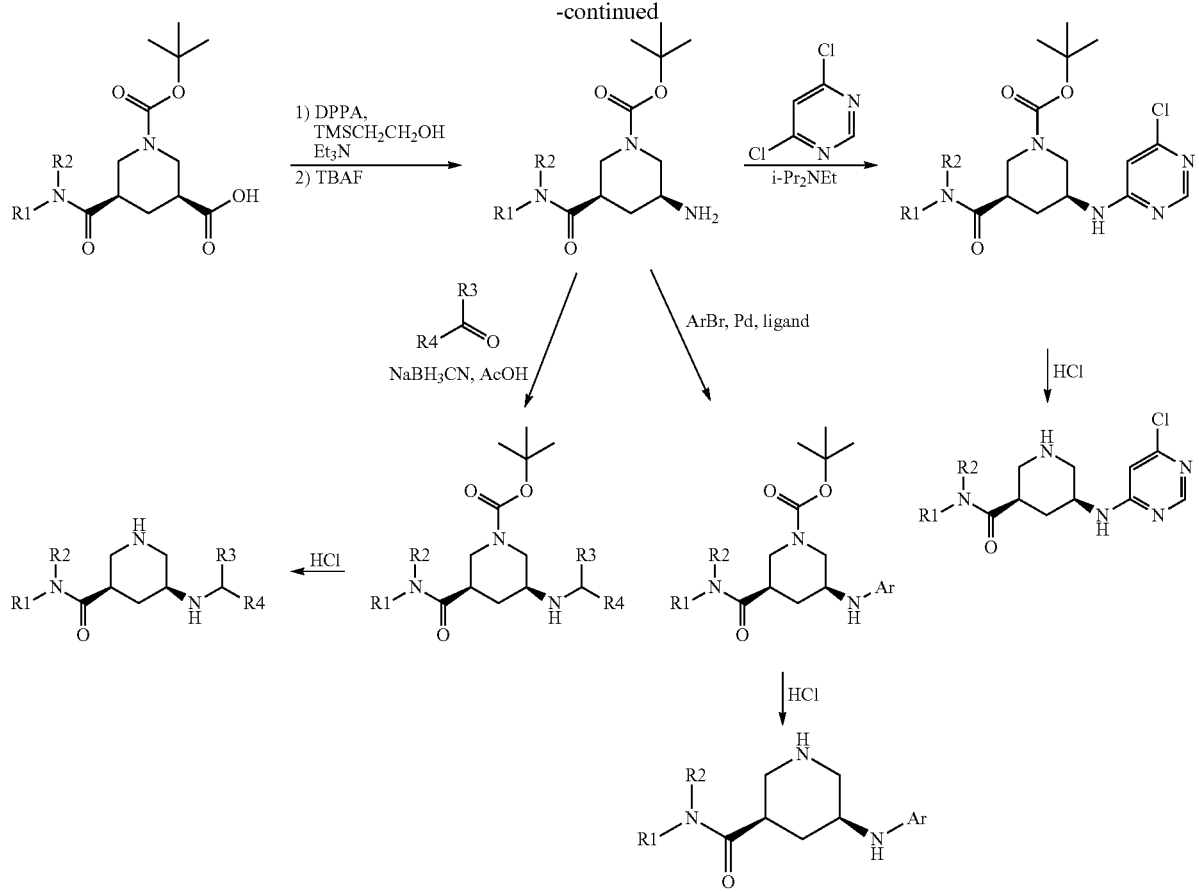

Example 164

(3R*,5S*)-5-Cyclohexylamino-piperidine-3-carboxylic acid cyclopropyl-[3-methoxy-5-(3-methoxy-propoxy)-benzyl]-amide

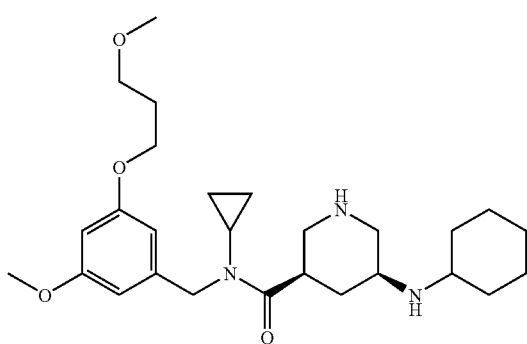

A mixture of (3S*,5R*)-3-Amino-5-{cyclopropyl-[3-methoxy-5-(3-methoxy-propoxy)-benzyl]-carbamoyl}-piperidine-1-carboxylic acid tert-butyl ester (42 mg, 0.085 mmol), cyclohexanone (8.4 mg, 0.086 mmol), and acetic acid (0.025 mL, 0.44 mmol) in MeOH is stirred at room temperature for 1 h. To the resulting mixture is added NaBH$_3$CN (6 mg, 0.095 mmol) and the mixture is stirred for 3 h. The mixture is purified by RP-HPLC to give the desired amine, which is treated with 4 N HCl-1,4-dioxane (1 mL) at room temperature for 1.5 h. Concentration under vacuum gives the title compound as a white amorphous solid. MS: 473 [M+H]$^+$; t$_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.38 min.

The starting material is prepared as follows:

A. (3S*,5R*)-3-Amino-5-{cyclopropyl-[3-methoxy-5-(3-methoxy-propoxy)-benzyl]-carbamoyl}-piperidine-1-carboxylic acid tert-butyl ester To a solution of Cyclopropyl-[3-methoxy-5-(3-methoxy-propoxy)-benzyl]-amine (1.18 g, 4.45 mmol) and triethylamine (0.68 mL, 4.90 mmol) in THF (20 mL) at room temperature is added 2,4-Dioxo-3-oxa-7-aza-bicyclo[3.3.1]nonane-7-carboxylic acid tert-butyl ester (1.07 g, 4.19 mmol). After stirred for 2 h, bulk of the solvent is concentrated. The residue is diluted with EtOAc, and washed with aq. KHSO$_4$, water, and brine, dried over Na$_2$SO$_4$, filtered, and concentrated. To a solution of a part of the residue (673 mg, 1.29 mmol) in toluene (5 mL) at room temperature are added triethylamine (0.2 mL, 1.44 mmol) and DPPA (0.31 mL, 1.43 mmol). After stirred for 40 min, TMSCH$_2$CH$_2$OH (0.9 mL, 6.31 mmol) is added. The reaction mixture is refluxed for 2 h. After dilution with EtOAc, the mixture is washed with aq. KHSO$_4$, water, aq. sat. NaHCO$_3$, and brine, dried over Na$_2$SO$_4$, filtered, and concentrated. The residue is purified by silica gel column chromatography to afford the desired carbamate (332 mg, 0.522 mmol), which is treated with TBAF (410 mg, 1.57 mmol) in THF (5 mL) at 50° C. for 2.5 h. After dilution with EtOAc, the mixture is washed with water (×2) and brine, dried over Na$_2$SO$_4$, filtered, and concentrated to afford the title compound as a pale yellow oil. MS: 491 [M+H]$^+$; $t_R$ (HPLC, ACQUITY UPLC™ BEH C$_{18}$ 1.7 μm, 50×2.1 mm; 5-100% CH$_3$CN+0.1% TFA/H$_2$O+0.1% TFA for 2 min then 100% CH$_3$CN+0.1% TFA for 1 min, flow 0.5 ml/min): 1.67 min.

The amine used in Example 164A is prepared as follows:

B. 3-Methoxy-5-(3-methoxy-propoxy)-benzoic acid methyl ester

To a mixture of 3-methoxy-5-hydroxybenzoic acid methyl ester (23.2 g, 127 mmol), toluene-4-sulfonic acid 3-methoxy-propyl ester (40.7 g, 167 mmol) and KI (2.23 g, 13.4 mmol) in DMF (350 mL), K$_2$CO$_3$ (53.1 g, 384 mmol) is added under N$_2$. After stirring at 60° C. for 17 h, the reaction mixture is supplemented with H$_2$O and extracted with Et$_2$O. The combined organic phases are washed with H$_2$O and dried (Na$_2$SO$_4$). Concentration under reduced pressure and silica gel flash chromatography give the title compound as colorless oil. MS: 255 [M+H]$^+$; $t_R$ (HPLC, CombiScreen ODS-AM 50×4.6 mm; 5-100% CH$_3$CN+0.1% TFA/H$_2$O+0.1% TFA for 5 min then 100% CH$_3$CN+0.1% TFA for 2 min, flow 2.0 ml/min): 3.80 min.

C. [3-Methoxy-5-(3-methoxy-propoxy)-phenyl]-methanol

A mixture of 3-Methoxy-5-(3-methoxy-propoxy)-benzoic acid methyl ester (5 g, 19.7 mmol) and LAH (528 mg, 20 mmol) in THF (110 mL) is stirred under N$_2$ at 0° C. for 3 h. After adding H$_2$O, the reaction mixture is extracted with EtOAc. The combined organic phases are washed with H$_2$O, brine and dried (Na$_2$SO$_4$). Concentration under reduced pressure and silica gel flash chromatography give the title compound as colorless oil. MS: 227 [M+H]$^+$; $t_R$ (HPLC, CombiScreen ODS-AM 50×4.6 mm; 5-100% CH$_3$CN+0.1% TFA/H$_2$O+0.1% TFA for 5 min then 100% CH$_3$CN+0.1% TFA for 2 min, flow 2.0 ml/min): 2.85 min.

D. 3-Methoxy-5-(3-methoxy-propoxy)-benzaldehyde

The title compound is synthesized by MnO$_2$ oxidation of [3-Methoxy-5-(3-methoxy-propoxy)-phenyl]-methanol (4.20 g, 18.6 mmol) in toluene at RT for 12 h. Yellow oil; MS: 225 [M+H]$^+$; $t_R$ (HPLC, CombiScreen ODS-AM 50×4.6 mm; 5-100% CH$_3$CN+0.1% TFA/H$_2$O+0.1% TFA for 5 min then 100% CH$_3$CN+0.1% TFA for 2 min, flow 2.0 ml/min): 3.59 min.

E. Cyclopropyl-[3-methoxy-5-(3-methoxy-propoxy)-benzyl]-amine

The title compound is synthesized by reductive amination of 3-Methoxy-5-(3-methoxy-propoxy)-benzaldehyde (2.50 g, 11.1 mmol) with cyclopropylamine (855 mg, 15.0 mmol) analogously to the preparation of Example 152. Yellow oil; MS: 266 [M+H]$^+$; $t_R$ (HPLC, CombiScreen ODS-AM 50×4.6 mm; 5-100% CH$_3$CN+0.1% TFA/H$_2$O+0.1% TFA for 5 min then 100% CH$_3$CN+0.1% TFA for 2 min, flow 2.0 ml/min): 2.48 min.

The cyclic anhydride used in Example 164A is prepared as follows:

F. Pyridine-3,5-dicarboxylic acid dimethyl ester 3,5-Pyridinedicarboxylic acid (1.5 g, 63 mmol) and conc. H$_2$SO$_4$ (0.9 mL) in MeOH (15 mL) are heated in a microwave oven at 120° C. for 2 h. The solvent is evaporated to give a residue with is partitioned between ethyl acetate and sat. aq. NaHCO$_3$. The organic phase is washed with brine, dried over Na$_2$SO$_4$, filtered and evaporated to give a light yellow solid. MS (LC-MS): 196 [M+H]$^+$ TLC, R$_f$ (ethyl acetate/hexane 1:1)=0.56.

G. Piperidine-3,5-dicarboxylic acid dimethyl ester

Pyridine-3,5-dicarboxylic acid dimethyl ester (5.3 g, 27 mmol) and Rh/PtO$_2$ (0.5 g) in MeOH (200 mL) are stirred under hydrogen overnight. The resulting mixture is filtered and the solvents are evaporated to leave a brown oil. MS (LC-MS): 202 [M+H]$^+$ H. Piperidine-1,3,5-tricarboxylic acid 1-tert-butyl ester 3,5-dimethyl ester A solution of piperidine-3,5-dicarboxylic acid dimethyl ester (5.4 g, 26.8 mmol) in CH$_2$Cl$_2$ (55 mL) is treated with Boc$_2$O (6.4 g, 29.5 mmol) and the reaction stirred at rt overnight. The reaction is quenched with 0.1N aq. HCl and the organic phase washed with 0.1N aq HCl. The combined aqueous phases are extracted 2 times with CH$_2$Cl$_2$/MeOH (9/1) before the combined organic phases are dried over Na$_2$SO$_4$, filtered and evaporated. The resulting residue is purified by flash chromatography on silica gel (eluent: CH$_2$Cl$_2$/MeOH 95:5) to give the title compound as a yellow solid. MS (LC-MS): 302 [M+H]$^+$. TLC, R$_f$ (CH$_2$Cl$_2$/MeOH 95:5)=0.5.

I. Piperidine-1,3,5-tricarboxylic acid 1-tert-butyl ester

To a solution of piperidine-1,3,5-tricarboxylic acid 1-tert-butyl ester 3,5-dimethyl ester (6.8 g, 22.5 mmol) in MeOH/water (4:1, 120 mL), K$_2$CO$_3$ (9.4 g, 68 mmol) is added. The reaction is stirred at reflux overnight. The MeOH is evaporated and the residue extracted with dichloromethane and 1N aq. HCl. The organic phase is dried over Na$_2$SO$_4$, filtered and evaporated to give a light yellow solid. MS (LC-MS): 274 [M+H]$^+$.

J. 2,4-Dioxo-3-oxa-7-aza-bicyclo[3.3.1]nonane-7-carboxylic acid tert-butyl ester A suspension of piperidine-1,3,5-tricarboxylic acid 1-tert-butyl ester (1 g, 3.6 mmol) in acetic anhydride (20 mL) is heated at reflux for 2 h. The reaction mixture is evaporated 3× times with toluene before it is dried under high vacuum at rt overnight to give a yellow solid. MS (LC-MS): 278 [M+Na]$^+$.

Example 165

(3R*,5S*)-5-m-Tolylamino-piperidine-3-carboxylic acid cyclopropyl-[3-methoxy-5-(3-methoxy-Propoxy)-benzyl]-amide

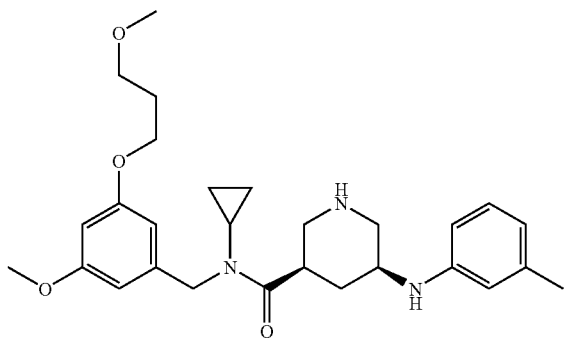

A mixture of (3S*,5R*)-3-Amino-5-{cyclopropyl-[3-methoxy-5-(3-methoxy-propoxy)-benzyl]-carbamoyl}-piperidine-1-carboxylic acid tert-butyl ester (40 mg, 0.081 mmol), 3-bromotoluene (16 mg, 0.094 mmol), (rac)-2,2'-bis(diphenylphosphino)-1,1'-binaphthalene (3.8 mg, 0.006 mmol), tris(dibenzylideneacetone)dipalladium(0) (3.8 mg, 0.004 mmol), and cesium carbonate (32 mg, 0.098 mmol) in toluene (0.6 mL) is heated at 110° C. for 36 h. The mixture is purified by RP-HPLC to give the desired amine, which is treated with 4 N HCl-1,4-dioxane (1 mL) at room temperature for 1 h. Concentration under vacuum gives the title compound as a white amorphous solid. MS: 481 [M+H]$^+$; $t_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 3.07 min.

Example 166

(3R*,5S*)-5-(6-Chloro-pyrimidin-4-ylamino)-piperidine-3-carboxylic acid cyclopropyl-[3-methoxy-5-(3-methoxy-propoxy)-benzyl]-amide

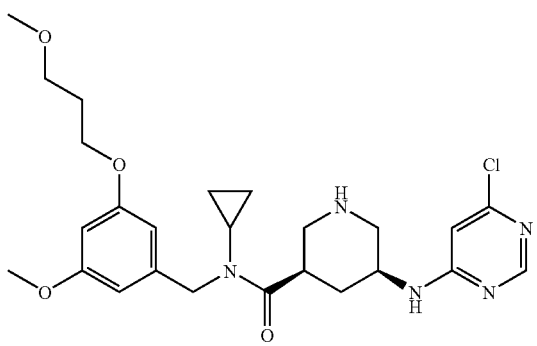

To a solution of (3S*,5R*)-3-Amino-5-{cyclopropyl-[3-methoxy-5-(3-methoxy-propoxy)-benzyl]-carbamoyl}-piperidine-1-carboxylic acid tert-butyl ester (50 mg, 0.10 mmol) in DMF (0.5 mL) are added i-Pr$_2$NEt (26 uL, 0.15 mmol) and 4,6-dichloropyrimidine (23 mg, 0.15 mmol). After stirring for 16 h, the reaction mixture is quenched by H$_2$O (30 mL) and extracted with EtOAc/Et$_2$O (c.a. 1:1, 60 mL). The organic phase is successively washed with 5% KHSO$_4$aq, 5% NaHCO$_3$aq, H$_2$O, and brine, then dried over Na$_2$SO$_4$. The solution is filtered and the solvent is evaporated in vacuo. The residue is purified by silica gel column chromatography to give Boc protected title compound. MS: 604 (Cl$^{35}$) [M+H]$^+$; t$_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 3.88 min. The Boc protected compound is treated with 4N HCl-1,4-dioxane to give the title compound as a white amorphous solid. MS: 504 (Cl$^{35}$) [M+H]$^+$; t$_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.66 min.

Example 167

(3R*,5S*)-5-(6-Chloro-pyrimidin-4-ylamino)-piperidine-3-carboxylic acid cyclopropyl-[1-(3-methoxy-propyl)-1H-indol-3-ylmethyl]-amide

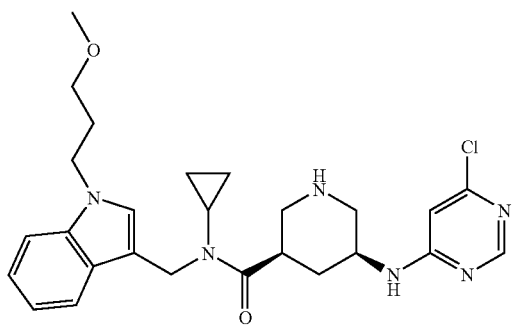

The title compound is prepared analogously as described in Example 154 using (3S*,5R*)-3-Amino-5-{cyclopropyl-[1-(3-methoxy-propyl)-1H-indol-3-ylmethyl]-carbamoyl}-piperidine-1-carboxylic acid tert-butyl ester and 4,6-dichloropyrimidine followed by deprotection of Boc using TMSOTf and 2,6-lutidine. MS: 497 (Cl$^{35}$) [M+H]$^+$; t$_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.77 min.

The starting material is prepared as follows:

A. (3S*,5R*)-3-Amino-5-{cyclopropyl-[1-(3-methoxy-propyl)-1H-indol-3-ylmethyl]-carbamoyl}-piperidine-1-carboxylic acid tert-butyl ester The title compound is prepared analogously as described in Example 152A using cyclopropyl-[1-(3-methoxy-propyl)-1H-indol-3-ylmethyl]-amine and 2,4-Dioxo-3-oxa-7-aza-bicyclo[3.3.1]nonane-7-carboxylic acid tert-butyl ester. MS: 485 [M+H]$^+$; t$_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 3.09 min.

Example 168

(3R*,5S*)-5-(2-Oxo-imidazolidin-1-yl)-piperidine-3-carboxylic acid cyclo propyl-[1-(3-methoxy-propyl)-1H-indol-3-ylmethyl]-amide

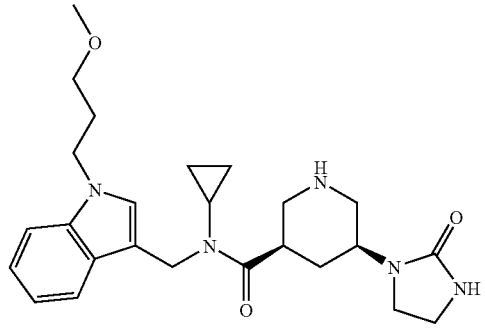

The title compound is prepared by deprotection of (3S*,5R*)-3-(2-Amino-ethylamino)-5-{cyclopropyl-[1-(3-methoxy-propyl)-1H-indol-3-ylmethyl]-carbamoyl}-piperidine-1-carboxylic acid tert-butyl ester using TMSOTf and 2,6-lutidine. MS: 246 [M+H]$^+$; t$_R$ (HPLC, ACQUITY UPLC™ BEH C$_{18}$ 1.7 µm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 4.54 min.

The starting materials are prepared as follows:

A. (3S*,5R*)-3-(2-Amino-ethylamino)-5-{cyclopropyl-[1-(3-methoxy-propyl)-1H-indol-3-ylmethyl]-carbamoyl}-piperidine-1-carboxylic acid tert-butyl ester A mixture of (3R*,5S*)-3-{Cyclopropyl-[1-(3-methoxy-propyl)-1H-indol-3-ylmethyl]-carbamoyl}-5-[2-(1,3-dioxo-1,3-dihydro-isoindol-2-yl)-ethylamino]-piperidine-1-carboxylic acid tert-butyl ester (160 mg, 0.24 mmol) and hydrazine monohydrate (18 uL, 0.37 mmol) in EtOH is stirred at 60° C. After 6 h, the reaction mixture is cooled down to room temperature. The solution is filtered through celite pad and the solvent is evaporated in vacuo to afford the title compound as yellow material. MS: 528 [M+H]$^+$; t$_R$ (HPLC, ACQUITY UPLC™ BEH C$_{18}$ 1.7 µm, 50×2.1 mm; 5%

CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 2.93 min.

B. (3R*,5S*)-3-{Cyclopropyl-[1-(3-methoxy-propyl)-1H-indol-3-ylmethyl]-carbamoyl}-5-[2-(1,3-dioxo-1,3-dihydro-isoindol-2-yl)-ethylamino]-piperidine-1-carboxylic acid tert-butyl ester To a solution of (3R*,5S*)-3-{Cyclopropyl-[1-(3-methoxy-propyl)-1H-indol-3-ylmethyl]-carbamoyl}-5-[[2-(1,3-dioxo-1,3-dihydro-isoindol-2-yl)-ethyl]-(2-nitro-benzenesulfonyl)-amino]-piperidine-1-carboxylic acid tert-butyl ester (250 mg, 0.3 mmol) in DMF (1 mL) are added thioglycolic acid (104 uL, 1.5 mmol) and DBU (224 uL, 1.5 mmol) at room temperature. After 2.5 h, the reaction mixture is quenched by H₂O (20 mL) and extracted with CH₂Cl₂ (50 mL). The organic phase is successively washed with H₂O and brine, then dried over Na₂SO₄ and concentrated in reduced pressure. The residue is purified by silica gel column chromatography to afford the title compound. MS: 658 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 3.60 min.

C. (3R*,5S*)-3-{Cyclopropyl-[1-(3-methoxy-propyl)-1H-indol-3-ylmethyl]-carbamoyl}-5-[[2-(1,3-dioxo-1,3-dihydro-isoindol-2-yl)-ethyl]-(2-nitro-benzenesulfonyl)-amino]-piperidine-1-carboxylic acid tert-butyl ester To a solution of (3R*,5S*)₃-{Cyclopropyl-[1-(3-methoxy-propyl)-1H-indol-3-ylmethyl]-carbamoyl}-5-(2-nitro-benzenesulfonylamino)-piperidine-1-carboxylic acid tert-butyl ester (400 mg, 0.60 mmol), 2-(2-hydroxyethyl) isoindole-1,3-dione (171 mg, 0.9 mmol), and PPh₃ (315 mg, 1.2 mmol) in THF is added DEAD (208 mg, 1.2 mmol) at room temperature, then the mixture is stirred at 60° C. After 13 h, the reaction mixture is quenched by H₂O (20 mL) and extracted with EtOAc (50 mL). The organic phase is successively washed with 5% aqueous KHSO₄, H₂O, and brine, then dried over Na₂SO₄ and concentrated in reduced pressure. The residue is purified by silica gel column chromatography to afford the title compound as yellow amorphous material. MS: 843 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 4.41 min.

D. (3R*,5S*)-3-{Cyclopropyl-[1-(3-methoxy-propyl)-1H-indol-3-ylmethyl]-carbamoyl}-5-(2-nitro-benzenesulfonylamino)-piperidine-1-carboxylic acid tert-butyl ester To a solution of (3S*,5R*)-3-Amino-5-{cyclopropyl-[1-(3-methoxy-propyl)-1H-indol-3-ylmethyl]-carbamoyl}-piperidine-1-carboxylic acid tert-butyl ester (400 mg, 0.83 mmol) in CH₂Cl₂ (1 mL) are added pyridine (1 mL) and o-nitrobenzenesulfonyl chloride (274 mg, 1.2 mmol) at 0° C., then the mixture is stirred at room temperature. After 20 h, the reaction mixture is quenched by H₂O (30 mL) and extracted with EtOAc (100 mL). The organic layer is successively washed with 5% aqueous KHSO₄, H₂O, and brine, then dried over Na₂SO₄ and concentrated in reduced pressure. The residue is purified by silica gel column chromatography to afford the title compound as brown amorphous material. MS: 670 [M+H]⁺; $t_R$ (HPLC, ACQUITY UPLC™ BEH C₁₈ 1.7 μm, 50×2.1 mm; 5% CH₃CN+0.1% TFA/H₂O+0.1% TFA for 0.5 min then 5-100% CH₃CN+0.1% TFA/H₂O+0.1% TFA for 5 min then 100% CH₃CN+0.1% TFA for 1.5 min, flow 0.5 ml/min): 4.14 min.

Scheme 10

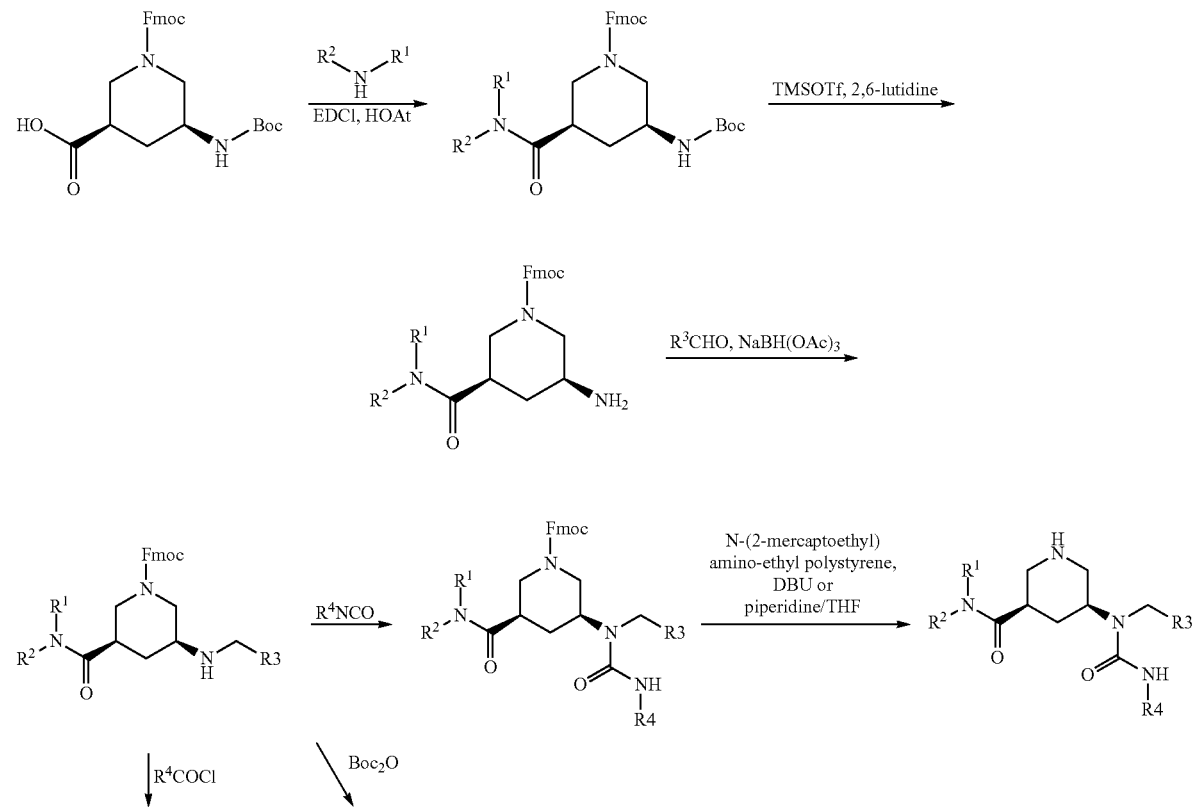

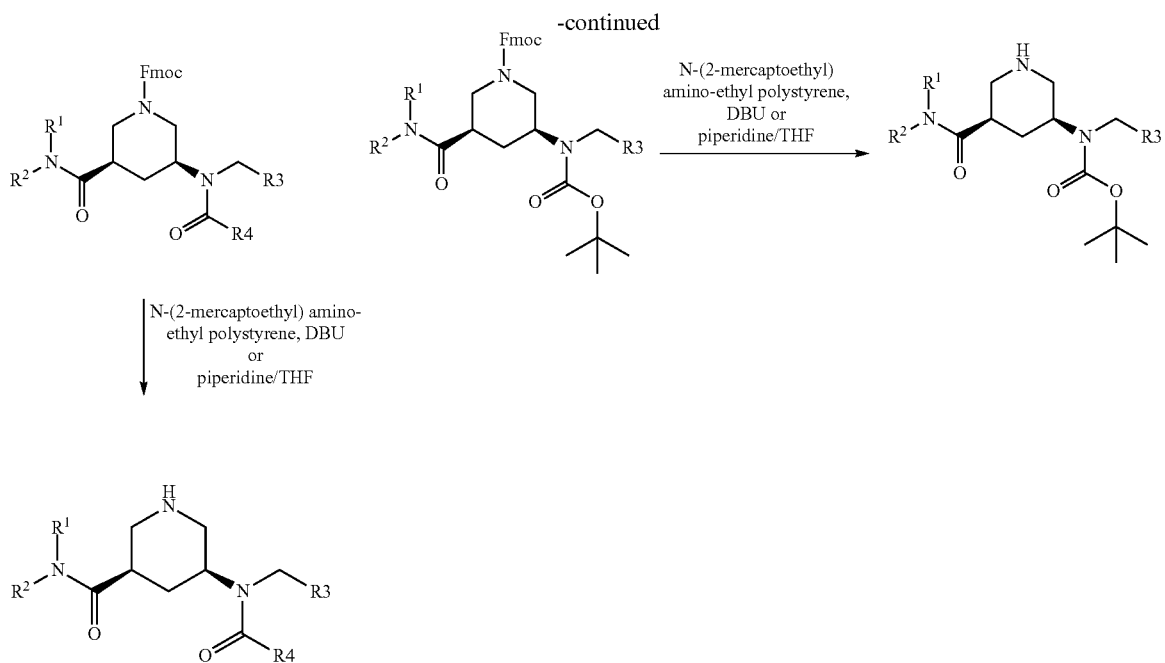

Example 169

(3R,5S)-5-[Benzyl-(2,2-dimethyl-propionyl)-amino]-piperidine-3-carboxylic acid cyclopropyl-[1-(3-methoxy-propyl)-1H-indol-3-ylmethyl]-amide

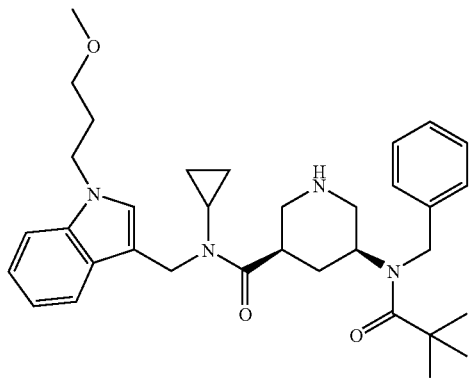

A solution of (3S,5R)-3-Benzylamino-5-{cyclopropyl-[1-(3-methoxy-propyl)-1H-indol-3-ylmethyl]-carbamoyl}-piperidine-1-carboxylic acid 9H-fluoren-9-ylmethyl ester (68.5 mg, 0.098 mmol) in $CH_2Cl_2$ is treated with i-$Pr_2$NEt (40.2 μL, 0.235 mmol) and pivaloylchloride (23.9 μL, 0.196 mmol). The solution is stirred at room temperature for 18 h. Additional i-$Pr_2$NEt (20 μL, 0.12 mmol) and pivaloylchloride (12 μL, 0.095 mmol) are added and stirring is continued for 9 h. The reaction mixture is partitioned between EtOAc and 1 M $NaHCO_3$, the organic layer is washed with 1 M $NaHCO_3$ and brine, dried over $MgSO_4$, filtered and concentrated in vacuo. The residue is dissolved in THF/piperidine (5:1) (6 mL), the solution is stirred at room temperature for 2.5 h and then concentrated in vacuo. The crude product is purified by RP-HPLC to afford the title compound. MS: 559 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.40 min.

Example 170

(3R,5S)-5-(Benzyl-cyclobutanecarbonyl-amino)-piperidine-3-carboxylic acid cyclopropyl-[1-(3-methoxy-propyl)-1H-indol-3-ylmethyl]-amide

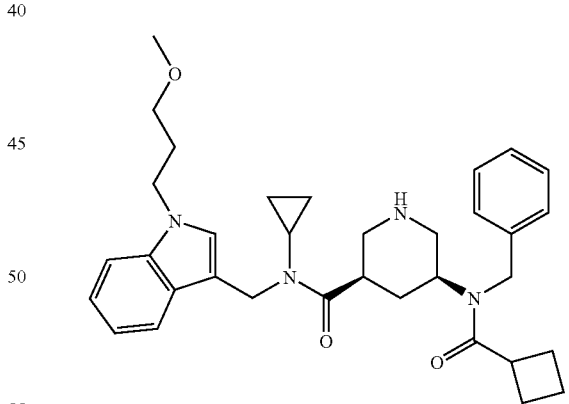

The title compound is prepared analogously as described in Example 134 using (3S,5R)-3-Benzylamino-5-{cyclopropyl-[1-(3-methoxy-propyl)-1H-indol-3-ylmethyl]-carbamoyl}-piperidine-1-carboxylic acid 9H-fluoren-9-ylmethyl ester and cyclobutanecarbonylchloride. MS: 557 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.34 min.

Example 171

(3R,5S)-5-[(2,2-Dimethyl-propionyl)-isobutyl-amino]-piperidine-3-carboxylic acid cyclopropyl-[1-(3-methoxy-propyl)-1H-indol-3-ylmethyl]-amide

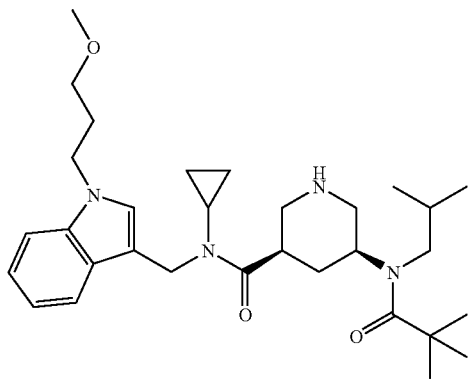

The title compound is prepared analogously as described in Example ??? using (3R,5S)-3-{Cyclopropyl-[1-(3-methoxy-propyl)-1H-indol-3-ylmethyl]-carbamoyl}-5-isobutylamino-piperidine-1-carboxylic acid 9H-fluoren-9-ylmethyl ester and pivaloylchloride. MS: 525 [M+H]$^+$; $t_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 3.29 min.

Example 172

(3R,5S)-5-(3-Benzyl-1-isobutyl-ureido)-piperidine-3-carboxylic acid cyclopropyl-[1-(3-methoxy-propyl)-1H-indol-3-ylmethyl]-amide

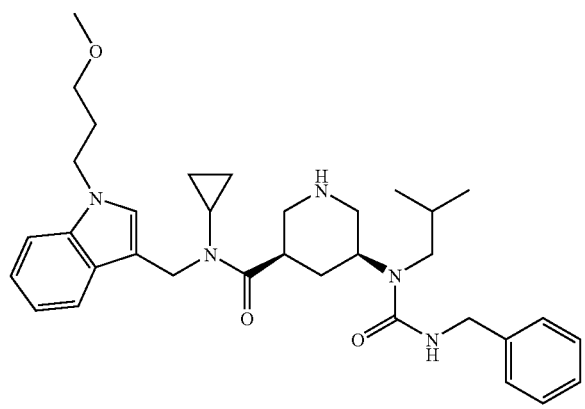

The title compound is prepared analogously as described in Example ??? using (3R,5S)-3-{Cyclopropyl-[1-(3-methoxy-propyl)-1H-indol-3-ylmethyl]-carbamoyl}-5-isobutylamino-piperidine-1-carboxylic acid 9H-fluoren-9-ylmethyl ester and benzylisocyanate. MS: 574 [M+H]$^+$; $t_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 3.34 min.

Example 173

(3R,5S)-5-[Cyclopropylmethyl-(2,2-dimethyl-propionyl)-amino]-piperidine-3-carboxylic acid cyclopropyl-[1-(3-methoxy-propyl)-1H-indol-3-ylmethyl]-amide

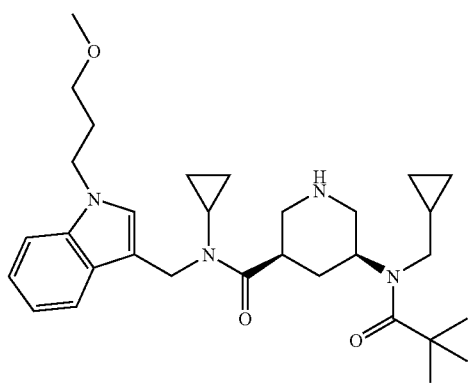

The title compound is prepared analogously as described in Example ??? using (3R,5S)-3-{Cyclopropyl-[1-(3-methoxy-propyl)-1H-indol-3-ylmethyl]-carbamoyl}-5-(cyclopropylmethyl-amino)-piperidine-1-carboxylic acid 9H-fluoren-9-ylmethyl ester and pivaloylchloride. MS: 523 [M+H]$^+$; $t_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 3.24 min.

Example 174

((3S,5R)-5-{Cyclopropyl-[1-(3-methoxy-propyl)-1H-indol-3-ylmethyl]-carbamoyl}-piperidin-3-yl)-cyclopropylmethyl-carbamic acid tert-butyl ester

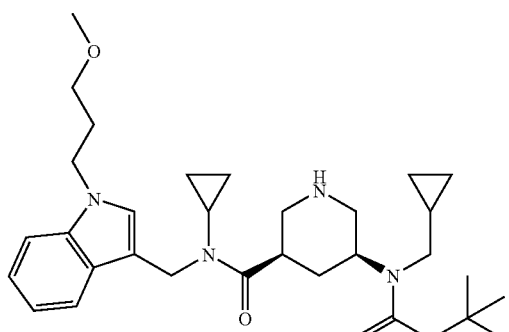

The title compound is prepared analogously as described in Example ??? using (3R,5S)-3-{Cyclopropyl-[1-(3-methoxy-propyl)-1H-indol-3-ylmethyl]-carbamoyl}-5-(cyclopropyl-methyl-amino)-piperidine-1-carboxylic acid 9H-fluoren-9- ylmethyl ester and di-tert-butyl dicarbonate. MS: 539 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.46 min.

The starting materials are prepared as follows:

A. (3S,5R)-3-Benzylamino-5-{cyclopropyl-[1-(3-methoxy-propyl)-1H-indol-3-ylmethyl]-carbamoyl}-piperidine-1-carboxylic acid 9H-fluoren-9-ylmethyl ester B. (3R,5S)-3-{Cyclopropyl-[1-(3-methoxy-propyl)-1H-indol-3-ylmethyl]-carbamoyl}-5-isobutylamino-piperidine-1-carboxylic acid 9H-fluoren-9-ylmethyl ester C. (3R,5S)-3-{Cyclopropyl-[1-(3-methoxy-propyl)-1H-indol-3-ylmethyl]-carbamoyl}-5-(cyclopropylmethyl-amino)-piperidine-1-carboxylic acid 9H-fluoren-9-ylmethyl ester A solution of (3S,5R)-3-Amino-5-{cyclopropyl-[1-(3-methoxy-propyl)-1H-indol-3-ylmethyl]-carbamoyl}-piperidine-1-carboxylic acid 9H-fluoren-9-ylmethyl ester (145 mg, 0.205 mmol) in $CH_2Cl_2$ is treated with corresponding aldehyde (0.205 mmol), stirred at room temperature for 10 min, followed by addition of NaBH(OAc)$_3$ (87 mg, 0.41 mmol). The mixture is stirred for 88 h, partitioned between EtOAc and 1 M NaHCO3. The organic layer is washed with 1 M NaHCO3 and brine, dried over MgSO4, filtered and concentrated in vacuo.

A. MS: 697 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 4.06 min.

B. MS: 663 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.98 min.

C. MS: 661 [M+H]$^+$; $t_R$ (HPLC, ACQUITY UPLC™ BEH $C_{18}$ 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.88 min.

Scheme 11

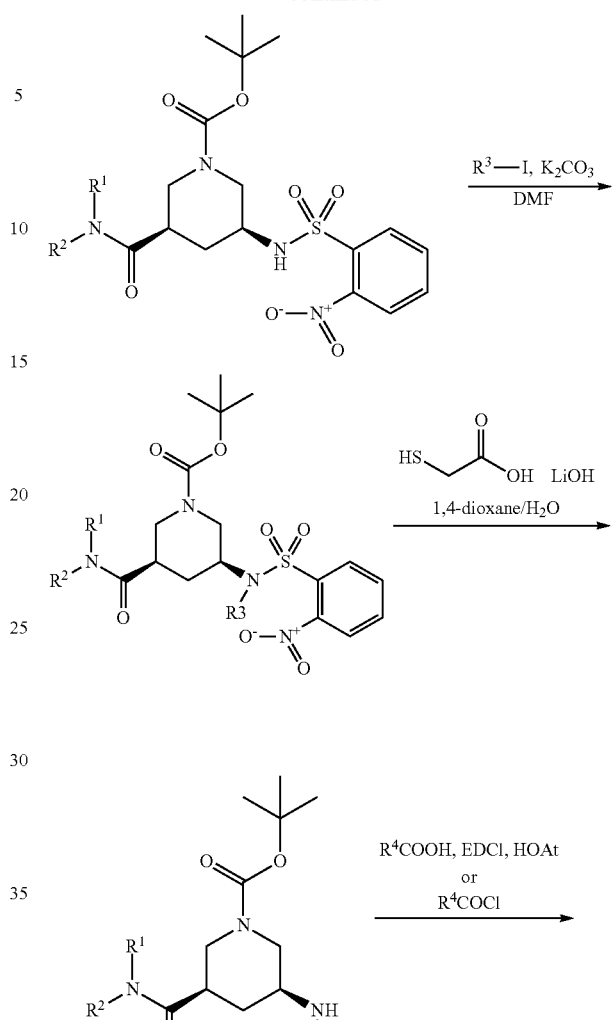

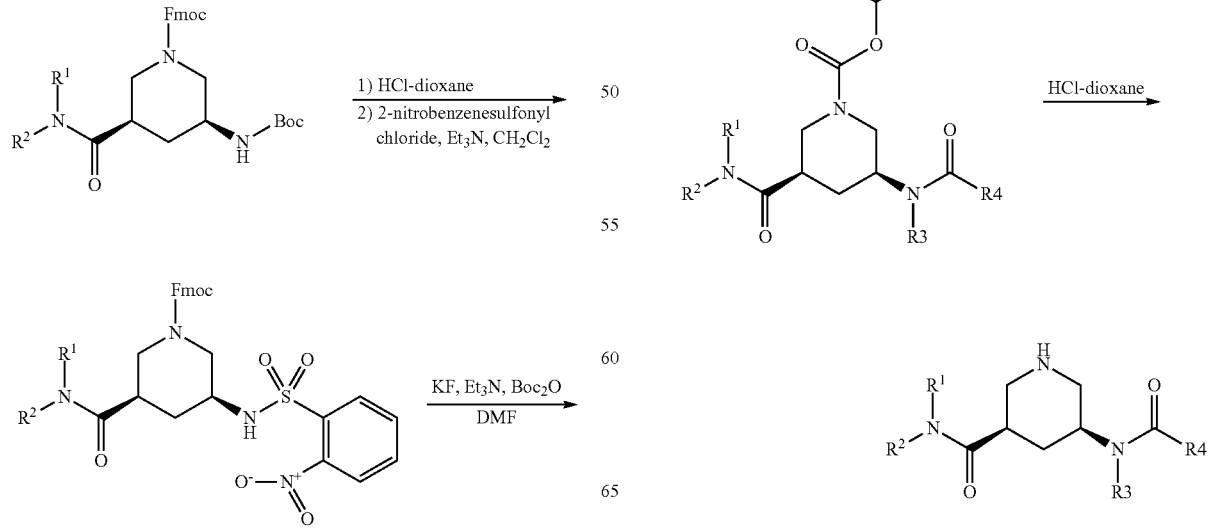

Example 175

(3R,5S)-5-[Methyl-(1-phenyl-cyclopropanecarbonyl)-amino]-Piperidine-3-carboxylic acid cyclopropyl-[4-(3-methoxy-propyl)-2,2-dimethyl-3-oxo-3,4-dihydro-2H-benzo[1,4]oxazin-6-yl]-amide

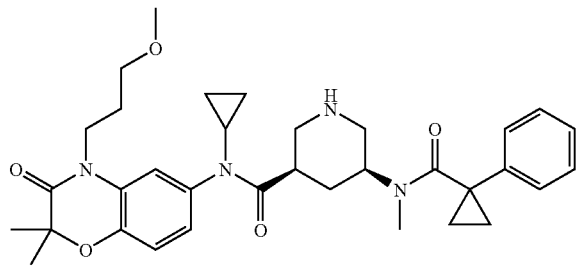

To a mixture of (3R,5S)-3-{Cyclopropyl-[4-(3-methoxy-propyl)-2,2-dimethyl-3-oxo-3,4-di hydro-2H-benzo[1,4]oxazin-6-yl]-carbamoyl}-5-methylamino-piperidine-1-carboxylic acid tert-butyl ester (110 mg, 0.2 mmol) and 1-phenyl-1-cyclopropanecarboxylic acid (40 mg, 0.24 mmol) in DMF (2 mL) are added EDCl. HCl (60 mg, 0.3 mmol) and HOAt (40 mg, 0.3 mmol) at 0° C. After stirred at rt overnight, the reaction mixture is diluted with EtOAc. The mixture is washed with water and dried over $Na_2SO_4$, filtered, and concentrated in vacuo. The residue is purified by silica gel column chromatography to afford (3R,5S)-3-[4-(3-Methoxy-propyl)-2,2-dimethyl-3-oxo-3,4-dihydro-2H-benzo[1,4]oxazin-6-ylcarbamoyl]-5-[(1-phenylcyclopropanecarbonyl)-amino]-piperidine-1-carboxylic acid tert-butyl ester as a white amorphous, which is treated with 4 N HCl in 1,4-dioxane (3 mL). The solution is concentrated under reduced pressure to give the title compound as a yellow powder. MS: 589 [M+H]$^+$; $t_R$ (HPLC, ACQUITY UPLC™ BEH C18 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.01 min.

The starting materials are prepared as follows:

A. (3R,5S)-3-{Cyclopropyl-[4-(3-methoxy-propyl)-2,2-dimethyl-3-oxo-3,4-di hydro-2H-benzo[1,4]oxazin-6-yl]-carbamoyl}-5-methylamino-piperidine-1-carboxylic acid tert-butyl ester To a solution of (3R,5S)-3-{Cyclopropyl-[4-(3-methoxy-propyl)-2,2-dimethyl-3-oxo-3,4-dihydro-2H-benzo[1,4]oxazin-6-yl]-carbamoyl}-5-(2-nitro-benzenesulfonylamino)-piperidine-1-carboxylic acid tert-butyl ester (550 mg, 0.78 mmol) in DMF (5 mL), iodomethane (81 μL, 0.94 mmol) and $K_2CO_3$ (320 mg, 2.3 mmol) are added at rt. After stirring overnight, the reaction mixture is diluted with $H_2O$ and extracted with EtOAc. The combined organic phases are washed with $H_2O$ and dried over $Na_2SO_4$. Concentration under reduced pressure and filtration through silica gel give crude product. To a solution of the crude product in DMF (3 mL), thioglycolic acid (160 μL, 2.3 mmol) and LiOH (93 mg, 3.9 mmol) are added at rt. After stirring for 4 hours, the reaction mixture is diluted with $H_2O$ and extracted with EtOAc. The combined organic phases are washed with $H_2O$ and dried over $Na_2SO_4$. Concentration under reduced pressure and filtration through silica gel give the title compound. MS: 545 [M+H]$^+$; $t_R$ (HPLC, ACQUITY UPLC™ BEH C18 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.05 min.

B. (3R,5S)-3-{Cyclopropyl-[4-(3-methoxy-propyl)-2,2-dimethyl-3-oxo-3,4-dihydro-2H-benzo[1,4]oxazin-6-yl]-carbamoyl}-5-(2-nitro-benzenesulfonylamino)-piperidine-1-carboxylic acid tert-butyl ester To a solution of (3S,5R)-3-Amino-5-{cyclopropyl-[4-(3-methoxy-propyl)-2,2-dimethyl-3-oxo-3,4-dihydro-2H-benzo[1,4]oxazin-6-yl]-carbamoyl}-piperidine-1-carboxylic acid 9H-fluoren-9-ylmethyl ester hydrochloride (1.0 g, 1.5 mmol) in $CH_2Cl_2$/$H_2O$ (5 mL/5 mL), 2-nitrobenzenesulfonyl chloride (400 mg, 1.8 mmol), sodium bicarbonate (480 mg, 4.5 mmol) are added at 0° C. After stirring for 2 hours at the temperature, the reaction mixture is diluted with $H_2O$ and extracted with EtOAc. The combined organic phases are washed with $H_2O$ and dried over $Na_2SO_4$. Purification Concentration under reduced pressure and filtration through silica gel give crude material. To the crude product (1.2 g, 1.46 mmol) in DMF (10 mL), KF (436 mg, 7.5 mmol), $Et_3N$ (0.41 mL, 3.0 mmol), and $Boc_2O$ (393 mg, 1.8 mmol) are added at rt. After stirring for 18 hours at rt, the reaction mixture is diluted with $H_2O$ and extracted with EtOAc. The combined organic phases are washed with $H_2O$ and dried over $Na_2SO_4$. Purification by column chromatography gives the title compound. MS: 716 [M+H]$^+$; $t_R$ (HPLC, ACQUITY UPLC™ BEH C18 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.94 min.

C. (3S,5R)-3-Amino-5-{cyclopropyl-[4-(3-methoxy-propyl)-2,2-dimethyl-3-oxo-3,4-dihydro-2H-benzo[1,4]oxazin-6-yl]-carbamoyl}-piperidine-1-carboxylic acid 9H-fluoren-9-ylmethyl ester hydrochloride (3S,5R)-3-tert-Butoxycarbonylamino-5-{cyclopropyl-[4-(3-methoxy-propyl)-2,2-dimethyl-3-oxo-3,4-dihydro-2H-benzo[1,4]oxazin-6-yl]-carbamoyl}-piperidine-1-carboxylic acid 9H-fluoren-9-ylmethyl ester (3.0 g, 4.0 mmol) is treated with 4N HCl in 1,4-dioxane (15 mL). The solution is concentrated under reduced pressure to give the title compound as a yellow powder. MS: 653 [M+H]$^+$; $t_R$ (HPLC, ACQUITY UPLC™ BEH C18 1.7 μm, 50×2.1 mm; 5% $CH_3CN$+0.1% TFA/$H_2O$+0.1% TFA for 0.5 min then 5-100% $CH_3CN$+0.1% TFA/$H_2O$+0.1% TFA for 5 min then 100% $CH_3CN$+0.1% TFA for 1.5 min, flow 0.5 ml/min): 3.46 min.

Example 176

(3R,5S)-5-[Methyl-(2-tetrahydro-pyran-4-yl-acetyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide

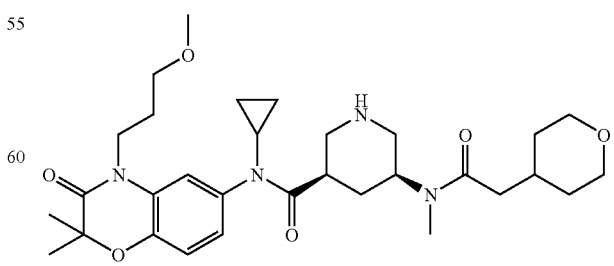

The title compound is prepared analogously as described in Example ??? (iwasaki) using (Tetrahydro-pyran-4-yl)-acetic acid as acid component and EDCI and HOAt for the acylation step. MS: 571 [M+H]$^+$; t$_R$ (HPLC, ACQUITY UPLC™ BEH C$_{18}$ 1.7 μm, 50×2.1 mm; 5% CH$_3$CN+0.1% TFA/H$_2$O+0.1% TFA for 0.5 min then 5-100% CH$_3$CN+0.1% TFA/H$_2$O+0.1% TFA for 5 min then 100% CH$_3$CN+0.1% TFA for 1.5 min, flow 0.5 ml/min): 2.51 min.

Example 177

Soft Capsules 5000 soft gelatin capsules, each comprising as active ingredient 0.05 g of any one of the compounds of formula I mentioned in any one of the preceding Examples, are prepared as follows:

| Composition | |
|---|---|
| Active ingredient | 250 g |
| Lauroglycol | 2 liters |

Preparation process: The pulverized active ingredient is suspended in Lauroglykol® (propylene glycol laurate, Gattefossé S.A., Saint Priest, France) and ground in a wet pulverizer to produce a particle size of about 1 to 3 μm. 0.419 g portions of the mixture are then introduced into soft gelatin capsules using a capsule-filling machine.

Example 178

Tablets Comprising Compounds of the Formula I

Tablets, comprising, as active ingredient, 100 mg of any one of the compounds of formula I in any one of the preceding Examples are prepared with the following composition, following standard procedures:

| Composition | |
|---|---|
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, stamp diameter 10 mm).

Avicel® is microcrystalline cellulose (FMC, Philadelphia, USA). PVPPXL is polyvinyl-polypyrrolidone, cross-linked (BASF, Germany). Aerosil® is silicon dioxide (Degussa, Germany).

The invention claimed is:
1. A compound of the formula I

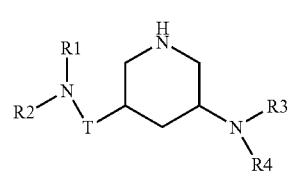

wherein
R1 is hydrogen, unsubstituted or substituted alkyl, unsubstituted or substituted alkenyl, unsubstituted or substituted alkynyl, unsubstituted or substituted aryl, unsubstituted or substituted heterocyclyl or unsubstituted or substituted cycloalkyl;
R2 is phenyl-C$_1$-C$_7$-alkyl, naphthyl-C$_1$-C$_7$-alkyl, di-(phenyl)-C$_1$-C$_7$-alkyl, indanyl-C$_1$-C$_7$-alkyl, (phenyl-C$_3$-C$_8$-cycloalkyl)-C$_1$-C$_7$-alkyl, (phenyl)-(pyridyl)-C$_1$-C$_7$-alkyl, indolyl-C$_1$-C$_7$-alkyl, 4H-benzo[1,4]oxazin-3-on-yl, (C$_1$-C$_7$-alkoxy)-di(phenyl)-C$_1$-C$_7$-alkyl or (C$_1$-C$_7$-alkoxycarbonyl)-di-(phenyl)-C$_1$-C$_7$-alkyl where each phenyl, naphthyl, pyridyl, indolyl or 4H-benzo[1,4]oxazin-3-on-yl mentioned for R2 is unsubstituted or substituted by one to three, moieties independently selected from the group consisting of C$_1$-C$_7$-alkyl, C$_1$-C$_7$ alkoxy-C$_1$-C$_7$-alkyl, phenyl, halo, hydroxy, C$_1$-C$_7$-alkoxy and C$_1$-C$_7$-alkoxy-C$_1$-C$_7$-alkoxy;
R3 is hydrogen, unsubstituted or substituted aryl or unsubstituted or substituted alkyl,
R4 is unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl, or acyl;
T is methylene or carbonyl;
or a salt thereof.
2. The compound of the formula I according to claim 1 wherein
R1 is hydrogen, unsubstituted or substituted alkyl or unsubstituted or substituted cycloalkyl;
R2 is phenyl-C$_1$-C$_7$-alkyl, naphthyl-C$_1$-C$_7$-alkyl, di-(phenyl)-C$_1$-C$_7$-alkyl, indanyl-C$_1$-C$_7$-alkyl, (phenyl-C$_3$-C$_8$-cycloalkyl)-C$_1$-C$_7$-alkyl, (phenyl)-(pyridyl)-C$_1$-C$_7$-alkyl, indolyl-C$_1$-C$_7$-alkyl, 4H-benzo[1,4]oxazin-3-on-yl, (C$_1$-C$_7$-alkoxy)-di(phenyl)-C$_1$-C$_7$-alkyl or (C$_1$-C$_7$-alkoxycarbonyl)-di-(phenyl)-C$_1$-C$_7$-alkyl where each phenyl, naphthyl, pyridyl, indolyl or 4H-benzo[1,4]oxazin-3-on-yl mentioned for R2 is unsubstituted or substituted by one to three, moieties independently selected from the group consisting of C$_1$-C$_7$-alkyl, C$_1$-C$_7$ alkoxy-C$_1$-C$_7$-alkyl, phenyl, halo, hydroxy, C$_1$-C$_7$-alkoxy and C$_1$-C$_7$-alkoxy-C$_1$-C$_7$-alkoxy;
R3 is hydrogen or unsubstituted or substituted alkyl,
R4 is unsubstituted or substituted alkyl, unsubstituted or substituted aryl, unsubstituted or substituted heterocyclyl, unsubstituted or substituted cycloalkyl, or acyl;
T is carbonyl (C(=O));
or a pharmaceutically acceptable salt thereof.
3. The compound of the formula I according to claim 1 wherein
R1 is hydrogen, unsubstituted or substituted alkyl or unsubstituted or substituted cycloalkyl;
R2 is phenyl-C$_1$-C$_7$-alkyl, naphthyl-C$_1$-C$_7$-alkyl, di-(phenyl)-C$_1$-C$_7$-alkyl, indanyl-C$_1$-C$_7$-alkyl, (phenyl-C$_3$-C$_8$-cycloalkyl)-C$_1$-C$_7$-alkyl, (phenyl)-(pyridyl)-C$_1$-C$_7$-alkyl, indolyl-C$_1$-C$_7$-alkyl, 4H-benzo[1,4]oxazin-3-onyl, (C₁-C₇-alkoxy)-di(phenyl)-C₁-C₇-alkyl or (C₁-C₇-alkoxycarbonyl)-di-(phenyl)-C₁-C₇-alkyl where each phenyl, naphthyl, pyridyl, indolyl or 4H-benzo[1,4]oxazin-3-on-yl mentioned for R2 is unsubstituted or substituted by one to three, moieties independently selected from the group consisting of C₁-C₇-alkyl, C₁-C₇ alkoxy-C₁-C₇-alkyl, phenyl, halo, hydroxy, C₁-C₇-alkoxy and C₁-C₇-alkoxy-C₁-C₇-alkoxy;

R3 is hydrogen or unsubstituted or substituted alkyl,

R4 is unsubstituted or substituted alkyl or acyl;

T is carbonyl (C(=O));

or a pharmaceutically acceptable salt thereof.

4. The compound of the formula I according to any one of claims 1 to 3 wherein the moieties T-NR1R2 and NR3R4 are bound in cis configuration with regard to the central piperidine, or a pharmaceutically acceptable salt thereof.

5. The compound of the formula I according to claim 1 wherein the moieties T-NR1R2 and NR3R4 are bound in trans configuration with regard to the central piperidine ring, or a pharmaceutically acceptable salt thereof.

6. The compound of the formula I according to claim 4 which has the configuration shown in the following formula IA,

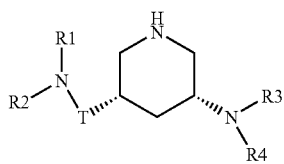

(IA)

or a pharmaceutically acceptable salt thereof.

7. The compound of the formula I according to claim 4 which has the configuration shown in the following formula IB,

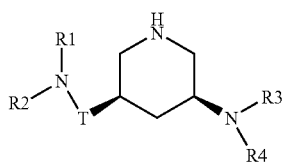

(IB)

or a pharmaceutically acceptable salt thereof.

8. The compound of the formula I according to claim 5 which has the configuration shown in the following formula IC,

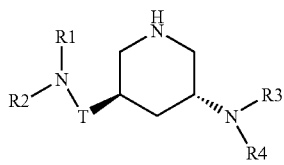

(IC)

or a pharmaceutically acceptable salt thereof.

9. The compound of the formula I according to claim 5 which has the configuration shown in the following formula ID,

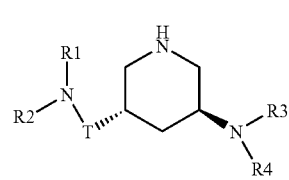

(ID)

or a pharmaceutically acceptable salt thereof.

10. The compound of the formula I according to claim 1 wherein R4 is selected from the group consisting of:
- acyl as shown in (a) to (o)
  (a) Unsubstituted or substituted mono- or bicyclic arylcarbonyl,
  (b) unsubstituted or substituted mono- or bicyclic heterocyclylcarbonyl,
  (c) unsubstituted or substituted mono- or bicyclic cycloalkylcarbonyl,
  (d) unsubstituted or substituted alkylcarbonyl,
  (e) unsubstituted or substituted mono- or bicyclic aryl-C₁-C₇-alkylcarbonyl,
  (f) unsubstituted or substituted mono- or bicyclic heterocyclyl-C₁-C₇-alkylcarbonyl,
  (g) unsubstituted or substituted mono- or bicyclic cycloalkyl-C₁-C₇-alkylcarbonyl,
  (h) unsubstituted or substituted alkyloxycarbonyl,
  (i) unsubstituted or substituted mono- or bicyclic heterocyclyloxycarbonyl,
  (j) unsubstituted or substituted mono- or bicyclic aryl-C₁-C₇-alkyloxycarbonyl,
  (k) N-mono- or N,N-di-(unsubstituted or substituted mono- or bicyclic aryl, unsubstituted or substituted mono- or bicyclic cycloalkyl, unsubstituted or substituted mono- or bicyclic aryl-C₁-C₇-alkyl and/or unsubstituted or substituted alkyl)-aminocarbonyl,
  (l) unsubstituted or substituted mono- or bicyclic arylsulfonyl,
  (m) unsubstituted or substituted mono- or bicyclic heterocyclylsulfonyl,
  (n) unsubstituted or substituted mono- or bicyclic aryl-C₁-C₇-alkylsulfonyl,
  (o) unsubstituted or substituted C₁-C₇-alkylsulfonyl, unsubstituted or substituted mono- or bicyclic aryl-C₁-C₇-alkyl,
unsubstituted or substituted mono- or bicyclic cycloalkyl,
unsubstituted or substituted mono- or bicyclic aryl, and
unsubstituted or substituted mono- or bicyclic heterocyclyl.

11. The compound of the formula I according to claim 1 wherein
R1 is hydrogen, C₁-C₇-alkyl, C₃-C₈-cycloalkyl or phenyl-C₁-C₇-alkyl,
R2 is phenyl-C₁-C₇-alkyl, naphthyl-C₁-C₇-alkyl, di-(phenyl)-C₁-C₇-alkyl, indanyl C₁-C₇-alkyl, (phenyl-C₃-C₈-cycloalkyl)-C₁-C₇-alkyl, (phenyl)-(pyridyl)-C₁-C₇-alkyl, indolyl-C₁-C₇-alkyl, 4H-benzo[1,4]oxazin-3-on-yl, (C₁-C₇-alkoxy)-di(phenyl)-C₁-C₇-alkyl or (C₁-C₇-alkoxycarbonyl)-di-(phenyl)-C₁-C₇-alkyl where each phenyl, naphthyl, pyridyl, indolyl or 4H-benzo[1,4]oxazin-3-on-yl mentioned for R2 is unsubstituted or substituted by one or more moieties independently selected from the group consisting of C₁-C₇-alkyl, C₁-C₇-alkoxy-C₁-C₇-alkyl, phenyl, halo, hydroxy, C₁-C₇-alkoxy and C₁-C₇-alkoxy-C₁-C₇-alkoxy;

R3 is hydrogen, $C_1$-$C_7$-alkyl or pheny-$C_1$-$C_7$-alkyl wherein phenyl is unsubstituted or substituted by one or more, especially up to three, moieties independently selected from the group consisting of $C_1$-$C_7$-alkyl, halo, hydroxy, $C_1$-$C_7$-alkoxy, carboxy, $C_1$-$C_7$-alkoxycarbonyl and cyano;

R4 is phenyl-$C_1$-$C_7$-alkyl wherein phenyl is unsubstituted or substituted by one to three, moieties independently selected from the group consisting of halo and $C_1$-$C_7$-alkoxy, especially 2-, 3- or 4-chlorophenylmethyl, $C_1$-$C_7$-alkanoyl that is unsubstituted or substituted by one to three, independently selected from the group consisting of hydroxy, amino, N-mono- or N,N-di-$C_1$-$C_7$-alkylamino and $C_1$-$C_7$-alkanoylamino, especially acetyl, 2-methyl-propionyl, 2-ethyl-butyryl, 3-methylbutyryl, 3,3-dimethyl-butyryl, 2,2-dimethyl-propionyl, 3,3-dimethyl-butyryl, 3-hydroxy-2,2-dimethyl-propionyl, N,N-dimethyl-amino-acetyl, 2-(N-acetylamino)-4-methyl-butyryl, unsubstituted or mono-, di- or tri-(halo, $C_1$-$C_7$-alkoxy and/or $C_1$-$C_7$-alkyl)-substituted benzoyl or naphthoyl, phenyl- or naphthyl-$C_2$-$C_7$-alkanoyl wherein phenyl or naphthyl is unsubstituted or substituted by one to three, $C_1$-$C_7$-alkoxy substitutents, $C_3$-$C_8$-cycloalkylcarbonyl that is unsubstituted or substituted by one to four, substituents independently selected from the group consisting of $C_1$-$C_7$-alkyl, carbamoyl and cyano, cyclopropylcarbonyl, 2,2,3,3-tetramethyl-cyclopropylcarbonyl, 1-carbamoyl-cyclopropylcarbonyl, cyclobutylcarbonyl or 1-cyano-cyclopropylcarbonyl, benzo[b]thiophenylcarbonyl, tetrahydrofuranylcarbonyl, piperidinylcarbonyl which is unsubstituted or substituted by $C_1$-$C_7$-alkanoyl,$C_1$-$C_7$-alkylsulfonyl, (phenyl- or naphthyl)-$C_1$-$C_7$-alkylsulfonyl, or (unsubstituted or [$C_1$-$C_7$-alkyl-, phenyl-, halo-lower alkyl-, halo, oxo-$C_1$-$C_7$-alkyl-, $C_1$-$C_7$-alkyloxy-, phenyl-$C_1$-$C_7$-alkoxy-, halo-$C_1$-$C_7$-alkyloxy-, phenoxy-, $C_1$-$C_7$-alkanoylamino-, $C_1$-$C_7$-alkylsulfonyl, cyano and/or $C_1$-$C_7$-alkylsulfonyl-]-(mono-, di- or tri-) substituted) (phenyl- or naphthyl)-sulfonyl wherein if more than one substituent is present the substituents are selected independently from those mentioned, especially methanesulfonyl, phenylmethanesulfonyl, phenylsulfonyl, naphthalene-1-sulfonyl, naphthalene-2-sulfonyl, toluene-4-sulfonyl, 4-isopropyl-benzenesulfonyl, biphenyl-4-sulfonyl, 2-trifluoromethyl-benzenesulfonyl, 3-trifluoromethyl-benzenesulfonyl, 4-trifluoromethylsulfonyl, 4-chloro-benzenesulfonyl, 3-chloro-benzenesulfonyl, 2-chloro-benzenesulfonyl, 2,4-difluoro-benzenesulfonyl, 2,6-difluoro-benzenesulfonyl, 2,5-dichloro-benzenesulfonyl, 2,4-dichlorobenzenesulfonyl, 3,4-dichloro-benzenesulfonyl, 3,5-dichloro-benzenesulfonyl, 2,3-dichloro-benzenesulfonyl, 3-methoxy-benzenesulfonyl, 4-methoxy-benzenesulfonyl, 2,5-dimethoxy-benzenesulfonyl, 2,4-dimethoxy-benzenesulfonyl, 4-trifluoromethoxy-benzenesulfonyl, 2-benzyloxy-benzenesulfonyl, 4-phenoxy-benzenesulfonyl, 4-(2-oxo-propyl)-benzenesulfonyl, 3-acetyl-benzenesulfonyl, 4-acetylamino-benzenesulfonyl, 4-cyano-benzenesulfonyl, 3-cyano-benzenesulfonyl, 2-cyano-benzenesulfonyl or 4-methanesulfonyl-benzenesulfonyl; halo-thiophene-2-sulfonyl, quinoline-sulfonyl, ($C_1$-$C_7$-alkanoylamino and/or $C_1$-$C_7$-alkyl)-substituted thiazol-sulfonyl, (halo and/or $C_1$-$C_7$-alkyl)-substituted pyrazolesulfonyl, pyridine-sulfonyl, N-mono- or N,N-di-($C_1$-$C_7$-alkyl, (unsubstituted or $C_1$-$C_7$-alkyl- and/or halo-substituted) phenyl or naphthyl, phenyl-$C_1$-$C_7$-alkyl, naphthyl-$C_1$-$C_7$-alkyl or $C_3$-$C_8$-cycloalkyl)-aminocarbonyl, $C_1$-$C_7$-alkylaminocarbonyl, N-phenyl-aminocarbonyl, N-(3-chlorophenyl)-aminocarbonyl or phenyl-$C_1$-$C_7$alkylaminocarbonyl, or ($C_1$-$C_7$-alkyl, phenyl, naphthyl, phenyl-$C_1$-$C_7$-alkyl and/or napthyl-$C_1$-$C_7$-alkyl)-oxycarbonyl; and T is C(O);

or a pharmaceutically acceptable salt thereof.

12. The compound of the formula I according to claim 1, selected from the group of compounds with the following names:

(3S*,5R*)-5-(toluene-4-sulfonylamino)-piperidine-3-carboxylic acid (2,2-diphenyl-ethyl)-amide, (3R*,5R*)-5-(toluene-4-sulfonylamino)-piperidine-3-carboxylic acid (2,2-diphenyl-ethyl)-amide, (3S*,5R*)-5-(4-methoxy-benzenesulfonylamino)-piperidine-3-carboxylic acid (2,2-diphenyl-ethyl)-amide, (3S*,5R*)-5-(5-chloro-thiophene-2-sulfonylamino)-piperidine-3-carboxylic acid (2,2-diphenyl-ethyl)-amide, (3S*,5R*)-5-(quinoline-8-sulfonylamino)-piperidine-3-carboxylic acid (2,2-diphenyl-ethyl)-amide, (3S*,5R*)-5-phenylmethanesulfonylamino-piperidine-3-carboxylic acid (2,2-diphenyl-ethyl)-amide, (3S*,5R*)-5-(4-chloro-benzenesulfonylamino)-piperidine-3-carboxylic acid (2,2-diphenyl-ethyl)-amide, (3S*,5R*)-5-(3-chloro-benzenesulfonylamino)-piperidine-3-carboxylic acid (2,2-diphenyl-ethyl)-amide, (3S*,5R*)-5-(2-chloro-benzenesulfonylamino)-piperidine-3-carboxylic acid (2,2-diphenyl-ethyl)-amide, (3S*,5R*)-5-(naphthalene-1-sulfonylamino)-piperidine-3-carboxylic acid (2,2-diphenyl-ethyl)-amide, (3S*,5R*)-5-(4-methanesulfonyl-benzenesulfonylamino)-piperidine-3-carboxylic acid (2,2-diphenyl-ethyl)-amide, (3S*,5R*)-5-(4-trifluoromethoxy-benzenesulfonylamino)-piperidine-3-carboxylic acid (2,2-diphenyl-ethyl)-amide, (3S*,5R*)-5-(4-isopropyl-benzenesulfonylamino)-piperidine-3-carboxylic acid (2,2-diphenyl-ethyl)-amide, (3S*,5R*)-5-methanesulfonylamino-piperidine-3-carboxylic acid (2,2-diphenyl-ethyl)-amide, (3S*,5R*)-5-(2-acetylamino-4-methyl-thiazole-5-sulfonylamino)-piperidine-3-carboxylic acid (2,2-diphenyl-ethyl)-amide, (3S*,5R*)-5-(5-chloro-1,3-dimethyl-1H-pyrazole-4-sulfonylamino)-piperidine-3-carboxylic acid (2,2-diphenyl-ethyl)-amide, (3S*,5R*)-5-(2,4-difluoro-benzenesulfonylamino)-piperidine-3-carboxylic acid (2,2-diphenyl-ethyl)-amide, (3S*,5R*)-5-[4-(2-oxo-propyl)-benzenesulfonylamino]-piperidine-3-carboxylic acid-(2,2-diphenyl-ethyl)-amide, (3S*,5R*)-5-(4-cyano-benzenesulfonylamino)-piperidine-3-carboxylic acid (2,2-diphenyl-ethyl)-amide, (3S*,5R*)-5-(2,6-difluoro-benzenesulfonylamino)-piperidine-3-carboxylic acid (2,2-diphenyl-ethyl)-amide, (3S*,5R*)-5-(2-cyano-benzenesulfonylamino)-piperidine-3-carboxylic acid (2,2-diphenyl-ethyl)-amide, (3S*,5R*)-5-(3-methoxy-benzenesulfonylamino)-piperidine-3-carboxylic acid (2,2-diphenyl-ethyl)-amide, (3S*,5R*)-5-(2-trifluoromethyl-benzenesulfonylamino)-piperidine-3-carboxylic acid (2,2-diphenyl-ethyl)-amide, (3S*,5R*)-5-(4-acetylamino-benzenesulfonylamino)-piperidine-3-carboxylic acid (2,2-diphenyl-ethyl)-amide, (3S*,5R*)-5-(pyridine-3-sulfonylamino)-piperidine-3-carboxylic acid (2,2-diphenyl-ethyl)-amide, (3S*,5R*)-5-(3-trifluoromethyl-benzenesulfonylamino)-piperidine-3-carboxylic acid (2,2-diphenyl-ethyl)-amide, (3S*,5R*)-5-(biphenyl-4-sulfonylamino)-piperidine-3-carboxylic acid (2,2-diphenyl-ethyl)-amide, (3S*,5R*)-5-(3-cyano-benzenesulfonylamino)-piperidine-3-carboxylic acid (2,2-diphenyl-ethyl)-amide,
(3S*,5R*)-5-(3,4-dichloro-benzenesulfonylamino)-piperidine-3-carboxylic acid (2,2-diphenyl-ethyl)-amide,
(3S*,5R*)-5-(2,5-dimethoxy-benzenesulfonylamino)-piperidine-3-carboxylic acid (2,2-diphenyl-ethyl)-amide,
(3S*,5R*)-5-(4-phenoxy-benzenesulfonylamino)-piperidine-3-carboxylic acid (2,2-diphenyl-ethyl)-amide,
(3S*,5R*)-5-(2,5-dichloro-benzenesulfonylamino)-piperidine-3-carboxylic acid (2,2-diphenyl-ethyl)-amide,
(3S*,5R*)-5-(3,5-dichloro-benzenesulfonylamino)-piperidine-3-carboxylic acid (2,2-diphenyl-ethyl)-amide,
(3S*,5R*)-5-benzenesulfonylamino-piperidine-3-carboxylic acid (2,2-diphenyl-ethyl)-amide,
(3S*,5R*)-5-(2,4-dichloro-benzenesulfonylamino)-piperidine-3-carboxylic acid (2,2-diphenyl-ethyl)-amide,
(3S*,5R*)-5-(naphthalene-2-sulfonylamino)-piperidine-3-carboxylic acid (2,2-diphenyl-ethyl)-amide,
(3S*,5R*)-5-(2,3-dichloro-benzenesulfonylamino)-piperidine-3-carboxylic acid (2,2-diphenyl-ethyl)-amide,
(3S*,5R*)-5-(2-benzyloxy-benzenesulfonylamino)-piperidine-3-carboxylic acid (2,2-diphenyl-ethyl)-amide,
(3S*,5R*)-5-(3-acetyl-benzenesulfonylamino)-piperidine-3-carboxylic acid (2,2-diphenyl-ethyl)-amide,
(3S*,5R*)-5-[bis-(3-chloro-benzyl)-amino]-piperidine-3-carboxylic acid (naphthalen-1-ylmethyl)-amide,
(3S*,5R*)-5-(4-methyl-benzoylamino)-piperidine-3-carboxylic acid (2,2-diphenyl-ethyl)-amide,
(3S*,5R*)-5-(2-chloro-benzylamino)-piperidine-3-carboxylic acid (2,2-diphenyl-ethyl)-amide,
(3S*,5R*)-5-(3-chloro-benzylamino)-piperidine-3-carboxylic acid (2,2-diphenyl-ethyl)-amide,
(3S*,5R*)-5-[3-(3-chloro-phenyl)-ureido]-piperidine-3-carboxylic acid (2,2-diphenyl-ethyl)-amide,
(3S*,5R*)-5-(toluene-4-sulfonylamino)-piperidine-3-carboxylic acid (5,6-diethyl-indan-2-yl)-amide,
(3R*,5S*)-5-(toluene-4-sulfonylamino)-piperidine-3-carboxylic acid (2-phenyl-2-pyridin-2-yl-ethyl)-amide,
(3S*,5R*)-5-(3-chloro-benzenesulfonylamino)-piperidine-3-carboxylic acid [1-(4-chloro-phenyl)-cyclopropylmethyl]-amide,
(3S*,5R*)-5-(toluene-4-sulfonylamino)-piperidine-3-carboxylic acid [2-(4-methoxy-phenyl)-2-phenyl-ethyl]-amide,
(3S*,5R*)-5-(toluene-4-sulfonylamino)-piperidine-3-carboxylic acid {2-[2-(4-methoxy-butoxy)-phenyl]-2-phenyl-ethyl}-amide,
(3S*,5R*)-5-(toluene-4-sulfonylamino)-piperidine-3-carboxylic acid (biphenyl-2-ylmethyl)-amide,
(3S*,5R*)-5-(toluene-4-sulfonylamino)-piperidine-3-carboxylic acid [3-(4-methoxy-phenyl)-2-phenyl-propyl]-amide,
(3S*,5R*)-5-(3-Chloro-benzenesulfonylamino)-piperidine-3-carboxylic acid (2-chloro-benzyl)-cyclopropyl-amide,
(3S*,5R*)-5-(3-chloro-benzenesulfonylamino)-piperidine-3-carboxylic acid cyclopropyl-(2,2-diphenyl-ethyl)-amide,
(3S*,5R*)-5-(toluene-4-sulfonylamino-piperidine-3-carboxylic acid benzyl-(3-methyl-2-phenyl-butyl)-amide,
(3S,5R)-5-(toluene-4-sulfonylamino)-piperidine-3-carboxylic acid (2,2-diphenyl-ethyl)-amide,
{(3R*,5S*)-5-[benzyl-(3-methyl-2-phenyl-butyl)-carbamoyl]-piperidin-3-yl}-carbamic acid tert-butyl ester,
((3R*, 5S*)-5-{cyclopropyl-[1-(3-methoxy-propyl)-1H-indol-3-ylmethyl]-carbamoyl}-piperidin-3-yl)-carbamic acid tert-butyl ester,
(3S*,5R*)-5-(3,3-dimethyl-butyrylamino)-piperidine-3-carboxylic acid cyclopropyl-[1-(3-methoxy-propyl)-1H-indol-3-ylmethyl]-amide,
((3R*,5S*)-5-{cyclopropyl-[1-(3-methoxy-propyl)-1H-indol-3-ylmethyl]-carbamoyl}-piperidin-3-yl)-carbamic acid isobutyl ester,
(3S*,5R*)-5-(2,2-dimethyl-propionylamino)-piperidine-3-carboxylic acid cyclopropyl-[1-(3-methoxy-propyl)-1H-indol-3-ylmethyl]-amide,
(3S*,5R*)-5-(3,3-dimethyl-butyrylamino)-piperidine-3-carboxylic acid cyclopropyl-[1-(3-methoxy-propyl)-1H-indol-3-ylmethyl]-amide,
(3S*,5R*)-5-(cyclobutylcarbonyl-amino)-piperidine-3-carboxylic acid cyclopropyl-[1-(3-methoxy-propyl)-1H-indol-3-ylmethyl]-amide,
(3S*,5R*)-5-(3-benzyl-ureido)-piperidine-3-carboxylic acid cyclopropyl-[1-(3-methoxy-propyl)-1H-indol-3-ylmethyl]-amide,
(3S*,5R*)-5-(3-cyclohexyl-ureido)-piperidine-3-carboxylic acid cyclopropyl-[1-(3-methoxy-propyl)-1H-indol-3-ylmethyl]-amide;
(3S*,5R*)-5-(3-tert-butyl-ureido)-piperidine-3-carboxylic acid cyclopropyl-[1-(3-methoxy-propyl)-1H-indol-3-ylmethyl]-amide;
(3S*,5R*)-5-[2-(3-methoxy-phenyl)-acetylamino]-piperidine-3-carboxylic acid cyclopropyl-[1-(3-methoxy-propyl)-1H-indol-3-ylmethyl]-amide;
(3S*,5R*)-5-[(benzo[b]thiophene-2-carbonyl)-amino]-piperidine-3-carboxylic acid cyclopropyl-[1-(3-methoxy-propyl)-1H-indol-3-ylmethyl]-amide;
(3S*,5R*)-5-benzoylamino-piperidine-3-carboxylic acid cyclopropyl-[1-(3-methoxy-propyl)-1H-indol-3-ylmethyl]-amide;
(3S*,5R*)-5-acetylamino-piperidine-3-carboxylic acid cyclopropyl-[1-(3-methoxy-propyl)-1H-indol-3-ylmethyl]-amide;
(3S*,5R*)-5-(3,4-dimethoxy-benzoylamino)-piperidine-3-carboxylic acid cyclopropyl-[1-(3-methoxy-propyl)-1H-indol-3-ylmethyl]-amide;
(3S*,5R*)-5-(3-phenyl-propionylamino)-piperidine-3-carboxylic acid cyclopropyl-[1-(3-methoxy-propyl)-1H-indol-3-ylmethyl]-amide;
(3S*,5R*)-5-(cyclohexanecarbonyl-amino)-piperidine-3-carboxylic acid cyclopropyl-[1-(3-methoxy-propyl)-1H-indol-3-ylmethyl]-amide;
(3S*,5R*)-5-(3-methyl-butyrylamino)-piperidine-3-carboxylic acid cyclopropyl-[1-(3-methoxy-propyl)-1H-indol-3-ylmethyl]-amide;
(3S*,5R*)-5-(2-ethyl-butyrylamino)-piperidine-3-carboxylic acid cyclopropyl-[1-(3-methoxy-propyl)-1H-indol-3-ylmethyl]-amide;
(3S*,5R*)-5-[(2,2,3,3-tetra methyl-cyclopropanecarbonyl)-amino]-piperidine-3-carboxylic acid cyclopropyl-[1-(3-methoxy-propyl)-1H-indol-3-ylmethyl]-amide;
(3S*,5R*)-5-[(tetrahydro-furan-2-carbonyl)-amino]-piperidine-3-carboxylic acid cyclopropyl-[1-(3-methoxy-propyl)-1H-indol-3-ylmethyl]-amide;
(3S*,5R*)-5-isobutyrylamino-piperidine-3-carboxylic acid cyclopropyl-[1-(3-methoxy-propyl)-1H-indol-3-ylmethyl]-amide;
(3S*,5R*)-5-(cyclopropanecarbonyl-amino)-piperidine-3-carboxylic acid cyclopropyl-[1-(3-methoxy-propyl)-1H-indol-3-ylmethyl]-amide;
(3S*,5R*)-5-(2-methoxy-acetylamino)-piperidine-3-carboxylic acid cyclopropyl-[1-(3-methoxy-propyl)-1H-indol-3-ylmethyl]-amide;
(3S*,5R*)-5-(2-methyl-2-phenyl-propionylamino)-piperidine-3-carboxylic acid cyclopropyl-[1-(3-methoxy-propyl)-1H-indol-3-ylmethyl]-amide;
(3S*,5R*)-5-((S)-2-acetylamino-4-methyl-pentanoylamino)-piperidine-3-carboxylic acid cyclopropyl-[1-(3-methoxy-propyl)-1H-indol-3-ylmethyl]-amide;

(3S*,5R*)-5-(2-dimethylamino-acetylamino)-piperidine-3-carboxylic acid cyclopropyl-[1-(3-methoxy-propyl)-1H-indol-3-ylmethyl]-amide;
(3S*,5R*)-5-(3-hydroxy-2,2-dimethyl-propionylamino)-piperidine-3-carboxylic acid cyclopropyl-[1-(3-methoxy-propyl)-1H-indol-3-ylmethyl]-amide; cyclopropane-1,1-dicarboxylic acid amide ((3R*,5S*)-5-{cyclopropyl-[1-(3-methoxy-propyl)-1H-indol-3-ylmethyl]-carbamoyl}-piperidin-3-yl)-amide;
(3S*,5R*)-5-[(1-cyano-cyclopropanecarbonyl)-amino]-piperidine-3-carboxylic acid cyclopropyl-[1-(3-methoxy-propyl)-1H-indol-3-ylmethyl]-amide;
((3R*,5S*)-5-{cyclopropyl-[1-(3-methoxy-propyl)-1H-indol-3-ylmethyl]-carbamoyl}-piperidin-3-yl)-carbamic acid benzyl ester;
((3R*,5S*)-5-{cyclopropyl-[1-(3-methoxy-propyl)-1H-indol-3-ylmethyl]-carbamoyl}-piperidin-3-yl)-carbamic acid 2-methoxy-ethyl ester;
(3S*,5R*)-5-(2,2-dimethyl-propionylamino)-piperidine-3-carboxylic acid [4-chloro-3-(3-methoxy-propoxy)-benzyl]-cyclopropyl-amide;
((3R*,5S*)-5-{[4-chloro-3-(3-methoxy-propoxy)-benzyl]-cyclopropyl-carbamoyl}-piperidin-3-yl)-carbamic acid tert-butyl ester;
(3S*,5R*)-5-(cyclopropanecarbonyl-amino)-piperidine-3-carboxylic acid [4-chloro-3-(3-methoxy-propoxy)-benzyl]-cyclopropyl-amide;
(3S*,5R*)-5-(cyclobutanecarbonyl-amino)-piperidine-3-carboxylic acid [4-chloro-3-(3-methoxy-propoxy)-benzyl]-cyclopropyl-amide;
(3S*,5R*)-5-isobutyrylamino-piperidine-3-carboxylic acid [4-chloro-3-(3-methoxy-propoxy)-benzyl]-cyclopropyl-amide;
(3S*,5R*)-5-(3-tert-butyl-ureido)-piperidine-3-carboxylic acid [4-chloro-3-(3-methoxy-propoxy)-benzyl]-cyclopropyl-amide;
(3S*,5R*)-5-(3-tert-Butyl-ureido)-piperidine-3-carboxylic acid cyclopropyl-[3-(3-methoxy-propoxy)-4-methyl-benzyl]-amide;
(3S*,5R*)-5-(3-benzyl-ureido)-piperidine-3-carboxylic acid cyclopropyl-[3-(3-methoxy-propoxy)-4-methyl-benzyl]-amide;
((3R*,5S*)-5-{cyclopropyl-[3-(3-methoxy-propoxy)-4-methyl-benzyl]-carbamoyl}-piperidin-3-yl)-carbamic acid isobutyl ester;
(3S*,5R*)-5-(2,2-dimethyl-propionylamino)-piperidine-3-carboxylic acid cyclopropyl-[3-(3-methoxy-propoxy)-4-methyl-benzyl]-amide;
(3S*,5R*)-5-(cyclobutanecarbonyl-amino)-piperidine-3-carboxylic acid cyclopropyl-[3-(3-methoxy-propoxy)-4-methyl-benzyl]-amide;
(3S*,5R*)-5-(3-tert-butyl-ureido)-piperidine-3-carboxylic acid cyclopropyl-[3-methoxy-5-(3-methoxy-propoxy)-benzyl]-amide;
(3S*,5R*)-5-(3-benzyl-ureido)-piperidine-3-carboxylic acid cyclopropyl-[3-methoxy-5-(3-methoxy-propoxy)-benzyl]-amide;
((3R*,5S*)-5-{cyclopropyl-[3-methoxy-5-(3-methoxy-propoxy)-benzyl]-carbamoyl}-piperidin-3-yl)-carbamic acid isobutyl ester;
((3R*,5S*)-5-{cyclopropyl-[3-methoxy-5-(3-methoxy-propoxy)-benzyl]-carbamoyl}-piperidin-3-yl)-carbamic acid tert-butyl ester;
(3S*,5R*)-5-(3,3-dimethyl-butyrylamino)-piperidine-3-carboxylic acid cyclopropyl-[3-methoxy-5-(3-methoxy-propoxy)-benzyl]-amide;
(3S*,5R*)-5-(cyclobutanecarbonyl-amino)-piperidine-3-carboxylic acid cyclopropyl-[3-methoxy-5-(3-methoxy-propoxy)-benzyl]-amide;
(3S*,5R*)-5-(2,2-dimethyl-propionylamino)-piperidine-3-carboxylic acid cyclopropyl-[3-methoxy-5-(3-methoxy-propoxy)-benzyl]-amide;
(3S*,5R*)-5-(3,3-dimethyl-butyrylamino)-piperidine-3-carboxylic acid cyclopropyl-(2,3-dichloro-benzyl)-amide;
{(3R*,5S*)-5-[cyclopropyl-(2,3-dichloro-benzyl)-carbamoyl]-piperidin-3-yl}-carbamic acid 2-methoxy-ethyl ester;
{(3R*,5S*)-5-[cyclopropyl-(2,3-dimethyl-benzyl)-carbamoyl]-piperidin-3-yl}-carbamic acid tert-butyl ester;
(3S*,5R*)-5-(3,3-dimethyl-butyrylamino)-piperidine-3-carboxylic acid cyclopropyl-(2,3-dimethyl-benzyl)-amide;
(3R,5S)-5-(2,2-dimethyl-propionylamino)-piperidine-3-carboxylic acid cyclopropyl-[1-(3-methoxy-propyl)-1H-indol-3-ylmethyl]-amide
(3R,5S)-5-(3-tert-butyl-ureido)-piperidine-3-carboxylic acid cyclopropyl-[1-(3-methoxy-propyl)-1H-indol-3-ylmethyl]-amide;
(3S*,5R*)-5-(2,2-dimethyl-propionylamino)-piperidine-3-carboxylic acid ethyl-[4-(3-methoxy-propyl)-3-oxo-3,4-dihydro-2H-benzo[1,4]oxazin-6-yl]-amide;
(3S*,5R*)-5-[methyl-(toluene-4-sulfonyl)-amino]-piperidine-3-carboxylic acid (2,2-diphenyl-ethyl)-amide,
(3S*,5R*)-5-(toluene-4-sulfonylamino)-piperidine-3-carboxylic acid [2-(4-chloro-phenyl)-2-phenyl-ethyl]-amide,
(3S*,5R*)-5-(toluene-4-sulfonylamino)-piperidine-3-carboxylic acid [2,2-bis-(4-methoxy-phenyl)-ethyl]-amide,
(3S*,5R*)-5-(toluene-4-sulfonylamino)-piperidine-3-carboxylic acid (2-cyclohexyl-2-phenyl-ethyl)-amide,
(3S*,5R*)-5-(toluene-4-sulfonylamino)-piperidine-3-carboxylic acid [2-(3-methoxymethyl-phenyl)-2-phenyl-ethyl]-amide,
(3S*,5R*)-5-(toluene-4-sulfonylamino)-piperidine-3-carboxylic acid (2,2-diphenyl-butyl)-amide,
(3S*,5R*)-5-(toluene-4-sulfonylamino)-piperidine-3-carboxylic acid [2-(4-chloro-phenyl)-3-methyl-butyl]-amide,
2,2-diphenyl-3-{[(3S*,5R*)-5-(toluene-4-sulfonylamino)-piperidine-3-carbonyl]-amino}-propionic acid ethyl ester,
(3S*,5R*)-5-(toluene-4-sulfonylamino)-piperidine-3-carboxylic acid (4-methyl-2-phenyl-pentyl)-amide,
(3S*,5R*)-5-(toluene-4-sulfonylamino)-piperidine-3-carboxylic acid {2-[2-(3-methoxy-propoxy)-phenyl]-2-phenyl-ethyl}-amide,
(3S*,5R*)-5-(toluene-4-sulfonylamino)-piperidine-3-carboxylic acid [2-(2-methoxy-phenyl)-2-phenyl-ethyl]-amide,
(3S*,5R*)-5-(toluene-4-sulfonylamino)-piperidine-3-carboxylic acid (5-methoxy-2,2-diphenyl-pentyl)-amide,
(3S*,5 R*)-5-(toluene-4-sulfonylamino)-piperidine-3-carboxylic acid {2-[2-(2-methoxy-ethoxy)-phenyl]-2-phenyl-ethyl}-amide,
{(3R*,5S*)-5-[cyclopropyl-(2,3-dichloro-benzyl)-carbamoyl]-piperidin-3-yl}-carbamic acid tert-butyl ester,
(3S*,5R*)-5-(3-chloro-benzenesulfonylamino)-piperidine-3-carboxylic acid (2,3-diphenyl-propyl)-amide,
(3S*,5R*)-5-(toluene-4-sulfonylamino)-piperidine-3-carboxylic acid cyclopropyl-(2,3-dichloro-benzyl)-amide,
{(3R*,5R*)-5-[cyclopropyl-(2,3-dichloro-benzyl)-carbamoyl]-piperidin-3-yl}-carbamic acid tert-butyl ester,
(3R*,5R*)-5-(3-chloro-benzenesulfonylamino)-piperidine-3-carboxylic acid cyclopropyl-(2,3-dichloro-benzyl)-amide, ((3R*,5R*)-5-{cyclopropyl-[1-(3-methoxy-propyl)-1H-indol-3-ylmethyl]-carbamoyl}-piperidin-3-yl)-carbamic acid tert-butyl ester,
(3R,5S)-5-Phenylacetylamino-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(2-Phenoxy-acetylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[(1-Phenyl-cyclopropanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(2-Hydroxy-4-methyl-pentanoylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(2-Hydroxy-3-phenyl-propionylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(2-Hydroxy-3-methyl-butyrylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[2-(Tetrahydro-pyran-4-yloxy)-acetylamino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
((3S,5R)-5-{Cyclopropyl-[4-(3-methoxy-propyl)-2,2-dimethyl-3-oxo-3,4-dihydro-2H-benzo[1,4]oxazin-6-yl]-carbamoyl}-piperidin-3-yl)-carbamic acid tetrahydro-pyran-4-yl ester,
(3R,5S)-5-(2-Hydroxymethyl-3-methyl-butyrylamino)-piperidine-3-carboxylic acid cyclopropyl-[4-(3-methoxy-propyl)-2,2-dimethyl-3-oxo-3,4-dihydro-2H-benzo[1,4]-oxazin-6-yl]-amide,
((3S,5R)-5-{Cyclopropyl-[4-(3-methoxy-propyl)-2,2-dimethyl-3-oxo-3,4-dihydro-2H-benzo[1,4]oxazin-6-yl]-carbamoyl}-piperidin-3-yl)-carbamic acid tert-butyl ester,
(3R,5S)-5-Acetylamino-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[2-(Pyridin-3-yloxy)-acetylamino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(2-Tetrahydro-pyran-4-yl-acetylamino)-piperidine-3-carboxylic acid cyclopropyl-[4-(3-methoxy-propyl)-2,2-dimethyl-3-oxo-3,4-dihydro-2H-benzo-[1,4]oxazin-6-yl]-amide,
(3R,5S)-5-(3-Hydroxy-3-methyl-butyrylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[(Tetrahydro-pyran-4-carbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
N-((3S,5R)-5-{Cyclopropyl-[4-(3-methoxy-propyl)-2,2-dimethyl-3-oxo-3,4-dihydro-2H-benzo[1,4]oxazin-6-yl]-carbamoyl}-piperidin-3-yl)-nicotinamide,
(3R,5S)-5-Methanesulfonylamino-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(2,2-Dimethyl-propionylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[(1-Cyano-cyclopropanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(4-Methyl-pentanoylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[(1-Cyano-cyclopentanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[2-(4-Hydroxy-tetrahydro-pyran-4-yl)-acetylamino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(4-Hydroxy-4-methyl-pentanoylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[(4-Cyano-tetrahydro-pyran-4-carbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[2-Methyl-2-(tetrahydro-pyran-4-yl)-propionylamino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-(2-Tetrahydro-pyran-4-yl-propionylamino)-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5S)-5-[(1-Pyridin-4-yl-cyclopropanecarbonyl)-amino]-piperidine-3-carboxylic acid [4-(3-methoxy-propyl)-2,2-dimethyl-3-oxo-3,4-dihydro-2H-benzo[1,4]oxazin-6-yl]-amide,
(3R,5S)-5-[(1-Pyridin-4-yl-cyclopropanecarbonyl)-amino]-piperidine-3-carboxylic acid [4-(3-methoxy-propyl)-2,2-dimethyl-3-oxo-3,4-dihydro-2H-benzo[1,4]oxazin-6-yl]-amide,
(3R,5S)-5-[(1-Pyridin-2-yl-cyclopentanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R,5R)-5-{2-Oxo-2-[1-(2H-tetrazol-5-yl)-cyclopropyl]-ethyl}-piperidine-3-carboxylic acid cyclopropyl-[4-(3-methoxy-propyl)-2,2-dimethyl-3-oxo-3,4-dihydro-2H-benzo[1,4]oxazin-6-yl]-amide,
(3R*,5S*)-5-Cyclohexylamino-piperidine-3-carboxylic acid cyclopropyl-[3-methoxy-5-(3-methoxy-propoxy)-benzyl]-amide,
(3R*,5S*)-5-m-Tolylamino-piperidine-3-carboxylic acid cyclopropyl-[3-methoxy-5-(3-methoxy-propoxy)-benzyl]-amide,
(3R*,5S*)-5-(6-Chloro-pyrimidin-4-ylamino)-piperidine-3-carboxylic acid cyclopropyl-[3-methoxy-5-(3-methoxy-propoxy)-benzyl]-amide,
(3R*,5S*)-5-(6-Chloro-pyrimidin-4-ylamino)-piperidine-3-carboxylic acid cyclopropyl-[1-(3-methoxy-propyl)-1H-indol-3-ylmethyl]-amide,
(3R*,5S*)-5-(2-Oxo-imidazolidin-1-yl)-piperidine-3-carboxylic acid cyclopropyl-[1-(3-methoxy-propyl)-1H-indol-3-ylmethyl]-amide, (3R,5S)-5-[Benzyl-(2,2-dimethyl-propionyl)-amino]-piperidine-3-carboxylic acid cyclopropyl-[1-(3-methoxy-propyl)-1H-indol-3-ylmethyl]-amide, (3R,5S)-5-(Benzyl-cyclobutanecarbonyl-amino)-piperidine-3-carboxylic acid cyclopropyl-[1-(3-methoxy-propyl)-1H-indol-3-ylmethyl]-amide, (3R,5S)-5-[(2,2-Dimethyl-propionyl)-isobutyl-amino]-piperidine-3-carboxylic acid cyclopropyl-[1-(3-methoxy-propyl)-1H-indol-3-ylmethyl]-amide, (3R,5S)-5-(3-Benzyl-1-isobutyl-ureido)-piperidine-3-carboxylic acid cyclopropyl-[1-(3-methoxy-propyl)-1H-indol-3-ylmethyl]-amide, (3R,5S)-5-[Cyclopropylmethyl-(2,2-dimethyl-propionyl)-amino]-piperidine-3-carboxylic acid cyclopropyl-[1-(3-methoxy-propyl)-1H-indol-3-ylmethyl]-amide, ((3S,5R)-5-{Cyclopropyl-[1-(3-methoxy-propyl)-1H-indol-3-ylmethyl]-carbamoyl}-piperidin-3-yl)-cyclopropylmethyl-carbamic acid tert-butyl ester, (3R,5S)-5-[Methyl-(1-phenyl-cyclopropanecarbonyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide, and (3R,5S)-5-[Methyl-(2-tetrahydro-pyran-4-yl-acetyl)-amino]-piperidine-3-carboxylic acid cyclopropyl-[4-(3-methoxy-propyl)-2,2-dimethyl-3-oxo-3,4-dihydro-2H-benzo[1,4]oxazin-6-yl]-amide, or a pharmaceutically acceptable salt thereof, respectively.

13. A pharmaceutical formulation, comprising a compound of the formula I, or a pharmaceutically acceptable salt thereof, as mentioned in claim 1 and at least one pharmaceutically acceptable carrier material.

14. A method of treating hypertension comprising administering to a warm-blooded animal in need of such treatment a pharmaceutically effective amount of a compound of the formula I, or a pharmaceutically acceptable salt thereof, as mentioned in claim 1.

15. A process for the manufacture of a compound of the formula I, or a pharmaceutically acceptable salt thereof, as given in claim 1, said process comprising a) for the manufacture of a compound of the formula I wherein R1 is hydrogen, and R2, R3, R4 and T are as defined for a compound of the formula I in claim 1, reacting a compound of the formula II,

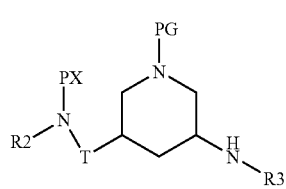

(II)

wherein R2, R3 and T are as defined for a compound of the formula I, PX is R1 as defined for a compound of the formula I, a protecting group or a bound resin and PG is a protecting group, with a compound of the formula III,

R4-A (III)

wherein R4 is as defined for a compound of the formula I in claim 1 and A is activated hydroxy; or b) reacting a compound of the formula IV,

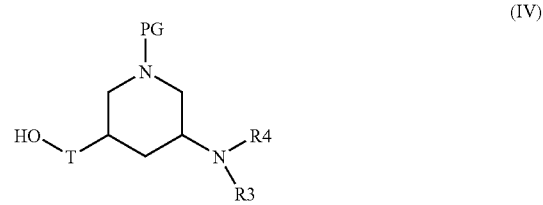

(IV)

wherein T is methylene or preferably carbonyl, PG is a protecting group and R3 and R4 are as defined for a compound of the formula I in claim 1, or an activated derivative thereof, with a compound of the formula V,

R1-NH-R2 (V)

wherein R1 and R2 are as defined for the formula I in claim 1; or c) for the manufacture of a compound of the formula I as given in claim 1 wherein R1 is hydrogen, R4 is N-mono- or N,N-di-(unsubstituted or substituted aryl, unsubstituted or substituted heterocyclyl, unsubstituted or substituted cycloalkyl or unsubstituted or substituted alkyl)-aminocarbonyl and R2, R3 and T are as defined for a compound of the formula I in claim 1, reacting a compound of the formula II as given under a) above with a compound of the formula VI,

R4*-NCO (VI)

wherein R4* is unsubstituted or substituted aryl, unsubstituted or substituted heterocyclyl, unsubstituted or substituted cycloalkyl or unsubstituted or substituted alkyl; or d) for the manufacture of a compound of the formula I wherein R1 is hydrogen, R4 is unsubstituted or substituted alkyl bound via a methylene group (which may be the alkyl of unsubstituted or substituted alkyl or form part of it) and R2, R3 and T are as defined for a compound of the formula I in claim 1, reacting a compound of the formula II as given under a) above with an oxo compound of the formula VII,

R4-C(=O)R4* (VII)

wherein R4 and R4* with the carbon atom binding independently are hydrogen or a moiety completing an unsubstituted or substituted alkyl moiety R4 as given for a compound of the claim 1 bound via the carbon carrying the oxo (=O) group in formula VII, under conditions of reductive amination;

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof.

* * * * *